(12) United States Patent
Pio et al.

(10) Patent No.: US 9,206,199 B2
(45) Date of Patent: Dec. 8, 2015

(54) INHIBITORS OF THE RENAL OUTER MEDULLARY POTASSIUM CHANNEL

(71) Applicants: Barbara Pio, West Orange, NJ (US); Alexander Pasternak, Princeton, NJ (US); Aurash Shahripour, Rahway, NJ (US); Haifeng Tang, Metuchen, NJ (US); Shawn Walsh, Bridgewater, NJ (US)

(72) Inventors: Barbara Pio, West Orange, NJ (US); Alexander Pasternak, Princeton, NJ (US); Aurash Shahripour, Rahway, NJ (US); Haifeng Tang, Metuchen, NJ (US); Shawn Walsh, Bridgewater, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/364,908

(22) PCT Filed: Dec. 11, 2012

(86) PCT No.: PCT/US2012/068964
§ 371 (c)(1),
(2) Date: Jun. 12, 2014

(87) PCT Pub. No.: WO2013/090271
PCT Pub. Date: Jun. 20, 2013

(65) Prior Publication Data
US 2014/0336177 A1  Nov. 13, 2014

Related U.S. Application Data

(60) Provisional application No. 61/576,879, filed on Dec. 16, 2011.

(51) Int. Cl.
| | |
|---|---|
| C07D 498/04 | (2006.01) |
| A61K 31/5383 | (2006.01) |
| A61P 7/12 | (2006.01) |
| A61P 9/02 | (2006.01) |
| A61P 9/04 | (2006.01) |
| C07D 513/04 | (2006.01) |
| A61K 31/4985 | (2006.01) |
| A61K 45/06 | (2006.01) |
| A61K 31/401 | (2006.01) |
| A61K 31/41 | (2006.01) |
| A61K 31/4178 | (2006.01) |
| A61K 31/4422 | (2006.01) |
| A61K 31/585 | (2006.01) |
| A61K 31/675 | (2006.01) |
| A61K 31/542 | (2006.01) |
| A61K 31/553 | (2006.01) |
| C07D 487/04 | (2006.01) |

(52) U.S. Cl.
CPC ............ *C07D 513/04* (2013.01); *A61K 31/401* (2013.01); *A61K 31/41* (2013.01); *A61K 31/4178* (2013.01); *A61K 31/4422* (2013.01); *A61K 31/4985* (2013.01); *A61K 31/5383* (2013.01); *A61K 31/542* (2013.01); *A61K 31/553* (2013.01); *A61K 31/585* (2013.01); *A61K 31/675* (2013.01); *A61K 45/06* (2013.01); *C07D 487/04* (2013.01); *C07D 498/04* (2013.01)

(58) Field of Classification Search
CPC .......................... A61K 31/5383; C07D 498/04
USPC .............. 544/90; 540/552; 514/230.5, 211.09
See application file for complete search history.

(56) References Cited

U.S. PATENT DOCUMENTS

| | | | |
|---|---|---|---|
| 2,988,551 | A | 6/1961 | Morren |
| 3,435,002 | A | 3/1969 | Holub |
| 3,632,608 | A | 1/1972 | Holub |
| 3,749,722 | A | 7/1973 | Holub |
| 4,579,863 | A | 4/1986 | Horwell et al. |
| 4,806,536 | A | 2/1989 | Cross et al. |

(Continued)

FOREIGN PATENT DOCUMENTS

| | | |
|---|---|---|
| EP | 0099148 B1 | 2/1988 |
| EP | 0175376 B1 | 4/1991 |

(Continued)

OTHER PUBLICATIONS

Felix et al. Assay and Drug Development Technologies,10(5),pp. 417-431 (2012).*

(Continued)

*Primary Examiner* — Venkataraman Balasubramanian
(74) *Attorney, Agent, or Firm* — Nicole M. Beeler; Catherine D. Fitch

(57) ABSTRACT

The present invention provides compounds of Formula I

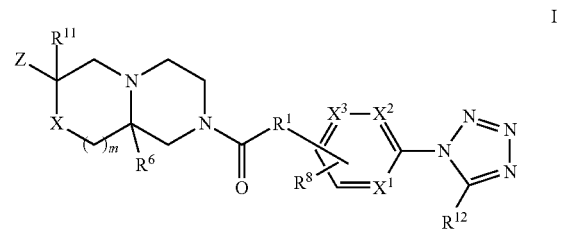

and the pharmaceutically acceptable salts thereof, which are inhibitors of the ROMK (Kir1.1) channel. The compounds act as diuretics and natriuretics and are valuable pharmaceutically active compounds for the therapy and prophylaxis of medical conditions including cardiovascular diseases such as hypertension and conditions resulting from excessive salt and water retention.

18 Claims, No Drawings

(56) References Cited

U.S. PATENT DOCUMENTS

| | | | |
|---|---|---|---|
| 4,992,547 | A | 2/1991 | Berner et al. |
| 5,145,885 | A | 9/1992 | Berner et al. |
| 5,215,989 | A | 6/1993 | Baldwin et al. |
| 5,614,526 | A | 3/1997 | Godel et al. |
| 5,736,546 | A | 4/1998 | Kawashima et al. |
| 6,258,813 | B1 | 7/2001 | Arlt et al. |
| 6,787,543 | B2 | 9/2004 | Take et al. |
| 2004/0204404 | A1 | 10/2004 | Zelle et al. |
| 2005/0215526 | A1 | 9/2005 | Hulme et al. |
| 2005/0267121 | A1 | 12/2005 | Li et al. |
| 2006/0183739 | A1 | 8/2006 | Tsaklakidis et al. |
| 2006/0183742 | A1 | 8/2006 | Mederski et al. |
| 2006/0211692 | A1 | 9/2006 | Mederski et al. |
| 2007/0004750 | A1 | 1/2007 | Lorsbach et al. |
| 2007/0093472 | A1 | 4/2007 | Mederski et al. |
| 2008/0003214 | A1 | 1/2008 | Cezanne et al. |
| 2010/0286123 | A1 | 11/2010 | Pasternak et al. |

FOREIGN PATENT DOCUMENTS

| | | | |
|---|---|---|---|
| EP | 1094063 | A1 | 4/2001 |
| EP | 1939175 | A1 | 7/2009 |
| FR | 2673182 | | 8/1992 |
| FR | 2673182 | A1 | 8/1992 |
| GB | 949088 | A | 2/1964 |
| GB | 1575310 | A | 9/1980 |
| GB | 2116967 | | 7/1986 |
| JP | 10203986 | | 8/1998 |
| WO | 9744329 | | 11/1997 |
| WO | 0051611 | A1 | 9/2000 |
| WO | 0232874 | | 4/2002 |
| WO | 0204314 | A1 | 6/2002 |
| WO | 0250061 | A1 | 6/2002 |
| WO | 2004020422 | A1 | 3/2004 |
| WO | 2004037817 | A1 | 5/2004 |
| WO | 2004046110 | | 6/2004 |
| WO | 2005037843 | | 4/2005 |
| WO | 2005044797 | | 5/2005 |
| WO | 2006034341 | A2 | 3/2006 |
| WO | 2006034769 | A1 | 4/2006 |
| WO | 2006098342 | A1 | 9/2006 |
| WO | 2006129199 | A1 | 12/2006 |
| WO | 2007075629 | A2 | 7/2007 |
| WO | 2008147864 | | 12/2008 |
| WO | 2008147864 | A2 | 12/2008 |
| WO | 2009149508 | | 11/2009 |
| WO | 2010129379 | A1 | 11/2010 |
| WO | 2012058116 | A1 | 5/2012 |
| WO | 2012058134 | A1 | 5/2012 |
| WO | 2013028474 | A1 | 2/2013 |
| WO | 2013039802 | A1 | 3/2013 |
| WO | 2013062892 | A1 | 5/2013 |
| WO | 2013062900 | A1 | 5/2013 |
| WO | 2013066714 | A1 | 5/2013 |
| WO | 2013066717 | A1 | 5/2013 |
| WO | 2013066718 | A2 | 5/2013 |
| WO | 2014015495 | A1 | 1/2014 |
| WO | 2014018764 | A1 | 1/2014 |

OTHER PUBLICATIONS

Cecil Textbook of Medicine, edited by Bennet, J.C., and Plum F., 20th edition, vol. 1, 1004-101 O, 1996.*

Freshney et al., Culture of Animal Cells, A Manual of Basic Technique, Alan R. Liss, Inc., 1983, New York, p. 4.*

Dermer et al., Bio/Technology, 1994, 12:320.*

ACCF/AHA Practice Guideline, 2009 Focused update incorporated into the ACC/AHA 2005 guidelines . . . , Circulation, 2009, e391-e436, 119.

Baltzly, R., The preparation of N-mono-substituted and unsymmetrically disubstituted piperazines, J. Am. Chemoc., 1944, 263-266, 66.

Bhave, G., Small-molecule modulators of inward rectifier K+ channels: recent advances and future possibilities, Future Med Chem, 2010, 757-774, 2(5).

Bhave, G., Development of a selective small-molecule inhibitor Kir1.1, the renal outer medullary potassium channel, Mol. Pharmacol., 2011, 42-50, 79.

Brater et al., Diuretic Therapy, Drug Therapy, 1998, 387-395, 339.

Brewster et al., Antihypertensive 1,4-bis (2-indol-3-ylethyl)piperazines, Chimie Ther., 1973, 169-172 (English trans.), 2.

Cerkvenik-Flajs V, Determination of residues of azaperone in the kidneys by liquid chromatography with fluorescence, Anal. Chim. Acta., 2007, 374-382, 586.

Chemical Abstracts (2004), Abstract No. 697771-49-6, "1,3-Isobenzofurandione 5-[[4-[(5-chloro-2-methoxyphenyl) sulfonyl]-1-...".

Cheymol et al., Increase in the effects of epinephrine and acetylcholine . . . , Comptes Rendus des seances de la Societe de Biologie, 1951, 496-499 (English trans.), 145.

Fallen, K., The Kir channel immunoglobuling domain is essential for Kir1.1 (ROMK) thermodynamic stability, trafficing and gating, Channels, 2009, 57-66, 3.

Felker et al, Diuretic strategies in patients with acute decompensated heart failure, New Eng. J. Med., 2011, 797-805, 364.

Frank, Managing hypertension using combination therapy, Am. Fam. Physician, 2008, 1279-1286, 77.

International Search Report and Written Opinion for PCT/US 12/68964, mailed Feb. 20, 2013, 13 pages.

Kulkarni, YD, Possible antifertility agents, part III. Synthesis of 4-(substituted aminomethyl)-5,6,7-trimethoxy phthalid . . . (abstract)), Biol. Mem., 1987, 141-144, 13.

Lanyi et al., Piperazine-Derivatives II, Res. Lab. of Chinoin-Fabrik Chemisch-Pharma. Prod., 1968, 1431-1435 (English trans.), 18.

Lewis, L. M., High-throughput screening reveals a small-molecule inhibitor of the Renal Outer Medullary Potassium Channel and Kir7.1, Mol. Pharncol., 2009, 1094-1103, 76.

Lutz, R. E., Antimalarials. Some Piperazine Derivatives, J. Org. Chem., 1947, 771-775, 12, BO.

Miyake et al., Synthesis of 1-substituted isochroman . . . , Takeda Res. Lab., 1982, 24-40 (English trans.), 41.

Sica, D. A., Diuretic use in renal disease, Nature, 2012, 100-109, 8.

Welling et al., A comprehensive guide to the ROMK potassium channel: form and function in health and disease, Am. J. Physiol. Renal Physiol., 2009, F849-F863, 297.

Zejc et al., Piperazine derivative of dimethylxanthines, Polish J. Pharmacol. & Pharm., 1975, 311-316 (English trans.), 27.

* cited by examiner

INHIBITORS OF THE RENAL OUTER MEDULLARY POTASSIUM CHANNEL

CROSS REFERENCE TO RELATED APPLICATIONS

This application is a U.S. National Phase application under 35 U.S.C. §371 of PCT Application No. PCT/US12/068964 filed Dec. 11, 2012, which claims priority from U.S. Provisional Application Ser. No. 61/576,879, filed Dec. 16, 2012.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K. potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are predicted to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first small molecule selective inhibitors of ROMK were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. However, continuing discovery of selective small molecule inhibitors of ROMK is still needed for the development of new treatments for hypertension and related disorders.

SUMMARY OF THE INVENTION

The present invention provides compounds of Formula I

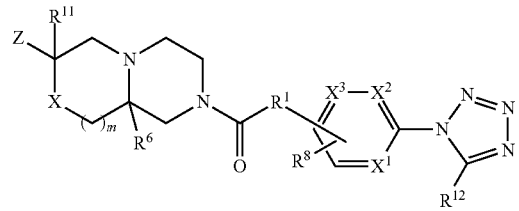

and the pharmaceutically acceptable salts thereof. The compounds of Formula I are inhibitors of the ROMK (Kir1.1) channel and can act as diuretics and natriuretics and are valuable pharmaceutically active compounds for the therapy and prophylaxis of medical conditions, including, but not limited to, cardiovascular diseases such as hypertension, heart failure and conditions resulting from excessive salt and water retention. Therefore, the invention provides methods of treatment comprising administering a therapeutically or prophylactically effective amount of a compound of Formula I to a patient in need of a diuretic and/or natriuretic agent. The invention further provides the use of compounds of Formula I in combination with other therapeutically effective agents, including other drugs useful for the treatment of hypertension, heart failure and conditions resulting from excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention is directed to compounds having structural Formula I:

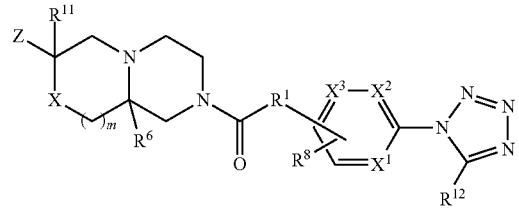

and the pharmaceutically acceptable salts thereof wherein:
X is O, NH, S or $SO_2$;
$R^1$ is $-C(R^9)(R^{10})-$ or $-N(R^{13})-$;
m is an integer selected from 1 or 2;
$X^1$, $X^2$ and $X^3$ are each independently selected from $C(R^7)$ or N, provided that at least one of $X^1$, $X^2$ and $X^3$ must be N and at most two of $X^1$ $X^2$ and $X^3$ are N;

Z is

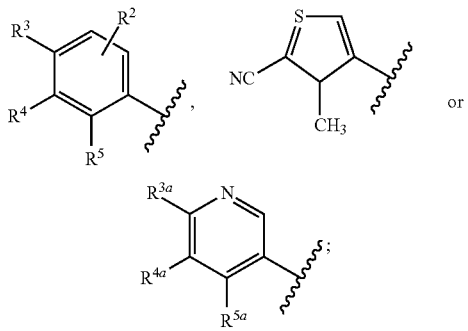

$R^2$ is —H, —F, —Cl, —$C_{1-6}$ alkyl, —$C_{3-6}$ cycloalkyl or —$OC_{1-6}$ alkyl;

$R^3$ and $R^{3a}$ are each independently —H, —F, —Cl, —CN, —$C_{1-6}$ alkyl, —$C_{3-6}$ cycloalkyl or —$OC_{1-6}$ alkyl;

$R^4$ and $R^{4a}$ are each independently —F, —Cl, —CN, —$C_{1-6}$ alkyl, —$C_{3-6}$ cycloalkyl, —$OC_{1-4}$alkyl or N-tetrazolyl;

or $R^3$ and $R^4$ are joined together with the carbon atoms in the phenyl ring to which they are attached to form:

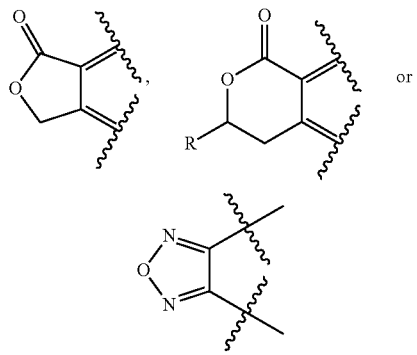

wherein R is —H or —$C_{1-4}$alkyl;

$R^5$ and $R^{5a}$ are each independently —H, —F, —Cl, —CN, —$C_{1-4}$alkyl, —$C_{3-6}$ cycloalkyl or —$OC_{1-4}$-alkyl;

provided that when $R^3$ and $R^4$ are not joined together, then one and only one of $R^3$, $R^4$ or $R^5$ is —CN;

and provided that one and only one of $R^{3a}$, $R^{4a}$ or $R^{5a}$ is —CN;

$R^6$ is —H or —$C_{1-4}$alkyl;

each $R^7$ is independently —H, —F, —Cl, —$CF_3$, —$C_{1-4}$alkyl or —$OC_{1-4}$alkyl; and $R^8$ is —H, —F, —Cl, —$CF_3$, —$C_{1-4}$alkyl or —$OC_{1-4}$alkyl;

$R^9$ is —H, —F or —$C_{1-4}$alkyl;

$R^{10}$ is —H or —F;

$R^{11}$ is —H or —$CH_3$;

$R^{12}$ is —H or —$CH_3$; and $R^{13}$ is —H or —$C_{1-4}$alkyl.

In another embodiment of this invention are compounds of Formula I having structural Formula II and the pharmaceutically acceptable salts thereof:

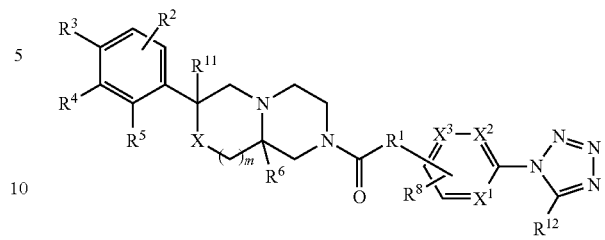

wherein the variables (X, $X^1$, $X^2$, $X^3$, R, $R^1$, $R^2$, $R^3$, etc.) are as defined in Formula I.

In another embodiment of this invention are compounds of Formula I having structural Formula III and the pharmaceutically acceptable salts thereof:

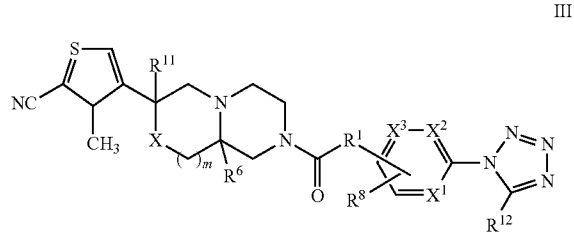

wherein the variables are as defined in Formula I.

In another embodiment of this invention are compounds of Formula I having structural Formula IV

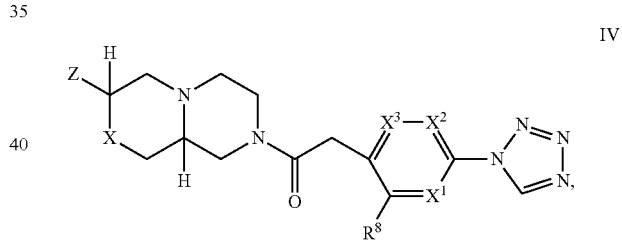

wherein X is O or NH. In an embodiment thereof are compounds of Formula IV wherein $X^1$, $X^2$ and $X^3$ are each independently selected from $C(R^7)$ or N, provided that at least one of $X^1$, $X^2$ and $X^3$ must be N and at most two of $X^1$ $X^2$ and $X^3$ are N;

Z is

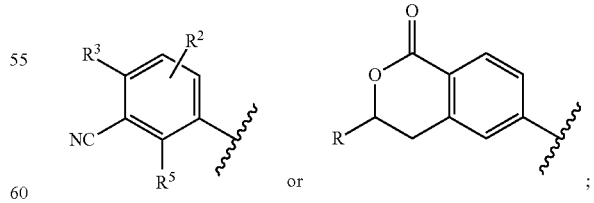

R is —H or —$C_{1-3}$ alkyl; $R^2$ is —H, —F, —Cl, —$C_{1-3}$ alkyl, cyclopropyl or —$OC_{1-3}$ alkyl;

$R^3$ is —H, —F, —Cl, —$C_{1-3}$ alkyl, cyclopropyl or —$OC_{1-3}$ alkyl; $R^5$ is —H, —F, —Cl, —$C_{1-3}$ alkyl, cyclopropyl or —$OC_{1-3}$ alkyl; $R^7$ is —H, —$CH_3$, —$CH_2CH_3$, —$OCH_3$, —F, —Cl, or —$CF_3$, or more particularly R⁷ is —H or —CH₃; and R⁸ is —H, —CH₃ or —OCH₃. In an embodiment thereof are compounds wherein X is O. In another embodiment thereof are compounds wherein X is NH.

In another embodiment of this invention are compounds of Formula I, II or III wherein X is O or NH. In separate embodiments, X is O; or X is NH; or X is S or SO₂.

In another embodiment of this invention are compounds of Formula I, II or III wherein R¹ is —C(R⁹)(R¹⁰)—; and particularly R⁹ is —H, —F or —CH₃ and R¹⁰ is —H or —F. More particularly, R¹ is —CH₂—. In another embodiment of this invention are compounds of Formula I, II or III wherein R¹ is —N(R¹³)—, and particularly it is —NH—.

In another embodiment of this invention are compounds of Formula I, II or III wherein m is 1.

In another embodiment of this invention are compounds of Formula I, II or IV wherein Z is

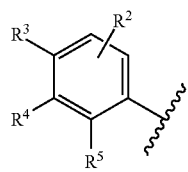

and one of R³ and R⁴ is —CN, and particularly wherein R⁴ is —CN.

In another embodiment of this invention are compounds of Formula I, II or IV wherein Z is

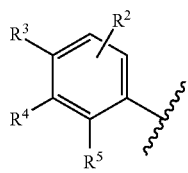

and R² is —H, —F, —Cl, —C₁₋₃ alkyl (particularly —CH₃), cyclopropyl or —OC₁₋₃ alkyl (particularly —OCH₃); R³ is —H, —F, —Cl, —CN, —C₁₋₃ alkyl (particularly —CH₃), cyclopropyl or —OC₁₋₃ alkyl (particularly —OCH₃); R⁴ is —F, —Cl, —CN, —C₁₋₃ alkyl (particularly —CH₃), cyclopropyl, —OC₁₋₃ alkyl (particularly —OCH₃) or N-tetrazolyl; and R⁵ is —H, —F, —Cl, —CN, —C₁₋₃ alkyl (particularly —CH₃), cyclopropyl or —OC₁₋₃ alkyl (particularly —OCH₃); provided that one and only one of R³, R⁴ or R⁵ is —CN. In a class of this embodiment, one of R³ and R⁴ is —CN. In a sub-class thereof, R⁴ is —CN.

In another embodiment of this invention are compounds of Formula I, II or IV wherein Z is

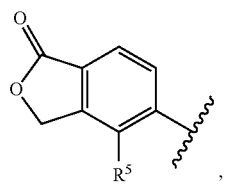

particularly wherein R⁵ is —H or —CH₃, or

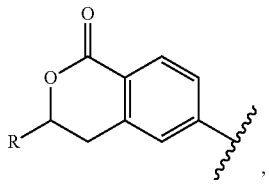

particularly wherein R is —H or —CH₃.

In another embodiment of this invention are compounds of Formula I, II, III or IV wherein Z is

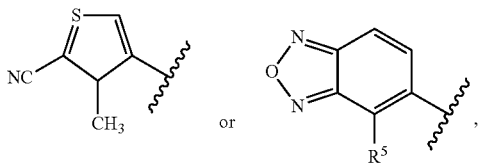

particularly wherein R⁵ is —H or —CH₃.

In another embodiment of this invention are compounds of Formula I, II, III or IV wherein R⁷ is —H, —CH₃, —CH₂CH₃, —OCH₃, —F, —Cl, or —CF₃. More particularly R⁷ is —H or —CH₃.

In another embodiment of this invention are compounds of Formula I or IV wherein Z is

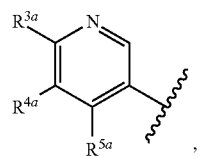

particularly wherein R⁴ᵃ is —CN.

In another embodiment of this invention are compounds of Formula I, II, III or IV wherein R⁶ is —H; and/or R⁸ is —H, —CH₃ or —OCH₃; and/or R¹¹ is —H; and/or R¹² is —H.

In Embodiment A of this invention are compounds of Formula I, II or III wherein:
X is O or NH;
R¹ is or —NH— or —C(R⁹)(R¹⁰)— wherein R⁹ is —H, —F, or —CH₃, and R¹⁰ is —H or —F;
m is 1;
R⁶ is —H;
R⁷ is —H, —CH₃, —CH₂CH₃, —OCH₃, —F, —Cl, or —CF₃ (particularly R⁷ is —H or —CH₃);
R⁸ is —H, —CH₃ or —OCH₃;
R¹¹ is —H; and
R¹² is —H.

In Embodiment A-1 are compounds of Embodiment A wherein Z is

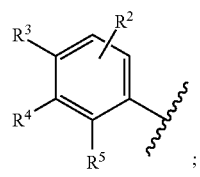

R² is —H, —F, —Cl, —C₁₋₃ alkyl (particularly —CH₃), cyclopropyl or —OC₁₋₃ alkyl (particularly —OCH₃);
R³ is —H, —F, —Cl, —CN, —C₁₋₃ alkyl (particularly —CH₃), cyclopropyl or —OC₁₋₃ alkyl (particularly —OCH₃);

R⁴ is —F, —Cl, —CN, —C₁₋₃ alkyl (particularly —CH₃), cyclopropyl or —OC₁₋₃ alkyl (particularly —OCH₃) or N-tetrazolyl; and R⁵ is —H, —F, —Cl, —C₁₋₃ alkyl (particularly —CH₃), cyclopropyl or —OC₁₋₃ alkyl (particularly —OCH₃); provided that one and only one of R³ and R⁴ is —CN (and particularly R⁴ is —CN).

In Embodiment A-2 are compounds of Embodiment A wherein Z is

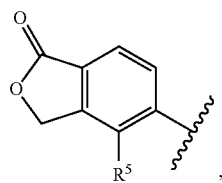

particularly wherein R⁵ is —H or —CH₃.

In Embodiment A-3 are compounds of Embodiment A wherein Z is

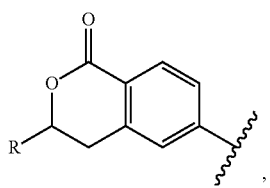

particularly wherein R is —H or —CH₃;

In Embodiment A-4 are compounds of Embodiment A wherein Z is

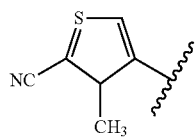

In Embodiment A-5 are compounds of Embodiment A wherein Z is

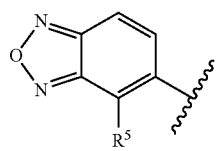

and particularly wherein R⁵ is —H or —CH₃.

In Embodiment B of this invention are compounds of Formula I, II or III or Embodiments A, A-1, A-2, A-3, A-4 or A-5 wherein

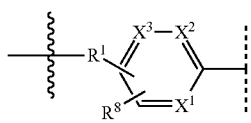

is:

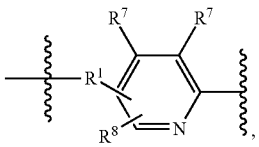
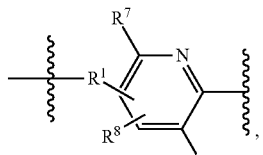
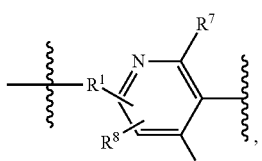
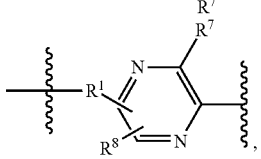
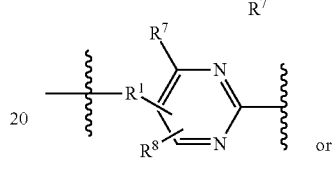

In Embodiment C of this invention are compounds of Formula I, II or III or Embodiment A, A-1, A-2, A-3, A-4, A-5 or B wherein:

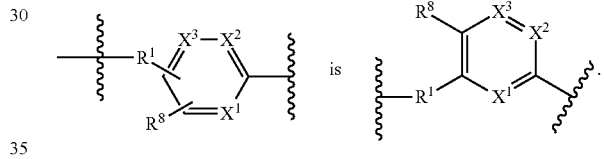

In Embodiment D of this invention are compounds of Formula I, II or III or Embodiments A, A-1, A-2, A-3, A-4, A-5 or B wherein:

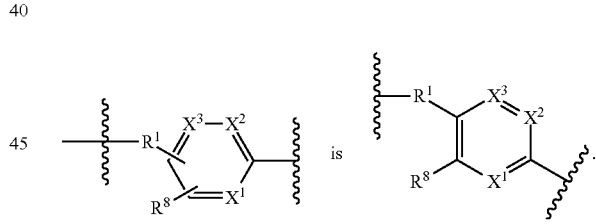

All structural Formulas, Embodiment A, A-1, A-2, A-3, A-4, A-5, B, C, D and other embodiments described above include the pharmaceutically acceptable salts of the compounds defined therein.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me).

"Cycloalkyl" is a cyclized alkyl ring having the indicated number of carbon atoms. Examples of cycloalkyl include cyclopropyl, cyclobutyl, cyclopentyl and cyclohexyl.

Unless expressly depicted or described otherwise, variables depicted in a structural formula with a "floating" bond, such as $R^1$, $R^2$ and $R^8$, are permitted on any available carbon atom in the ring to which the variable is attached.

The present invention encompasses all stereoisomeric forms of the compounds of Formula I. Centers of asymmetry that are present in the compounds of Formula I can all independently of one another have (R) or (S) configuration. When bonds to the chiral carbon are depicted as straight lines in the structural Formulas of the invention, or when a compound name is recited without a chiral designation for a chiral carbon, it is understood that both the (R) and (S) configurations of the chiral carbon and hence both enantiomers and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

The compounds of the instant invention have at least two chiral (i.e., asymmetric) centers from the central fused bicyclic ring of Formula I, as indicated by the asterisk at each chiral center in example A.

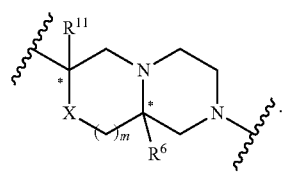

A)

Additional chiral centers may be present depending upon the nature of the various substituents on a molecule. In some of the chemical structures shown in the examples an asterisk may be used to identify one or more chiral centers.

Reference to the compounds of Formula I herein encompasses the compounds of Formulas II, III and IV and all embodiments thereof. Reference to the compounds of this invention as those of a specific formula or embodiment, e.g., Formula I, II, III or IV or embodiments thereof, or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding pharmaceutically acceptable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$ alkyl esters and —$C_{1-6}$ alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. The inhibition of ROMK by the compounds of Formula I can be examined, for example, in the Thallium Flux Assay and/or Electrophysiology Assay described below. Moreover, this invention also relates to the use of the compounds of Formula I or salts thereof to validate in vitro assays, for example but not limited to the Thallium Flux and Electrophysiology Assays described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, particularly essential hypertension (also known as primary or idiopathic hypertension) which is a form of hypertension for which no cause can be found, heart failure (acute and/or chronic, the latter also known as congestive heart failure) and/or other conditions associated with excessive salt and water retention. Furthermore, the compounds of Formula I could be used in methods for treatment of, prevention of or reduction of risk for developing one or more disorders such as pulmonary hypertension, particularly pulmonary arterial hypertension (PAH), cardiovascular disease, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute and chronic kidney insufficiency (also referred to as chronic kidney disease, or more generally as renal impairment), acute tubular necrosis, hypercalcemia, idiopathic edema, Dent's disease, Meniere's disease, edematous states, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

In general, compounds that are ROMK inhibitors can be identified as those compounds which, when tested, have an $IC_{50}$ of 5 µM or less, preferably 1 µM or less, and more preferably 0.25 µM or less, in at least one of the following assays: 1) Thallium Flux Assay, 2) Electrophysiology Assay. These assays are described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately from 0.001 to 100 mg/kg, preferably from 0.001 to 30 mg/kg, in particular from 0.01 to 14 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention or reduction of risk of myocardial infarction or prevention and reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from 0.1 mg to 1 g, particularly from 0.1 to 200 mg, more particularly from 0.1 to 100 mg, and even more particularly from 0.1 to 50 mg, per dose on a free acid/free base weight basis, but depending on the type of the pharmaceutical composition, potency of the active ingredient and/or the medical condition being treated, it could also be lower or higher. Pharmaceutical compositions usually comprise 0.5 to 90 percent by weight of the active compound on a free acid/free base weight basis.

The compounds of Formula I inhibit ROMK. On account of this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g., olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

Several methods for preparing the compounds of this invention are described in the examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products.

Compounds of the formula I may be prepared as shown in Scheme 1 by coupling of appropriately substituted piperazines 1 with carboxylic acids of the structure 2 to form amides. This can be accomplished in many ways well-known to the chemist, including by using EDC in the presence or absence of HOBt and a base such as triethylamine, or by using a variety of other amide coupling reagents such as HATU.

Scheme 1

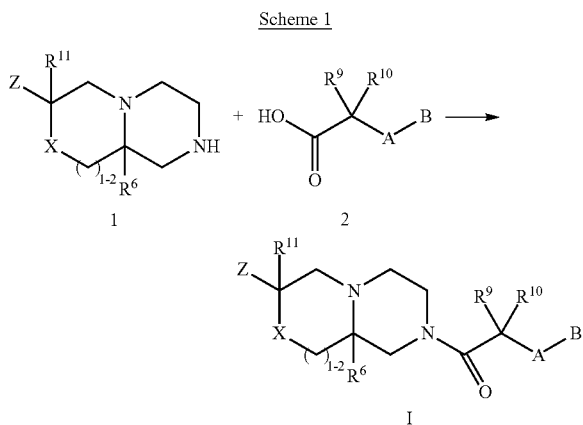

Alternatively, compounds of the formula I may also be prepared as shown in Scheme 2 by coupling of appropriately substituted piperazines 1 with activated carbamates such as phenyl carbamate 3 or para-nitrophenyl carbamates to form ureas. This can be done in the presence or absence of a base such as triethyl amine or diethylisopropylamine. Ureas may be assembled from piperazines 1 by numerous other methods known to the chemist. For example, piperazines 1 can be coupled to amines (N(H)(R)-A-B; where A is heteroaryl and B is tetrazolyl) using phosgene, triphosgene, disuccidinidyl carbonate, para-nitrophenyl chloroformate and other reagents.

Scheme 2

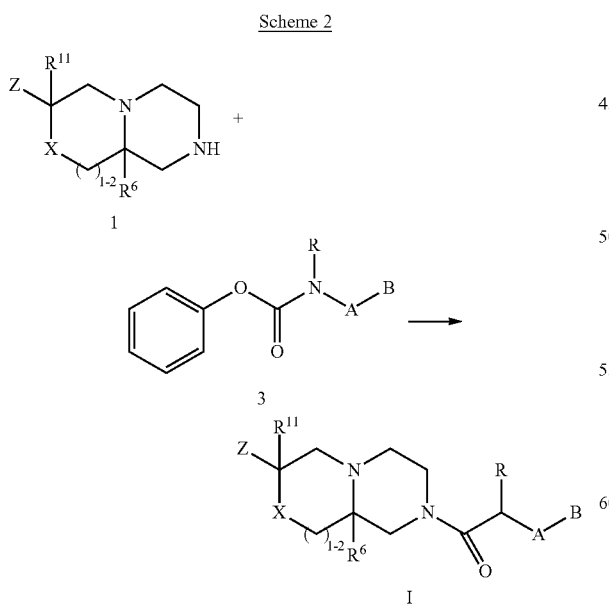

Piperazines 1 can be prepared according to Scheme 3. Epoxides 4 can be coupled with appropriately protected (Greene, T.; Wuts, P. G. M. *protective Groups in Organic Synthesis*, John Wiley and Sons, Inc., New York, N.Y. 1991) hydroxyalkylpiperazines 5 by heating in a solvent such as ethanol, DMSO, or toluene to afford the diols 6 (Nomura, Y. et al. Chemical & Pharmaceutical Bulletin, 1995, 43(2), 241-6). Heating can be by conventional thermal bath or by microwave irradiation. The diols 6 can be cyclized to afford 6 or 7-membered rings 7 by a variety of ways, including by heating with the reagent cyanomethylene tri-n-butylphosphorane in a suitable solvent such as benzene or toluene. Heating can be by conventional thermal bath or by microwave irradiation. The resulting compounds 7 are generally mixtures of cis and trans isomers. The protective group can then be removed. For example when the protective group is Boc as shown in Scheme 3, removal can be achieved by treatment with an acid such as TFA or HCl to afford piperazines 1A. Alternatively compounds 7 can be separated by means of silica chromatography or preparative high pressure liquid chromatography employing a chiral column to afford the separated cis 7 (cis) and trans 7 (trans) isomers. The protective group of the pure cis and trans isomers can be removed by treatment with an acid such as TFA or HCl, in the case of a Boc group, to afford piperazines 1A as pure cis and trans isomers 1A (cis) and 1A (trans). If a single enantiomer of the hydroxyalkylpiperazines 5 is employed, then single enantiomer cis and trans isomers 1A (cis), and 1A (trans) can be obtained.

Scheme 3

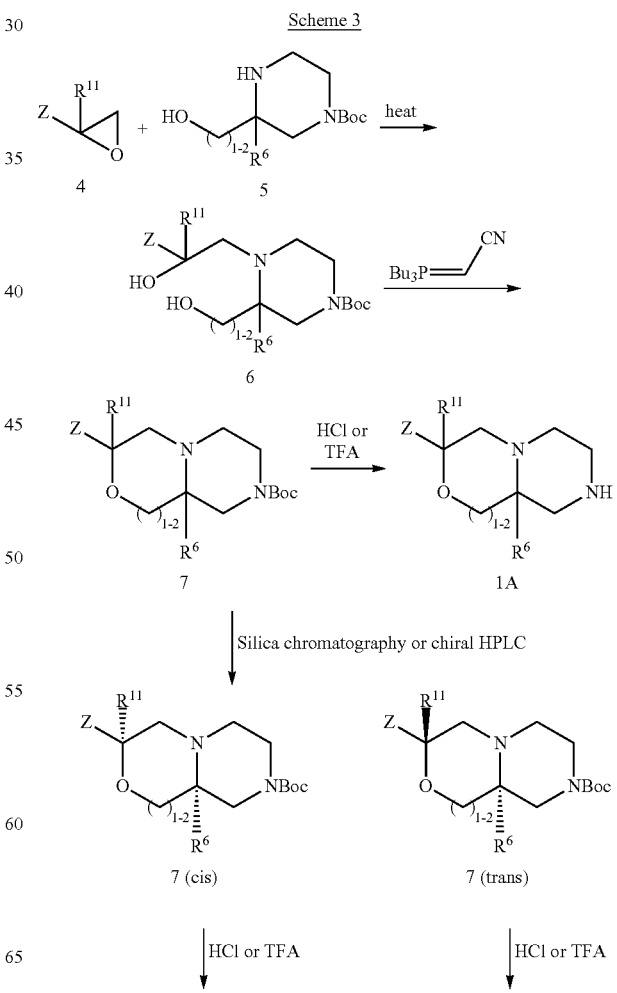

-continued

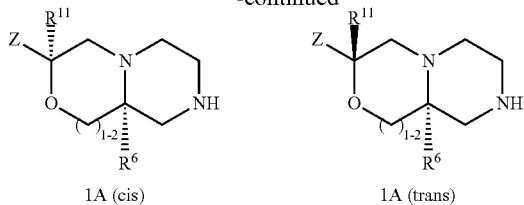

1A (cis)      1A (trans)

Protected piperazines 7 can also be prepared according to Scheme 4 by initially coupling hydroxyalkylpiperazines 5 with bromomethylketones (or chloromethyl ketones) 8 to afford hemiketals 9. This is typically accomplished in the presence of a base such as triethylamine or diethylisopropylamine. The resulting hemiketals 9 can be converted directly to piperazines 1A by reduction using, for example, triethylsilane in the presence of an acid catalyst such as trifluoroacetic acid. If separation of the cis and trans isomers is desired, a protective group such as Boc may be installed using, for example, Boc$_2$O, to give intermediates 7A which can be separated into cis and trans isomers as described in Scheme 3. Alternatively, the hemiketals 9 may be reduced by a three step sequence involving formation of a mesylate with methane sulfonyl chloride and a base such as triethylamine, followed by elimination in the presence of base to give enol ethers 10. Enol ethers 10 can then be reduced by hydrogenation in the presence of a catalyst such as palladium on carbon to afford protected piperazines 7A which can be separated into cis and trans isomers as described in Scheme 3. These may then be converted to piperazine intermediates 1A (cis) and 1A (trans) as described in Scheme 3.

Alternatively, a subclass of intermediates 1, piperazines 1B, can be prepared as described in Scheme 5. The Boc protective group of intermediates 6 (prepared as described in Scheme 3) are switched to benzyl carbamate (Cbz) groups by initial treatment with an acid such as TFA or HCl, followed by coupling with benzyl chloroformate in the presence of a base such as triethylamine. The resulting Cbz-piperazine diols 6B are converted to the corresponding dichloro intermediates by heating with thionyl chloride, then are heated with allylamine in the presence of sodium iodide to afford the allyl substituted fused piperazines 11. The allyl groups may be removed in several ways, including by warming with 1,3-dimethylpyrimidine-2,4,6(1H,3H,5H)-trione in the presence of a catalyst such as palladium tetrakis triphenylphosphine. The revealed amines are then re-protected with tert-butoxycarbamate groups by treatment with Boc$_2$O in the presence of an amine such as triethylamine to provide intermediates 7B, generally as mixtures of cis and trans isomers. The cis and trans isomers can be separated as described in Scheme 3 by silica chromatography or by chiral preparative HPLC. If intermediates 6 are single enantiomers (as described in Scheme 3), then the resulting intermediates 7B (cis) and 7B (trans) are also single isomers. Alternatively, separation of the cis and trans isomers can be performed at an earlier stage by separation of the cis/trans isomers of intermediates 11. The Cbz protective groups of intermediates 7B (cis) and 7B (trans) can be removed, for example, by hydrogenolysis in the presence of a catalyst such as palladium on carbon to afford intermediates 1B (cis) and 1B (trans).

Scheme 4

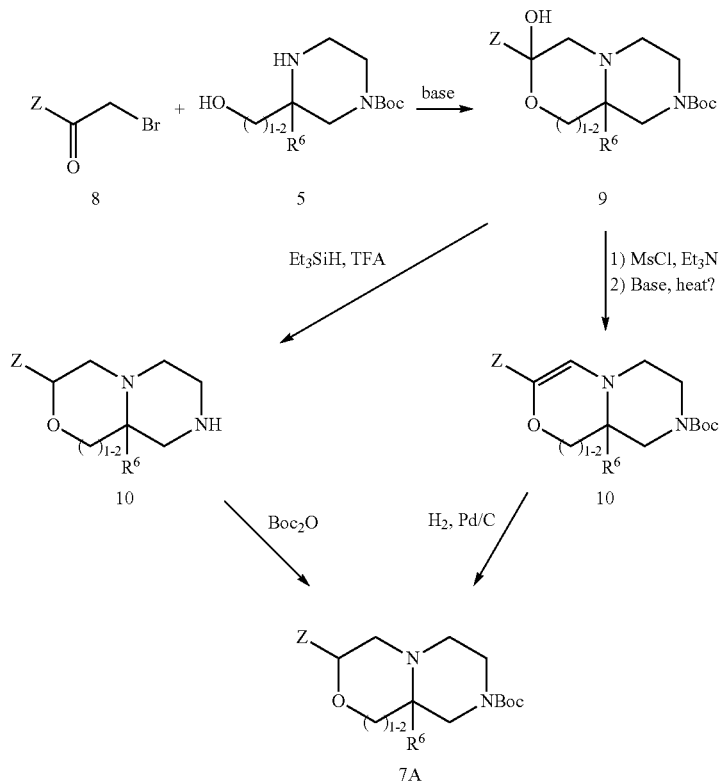

Scheme 5

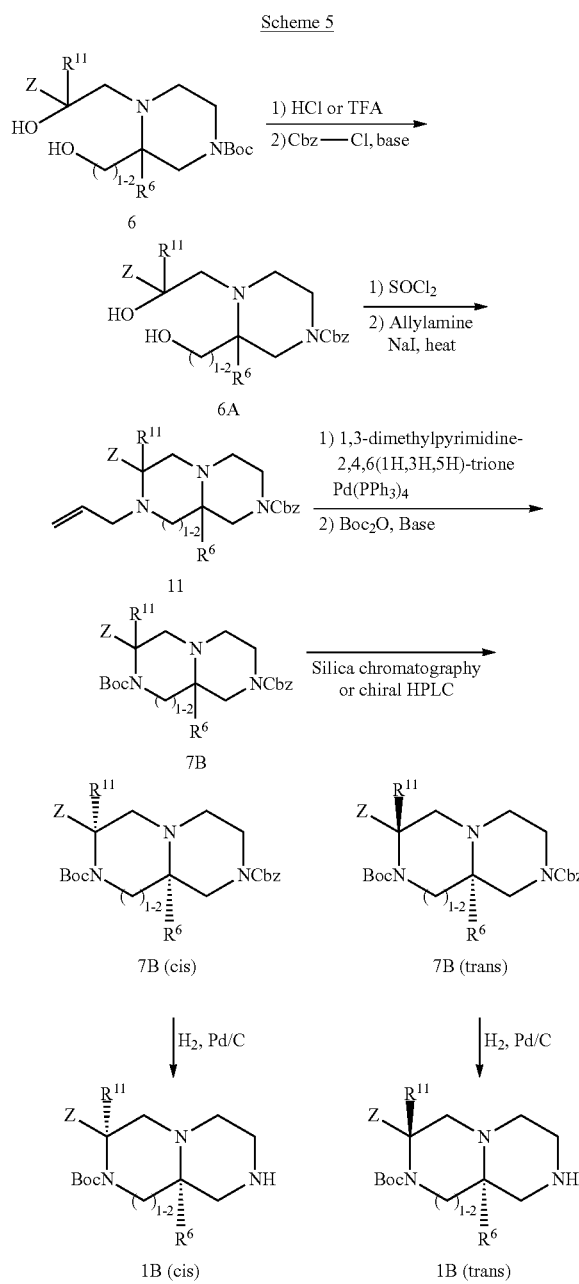

Scheme 6

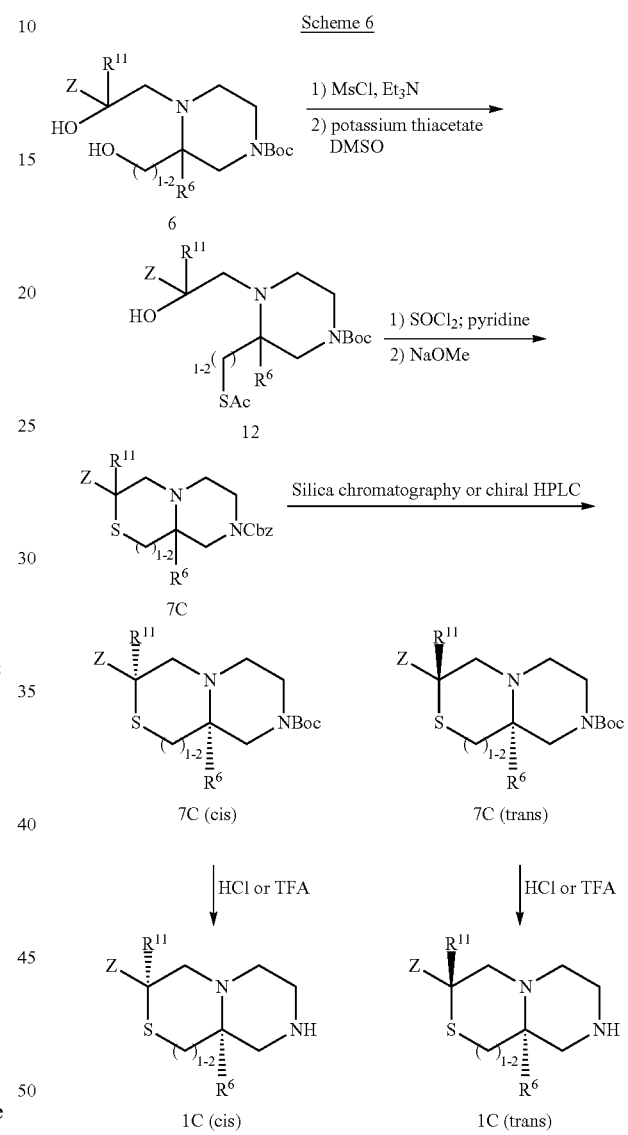

enantiomer hydroxyalkylpiperazines 5 are employed, the resulting intermediates 7C are obtained as a mixture of two isomers (cis and trans), which can then be separated to single isomers 7C (cis) and 7C (trans) by silica chromatography or by chiral preparative HPLC. Removal of the tert-butyl carbamate protective group can then be achieved by treatment with an acid such as TFA or HCl to provide the piperazines 1C (cis) and 1C (trans).

Alternatively, a sub-class of intermediates 1 (1C) may be prepared according to Scheme 6. Diols 6 are initially converted to their corresponding mono-mesylates by treatment with methanesulfonyl chloride, a base such as triethyl amine, and a catalyst such as 4-dimethylaminopyridine. Subsequent reaction with potassium thioacetate in a solvent such as dimethyl sulfoxide (DMSO) provides intermediates 12. The remaining hydroxyl group of 12 is then converted to the corresponding chloro intermediate by treatment with, for example, thionyl chloride, followed by addition of a base such as pyridine. The resulting chloro intermediate is then treated with sodium methoxide to afford the cyclized sulfides 7C. When the starting diols 6 used are single isomers (starting from enantiomerically pure epoxides 4 and enantiomerically pure hydroxyalkylpiperazines 5), as described in Scheme 3, the resulting intermediates 7C may be obtained as single isomers. Alternatively, when racemic epoxides 4, and single Intermediates 2 may be prepared in a variety of ways. A sub-class (2A) of carboxylic acids of the structure 2 may be prepared according to Scheme 7. By this route malonates 13 are reacted in the presence of a base such as sodium hydride with nitro-substituted heterocyclic groups bearing a halogen leaving group such as a fluoro, chloro (14 shown), or bromo. The resulting coupled products 15 are decarboxylated with hydrolysis of the remaining ester to afford carboxylic acids 16. Reduction of the nitro group can be achieved in a variety of ways. One approach is to reduce with hydrogen gas in the presence of a catalyst such as Pd on carbon. The anilines 17 may then be cyclized to the tetrazoles (2A) by a number of different methods, including reaction (often with heating) with sodium azide and triethylorthoformate in a solvent such as acetic acid. Alternatively, the tetrazoles 2A may be formed by reaction with trimethylsilyl azide, trimethylsilyl trifluoroacetate, and triethyl orthoformate.

Scheme 7

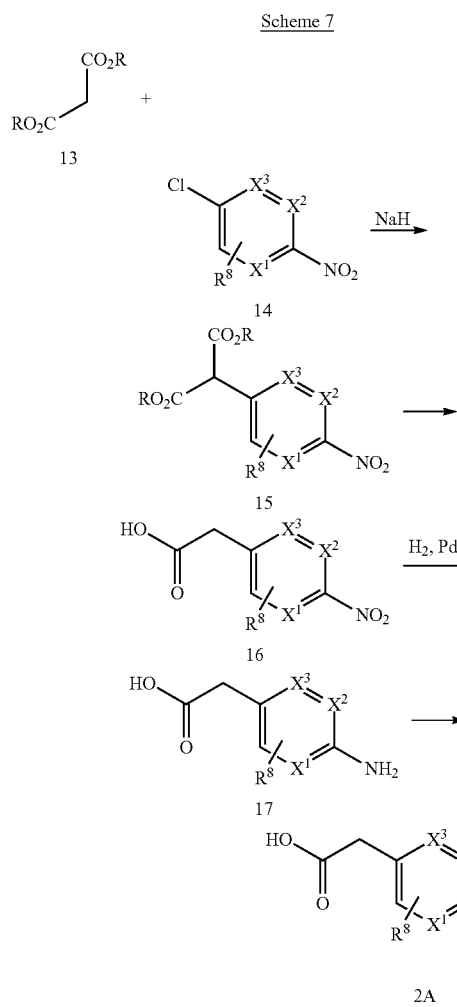

X = independently CR[7] or N (as defined in formula I)

Alternatively, intermediates of the sub-class 2A may be prepared according to Scheme 8. In this case, a mixed malonate 13a is used to afford compounds 15A in a similar fashion as described in Scheme 7. Decarboxylation under acidic conditions with, for example TFA, provides the esters 18. Reduction, under conditions described for Scheme 7, provides amines 19. Cyclization to afford the tetrazoles 20 again could be accomplished as described above for Scheme 7. Finally ester hydrolysis using a base such as lithium hydroxide or sodium hydroxide with water and an organic solvent such as THF or dioxane affords the intermediates 2A.

Scheme 8

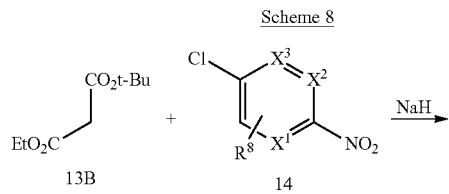

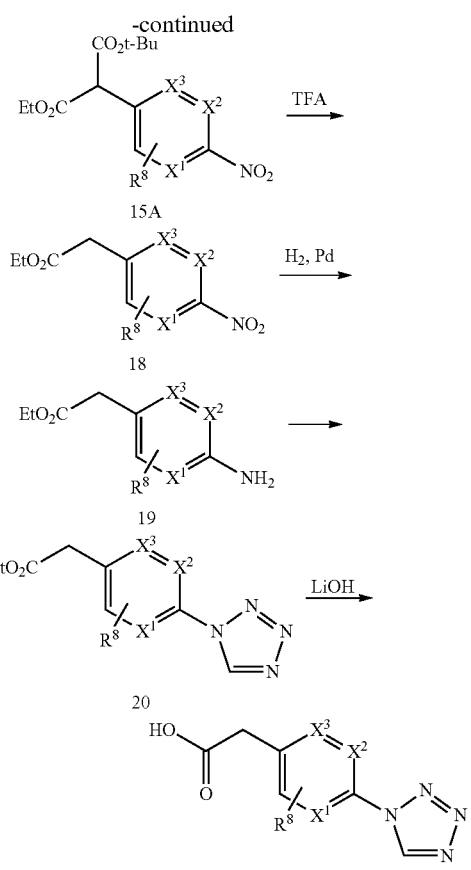

Similarly, acids 2A may be prepared according to Scheme 9. In this case, haloheterocyclic amines 22 are coupled to (2-tert-butoxy-2-oxoethyl)(chloro)zinc (21) in the presence of a palladium catalyst such as palladium Tetrakis triphenylphosphine to provide the coupled products 23. Cyclization to afford the tetrazoles 24 again could be accomplished as described above for Scheme 7. Hydrolysis is then achieved under acidic conditions with, for example, TFA to afford the acids 2A.

Scheme 9

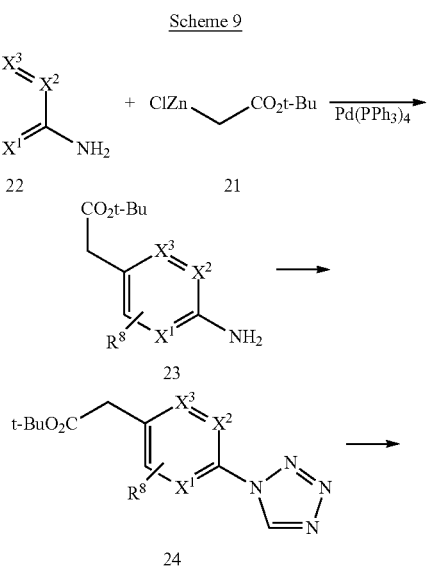

-continued

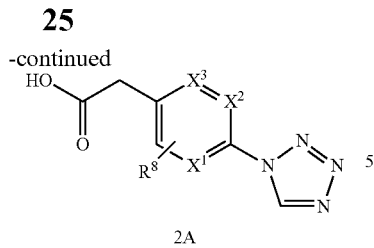

2A

Epoxides 4 may be prepared by a variety of methods. One approach is described by Scheme 10. Aryl or heterocycle halides (bromide 25 shown) may be coupled to form alkene products 26 in a number of ways, for example by Heck reaction or by reaction with vinyl tetrafluoroborate (Molander, G.; Luciana, A. Journal of Organic Chemistry, 2005, 70(10), 3950-3956) under palladium catalyzed coupling conditions with an appropriate phosphine ligand (Molander, G.; Brown, A. Journal of Organic Chemistry, 2006, 71(26), 9681-9686). The alkenes 26 can then be converted to the corresponding epoxides 4 by several ways, including treatment with meta-chloroperoxybenzoic acid (Fringuelli, F. et al. Organic Preparations and Procedures International, 1989, 21(6), 757-761).

Scheme 10

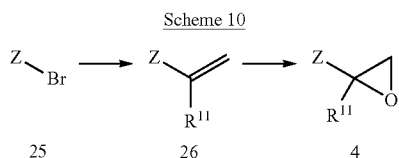

Bromomethylketones 8 may be prepared in a variety of ways; one route is depicted in Scheme 11. According to the Scheme, aryl or heterocyclic halides (bromide shown) can be reacted with tributyl(1-ethoxyvinyl)tin in the presence of a metal catalyst such as $PdCl_2(PPh_3)_2$ to provide an intermediate ethylenolether. This is subsequently treated in the same reaction vessel with N-bromosuccinimide (NBS) with added tetrahydrofuran and water to provide bromomethylketones 8. Chloromethyl ketones can similarly be prepared by employing N-chlorosuccinimide in place of N-bromosuccinimide.

Scheme 11

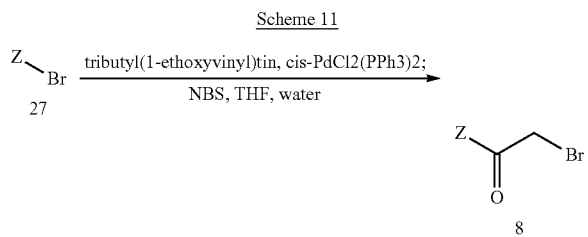

Intermediate carbamates 3 can be prepared by a variety of ways. A typical route is depicted in Scheme 12 where amines 28 are reacted with phenyl chloroformate 29 in the presence of a base such as pyridine to afford intermediates 3.

Scheme 12

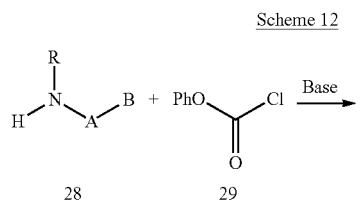

-continued

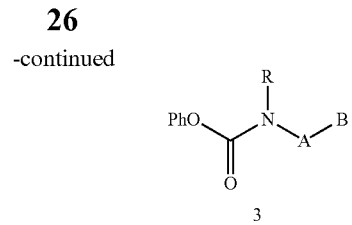

3

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry.

The subject compounds may be prepared by modification of the procedures disclosed in the Examples as appropriate. Starting materials are commercially available or made by known procedures or as illustrated. The following examples are provided for the purpose of further illustration only and are not intended to be limitations on the disclosed invention.

Reactions sensitive to moisture or air were performed under nitrogen or argon using anhydrous solvents and reagents. The progress of reactions was determined by either analytical thin layer chromatography (TLC) usually performed with E. Merck precoated TLC plates, silica gel 60 F-254, layer thickness 0.25 mm or liquid chromatography-mass spectrometry (LC-MS).

Typically, the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 μm. The flow rate was 1 mL/min, and the injection volume was 10 μL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage.

Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual CH₃OH peak or TMS was used as internal reference in CD₃OD solutions. Coupling constants (J) were reported in hertz (Hz).

Chiral analytical chromatography was usually performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography. Alternatively, chiral preparative chromatography was by supercritical fluid (SFC) conditions using one of Chiralpak AS, Chiralpak AD-H, Chiralcel OD-H, Chiralpak IC, or Chiralcel OJ-H columns (250×21.2 mm) (Daicel Chemical Industries, Ltd.). Where retention times are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used.

Flash chromatography was carried out on silica gel (230-400 mesh). NMR spectra were obtained in CDCl₃ solution unless otherwise noted. Coupling constants (J) are in hertz (Hz).

Abbreviations used herein: ethyl acetate (EtOAc), dichloromethane (DCM), starting material (SM), diethyl ether (ether), trifluoroacetic acid (TFA), triethylamine (TEA), N,N-diisopropylethylamine (DIEA, Hunig's base, DIPEA), 1-ethyl-3-(3-dimethylaminopropyl), carbodiimide (EDC, EDAC, or EDCI), 2-(7-Aza-1H-benzotriazole-1-yl)-1,1,3,3-tetramethyluronium hexafluorophosphate (HATU), 1-Hydroxybenzotriazole hydrate (HOBt), methyl tert-butyl ether (MTBE), Cyclopentyl methyl ether (CPME), 1,3-Bis(diphenylphosphino)propane (DPPP), 2-Dicyclohexylphosphino-2',4',6'-triisopropylbiphenyl (X-Phos), 1,2-dichloroethane (DCE), N-bromo succinimide (NBS), N-iodosuccinimide (NIS), lithium diisopropylamide (LDA), tetrahydrofuran (THF), dimethylsulfoxide (DMSO), isopropanol (IPA), t-butyloxycarbonyl (Boc or BOC), di-t-butyl dicarbonate (BOC₂O, Boc₂O), acetic acid (AcOH; HOAc), N; N-dimethylformamide (DMF), 4-dimethylaminopyridine (DMAP), mCPBA (3-chloroperoxybenzoic acid), nicotinamide adenine dinucleotide phosphate (NADP), petroleum ether (PE), lithium aluminum hydride (LAH), di-isopropylamine (DIPA), Carbonyldiimidazole (CDI), p-toluenesulfonic acid (TsOH), p-toluene-SO₂— (tosyl or Ts), methane sulfonyl chloride or mesyl chloride (Ms-Cl), methanesulfonic acid (MsOH), CH₃SO₂-(mesyl or Ms), dimethoxyethane (DME), Pd(dppf)Cl₂ or PdCl₂(dppf) is 1,1'-Bis(diphenylphosphino) ferrocene]dichloropalladium(II) which may be complexed with CH₂Cl₂, hexamethylphosphoramide (HMPA), isopropyl acetate (IPAc) round-bottom flask (RB or RBF), saturated aqueous (sat'd), medium pressure liquid chromatography (MPLC), high pressure liquid chromatography (HPLC), liquid chromatography (LC), thin layer chromatography (TLC), liquid chromatography-mass spectrometry (LC-MS or LC/MS), column volume (CV), room temperature (rt, r.t. or RT), hour(s) (h or hr), minute(s) (min). Celite is a trademark name for diatomaceous earth, and Solka Floc is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention.

Intermediates 1A and 1B

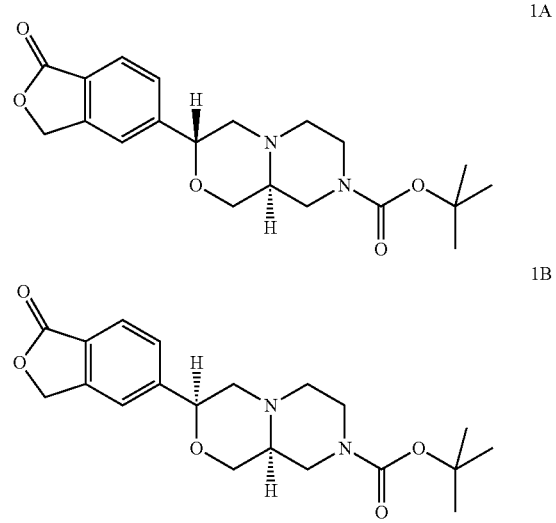

1A: tert-butyl(3R,9aS)-3-(1-oxo-1,3-dihydro-2-benzofuran-5-yl)hexahydropyrazino[2,1-c][1,4]oxazine-8(1H)-carboxylate; 1B: tert-butyl(3S,9aS)-3-(1-oxo-1,3-dihydro-2-benzofuran-5-yl)hexahydropyrazino [2,1-c][1,4]oxazine-8(1H)-carboxylate Step A: 5-ethenyl-2-benzofuran-1(3H)-one 5-Bromophthalide (50 g, 235 mmol), potassium vinyl trifluoroborate (62.9 g, 469 mmol), and PdCl₂(dppf)-CH₂Cl₂ Adduct (9.58 g, 11.7 mmol) were added to ethanol (500 mL) then TEA (65.4 mL, 469 mmol) was added. The reaction mixture was degassed then heated at reflux for 8 h. The reaction was worked up by diluting with ethyl acetate and washing with brine twice. The organic layer was dried and evaporated to dryness. The crude product was purified by MPLC (silica, 600 g column) with 25% EtOAc/hexane (3 L) then with 30% EtOAc/Hexane (2 L) to yield the title compound.

Step B: 5-(oxiran-2-yl)-2-benzofuran-1(3H)-one

5-Ethenyl-2-benzofuran-1(3H)-one (28.4 g, 177 mmol) was dissolved in DCM (400 mL) then mCPBA (47.7 g, 213 mmol) was added. The mixture was stirred at room temperature overnight. Some starting olefin remained. Another 25 g of mCPBA was added and the mixture was stirred overnight. The mixture was poured into ice cold Na₂SO₃ solution (saturated). The layers were separated and the organic layer was washed with 5% NaOH solution, brine, then was dried (MgSO₄). The crude product was purified by MPLC (330 g column, eluting with 40% EtOAc/hexane, 2 L, then with 45% EtOAc/hexane, 2 L, to afford 5-(oxiran-2-yl)-2-benzofuran-1(3H)-one. LC-MS: M+1=177.

Step C: tert-butyl(3S)-3-(hydroxymethyl)-4-[2-hydroxy-2-(1-oxo-1,3-dihydro-2-benzofuran-5-yl)ethyl]piperazine-1-carboxylate 5-(Oxiran-2-yl)-2-benzofuran-1(3H)-one (1.5 g, 8.5 mmol) and commercially available (S)-4-N—BOC-2-hydroxymethyl piperazine (2.394 g, 11.07 mmol) were combined in ethanol (10 mL) in a microwave tube. The mixture was degassed then heated for 60 min at 150° C. LC-MS showed the product peak. The reaction was worked up by adding ethyl acetate and washing once with brine. The organic layer was separated, dried, and concentrated to dryness. The crude product was purified by MPLC using an 80 g Redi-sep column and eluted with 50%-100% EtOAc/hexane yielding the title compound.

Step D: tert-butyl(9aS)-3-(1-oxo-1,3-dihydro-2-benzofuran-5-yl)hexahydropyrazino[2,1-c][1,4]oxazine-8(1H)-carboxylate tert-Butyl(3S)-3-(hydroxymethyl)-4-[2-hydroxy-2-(1-oxo-1,3-dihydro-2-benzofuran-5-yl)ethyl]piperazine-1-carboxylate (3.3 g, 8.4 mmol) and cyanomethylene tri-n-butylphosphorane (3.65 g, 15.1 mmol) were dissolved in 30 mL of benzene, the solution was degassed, and then heated to 100° C. for 3 h. LC-MS showed the product peak (M+1=389). The reaction mixture was cooled and evaporated to dryness. The residue was purified by MPLC through a 330 g Redi-sep column and eluted with a 15% acetone/85% hexane mixture to yield a cis-trans mixture of the title compound.

Step E: tert-butyl(3R,9aS)-3-(1-oxo-1,3-dihydro-2-benzofuran-5-yl)hexahydropyrazino[2,1-c][1,4]oxazine-8(1H)-carboxylate and tert-butyl(3S,9aS)-3-(1-oxo-1,3-dihydro-2-benzofuran-5-yl)hexahydropyrazino[2,1-c][1,4]oxazine-8(1H)-carboxylate The cis-trans isomer mixture from the prior step was separated using a ChiralCEL OD 4.6×250 mm 10 μcolumn eluting with a 45% IPA/55% heptane solvent system. The trans-isomer 1A eluted first at 11.46 min and the cis-isomer 1B second at 17.43 min. 1A: $^1$H-NMR (500 MHz, CDCl$_3$): δ ppm 7.915 (d, J=8 Hz, 1H), 7.56 (s, 1H), 7.52 (d, J=8 Hz, 1H), 5.33 (s, 2H), 4.81 (dd, J=2 Hz, 10.5 Hz, 1H), 4.03-4.07 (m, 2H), 4.00 (dd, J=3, 11.25 Hz, 1H), 3.51 (t, J=10.5 Hz, 1H), 3.04 (b, 1H), 2.96 (dd J=2, 11.75 Hz, 1H), 2.76 (d, J=10.5 Hz, 1H), 2.57 (b, 1H), 2.21-2.32 (m, 3H), 1.5 (s, 9H). 1B: $^1$H-NMR (500 MHz, CDCl$_3$): δ ppm 7.95 (d, J=8 Hz, 1H), 7.72 (d, J=8 Hz, 1H), 7.70 (s, 1H), 5.37 (s, 2H), 4.91 (t, J=3.5 Hz, 1H), 3.65-4.07 (b, 2H), 3.64 (dd, J=3, 11.5 Hz, 1H), 3.40 (t, J=11.5 Hz, 1H), 3.29 (dd, J=3.5, 12 Hz, 1H), 3.02 (b, 1H), 2.82 (dd, J=3.5, 12 Hz, 2H), 2.66-2.67 (b, 1H), 2.50 (t, J=11 Hz, 2H), 1.5 (s, 9H).

Intermediate 2

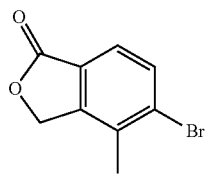

5-bromo-4-methyl-2-benzofuran-1(3H)-one

Step A: (3-bromo-2-methylphenyl)methanol

To a solution of 3-bromo-2-methyl benzoic acid (35.0 g, 163 mmol) in THF (200 mL) was added Borane THF Complex (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol.

Step B: 5-bromo-4-methyl-2-benzofuran-1(3H)-one

To a flask charged with (3-bromo-2-methylphenyl)methanol (6.0 g, 30 mmol) was added a 1M TFA solution of thallium trifluoroacetate (16.2 g, 29.8 mmol). The mixture was stirred at RT overnight. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The solution was filtered through a Celite pad, washed with EtOAc, adsorbed onto silica and purified by silica gel chromatography to afford the title compound: $^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

Intermediate 3

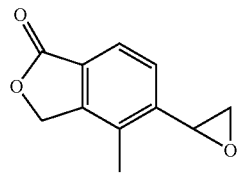

4-methyl-5-oxiran-2-yl-2-benzofuran-1(3H)-one

Step A: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmol), PdCl$_2$(dppf)-CH$_2$Cl$_2$ Adduct (182 mg, 0.223 mmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% ETOAC/Hexane solvent system to yield 5-ethenyl-4-methyl-2-benzofuran-1(3H)-one. LC-MS: M+1=175.

Step B: 4-methyl-5-oxiran-2-yl-2-benzofuran-1(3H)-one

5-Ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at RT overnight. The reaction mixture was washed once each with saturated aqueous Na₂S₂O₃, NaHCO₃, and brine. The organic layer was dried over Na₂SO₄, filtered, and evaporated to dryness. The crude material was purified by MPLC through a 120 g Redi-sep column eluting with 0-80% EtOAc/hexane solvent system to yield target 4-methyl-5-oxiran-2-yl-2-benzofuran-1(3H)-one. ¹H-NMR (500 MHz, CDCl₃): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H); LC-MS: M+1=191.

Intermediates 3A and 3B (Method 1)

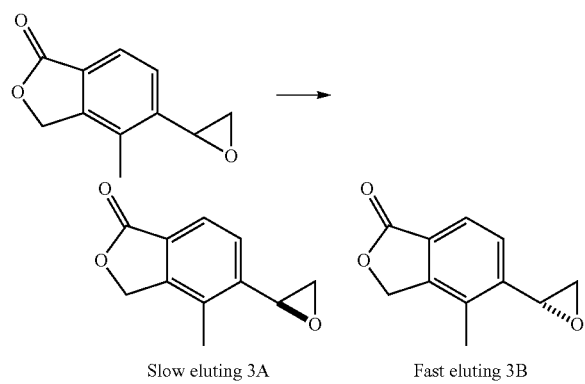

Slow eluting 3A    Fast eluting 3B

3A: 4-methyl-5-[(2S)-oxiran-2-yl]-2-benzofuran-1(3H)-one and 3B: 4-methyl-5-[(2R)-oxiran-2-yl]-2-benzofuran-1(3H)-one Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/CO₂, flow rate 200 mL/min, 100 bar, 25° C. 500 ul Injections were spaced every 2.12 mins. The faster eluting epoxide 3B eluted at 5.2 min, and the slower eluting epoxide 3A eluted at 5.6 min.

Alternatively, the resolution could also be achieved using a mobile phase of 8% MeOH/98% CO₂ with a flow rate of 100 ml/min. In that case the sample was prepared by dissolving in methanol, 20 mg/ml, and using a 1 mL volume per injection. After separation, the fractions were dried off via rotary evaporator at bath temperature 40° C.

The absolute stereochemistry of each enantiomer 3A and 3B was inferred based on the X-ray crystal structure determination of a final compound made with 3B, and by Mosher ester and Trost ester HNMR analysis of esters made starting from 3B (used tert-butyl-4-[(2R-2-hydroxy-2-(4-methyl-1-oxo-1,3-dihydro-2-benzofuran-5-yl)ethyl}piperazine-1-carboxylate).

Intermediate 3B (Method 2)

Step A: 3-hydroxymethyl-2-methyl phenol

To a 5 L 3 neck RB equipped with overhead stirrer was charged NaBH₄ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which BF₃—OEt₂ (321 mL, 2.53 mol) was added slowly over 1.5 hours. The slurry was aged at 10° C.-15° C. for 2 h then assayed for reaction completion (98.5% conversion). The slurry was cooled to <10° C. and quenched with 931 mL MeOH slowly over 1.5 h (gas evolution). The resulting slurry was aged overnight at RT. The batch was cooled to <10° C. then quenched with 1 N HCl (1.5 L) to get a homogeneous solution (pH solution ~1), which was aged for 30 min and then the organic solvents were removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol.

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL) and trifluoroacetic acid (750.0 mL, 9.735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5.358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the solids were washed with 4:1 heptane:MTBE (500 mL), followed by heptane (500 mL). The solid was dried under vacuum, providing 4-bromo-3-hydroxymethyl-2-methyl phenol.

Step C: 5-Hydroxy-4-methyl-3H-isobenzofuran-1-one

To a 2 L 3 neck flask equipped with overhead stirrer, N₂ inlet, and condenser were charged 4-bromo-3-hydroxymethyl-2-methyl phenol (100 g, 461 mmol), CuCN (83.0 g, 921 mmol), and DMF (500 mL). The solution was sparged with N₂ for 15 min then heated to 145° C. to obtain a homogeneous solution. The solution was aged at 145° C. for 2 h, then the reaction mixture was cooled to 95° C. 41.5 mL water was added (sparged with N₂), and the reaction aged for 20 h. The reaction was cooled to RT then the solids filtered through solka flok and the cake washed with 50 mL DMF. To a 3 L flask containing 1 L EtOAc was added the DMF filtrate. A precipitate coating formed in bottom of flask. The DMF/EtOAc suspension was filtered through solka flok and the cake was washed with 250 mL EtOAc. The resulting filtrate was washed with 5% brine solution (3×500 mL). The aqueous layers were extracted with 500 mL EtOAc and the combined organics were dried over MgSO₄, filtered and evaporated. The solids were slurried in 250 mL MTBE at RT then filtered and washed with 100 mL MTBE. The solids were dried under vacuum at RT, providing 5-hydroxy-4-methyl-3H-isobenzofuran-1-one.

Step D: Trifluoromethanesulfonic acid 4-methyl-1-oxo-1,3-dihydro-isobenzofuran-5-yl ester 5-Hydroxy-4-methyl-3H-isobenzofuran-1-one (46.8 g, 285 mmol) was suspended in dichloromethane (935 mL) in 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature <10° C. After stirring the reaction mixture for an additional 15 min, the reaction mixture was quenched with water (200 mL), then stirred with DARCO® KB (activated carbon, 25 g) for 15 min. The biphasic mixture was filtered over Solka Floc, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The solid was adsorbed onto silica gel (27.5 g) and eluted through a pad of silica gel (271 g) with 25% ethyl acetate/hexanes. The resulting solution was concentrated under vacuum with the product precipitating during concentration. The suspension was filtered, the solid washed with heptane and dried under vacuum and nitrogen, providing the title compound.

Step E: 5-(1-Butoxy-vinyl)-4-methyl-3H-isobenzofuran-1-one

To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol) then Et$_3$N (35.6 mL, 255 mmol). The solution was sparged with N$_2$ for 20 min. To the solution was added Pd(OAc)$_2$ (1.19 g., 5.32 mmol) and DPPP (2.41 g., 5.85 mmol) and sparged for an additional 10 min then heated to 80° C. After a 1 hr age, the solution was cooled to <10° C. then quenched with 630 mL EtOAc and washed with 5% NH$_4$Cl (2×315 mL), 10% brine (2×315 mL), dried over MgSO$_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one.

Step F: 5-(2-Bromo-acetyl)-4-methyl-3H-isobenzofuran-1-one

To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portionwise while maintaining Tmax=19° C. The solution was then warmed to RT for 30 minutes. HBr (48%, 0.241 mL) was added and the reaction was aged at RT for approximately 1 h after which 236 mL water was then added to the batch. A water bath is used to maintain temp at 20° C. Another 315 mL of water was added (solvent composition 1:2 THF:water) and the slurry was cooled to 15° C. The resulting solids were filtered and washed with cold 1:2 THF:water (15° C.): 150 mL displacement wash followed by 100 mL slurry wash. The solids were dried under vacuum at RT to provide 5-(2-bromo-acetyl)-4-methyl-3H-isobenzofuran-1-one.

Step G: 4-methyl-5-[(2R)-oxiran-2-yl]-2-benzofuran-1(3H)-one 5-(2-Bromo-acetyl)-4-methyl-3H-isobenzofuran-1-one (48.8 g., 181 mmol) was charged to a 5 L 3 neck RB flask equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT then extracted with 1.22 L isopropyl acetate (IPAc). The aqueous layer was re-extracted with 400 mL IPAc and the combined organics were washed with 400 mL 20% brine solution, dried over MgSO$_4$, filtered and concentrated by rotary evaporation. The resulting solids were taken up in 100 mL IPAc (thick slurry). Hexanes were added (400 mL) and the suspension aged at RT then filtered and washed w/5:1 Hexanes:IPAc solution (150 mL). The solids were dried under vacuum at RT to provide 4-methyl-5-[(2R)-oxiran-2-yl]-2-benzofuran-1(3H)-one. $^1$H NMR (400 MHz, CDCl$_3$): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H)

Intermediates 4A and 4B

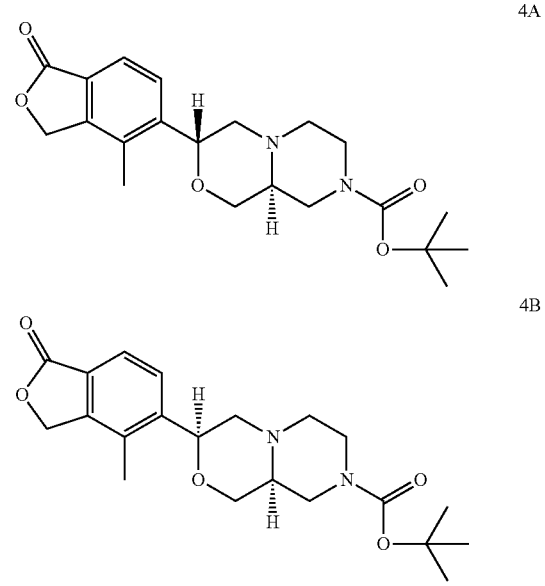

4A: tert-butyl(3R,9aS)-3-(4-methyl-1-oxo-1,3-dihydro-2-benzofuran-5-yl)hexahydropyrazino[2,1-c][1,4]oxazine-8(1H)-carboxylate and 4B: tert-butyl(3S,9aS)-3-(4-methyl-1-oxo-1,3-dihydro-2-benzofuran-5-yl)hexahydropyrazino[2,1-c][1,4]oxazine-8(1H)-carboxylate Step A: tert-butyl(3S)-3-(hydroxymethyl)-4-[2-hydroxy-2-(4-methyl-1-oxo-1,3-dihydro-2-benzofuran-5-yl)ethyl]piperazine-1-carboxylate 4-Methyl-5-oxiran-2-yl-2-benzofuran-1(3H)-one (3.00 g, 15.8 mmol) and (S)-4-N—BOC-2-hydroxymethylpiperazine (5.12 g. 23.7 mmol) were suspended in ethanol (10 mL) in a 20 mL microwave tube. The reaction mixture was degassed and heated in a microwave apparatus for 30 min at 150° C. The reaction mixture was evaporated to dryness, then chromatographed through a 330 g Redi-sep column and eluted with a solvent system of 1:1 EtOAc/hexane to 100% EtOAc to yield the title compound. LC-MS: M+1=407.

Step B: tert-butyl(9aS)-3-(4-methyl-1-oxo-1,3-dihydro-2-benzofuran-5-yl)hexahydropyrazino[2,1-c][1,4]oxazine-8(1H)-carboxylate tert-Butyl(3S)-3-(hydroxymethyl)-4-[2-hydroxy-2-(4-methyl-1-oxo-1,3-dihydro-2-benzofuran-5-yl)ethyl]piperazine-1-carboxylate (3.3 g, 8.2 mmol) and cyanomethylene tri-n-butylphosphorane (2 equivalents) were dissolved in 45 mL benzene in a sealed and degassed tube. The mixture was heated to 100° C. for 3 h. The reaction mixture was cooled and evaporated to dryness. The residue was purified by chromatography through a 330 g Redi-sep column and eluted with 30% acetone/70% hexane mixture to yield the title compound as a cis-trans mixture. LC-MS: M+1=389.

Step C: Intermediates 4A and 4B

The cis/trans mixture of the product of Step B was separated using a Chiralpak AD 4.6×250 mm 10 μcolumn with a 30% IPA/70% heptane solvent system. The trans isomer 4A eluted first at 15.7 min and the cis-isomer 4B second at 24.9 min. 4A: $^1$H-NMR (500 MHz, CDCl$_3$): δ ppm 7.82 (d, J=8 Hz, 1H) 7.73 (d, J=8 Hz, 1H), 5.28 (s, 2H), 4.97 ppm (dd, J=2.5, 10 Hz, 1H), 4.02 (dd, J=2.5, 11 Hz, 1H), 3.87-4.18 ppm (b, 2H) 3.53 ppm (t, J=11 Hz, 1H), 3.04 (b, 1H), 2.88 ppm (d, J=12 Hz, 1H), 2.76 (d, J=11.5 Hz, 1H), 2.54-2.59 (b, 1H), 2.36 (s, 3H), 2.22-2.34 (m, 3H), 1.50 (s, 9H): LC-MS: M+1=389.

4B: $^1$H-NMR (500 MHz, CDCl$_3$): δ ppm 8.12 (d, J=8 Hz, 1H), 7.79 (d, J=8 Hz, 1H), 5.29 (s, 2H), 5.01 (t, J=4 Hz, 1H), 3.69-4.03 (b, 2H), 3.62 (t, J=8.5 Hz, 1H), 3.38 (t, J=7.5 Hz, 1H), 3.23 (dd, J=4, 12 Hz, 1H), 3.09-3.20 ppm (b, 1H), 2.81 (dd, J=4, 12 Hz, 1H), 2.69-2.90 ppm (b, 2H), 2.55-2.58 (b, 2H), 2.38 ppm (s, 3H), 1.50 ppm (s, 9H): LC-MS: M+1=389.

Intermediates 4C and 4D

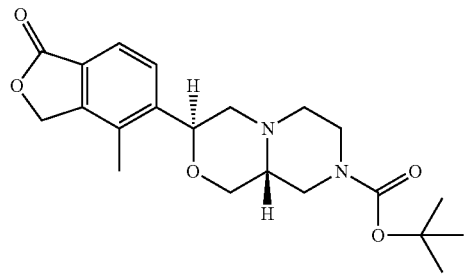

4C

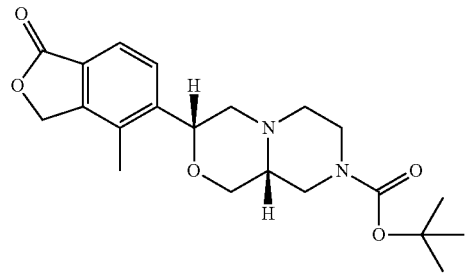

4D

4C: tert-butyl(3S,9aR)-3-(4-methyl-1-oxo-1,3-dihydro-2-benzofuran-5-yl)hexahydropyrazino[2,1-c][1,4]oxazine-8(1H)-carboxylates 4D: tert-butyl(3R,9aR)-3-(4-methyl-1-oxo-1,3-dihydro-2-benzofuran-5-yl)hexahydropyrazino[2,1-c][1,4]oxazine-8(1H)-carboxylate Intermediates 4C and 4D were made in a similar fashion to that described above for 4A and 4B, except (R)-4-N—BOC-2-hydroxymethylpiperazine was used in place of (S)-4-N—BOC-2-hydroxymethylpiperazine. The cis-trans isomers 4C and 4D were separated using a ChiralCEL OD 4.6×250 mm 10 μcolumn with the 20% IPA/80% heptane solvent system. The trans-isomer 4C eluted first at 22.8 min. and the cis-isomer 4D eluted at 37.8 min.: 4C: $^1$H-NMR (500 MHz, CDCl$_3$): δ ppm 7.82 (d, J=8 Hz, 1H) 7.73 (d, J=8 Hz, 1H), 5.28 (s, 2H), 4.97 (dd, J=2.5, 10 Hz, 1H), 4.02 (dd, J=3, 11 Hz, 1H), 4.05-4.20 (b, 2H) 3.53 (t, J=4 Hz, 1H), 3.05 (b, 1H), 2.88 (dd, J=2, 11.7 Hz, 1H), 2.75 (d, J=10.5 Hz, 1H), 2.55 (b, 1H), 2.36 (s, 3H), 2.22-2.36 (m, 3H), 1.51 (s, 9H); LC-MS: M+1=389.4D: $^1$H-NMR (500 MHz, CDCl$_3$): δ ppm 8.12 (d, J=7.8 Hz, 1H), 7.79 (d, J=8 Hz, 1H), 5.30 (d, J=1.8, 2H), 5.02 (t, J=3.85 Hz, 1H), 3.70-4.05 (b, 2H), 3.62 (dd, J=3, 11.65 Hz, 1H), 3.37 (t, J=9 Hz, 1H), 3.23 (dd, J=4, 12 Hz, 1H), 3.10 (b, 1H), 2.80-2.86 (m, 3H), 2.57 (b, 2H), 2.38 ppm (s, 3H), 1.50 ppm (s, 9H); LC-MS: M+1=389.

Intermediate 5

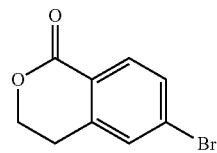 [SMILES: O=C1OCCc2cc(Br)ccc21]

6-bromo-3,4-dihydro-1H-isochromen-1-one

Method A:
A 250-mL, three-necked, round-bottomed flask equipped with a septum, nitrogen inlet needle, and thermocouple was charged with diisopropylamine (3.10 g, 30.6 mmol) and 30 mL of THF. The reaction mixture was cooled at −20° C. while n-BuLi (2.5 M, 12.2 mL, 30.6 mmol) was added dropwise via syringe keeping the internal temperature below 0° C. The resulting reaction mixture was stirred at 0° C. for 15 min. The reaction mixture was then cooled at −40° C. while 4-bromo-2-methylbenzonitrile (4.00 g, 20.4 mmol) in 10 mL of THF was added dropwise via syringe over 1 h. An internal temperature of ca. −40° C. was maintained during the addition.

The resulting reaction mixture was stirred at −40° C. for 30 min and then charged with DMF (2.98 g, 40.8 mmol, ca. 50 ppm water) in one portion. The reaction mixture was stirred at −40° C. for 15 min. The reaction mixture was quenched with MeOH (5 vol., 20 mL) and then charged with NaBH$_4$ (0.770 g, 20.4 mmol) in one portion and allowed to warm to room temperature. After complete reduction of intermediate aldehyde (as judged by HPLC analysis), the reaction mixture was carefully quenched with 5 M HCl (with cooling) to adjust the pH to 2-3. The reaction mixture was extracted with EtOAc and then solvent-switched to EtOH (40 mL). H$_2$SO$_4$ (98%, 20.0 g, 204 mmol) was added in one portion and the resulting reaction mixture was stirred at reflux for 24 h. After complete cyclization (monitored by HPLC analysis), the reaction mixture was cooled to room temperature and then solvent-switched to EtOAc. The resulting organic layer was washed with water, brine, and solvent-switched to MTBE. Precipitation from 1:1 MTBE:heptane afforded 6-bromo-3,4-dihydro-1H-isochromen-1-one.

Method B:

A solution of DIPA (4 M, 270 mL, 1080 mmol) in THF (900 mL) was cooled to −65° C. and hexyl lithium (2.1 M, 505 mL, 1060 mmol) was added dropwise over 15 min maintaining the internal temp <−55° C. Upon completion of the addition, the reaction mixture was warmed up to −40° C. where it was stirred 30 min. To the resulting solution of LDA was added 4-bromo-2-methylbenzoic acid (90 g, 419 mmol) slowly (over 15 min) as a solution in THF (400 mL). The reaction mixture was stirred for 30 min at −40° C. and then warmed to 15° C. at which point paraformaldehyde (50.30 g, 1674 mmol) was added in 3 portions as a solid keeping the internal temperature (ice water bath) below <18° C. Stirring was then continued at room temperature for 1 hour. After a second hour of stirring, the vessel was immersed in an ice water bath and 3N HCl (650 mL) was added at such a rate to keep the internal temperature less than 30° C. The contents of the reaction vessel was subsequently transferred to a separatory funnel where it was extracted 3×400 mL EtOAc and the combined organic phases were then concentrated to ~800 mL total volume. To this was added Amberlyst 15 resin (12 g) and the resulting mixture stirred at 48° C. overnight (~14 h). HPLC analysis the following morning indicated that cyclization to the desired 6-bromo-3,4-dihydro-1H-isochromen-1-one was nearly complete. The resin was removed by filtration and the solution concentrated to ~200 mL total volume at which point the desired product began to precipitate and the solids were then collected by filtration. The cake was subsequently washed with MTBE (2×80 mL) to give the first crop of product. Additional material was salvaged by washing the collected supernatant 2× with 200 mL 10% K$_2$CO$_3$, aq followed by 200 mL 1M H$_3$PO$_4$. After concentration to ~100 mL the precipitated material was collected by filtration, washed with MTBE and then combined with the first crop of 6-bromo-3,4-dihydro-1H-isochromen-1-one and dried.

Intermediate 6A and 6B

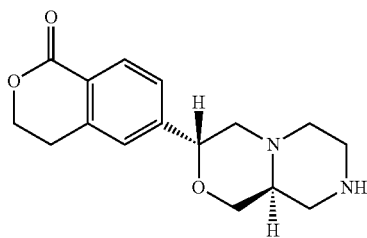

6A

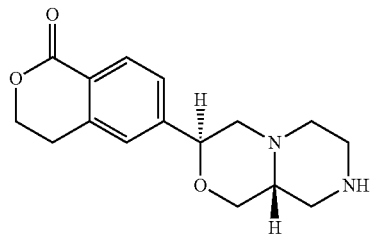

6B

6A: 6-[(3R,9aS)-octahydropyrazino[2,1-c][1,4]oxazin-3-yl]-3,4-dihydro-1H-isochromen-1-one Step A:
6-(bromoacetyl)-3,4-dihydro-1H-isochromen-1-one 6-Bromo-3,4-dihydro-1H-isochromen-1-one (6.90 g, 30.4 mmol), tributyl(1-ethoxyethenyl)stannane (10.8 mL, 31.9 mmol, 1.05 equiv), and PdCl$_2$(PPh$_3$)$_2$(1.07 g, 1.52 mmol, 0.05 equiv) were weighed into a 250 mL round bottom flask. To this was added dioxane (70 mL) and the resulting mixture stirred at 80° C. for 4 h. The reaction was not complete by HPLC, therefore another 0.1 equiv of tin reagent was added. After 30 min 6-bromo-3,4-dihydro-1H-isochromen-1-one had been fully consumed as indicated by HPLC. The reaction mixture was cooled to 0° C. and 35 mL THF followed by 14 mL H$_2$O were added. To this was introduced solid N-bromosuccinimide (5.68 g, 31.9 mmol, 1.05 equiv), added in portions over 5 min. After stirring for 30 min there was still evidence of remaining enol ether, therefore NBS was added in small portions (~300 additional mg added) until it was consumed as evidenced by HPLC. Water was then added and the mixture extracted with EtOAc. The aqueous layer was extracted 2 additional times with EtOAc, the combined organics dried with MgSO$_4$, filtered and concentrated in vacuo. This was transferred with EtOAc to a 100 mL round bottom flask, the resulting solution concentrated to ~25 mL total volume, at which point hexane (50 mL) was added dropwise. When complete the heterogeneous mixture was stirred for 30 min, then cooled to 0° C. and stirred for 10 min, then filtered and washed twice with hexanes. The desired product was dried under a nitrogen bag, then purified by flash chromatography (12 to 100% EtOAc/Hex) to provide the title compound.

Step B: tert-butyl(9aS)-3-hydroxy-3-(1-oxo-3,4-dihydro-1H-isochromen-6-yl)hexahydropyrazino[2,1-c][1,4]oxazine-8(1H)-carboxylate 6-(Bromoacetyl)-3,4-dihydro-1H-isochromen-1-one (~1.54 g, ~5.72 mmol, presence of α-chloroketone was noted, ~10%) and commercially available (S)-4-N—BOC-2-hydroxymethylpiperazine (1.24 g, 5.72 mmol) were added to a round bottom flask and diluted with THF (50 mL). Diisopropylethylamine (1.30 mL, 7.44 mmol) was then introduced and the mixture left stirring for 14 h at RT during which time a considerable amount of solid had formed (presumably HBr salt of DIPEA). The reaction mixture was diluted with EtOAc, then washed with saturated NH$_4$Cl$_{aq}$ followed by H$_2$O. Both aqueous layers were sequentially back extracted once with another portion of EtOAc, the organics were then combined, dried with MgSO$_4$, filtered, and concentrated in vacuo. The recovered crude product was subjected to purification by flash chromatography (Biotage, 50% EtOAc/Hex) to afford the title compound.

Step C: 6-[(3R,9aS)-octahydropyrazino[2,1-c][1,4]oxazin-3-yl]-3,4-dihydro-1H-isochromen-1-one tert-Butyl(9aS)-3-hydroxy-3-(1-oxo-3,4-dihydro-1H-isochromen-6-yl)hexahydropyrazino[2,1-c][1,4]oxazine-8(1H)-carboxylate (1.84 g, 4.55 mmol) was diluted with TFA (18 mL, 234 mmol) and cooled to 0° C. Some off gassing was apparent and after a few minutes a homogenous solution had been formed. Approximately 5 minutes post-TFA addition, Et₃SiH (5.09 mL, 31.8 mmol) was added and the reaction mixture allowed to slowly warm to RT (allowed to warm naturally in the ice bath) where it was stirred for 18 h. The trans:cis diastereomeric ratio appeared to be ~95:5. The reaction vessel was transferred to a rotary evaporator and concentrated in vacuo to a two phase liquid. This crude material was diluted with CH₂Cl₂ washed with NaHCO₃, aq then water. The separately kept aqueous layers were subsequently extracted once with the same portion of CH₂Cl₂, the combined organics dried with MgSO₄, filtered and concentrated in vacuo. The crude residue was dried under house vacuum then the mixture was further purified by flash chromatography (2% MeOH 2% Et₃N in CH₂Cl₂) to afford the title compound.

6B: 6-[(3S,9aR)-octahydropyrazino[2,1-c][1,4]oxazin-3-yl]-3,4-dihydro-1H-isochromen-1-one The same procedure described above to prepare 6-[(3R,9aS)-octahydropyrazino[2,1-c][1,4]oxazin-3-yl]-3,4-dihydro-1H-isochromen-1-one was used to prepare the title compound starting from 6-(bromoacetyl)-3,4-dihydro-1H-isochromen-1-one and commercially available (R)-4-N—BOC-2-hydroxymethylpiperazine; LC-MS (IE, m/z): 289.1 [M+1]⁺.

Intermediate 7 and Isomers 7A and 7B

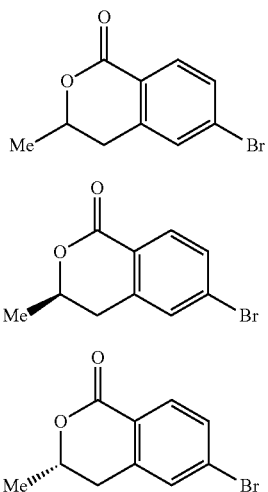

6-bromo-3-methyl-3,4-dihydro-1H-isochromen-1-one and individual isomers (3R)-6-bromo-3-methyl-3,4-dihydro-1H-isochromen-1-one and (3S)-6-bromo-3-methyl-3,4-dihydro-1H-isochromen-1-one A −78° C. solution of diisopropylamine (13.3 mL, 93.0 mmol)) in THF (155 mL) was treated with n-BuLi (1.6 M in Hexanes; 58 mL, 93 mmol) over a period of 15 minutes using a syringe pump. In a separate flask, a solution of 2-methyl-4-bromo benzoic acid (10.0 g, 46.5 mmol) and HMPA (8.33 mL, 46.5 mmol) in THF (155 mL) was cooled to −78° C. Methyl Lithium (29.1 mL, 46.5 mmol) was added slowly via syringe to the cooled solution. The resulting solution was stirred for 10 minutes and then transferred via cannula to the LDA solution at −78° C. The resulting solution was stirred at −78° C. for an additional 1 h before being quenched with anhydrous acetaldehyde (7.88 mL, 140 mmol) and the reaction was then taken out of the dry ice acetone bath and allowed to stir for an additional 1 h. The flask containing the reaction mixture was then resubmerged in the dry ice acetone bath before it was quenched with 4M HCl in dioxane (50 mL) followed by 25 mL of MeOH. The reaction was stirred at room temp for an additional 1 h. The crude reaction mixture was partitioned between 200 mL ethyl acetate and 200 mL water. The organic layer was washed with water, brine, dried with magnesium sulfate, filtered and concentrated. Purification via MPLC (30-70% DCM/Hexanes) afforded 7 as a racemic mixture which was separable by chiral SFC HPLC using, for example, a Chiralpak AS column to obtain 7A and 7B. ¹H NMR (500 MHz; CDCl₃): δ 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H); LC-MS (IE, m/z): 241 [M+1]⁺.

Intermediate 7A (Method 2)

(3R)-6-bromo-3-methyl-3,4-dihydro-1H-isochromen-1-one

Step A: 4-bromo-N,N-diethyl-2-methylbenzamide

A solution of 4-bromo-2-methylbenzoic acid (25.0 g, 116 mmol) in DCM (400 mL) was treated with oxalyl chloride (11.7 mL, 134 mmol) and a catalytic amount of dry DMF (0.1 mL). The reaction was allowed to stir under nitrogen for 2 hours at room temperature. Removal of excess solvent gave crude acid chloride which was redissolved in DCM (400 mL). The mixture was then cooled to 0° C. and triethyl amine (40.5 mL, 291 mmol) was added followed by the slow addition of diethyl amine (24.3 mL, 233 mmol). The reaction was then allowed to warm to room temperature overnight. The crude mixture was then diluted with 400 mL of water and extracted with DCM (3×500 mL). The combined organic layers were then washed with brine (200 mL), dried over magnesium sulfate, filtered and then concentrated. The crude material was purified via MPLC (10% EtOAc/Hex) to afford 4-bromo-N,N-diethyl-2-methylbenzamide: LC-MS: (M+H)⁺270.

Step B: 4-bromo-N,N-diethyl-2-(2-oxopropyl)benzamide

A 2M solution of LDA (35.2 mL, 70.3 mmol) in THF (176 mL) cooled to −78° C. was treated with slow addition of 4-bromo-N,N-diethyl-2-methylbenzamide (19 g, 70.3 mmol) in dry THF (176 mL). The reaction was allowed to stir at −78° C. for 1 hour before it was quenched with N-methoxy-N-methylacetamide (22.43 mL, 211 mmol) and allowed to slowly warm to room temp. The reaction was stirred overnight and then partitioned between 1N HCl (200 mL) and EtOAc (400 mL). The aqueous layer was further extracted with EtOAc (2×150 mL). The combined organic layers were washed with brine (150 mL), dried over magnesium sulfate, filtered and concentrated. The crude material was an oil out of which the product precipitated. The oil was decanted off and the solid was washed with hexanes and dried using a buchner funnel to afford 4-bromo-N,N-diethyl-2-(2-oxopropyl)benzamide: LC-MS: (M+H)⁺312.

Step C: 4-bromo-N,N-diethyl-2-[(2R)-2-hydroxypropyl]benzamide

A flask equipped with an overhead stirrer was charge with pH=8 Phosphate Buffer (156 mL, 31.2 mmol) followed by D-glucose (1.298 g, 7.21 mmol) and then warmed to 30° C. Next, 135 mg glucose dehydrogenase and 270 mg NADP+ disodium was added to the glucose/buffer solution at once, a homogeneous solution was obtained after 1 min agitating. Next, 577 mg of keto-reductase enzyme KRED P1B2 (available from Codexis, Inc., 200 Penobscot Drive, Redwood City, Calif. 94063, www.codexis.com, tel. 1-650-421-8100) was added to the reaction vessel and stirred at 500 rpm at 30° C. until enzyme was wetted (about 40 min). Lastly, a solution of 4-bromo-N,N-diethyl-2-(2-oxopropyl)benzamide (1.5 g, 4.80 mmol) dissolved in DMSO (14.56 mL) (pre-warmed on stir plate to 30° C.) was added to the reaction over ~3 min and agitate at 30° C. (400 rpm) overnight.

After 48 hours the reaction was cooled to room temperature and then 75 g of potassium carbonate was added to the reaction in portions and stirred for 15 minutes until enzyme clumps together when stirring is stopped. Next, acetonitrile (50 mL) was poured into the reaction flask and the layers were thoroughly mixed. Stirring was stopped after 15-20 minutes, the layers allowed to separate and the upper layer decanted off. This was repeated two more times with additional 50 mL of acetonitrile. The combined organic layers were then filtered through a medium porosity funnel, concentrated and then 50 ml MTBE was added to the concentrate and stirred for 5 min and then transferred to a separatory funnel and the layers separated. The aqueous layer was extracted further another 50 mL MTBE. The combined organic extracts were dried over magnesium sulfate, filtered and concentrated. Purification via MPLC (30-70% EtOAc/Hex) afforded 4-bromo-N,N-diethyl-2-[(2R)-2-hydroxypropyl]benzamide.

Step D: (3R)-6-bromo-3-methyl-3,4-dihydro-1H-isochromen-1-one

A solution of 4-bromo-N,N-diethyl-2-[(2R)-2-hydroxypropyl]benzamide (12.2 g, 38.8 mmol) dissolved in 4N HCl in dioxane (200 mL) was stirred at room temperature and monitored by TLC. After 3 days the reaction was partitioned between EtOAc (300 mL) and water (300 mL). The aqueous phase was further extracted with EtOAc (2×250 mL). The combined organic layers were then washed with water (200 mL), brine (200 mL), dried over magnesium sulfate, filtered and concentrated. The crude material was then purified via MPLC (15-30% EtOAc/Hexane) to afford (3R)-6-bromo-3-methyl-3,4-dihydro-1H-isochromen-1-one: $^1$H NMR (500 MHz; CDCl$_3$): 7.98 (d, J=8.2 Hz, 1H), 7.56 (dd, J=1.5, 8.2 Hz, 1H), 7.45 (s, 1H), 4.71 (m, 1H), 2.94 (m, 2H), 1.55 (d, J=6.3 Hz, 3H); LC-MS: (M+1)$^+$241.

Intermediate 7B (Method 2)

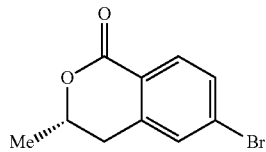 [SMILES: C[C@H]1Cc2cc(Br)ccc2C(=O)O1]

(3S)-6-bromo-3-methyl-3,4-dihydro-1H-isochromen-1-one (3S)-6-Bromo-3-methyl-3,4-dihydro-1H-isochromen-1-one was prepared in a similar manner as (3R)-6-Bromo-3-methyl-3,4-dihydro-1H-isochromen-1-one except using keto-reductase enzyme KRED P1H9 (available from Codexis, Inc., 200 Penobscot Drive, Redwood City, Calif. 94063, www.codexis.com, tel. 1-650-421-8100) in Step C, which gave the opposite enantiomer of the resulting alcohol.

Intermediates 8A and 8B

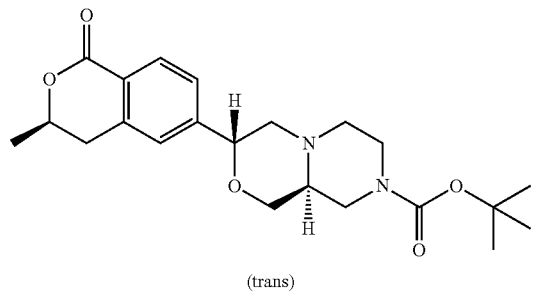

(trans)

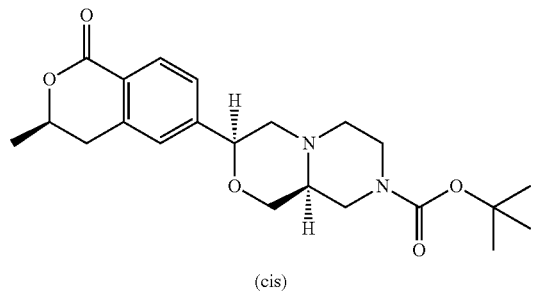

(cis)

8A: tert-Butyl (3R,9aS)-3-[(3R)-3-methyl-1-oxo-3,4-dihydro-1H-isochromen-6-yl]hexahydropyrazino[2,1-c][1,4]oxazine-8(1H)-carboxylate 8B: tert-Butyl (3S,9aS)-3-[(3R)-3-methyl-1-oxo-3,4-dihydro-1H-isochromen-6-yl]hexahydropyrazino[2,1-c][1,4]oxazine-8(1H)-carboxylate

Step A: (3R)-6-ethenyl-3-methyl-3,4-dihydro-1H-isochromen-1-one

A solution of (3R)-6-bromo-3-methyl-3,4-dihydro-1H-isochromen-1-one (2.4 g, 9.96 mmol) and triethylamine (2.78 mL, 19.91 mmol) in EtOH (39.8 mL) was added to a microwave vial containing PdCl$_2$(dppf)-CH$_2$Cl$_2$, (0.406 g, 0.498 mmol) and potassium vinyltrifluoroborate (2.000 g, 14.93 mmol). The contents of the vial were heated to 100° C. for 1 hour after which the mixture was cooled, diluted with chloroform (50 mL) and washed with aqueous ammonium chloride (25 mL). The organic layer was then dried over magnesium sulfate, filtered and the solvent was evaporated under reduced pressure. MPLC purification (15-60% EtOAc/Hex) gave the title compound.

Step B: (3R)-3-methyl-6-(oxiran-2-yl)-3,4-dihydro-1H-isochromen-1-one

A solution of 6-ethenyl-3-methyl-3,4-dihydro-1H-isochromen-1-one (1.69 g, 8.98 mmol) in DCM (60 mL) was treated with mCPBA (3.100 g, 17.96 mmol) overnight at room temperature. The reaction was then diluted with water (50 mL) and DCM (50 mL). The organic layer was further washed successively with saturated aqueous sodium bicarbonate (30 mL), water (30 mL), and brine (30 mL). The organic layer was then dried over magnesium sulfate, filtered and concentrated. The residue was purified via MPLC (15-40% EtOAc/Hex) to give the title compound.

Step C: tert-butyl (3S)-3-(hydroxymethyl)-4-{2-hydroxy-2-[(3R)-3-methyl-1-oxo-3,4-dihydro-1H-isochromen-6-yl]ethyl}piperazine-1-carboxylate A solution of (3R)-3-methyl-6-(oxiran-2-yl)-3,4-dihydro-1H-isochromen-1-one (325 mg, 1.59 mmol) and tert-butyl (3S)-3-(hydroxymethyl)piperazine-1-carboxylate (345 mg, 1.59 mmol dissolved in EtOH (7 mL)) was heated in a sealed tube to 155° C. for 3 hours in the microwave. The reaction was cooled and concentrated to give crude product which was purified via MPLC (40-100% EtOAc/Hexane) to give the title compound as a mixture of diastereomers.

Step D: tert-Butyl (3R,9aS)-3-[(3R)-3-methyl-1-oxo-3,4-dihydro-1H-isochromen-6-yl]hexahydropyrazino[2,1-c][1,4]oxazine-8(1H)-carboxylate and tert-Butyl (3S,9aS)-3-[(3R)-3-methyl-1-oxo-3,4-dihydro-1H-isochromen-6-yl]hexahydropyrazino[2,1-c][1,4]oxazine-8(1H)-carboxylate A sealed tube containing tert-butyl (3S)-3-(hydroxymethyl)-4-{2-hydroxy-2-[(3R)-3-methyl-1-oxo-3,4-dihydro-1H-isochromen-6-yl]ethyl}piperazine-1-carboxylate as a mixture of diastereomers (530 mg, 1.26 mmol) and cyanomethylenetributylphosphorane (304 mg, 1.26 mmol) dissolved in anhydrous benzene (8 mL) was degassed twice with nitrogen and then heated using a microwave to 135° C. for 2.5 hours. The reaction was allowed to cool and the crude mixture was concentrated and purified on MPLC (20-65% EtOAc/Hex) to afford a mixture of diastereomers as well as recovered starting material. The cis/trans mixture was purified via chiral HPLC (10% EtOH/Heptane) using AS column to give the trans isomer as the faster eluting peak and the cis isomer as the slower eluting peak. Alternatively, the mixture can be separated by chiral SFC-HPLC (40% 2:1 MeOH:MeCN/CO$_2$) using an IC column.

8A: $^1$H NMR (500 MHz; CDCl$_3$): 8.08 (d, J=8.1 Hz, 1H), 7.35 (d, J=8.0 Hz, 1H), 7.28 (s, 1H), 4.70 (m, 2H), 4.00 (bs, 2H), 3.96 (dd, J=3.0, 11.3 Hz, 2H), 3.48 (t, J=10.7 Hz, 1H), 2.95 (m, 4H), 2.74 (d, J=10.5 Hz, 1H), 2.2 (m, 3H), 1.53 (d, J=6.4 Hz, 3H), 1.49 (s, 9H);
LC-MS: (M+1)$^+$403; 8B: $^1$H NMR (500 MHz; CDCl$_3$): 8.10 (d, J=8.2 Hz, 1H), 7.54 (d, J=8.0 Hz, 1H), 7.40 (s, 1H), 4.81 (bt, 1H), 4.71 (m, 1H), 3.62 (dd, J=2.8, 11.5 Hz, 1H), 3.41 (m, 1H), 3.25 (dd, J=3.7, 12.1 Hz, 1H), 2.95 (m, 4H), 2.76 (m, 3H), 2.50 (m, 2H), 2.28 (m, 1H), 1.54 (d, J=6.2 Hz, 3H), 1.49 (s, 9H); LC-MS: (M+1)$^+$403.

Intermediates 8C and 8D

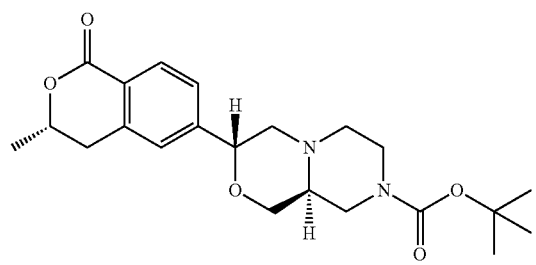

8C

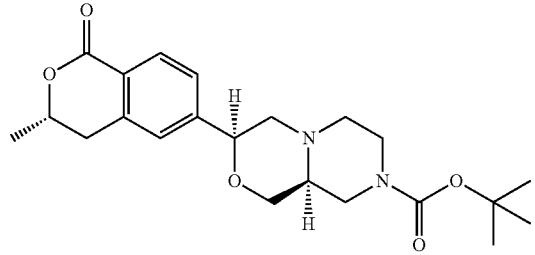

8D

8C: tert-Butyl (3R,9aS)-3-[(3S)-3-methyl-1-oxo-3,4-dihydro-1H-isochromen-6-yl]hexahydropyrazino[2,1-c][1,4]oxazine-8(1H)-carboxylate 8D: tert-Butyl (3S,9aS)-3-[(3S)-3-methyl-1-oxo-3,4-dihydro-1H-isochromen-6-yl]hexahydropyrazino[2,1-c][1,4]oxazine-8(1H)-carboxylate 8C and 8D were prepared in a similar manner as Intermediates 8A and 8B except (3S)-6-Bromo-3-methyl-3,4-dihydro-1H-isochromen-1-one was used as the starting material. The cis/trans mixture was purified via chiral HPLC (30% 2:1 MeOH:MeCN/CO$_2$) on an AD column. The faster eluting diastereomer was the trans isomer. 8C: $^1$H NMR (500 MHz; CDCl$_3$): 8.07 (d, J=8.1 Hz, 1H), 7.35 (d, J=8.0 Hz, 1H), 7.28 (s, 1H), 4.72 (dd, J=1.8, 10.5 Hz, 1H), 4.68 (m, 1H), 4.1-3.8 (bs, 2H), 3.96 (dd, J=3.0, 11.3 Hz, 2H), 3.48 (t, J=10.7 Hz, 1H), 2.95 (m, 4H), 2.74 (d, J=10.5 Hz, 1H), 2.2 (m, 3H), 1.54 (d, J=6.2 Hz, 3H), 1.49 (s, 9H); LC-MS: (M+1)$^+$403; 8D: $^1$H NMR (500 MHz; CDCl$_3$): 8.10 (d, J=8.2 Hz, 1H), 7.54 (d, J=8.0 Hz, 1H), 7.39 (s, 1H), 4.81 (bt, 1H), 4.71 (m, 1H), 3.62 (dd, J=2.8, 11.5 Hz, 1H), 3.41 (m, 1H), 3.25 (dd, J=3.7, 12.1 Hz, 1H), 2.95 (m, 4H), 2.76 (m, 3H), 2.50 (m, 2H), 2.28 (m, 1H), 1.54 (d, J=6.2 Hz, 3H), 1.48 (s, 9H); LC-MS: (M+1)$^+$ 403.

Intermediates 8E and 8F

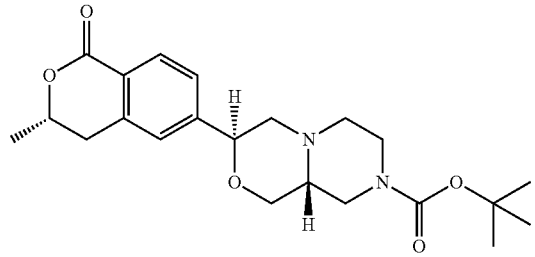

8E

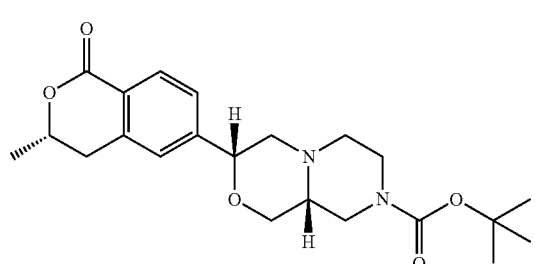

8F

8E: tert-Butyl (3S,9aR)-3-[(3S)-3-methyl-1-oxo-3,4-dihydro-1H-isochromen-6-yl]hexahydropyrazino[2,1-c][1,4]oxazine-8(1H)-carboxylate 8F: tert-Butyl (3R,9aR)-3-[(3S)-3-methyl-1-oxo-3,4-dihydro-1H-isochromen-6-yl]hexahydropyrazino[2,1-c][1,4]oxazine-8(1H)-carboxylate Intermediates 8E and 8F were prepared in a similar manner as Intermediates 8A and 8B except (3S)-6-Bromo-3-methyl- 3,4-dihydro-1H-isochromen-1-one and tert-butyl (3R)-3-(hydroxymethyl)piperazine-1-carboxylate were used as the starting materials. The cis/trans mixture was purified via MPLC (20-65% EtOAc/Hex). The faster eluting diastereomer was the trans isomer: 8E: ¹H NMR (500 MHz; CDCl₃): 8.07 (d, J=8.2 Hz, 1H), 7.35 (d, J=8.0 Hz, 1H), 7.27 (s, 1H), 4.71 (dd, J=2.0, 10.7 Hz, 1H), 4.68 (m, 1H), 4.0 (bs, 2H), 3.97 (dd, J=3.1, 11.1 Hz, 2H), 3.48 (t, J=10.8 Hz, 1H), 2.99 (m, 4H), 2.74 (d, J=10.5 Hz, 1H), 2.2 (m, 3H), 1.53 (d, J=6.4 Hz, 3H), 1.49 (s, 9H). (M+1)⁺403.8F: ¹H NMR (500 MHz; CDCl₃): 8.09 (d, J=8.9 Hz, 1H), 7.53 (d, J=8.3 Hz, 1H), 7.39 (s, 1H), 4.81 (t, J=3.6 Hz, 1H), 4.69 (m, 1H), 3.62 (dd, J=3.0, 11.5 Hz, 1H), 3.42 (m, 1H), 3.24 (dd, J=3.6, 12.1 Hz, 1H), 2.97 (m, 4H), 2.76 (m, 3H), 2.50 (m, 2H), 2.28 (m, 1H), 1.54 (d, J=6.2 Hz, 3H), 1.47 (s, 9H). (M+1)⁺403.

Intermediates 8G and 8H

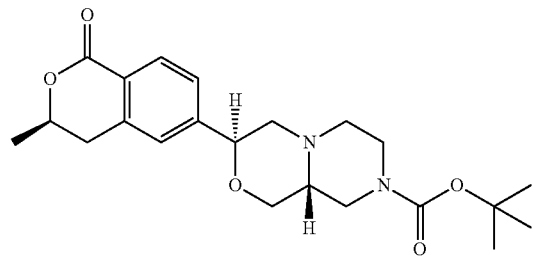

8G

8G: tert-Butyl (3S,9aR)-3-[(3R)-3-methyl-1-oxo-3,4-dihydro-1H-isochromen-6-yl]hexahydropyrazino[2,1-c][1,4]oxazine-8(1H)-carboxylate

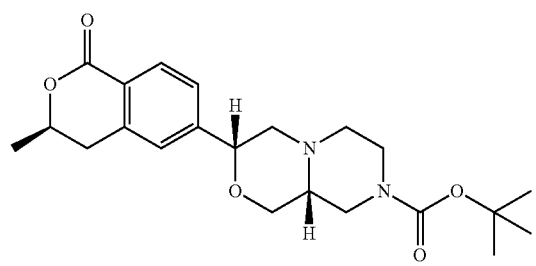

8H

8H: tert-Butyl (3R,9aR)-3-[(3R)-3-methyl-1-oxo-3,4-dihydro-1H-isochromen-6-yl]hexahydropyrazino[2,1-c][1,4]oxazine-8(1H)-carboxylate 8G and 8H were prepared in a similar manner as 8A and 8B except (3R)-6-Bromo-3-methyl-3,4-dihydro-1H-isochromen-1-one and tert-butyl (3R)-3-(hydroxymethyl)piperazine-1-carboxylate were used as the starting materials. The cis/trans mixture was purified via chiral HPLC (20% 2:1 MeOH:MeCN/CO₂) on OJ column. The slower eluting diastereomer was the trans isomer: 8G LC-MS: (M+1)+403; 8H: LC-MS: (M+1)+403.

Intermediates 9A and 9B

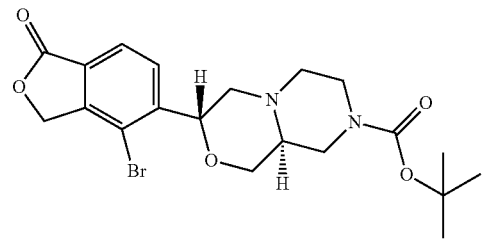

9A (trans)

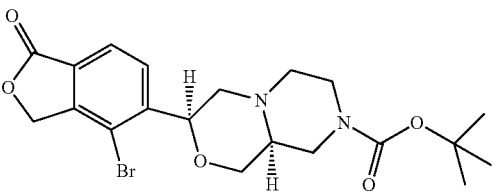

9B (cis)

9A: tert-butyl(3R,9aS)-3-(4-bromo-1-oxo-1,3-dihydro-2-benzofuran-5-yl)hexahydropyrazino[2,1-c][1,4]oxazine-8(1H)-carboxylate 9B: tert-butyl(3S,9aS)-3-(4-bromo-1-oxo-1,3-dihydro-2-benzofuran-5-yl)hexahydropyrazino[2,1-c][1,4]oxazine-8(1H)-carboxylate Step A: 4,5-dibromo-2-benzofuran-1(3H)-one To a flask containing a stir bar was added commercially available 5-bromo-2-benzofuran-1(3H)-one (12.0 g, 56.3 mmol) and NBS (15 g, 84 mmol). Triflic acid (50 mL) was added at 0° C. and the resulting mixture was stirred for 2 days. TLC analysis of the reaction mixture showed a complete reaction; the reaction mixture was poured into an ice and the organic layer separated. The organic layer was washed with aq. NaCl, water, dried over Na₂SO₄, filtered and concentrated to dryness, it was then absorbed onto silica gel and subjected for purification over a silica column to give the title compound.

Step B: 4-bromo-5-ethenyl-2-benzofuran-1(3H)-one 4,5-Dibromo-2-benzofuran-1(3H)-one (3.00 g, 10.3 mmol), Potassium vinyltrifluoroborate (12.7 g, 20.6 mmol) and Pd(dppf)Cl₂ (839 mg, 1.03 mmol) in TEA (2.7 mL) and EtOH (15 mL) were added to a flask containing a stir bar. The flask was then heated at 60° C. for 2 h. TLC showed clean and complete reaction. The organic residue was dissolved in EtOAc (500 mL) and the solution was washed with brine, dried over sodium sulfate, filtered and concentrated. The resulting organic residue was subjected to purification over silica gel to give 4-bromo-5-ethenyl-2-benzofuran-1(3H)-one.

Step: 4-bromo-5-(oxiran-2-yl)-2-benzofuran-1(3H)-one

To a solution of 4-bromo-5-ethenyl-2-benzofuran-1(3H)-one (2.00 g, 8.37 mmol) in DCM (20 mL) was slowly added mCPBA (2.6 g, 8.4 mmol) at 0° C. The flask was warmed to room temperature; the mixture was then stirred for 12 hours. The mixture was washed with aq. $Na_2S_2O_3$, aq. $NaHCO_3$, and water. The organic layers was washed with brine and then concentrated to dryness. The residue was purified over silica gel to give the title compound.

Steps D-E: tert-butyl(3R,9aS)-3-(4-bromo-1-oxo-1,3-dihydro-2-benzofuran-5-yl)hexahydropyrazino[2,1-c][1,4]oxazine-8(1H)-carboxylate and tert-butyl (3S,9aS)-3-(4-bromo-1-oxo-1,3-dihydro-2-benzofuran-5-yl)hexahydropyrazino[2,1-c][1,4]oxazine-8(1H)-carboxylate The title compounds were prepared from 4-bromo-5-(oxiran-2-yl)-2-benzofuran-1(3H)-one in two steps in an analogous fashion as that described for the synthesis of 4A: tert-butyl(3R,9aS)-3-(4-methyl-1-oxo-1,3-dihydro-2-benzofuran-5-yl)hexahydropyrazino[2,1-c][1,4]oxazine-8(1H)-carboxylate and 4B: tert-butyl(3S,9aS)-3-(4-methyl-1-oxo-1,3-dihydro-2-benzofuran-5-yl)hexahydropyrazino[2,1-c][1,4]oxazine-8(1H)-carboxylate. 9A, $^1$H-NMR ($CDCl_3$, 500 MHz), δ 7.93 (d, J=7.5 Hz, 1H), 7.81 (d, J=7.5 Hz, 1H), 5.25 (s, 2H), 5.10 (d, J=10 Hz, 1H), 4.07-4.01 (m, 4H), 3.57-3.53 (m, 2H), 3.09 (d, J=10.5 Hz, 1H), 2.78-2.77 (m, 2H), 2.39-2.06 (m, 2H), 1.51 (s, 9H): 9B (after Boc was removed with 4M HCl) $^1$H-NMR (DMSO, 500 MHz), δ 7.93-7.92 (m, 2H), 5.33 (m, 2H), 5.21 (d, J=7.5 Hz, 1H), 4.00-3.89 (m, 4H), 3.07-3.48 (m, 3H), 3.33-3.31 (m, 3H), 3.21 (d, J=11.5 Hz, 1H), 3.12 (d, J=11.5 Hz, 1H).

Intermediate 10A and 10B

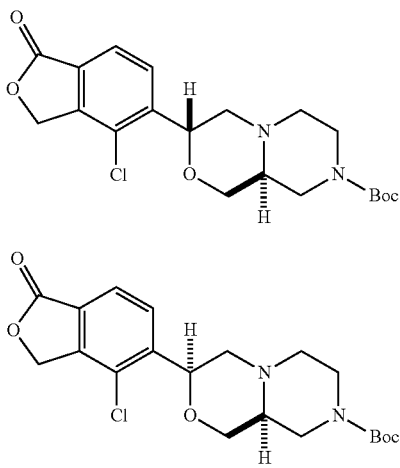

10A

10B

10A: tert-butyl (3R,9aS)-3-(4-chloro-1-oxo-1,3-dihydro-2-benzofuran-5-yl)hexahydropyrazino[2,1-c][1,4]oxazine-8(1H)-carboxylate 10B: tert-butyl (3S,9aS)-3-(4-chloro-1-oxo-1,3-dihydro-2-benzofuran-5-yl)hexahydropyrazino[2,1-c][1,4]oxazine-8(1H)-carboxylate Step A: 2-chloro-3-(hydroxymethyl)phenol To a solution of 2-chloro-3-hydroxybenzaldehyde (8.10 g, 51.7 mmol) in MeOH was added $NaBH_4$ (1.96 g, 51.7 mmol) at 0° C. The reaction was allowed to stir for 30 minutes. TLC showed clean conversion to a more polar spot. The reaction was diluted with EtOAc (400 mL), washed with water and brine, dried over sodium sulfate, and concentrated. The crude product was used in Step B without further purification.

Step B: 4-bromo-2-chloro-3-(hydroxymethyl)phenol

To the flask charged with 2-chloro-3-(hydroxymethyl)phenol from Step A and a stir bar was added NBS (10.8 g, 60.5 mmol) and TFA (50 mL). The reaction was allowed to stir for 16 hours at RT. TLC showed complete reaction at that point. The solvent was removed under vacuum. The residue was re-dissolved in EtOAc, washed with water, and purified by silica gel flash chromatography. A pair of regio-isomers was collected from the separation. The less polar spot was the desired 4-bromo-2-chloro-3-(hydroxymethyl)phenol according to one NMR analysis.

Step C: 4-chloro-5-hydroxy-2-benzofuran-1(3H)-one

To a flask charged with 4-bromo-2-chloro-3-(hydroxymethyl)phenol (2.44 g, 10.3 mmol) and a stir bar was added CuCN (2.76 g, 30.8 mmol) and DMF (25 mL). The flask was fitted with a condenser and purged three times with Nitrogen. The solution was then heated to 145° C. for 2 hours. At that point, water (0.555 mL, 30.8 mmol) was added to the reaction via a syringe, and the reaction was kept at 100° C. for another 24 hours. The reaction was cooled to RT, diluted with DCM (100 mL), and filtered through a pad of celite to remove the solids. The filtrate was washed with saturated $NH_4OAc$, dried over sodium sulfate, concentrated and purified by silica gel flash chromatography. 4-Chloro-5-hydroxy-2-benzofuran-1(3H)-one was collected after removal of solvents.

Step D: 4-chloro-5-ethenyl-2-benzofuran-1(3H)-one

To a cold solution of 4-chloro-5-hydroxy-2-benzofuran-1(3H)-one (1.39 g, 7.53 mmol) in DCM (25 mL) was added Hunig's Base (3.29 mL, 18.8 mmol) and trifluoromethanesulfonic anhydride (2.54 mL, 15.1 mmol). The mixture was allowed to stir for 16 hours. Analysis by TLC showed complete consumption of all SM. The reaction was diluted with Hexane and washed with water. The solution was dried with sodium sulfate, concentrated, and purified by flash chromatography on a silica column. The solvent was removed under reduced pressure to give intermediate triflate: LC-MS (M+1=317). To the triflate was added a stir bar, potassium vinyltrifluoroborate (1.33 g, 9.90 mmol), $PdCl_2(dppf)$ (0.243 g, 0.332 mmol), triethylamine (1.89 mL, 13.3 mmol), and iso-propanol (50 mL). The mixture was purged three times with nitrogen, and heated to 60° C. for 2 hours. TLC showed complete reaction at that point. Most of the solvent was removed under vacuum. The crude residue was diluted with EtOAc (200 mL), washed with brine, dried over sodium sulfate, adsorbed onto silica gel, and purified by flash chromatography to give the title compound.

Step E: 4-chloro-5-oxiran-2-yl-2-benzofuran-1(3H)-one

To a solution of 4-chloro-5-ethenyl-2-benzofuran-1(3H)-one (1.1 g, 5.7 mmol) in DCM (40 mL) was added m-CPBA (1.9 g, 8.5 mmol). The solution was stirred at RT for 16 hours. Analysis by TLC and LC showed formation of the desired product, along with some untouched starting material. The reaction was diluted with DCM (200 mL), washed with aqueous $Na_2S_2O_3$ and $Na_2CO_3$, dried over sodium sulfate, concentrated, and purified by silica gel flash chromatography to afford the title compound.

Step F-G: tert-butyl (3R,9aS)-3-(4-chloro-1-oxo-1,3-dihydro-2-benzofuran-5-yl)hexahydropyrazino[2,1-c][1,4]oxazine-8(1H)-carboxylate and tert-butyl (3S,9aS)-3-(4-chloro-1-oxo-1,3-dihydro-2-benzofuran-5-yl)hexahydropyrazino[2,1-c][1,4]oxazine-8(1H)-carboxylate The title compounds were prepared from 4-chloro-5-(oxiran-2-yl)-2-benzofuran-1(3H)-one in two steps in an analogous fashion as that described for the synthesis of 4A: tert-butyl(3R,9aS)-3-(4-methyl-1-oxo-1,3-dihydro-2-benzofuran-5-yl)hexahydropyrazino[2,1-c][1,4]oxazine-8(1H)-carboxylate and 4B: tert-butyl(3S,9aS)-3-(4-methyl-1-oxo-1,3-dihydro-2-benzofuran-5-yl)hexahydropyrazino[2,1-c][1,4]oxazine-8(1H)-carboxylate. The crude product mixture was adsorbed onto silica gel, and purified by flash chromatography. The top product spot was determined by NMR to be the trans-isomer tert-butyl (3R,9aS)-3-(4-chloro-1-oxo-1,3-dihydro-2-benzofuran-5-yl)hexahydropyrazino[2,1-c][1,4]oxazine-8(1H)-carboxylate 10A, and more polar product spot was the cis-isomer tert-butyl (3S,9aS)-3-(4-chloro-1-oxo-1,3-dihydro-2-benzofuran-5-yl)hexahydropyrazino[2,1-c][1,4]oxazine-8(1H)-carboxylate 10B: $^1$H-NMR (500 MHz, CDCl$_3$) δ ppm 10A: 7.83 (d, J=7.5 Hz, 1H), 7.78 (d, J=8.0 Hz, 1H), 5.26 (s, 2H), 5.10 (d, J=10.5 Hz, 1H), 3.98 (d, J=11.5 Hz, 1H), 3.90 (broad, 1H), 3.52 (t, J=10.5 Hz, 1H), 3.05 (d, J=11.5 Hz, 1H), 3.03 (broad, 1H), 2.75 (d, J=11 Hz, 1H), 2.54 (broad, 1H), 2.30 (t, J=10 Hz, 1H), 2.22 (t, J=11 Hz, 1H), 2.07 (t, J=10.5 Hz, 1H), 1.46 (s, 9H); 10B: 8.20 (d, J=7.5 Hz, 1H), 7.82 (d, J=8.0 Hz, 1H), 5.28 (s, 2H), 5.13 (s, 1H), 3.85 (broad, 1H), 3.71 (d, J=11.5 Hz, 1H), 3.49 (m, 1H), 3.09 (dd, J=12, 5.0 Hz, 1H), 3.05 (m, 1H), 2.91 (m, 1H), 2.88-2.80 (m, 2H), 2.64 (m, 1H), 1.47 (s, 9H).

Intermediate 11A

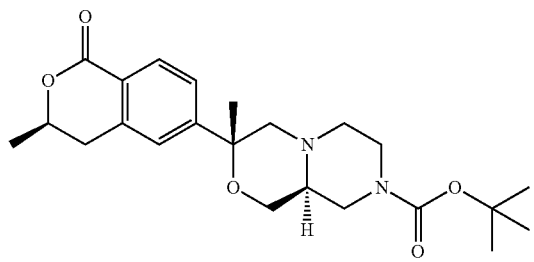 [SMILES: C[C@@H]1Cc2cc([C@]3(C)CN4CCN(C(=O)OC(C)(C)C)C[C@H]4CO3)ccc2C(=O)O1]

tert-butyl (3R,9aS)-3-methyl-3-[(3R)-3-methyl-1-oxo-3,4-dihydro-1H-isochromen-6-yl]hexahydropyrazino[2,1-c][1,4]oxazine-8(1H)-carboxylate Step A: (3R)-3-methyl-6-(prop-1-en-2-yl)-3,4-dihydro-1H-isochromen-1-one A 0.5 molar solution of zinc chloride (1.696 g, 12.44 mmol) in dry THF (16.59 mL) was cooled to 0° C. A solution of isopropenylmagnesium bromide (24.89 mL, 12.44 mmol) was added via syringe. The reaction was stirred at 0° C. for 30 minutes before being cannulated into a sealed tube containing (3R)-6-bromo-3-methyl-3,4-dihydro-1H-isochromen-1-one (2.00 g, 8.30 mmol), PdOAc$_2$ (0.093 g, 0.42 mmol), and X—PHOS (0.395 g, 0.830 mmol) in THF (16.6 mL) under N$_2$ atmosphere. The tube was heated to 70° C. overnight. The reaction was then cooled and partitioned between water (100 mL) and EtOAc (220 mL). The organic layer was then washed with brine, dried over magnesium sulfate, filtered and concentrated. MPLC purification (10-50% EtOAc/Hex) gave (3R)-3-methyl-6-(prop-1-en-2-yl)-3,4-dihydro-1H-isochromen-1-one:
LC-MS: (M+H)$^+$203;

Step B: (3R)-3-methyl-6-(2-methyloxiran-2-yl)-3,4-dihydro-1H-isochromen-1-one mCPBA (774 mg, 4.49 mmol) was added to a solution of (3R)-3-methyl-6-(prop-1-en-2-yl)-3,4-dihydro-1H-isochromen-1-one (605 mg, 2.99 mmol) in DCE (15 mL). The reaction was stirred at room temp for 3 h before it was complete by TLC. The reaction was then partitioned between saturated sodium bicarbonate solution and DCM. The aq. layer was further extracted with DCM (2×75 mL) the combined organic layers were dried over magnesium sulfate, filtered, and purified via MPLC (10-50% EtOAc/Hex) to give the title compound: LC-MS: (M+H)$^+$219;

Step C: tert-butyl (3R)-3-(hydroxymethyl)-4-{2-hydroxy-2-[(3S)-3-methyl-1-oxo-3,4-dihydro-1H-isochromen-6-yl]propyl}piperazine-1-carboxylate A solution of (3R)-3-methyl-6-(2-methyloxiran-2-yl)-3,4-dihydro-1H-isochromen-1-one (598 mg, 2.74 mmol) and tert-butyl (3S)-3-(hydroxymethyl)piperazine-1-carboxylate (770 mg, 3.56 mmol) dissolved in EtOH (15 mL) was heated in a sealed tube to 110° C. for 14 hours. The reaction was cooled and concentrated to give crude product which was purified via MPLC (30-80% EtOAc/Hexane) to give the title compound as a mixture of diastereomers: LC-MS: (M+1)+ 435;

Step D: tert-butyl (3R,9aS)-3-methyl-3-[(3R)-3-methyl-1-oxo-3,4-dihydro-1H-isochromen-6-yl]hexahydropyrazino[2,1-c][1,4]oxazine-8(1H)-carboxylate A sealed tube containing tert-butyl (3R)-3-(hydroxymethyl)-4-{2-hydroxy-2-[(3S)-3-methyl-1-oxo-3,4-dihydro-1H-isochromen-6-yl]propyl}piperazine-1-carboxylate (175 mg, 0.403 mmol) and cyanomethylenetributylphosphorane (117 mg, 0.483 mmol) dissolved in anhydrous benzene (3 mL) was degassed twice with nitrogen and then heated using a microwave to 135° C. for 2.5 hours. The reaction was allowed to cool and the crude mixture was concentrated and purified on MPLC (30-75% EtOAc/Hex) to afford the minor isomer as the faster eluting peak and the major isomer as the slower eluting peak: Major, slower eluting isomer: LC-MS: (M+1)$^+$417.

Intermediate 11B

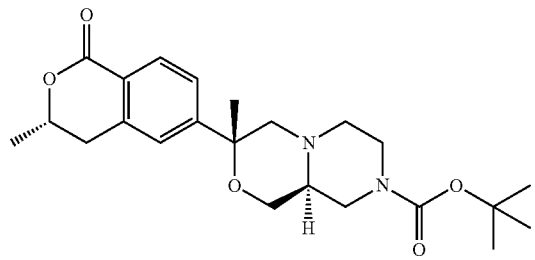 [SMILES: C[C@H]1Cc2cc([C@]3(C)CN4CCN(C(=O)OC(C)(C)C)C[C@H]4CO3)ccc2C(=O)O1]

tert-butyl (3R,9aS)-3-methyl-3-[(3S)-3-methyl-1-oxo-3,4-dihydro-1H-isochromen-6-yl]hexahydropyrazino[2,1-c][1,4]oxazine-8(1H)-carboxylate The title compound was made following the procedure as outlined for tert-butyl (3R,9aS)-3-methyl-3-[(3R)-3-methyl- 1-oxo-3,4-dihydro-1H-isochromen-6-yl]hexahydropyrazino[2,1-c][1,4]oxazine-8(1H)-carboxylate, except using (3S)-6-bromo-3-methyl-3,4-dihydro-1H-isochromen-1-one in Step A. The crude product was purified via MPLC (30-75% EtOAc/Hex): LC-MS: (M+1)$^+$417.

Intermediate 12A

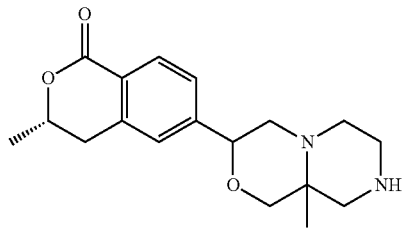 [SMILES: C[C@H]1Cc2cc(C3CN4CCNCC4(C)CO3)ccc2C(=O)O1]

(3S)-3-Methyl-6-(9a-methyloctahydropyrazino[2,1-c][1,4]oxazin-3-yl)isochroman-1-one Step A: Benzyl 4-(2-hydroxy-2-((S)-3-methyl-1-oxoisochroman-6-yl)ethyl)-3-(hydroxymethyl)-3-methylpiperazine-1-carboxylate To a solution of racemic benzyl 3-(hydroxymethyl)-3-methylpiperazine-1-carboxylate (1.0 g, 3.8 mmol) (prepared as described in US Patent Application Publication No. US2007/0088039A1, Example 10) in EtOH (13 mL) was added (3S)-3-methyl-6-(oxiran-2-yl) isochroman-1-one (773 mg, 3.80 mmol), the resulting mixture was heated at 80° C. for 16 h, the reaction mixture was concentrated to dryness and purified on silica gel to afford the title compound: LC/MS: m/e 469.2 (M+H)$^+$.

Step B: Benzyl 9a-methyl-3-((S)-3-methyl-1-oxoisochroman-6-yl) hexahydropyrazino[2,1-c][1,4]oxazine-8(1H)-carboxylate The mixture of benzyl 4-(2-hydroxy-2-((S)-3-methyl-1-oxoisochroman-6-yl)ethyl)-3-(hydroxymethyl)-3-methylpiperazine-1-carboxylate (762 mg, 1.60 mmol) and cyanomethylenetributylphosphorane (471 mg, 1.90 mmol) in dry benzene was degassed and heated to 135° C. in a microwave reactor for 3.5 h. After which point, the reaction mixture was cooled down to rt, concentrated to dryness and purified on silica gel to afford the title compound (cis or trans): MS: m/e 451.2 (M+H)$^+$.

Step C: (3S)-3-Methyl-6-(9a-methyloctahydropyrazino[2,1-c][1,4]oxazin-3-yl)isochroman-1-one The mixture of Benzyl 9a-methyl-3-((S)-3-methyl-1-oxoisochroman-6-yl)hexahydropyrazino[2,1-c][1,4]oxazine-8(1H)-carboxylate (215 mg, 0.500 mmol) and 10% Pd—C (56 mg, 0.05 mmol) in MeOH (10 mL) was stirred under a hydrogen balloon for 16 h. After which point, the solution was filtered through Celite and the resulting filtrate was concentrated to afford the title compound: LC/MS: m/e 317.2 (M+H)$^+$.

Intermediate 12B

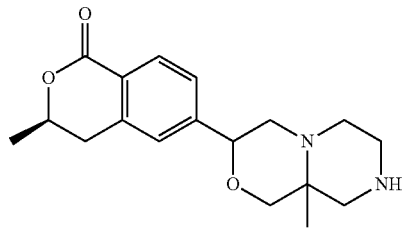 [SMILES: C[C@@H]1Cc2cc(C3CN4CCNCC4(C)CO3)ccc2C(=O)O1]

(3R)-3-Methyl-6-(9a-methyloctahydropyrazino[2,1-c][1,4]oxazin-3-yl)isochroman-1-one The title compound was prepared in an analogous fashion to that described for (3S)-3-Methyl-6-(9a-methyloctahydropyrazino[2,1-c][1,4]oxazin-3-yl)isochroman-1-one starting from (3R)-3-methyl-6-(oxiran-2-yl) isochroman-1-one. LC/MS: m/e 317.2 (M+H)$^+$.

Intermediate 13 (Trans)

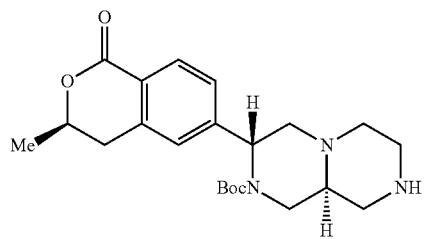 [SMILES: C[C@@H]1Cc2cc([C@@H]3CN4CCNC[C@H]4CN3C(=O)OC(C)(C)C)ccc2C(=O)O1]

(3R,9aS)-tert-butyl 3-((R)-3-methyl-1-oxoisochroman-6-yl)hexahydro-1H-pyrazino[1,2-a]pyrazine-2(6H)-carboxylate Step A: (3S)-tert-butyl 4-(2-hydroxy-2-((R)-3-methyl-1-oxoisochroman-6-yl)ethyl)-3-(hydroxymethyl)piperazine-1-carboxylate (3R)-3-methyl-6-(oxiran-2-yl)isochroman-1-one (0.750 g, 3.62 mmol) and (S)-tert-butyl 3-(hydroxymethyl)piperazine-1-carboxylate (0.953 g, 4.41 mmol) in ethanol (12 mL) was heated in microwave at 150° C. for 1.5 h. The reaction solution was concentrated and the residue was purified on Biotage using 40-100% ethyl acetate/hexane to give the title compound: LC/MS: (M+1)$^+$: 421.15;

Step B: (3S)-benzyl 4-(2-hydroxy-2-((R)-3-methyl-1-oxoisochroman-6-yl)ethyl)-3-(hydroxymethyl)piperazine-1-carboxylate To the solution of (3S)-tert-butyl 4-(2-hydroxy-2-((R)-3-methyl-1-oxoisochroman-6-yl)ethyl)-3-(hydroxymethyl)piperazine-1-carboxylate (2630 mg, 6.25 mmol) in methylene chloride (10 mL) was added trifluoroacetic acid (10 mL, 130 mmol) at rt for 1 h. After removing the volatile the residue was dissolved in methylene chloride (100 mL). To the above solution was added triethylamine (4.36 mL, 31.3 mmol) and benzyl chloroformate (0.986 mL, 6.56 mmol) at 0° C. for 0.5 h. The reaction was quenched by water followed by addition of saturated sodium carbonate. The mixture was extracted with methylene chloride, dried over sodium sulfate, concentrated and the residue was purified on Biotage using 40-100% EtOAc/hexane to give the title compound: LC/MS: (M+1)⁺: 455.10.

Step C: (9aR)-benzyl 8-allyl-7-((R)-3-methyl-1-oxoisochroman-6-yl)hexahydro-1H-pyrazino[1,2-a]pyrazine-2(6H)-carboxylate A solution of (3S)-benzyl 4-(2-hydroxy-2-((R)-3-methyl-1-oxoisochroman-6-yl)ethyl)-3-(hydroxymethyl)piperazine-1-carboxylate (2.07 g, 4.55 mmol) in thionyl chloride (30.0 mL, 411 mmol) was heated at reflux for 1 h. After removing the volatiles, the residue was dissolved in N,N-dimethylformamide (20 mL) and treated with allylamine (1.879 mL, 25.05 mmol) at 0° C. The resulting solution was treated with sodium iodide (0.0680 g, 0.455 mmol) and heated at 90° C. for 1 h. The solution was diluted in ethyl acetate (300 mL) and was washed with saturated sodium bicarbonate three times, dried over sodium sulphate concentrated and the residue was purified on Biotage using 40-100% ethyl acetate/hexane to give the title compound: LC/MS: (M+1)⁺: 476.14.

Step D: (3R,9aS)-8-benzyl 2-tert-butyl 3-((R)-3-methyl-1-oxoisochroman-6-yl)tetrahydro-1H-pyrazino[1,2-a]pyrazine-2,8(9H,9aH)-dicarboxylate and (3S,9aS)-8-benzyl 2-tert-butyl 3-((R)-3-methyl-1-oxoisochroman-6-yl)tetrahydro-1H-pyrazino[1,2-a]pyrazine-2,8(9H,9aH)-dicarboxylate The mixture of (9aR)-benzyl 8-allyl-7-((R)-3-methyl-1-oxoisochroman-6-yl)hexahydro-1H-pyrazino[1,2-a]pyrazine-2(6H)-carboxylate (1160 mg, 2.439 mmol), 1,3-dimethylpyrimidine-2,4,6(1H,3H,5H)-trione (1143 mg, 7.320 mmol) and tetrakis(triphenylphosphine)palladium (0) (141 mg, 0.122 mmol) in methylene chloride (10 mL) was heated at 35° C. for 4 h. After cooling to rt, di-tert-butyl dicarbonate (639 mg, 2.93 mmol) and triethylamine (1371 μL, 9.760 mmol) was added and the resulting solution was stirred at rt overnight. After concentration, the residue was purified on Biotage using 20-100% EtOAc/hexane to give (3S,9aS)-8-benzyl 2-tert-butyl 3-((R)-3-methyl-1-oxoisochroman-6-yl) tetrahydro-1H-pyrazino[1,2-a]pyrazine-2,8(9H,9aH)-dicarboxylate (less polar). LC/MS: (M+1)⁺: 536.27, ¹HNMR (500 MHz, CDCl₃) δ 8.092-8.066 (m, 1H), 7.579-7.564 (m, 1H), 7.478-7.7.462 (m, 1H), 7.391-7.315 (m, 5H), 5.419 (broad, 1H), 5.162 (s, 2H), 4.722-4.705 (broad, 1H), 4.109-3.967 (m, 2H), 3.820-3.790 (m, 1H), 3.350-3.237 (m, 1H), 3.016-2.929 (m, 3H), 2.904-2.773 (broad, 1H), 2.655-2.531 (m, 3H), 2.202-2.113 (m, 2H), 1.600 (s, 3H), 1.523 (s, 9H); and (3R,9aS)-8-benzyl 2-tert-butyl 3-((R)-3-methyl-1-oxoisochroman-6-yl)tetrahydro-1H-pyrazino[1,2-a]pyrazine-2,8(9H,9aH)-dicarboxylate (more polar). LC/MS: (M+1)⁺: 536.27,
¹HNMR (500 MHz, CDCl₃) δ 8.054-8.038 (d, J=8.1 Hz, 1H), 7.701-7.660 (m, 1H), 7.495-7.474 (m, 1H), 7.375 (broad, 5H), 5.158 (s, 2H), 4.695-4.653 (m, 1H), 4.606 (broad, 1H), 4.152-4.034 (m, 2H), 3.839-3.806 (m, 1H), 3.043-2.916 (m, 5H), 2.893-790(broad, 2H), 2.338-2.226 (m, 3H), 1.533-1.521 (d, 6.3 Hz, 3H), 1.209 (s, 9H).

Step E: (3R,9aS)-tert-butyl 3-((R)-3-methyl-1-oxoisochroman-6-yl)hexahydro-1H-pyrazino[1,2-a]pyrazine-2(6H)-carboxylate To the solution of (3R,9aS)-8-benzyl 2-tert-butyl 3-((R)-3-methyl-1-oxoisochroman-6-yl)tetrahydro-1H-pyrazino[1,2-a]pyrazine-2,8(9H,9aH)-dicarboxylate (0.590 g, 1.10 mmol) in methanol (20 mL) was added palladium on carbon (10%, 0.117 g, 0.110 mmol) and the mixture was subjected to hydrogenation at rt overnight. After filtration the filtrate was concentrated to give the title compound.
LC/MS: (M+1)⁺: 402.18.

Intermediate 14 (Cis)

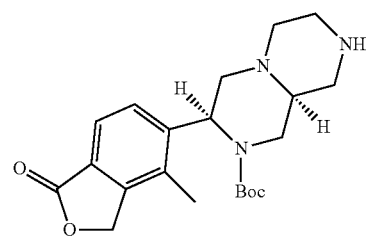 [SMILES: Cc1c([C@H]2CN3CCNC[C@H]3CN2C(=O)OC(C)(C)C)ccc2c1COC2=O]

(3S,9aS)-tert-butyl 3-(4-methyl-1-oxo-1,3-dihydroisobenzofuran-5-yl)hexahydro-1H-pyrazino[1,2-a]pyrazine-2(6H)-carboxylate The intermediate was synthesized following an analogous procedure to that used for the synthesis of (3R,9aS)-tert-butyl 3-((R)-3-methyl-1-oxoisochroman-6-yl)hexahydro-1H-pyrazino[1,2-a]pyrazine-2(6H)-carboxylate. In this case, the cis isomer was isolated and incorporated to make ROMK inhibitors. LC/MS: (M+1)⁺: 388.10.

Intermediate 15

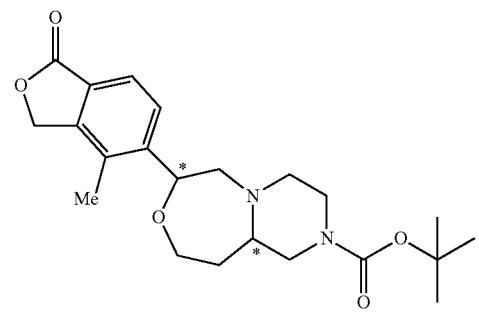 [SMILES: Cc1c(C2CN3CCN(C(=O)OC(C)(C)C)CC3CCO2)ccc2c1COC2=O]

tert-butyl 7-(4-methyl-1-oxo-1,3-dihydro-2-benzofuran-5-yl)octahydro-2H-pyrazino[1,2-d][1,4]oxazepine-2-carboxylate, and four separated isomers Step A: tert-butyl 3-(2-hydroxyethyl)piperazine-1-carboxylate tert-Butyl 3-(2-methoxy-2-oxoethyl)piperazine-1-carboxylate (7.28 g, 28.2 mmol) was dissolved in THF (100 mL) at 0° C. then added LAH (21.14 mL, 21.14 mmol). The reaction was monitored by TLC. After 30 mins, the reaction was first quenched with 0.8 mL water, then added 1.6 mL 2N NaOH followed by 4 mL water. The above slurry was diluted with ethyl acetate and MgSO$_4$ was added. The mixture was stirred at RT for ½ h, then filtered and concentrated to yield the title compound: LC-MS (IE, m/z): 231 [M+1]$^+$.

Step B: tert-butyl 3-(2-hydroxyethyl)-4-(2-(4-methyl-1-oxo-1,3-dihydroisobenzofuran-5-yl)-2-oxoethyl)piperazine-1-carboxylate tert-Butyl 3-(2-hydroxyethyl)piperazine-1-carboxylate (6.91 g, 30.0 mmol) and 5-(2-bromoacetyl)-4-methylisobenzofuran-1(3H)-one (6.73 g, 25 mmol) were dissolved in tetrahydrofuran (100 mL) then added Hunig's base (8.73 mL, 50.0 mmol) and stirred at RT overnight. The reaction was poured into brine and extracted with EtOAc (2×). The combined organic layer was dried over Na$_2$SO$_4$, filtered and evaporated to dryness. The crude product was chromatographed through an ISCO Redi-Sep 330 g column and eluted with 5% MeOH/DCM solvent system to the title compound. LC-MS (IE, m/z): 419 [M+1]$^+$.

Step C: tert-butyl 4-(2-hydroxy-2-(4-methyl-1-oxo-1,3-dihydroisobenzofuran-5-yl)ethyl)-3-(2-hydroxyethyl)piperazine-1-carboxylate tert-Butyl 3-(2-hydroxyethyl)-4-(2-(4-methyl-1-oxo-1,3-dihydroisobenzofuran-5-yl)-2-oxoethyl)piperazine-1-carboxylate (6.16 g, 14.7 mmol) was dissolved in methanol (100 mL) at 0° C. and then NaBH$_4$ (1.67 g, 44.2 mmol) was added. The reaction mixture was warmed up to RT. After ten minutes, TLC showed no SM left. The methanol was evaporated and the residue was taken up with brine and extracted with ethyl acetate twice. The combined organic layers were dried with MgSO$_4$, filtered and concentrated. The crude product was chromatographed through an ISCO 330 g Redi-sep column and eluted with 5% MeOH/DCM to yield the title compound: LC-MS (IE, m/z): 421[M+1]$^+$.

Step D: tert-butyl 7-(4-methyl-1-oxo-1,3-dihydro-2-benzofuran-5-yl)octahydro-2H-pyrazino[1,2-d][1,4]oxazepine-2-carboxylate tert-Butyl 4-(2-hydroxy-2-(4-methyl-1-oxo-1,3-dihydroisobenzofuran-5-yl)ethyl)-3-(2-hydroxyethyl)piperazine-1-carboxylate (2.22 g, 5.30 mmol) was dissolved in benzene (30 mL) and then cyanomethylene tributyl phosphorane (2.31 g, 9.55 mmol) was added, which was then heated to 100° C. overnight. The benzene was removed by rotary evaporation, and the residue was chromatographed through an ISCO redi-sep 330 g column and eluted with 15% acetone: 85% DCM. This separated the cis-diastereomers from the trans-diastereomers of the title compound. The cis-diastereomers were further separated to S,S and R,R diastereomers using the following conditions: Chiralpak AD column: 30×250 mm, 30% (2:1 MeOH:CH$_3$CN)/CO$_2$, 70 mL/min, 100 bar, 41 mg/mL in MeOH/MeCN/DCM, 35° C., 254 nm: cis-diastereomer A (retention time 3.2 mins): $^1$H-NMR (500 MHz, CDCl$_3$) δ ppm 7.83 (d, J=8 HZ, 1H), 7.78 (d, J=8 Hz, 1H), 5.27 (s, 2H), 4.97 (dd, J=4.75, 2.8 Hz, 1H), 4.13 (t, J=3.45 Hz, 0.5H), 4.10 (t, J=3.45 Hz, 0.5H), 3.91 (t, J=12 Hz, 1H), 3.82 (b, 2H), 3.17 (d, J=5.3 Hz, 0.5H), 3.13 (d, J=5.1 Hz, 0.5H), 2.93 (d, J=2.9 Hz, 0.5H), 2.90 (d, J=2.9 Hz, 0.5H), 2.88 (b, 1H), 2.69 (b, 4H), 2.31 (s, 3H), 1.89-1.92 (m, 2H), 1.49 (s, 9H): cis-diastereomer B (retention time 4.21 min): $^1$H-NMR (500 MHz, CDCl$_3$) δ ppm 7.83 (d, J=8 HZ, 1H), 7.78 (d, J=8 Hz, 1H), 5.27 (s, 2H), 4.97 (dd, J=4.75, 2.75 Hz, 1H), 4.13 (t, J=3.45 Hz, 0.5H), 4.10 (t, J=3.45 Hz, 0.5H), 3.91 (t, J=10.12 Hz, 1H), 3.82 (b, 2H), 3.17 (d, J=5.1 Hz, 0.5H), 3.14 (d, J=5.1 Hz, 0.5H), 2.93 (d, J=2.9 Hz, 0.5H), 2.90 (d, J=2.9 Hz, 0.5H), 2.88 (b, 1H), 2.69 (b, 4H), 2.31 (s, 3H), 1.89-1.92 (m, 2H), 1.49 (s, 9H): The trans-diastereomers were further separated to the S,R and R,S diastereomers using the following condition: Chiralpak AD column: 30×250 mm, 20% (2:1 MeOH: CH$_3$CN)/CO$_2$, 70 ml/min, 100 bar, 33 mg/mL in MeOH/MeCN/DCM, 35° C., 254 nm. The retention times of trans-diastereomer A and trans-diastereomer B were 6.68 mins and 8.08 mins on the analytical column Chiralpak AD: 4.6×250 mm, 15% (2:1 MeOH: CH$_3$CN)/CO$_2$, 2.1 ml/min, 100 bar, 35° C. 254 nm: trans-diastereomer A: $^1$H-NMR (500 MHz, CDCl$_3$) δ ppm 7.78 (d, J=8 HZ, 1H), 7.69 (d, J=8 Hz, 1H), 5.27 (s, 2H), 5.13 (d, J=8.8 Hz, 1H), 3.99-4.12 (m, 2H), 3.78-3.95 (b, 2H), 3.02 (b, 1H), 2.87 (d, J=9.1 Hz, 0.5H), 2.84 (d, J=9.0 Hz, 0.5H), 2.77 (b, 2H), 2.65 (d, J=14.5 Hz, 1H), 2.40-2.44 (m, 2H), 2.34 (s, 3H), 2.02-2.08 (m, 1H), 1.92-1.98 (m, 1H), 1.50 (s, 9H): trans-diastereomer B: $^1$H-NMR (500 MHz, CDCl$_3$) δ ppm 7.78 (d, J=8 HZ, 1H), 7.68 (d, J=8 Hz, 1H), 5.27 (s, 2H), 5.13 (d, J=8.8 Hz, 1H), 4.00-4.12 (m, 2H), 3.98 (b, 2H), 3.01 (b, 1H), 2.86 (d, J=9.1 Hz, 0.5H), 2.83 (d, J=9.0 Hz, 0.5H), 2.76 (b, 2H), 2.65 (d, J=13 Hz, 1H), 2.40-2.44 (m, 2H), 2.34 (s, 3H), 2.03-2.08 (m, 1H), 1.94-1.97 (m, 1H), 1.50 (s, 9H).

Intermediates 16 (Isomer Mixture), 16A and 16B isomeric Mixture (Step F)

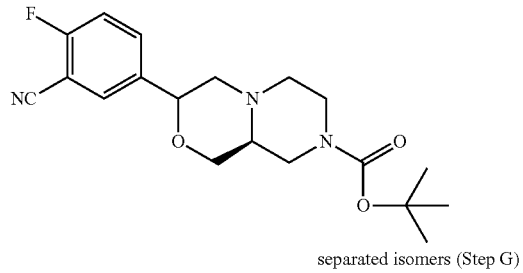

separated isomers (Step G)

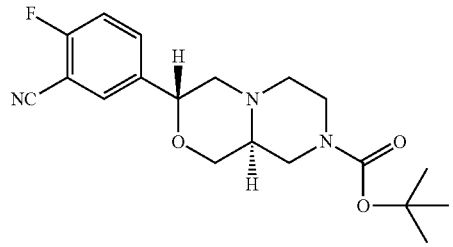

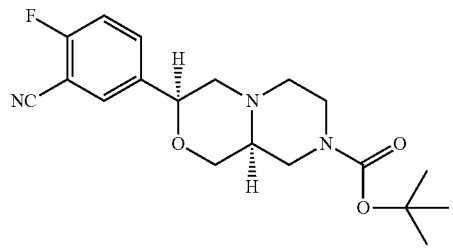

tert-butyl (3R,9aS)-3-(3-cyano-4-fluorophenyl)hexahydropyrazino[2,1-c][1,4]oxazine-8(1H)-carboxylate and tert-butyl (3S,9aS)-3-(3-cyano-4-fluorophenyl)hexahydropyrazino[2,1-c][1,4]oxazine-8(1H)-carboxylate Step A: 2-fluoro-5-(1-hydroxyethyl)benzonitrile 3-Cyano-4-fluorobenzaldehyde (2.17 g, 14.7 mmol) was dissolved in THF (50 mL) then cooled to −70° C. To this mixture was added methyl magnesium bromide (5.34 mL, 16.0 mmol). The mixture was stirred for 1 h, then was quenched with brine and extracted with ether. The ethereal layer was separated, dried over $Na_2SO_4$, filtered, and evaporated to dryness. The residue was purified by MPLC chromatography through a 120 g Redi-sep column using 0-50% EtOAc/hexane eluent to yield 2-fluoro-5-(1-hydroxyethyl) benzonitrile: LC-MS: M+1=166.

Step B: 5-acetyl-2-fluorobenzonitrile

2-Fluoro-5-(1-hydroxyethyl)benzonitrile (0.80 g, 4.8 mmol) was dissolved in DCM (50 mL). To this mixture was added pyridinium dichromate (2.73 g, 7.27 mmol) and the mixture was stirred at RT overnight. Florisil (26 g) was added to the reaction mixture which was then diluted with 50 mL of ether and filtered through a pad of Celite. The filtrate was evaporated to dryness and the residue was purified by MPLC through a 120 g Redi-sep column, eluting with 0-100% EtOAc/hexane to yield 5-acetyl-2-fluorobenzonitrile.

Step C: 5-(bromoacetyl)-2-fluorobenzonitrile

5-Acetyl-2-fluorobenzonitrile (400 mg, 2.45 mmol) was dissolved in THF (20 mL) then copper (II) bromide (1.10 g, 4.90 mmol) was added and the mixture was stirred at RT for 48 h. The reaction mixture was diluted with 20 mL of ether then washed with water, followed by brine. The organic layer was separated, dried over $Na_2SO_4$, and filtered. The filtrate was evaporated to dryness then purified by MPLC chromatography through an 80 g Redi-sep column with 0-50% ethyl acetate/hexane eluent to yield 5-(bromoacetyl)-2-fluorobenzonitrile: LC-MS: M+1=244.

Step D: tert-butyl (3S)-4-[2-(3-cyano-4-fluorophenyl)-2-oxoethyl]-3-(hydroxymethyl)piperazine-1-carboxylate 5-(Bromoacetyl)-2-fluorobenzonitrile (590 mg, 2.44 mmol) and (S)-4-N—BOC-2-hydroxymethyl-piperazine (527 mg, 2.44 mmol) were dissolved in THF (40 mL) at 0° C. then TEA (247 mg, 2.44 mmol) was added. The reaction mixture was stirred at RT for 16 h, then poured into water and extracted with ethyl acetate. The organic layer was dried over $Na_2SO_4$, filtered, and evaporated to dryness. The crude product was purified by MPLC through an 80 g Redi-sep column using 0-100% EtOAc/hexane to yield the title compound.

Step E: tert-butyl (3S)-4-[2-(3-cyano-4-fluorophenyl)-2-hydroxyethyl]-3-(hydroxymethyl)piperazine-1-carboxylate tert-Butyl (3S)-4-[2-(3-cyano-4-fluorophenyl)-2-oxoethyl]-3-(hydroxymethyl)piperazine-1-carboxylate (800 mg, 2.12 mmol) was dissolved in ethanol (50 mL) then sodium borohydride (321 mg, 8.48 mmol) was added and the mixture was stirred at RT for 16 h. LC-MS analysis showed product to be present. The ethanol was removed and the residue was redissolved in EtOAc and stirred with 1N HCl for 5 min. The mixture was then neutralized with saturated aqueous $NaHCO_3$ and extracted twice with EtOAc. The organic layers were washed with brine, dried over $Na_2SO_4$, filtered, and evaporated to dryness to yield the title compound. LC-MS: M+1=280.

Step F: tert-butyl (9aS)-3-(3-cyano-4-fluorophenyl) hexahydropyrazino[2,1-c][1,4]oxazine-8(1H)-carboxylate tert-Butyl (3S)-4-[2-(3-cyano-4-fluorophenyl)-2-hydroxyethyl]-3-(hydroxymethyl)piperazine-1-carboxylate (358 mg, 0.944 mmol) was dissolved in DCM (25 mL) and cooled to 0° C. To this mixture was added TEA (0.197 mL, 1.42 mmol) followed by methanesulfonyl chloride (0.096 mL, 1.2 mmol). The mixture was warmed to RT and stirred overnight. The reaction mixture was washed twice with brine, dried, and evaporated to dryness. The residue was purified by chromatography through a 40 g Redi-sep column, eluting with EtOAc/Hex 0-100% to yield the intermediate chloride (470 mg, 1.81 mmol). This chloride was then dissolved in THF (25 mL) and tetrabutylammonium chloride (436 mg, 1.18 mmol) was added at 0° C. followed by NaH (47.2 mg, 1.18 mmol) then the mixture was stirred at reflux overnight. The reaction mixture was diluted with EtOAc and washed with brine. The organic layer was dried over $Na_2SO_4$, filtered, and evaporated to dryness. The crude residue was purified by MPLC chromatography through a 40 g Redi-sep column, eluting with 0-100% ethyl acetate to yield the title compound as a mixture of two isomers: $^1$H-NMR (500 MHz, $CDCl_3$): δ ppm 7.86 (d, J=5.5 Hz, 0.5H), 7.75-7.81 (m, 0.5H), 7.65 (d, J=6 Hz, 1H), 7.58-7.61 (m, 0.5H), 7.19-7.24 (q, 1H), 4.79 (s, 0.5H), 4.66 d, J=10.5 Hz, 0.5H), 3.96 (dd, J=3, 11 Hz, 1H), 3.55-4.0 (b, 2H), 3.54 (dd, J=2.5, 11.5 Hz, 0.5H), 3.46 (t, J=10.5 Hz, 0.5H), 3.24 (t, J=8.5 Hz, 0.5H), 3.18 (d, J=2.5 Hz, 0.5H)$_3$. (b, 2H), 2.89 (dd, J=2.1, 11.5 Hz, 0.5H), 2.7-2.8 (m, 2H), 2.5 (b, 1H), 2.38-2.45 (m, 1H), 2.25 (t, J=8.5 Hz, 1H), 2.17 (t, J=11 Hz, 1H), 1.48 (s, 9H); LC-MS: M+1=362.

Step G: tert-butyl (3R,9aS)-3-(3-cyano-4-fluorophenyl)hexahydropyrazino[2,1-c][1,4]oxazine-8(1H)-carboxylate and tert-butyl (3S,9aS)-3-(3-cyano-4-fluorophenyl)hexahydropyrazino[2,1-c][1,4]oxazine-8(1H)-carboxylate The title compounds were obtained by preparative HPLC separation of the mixture of isomers obtained in the prior step.

Intermediates 16C and 16D

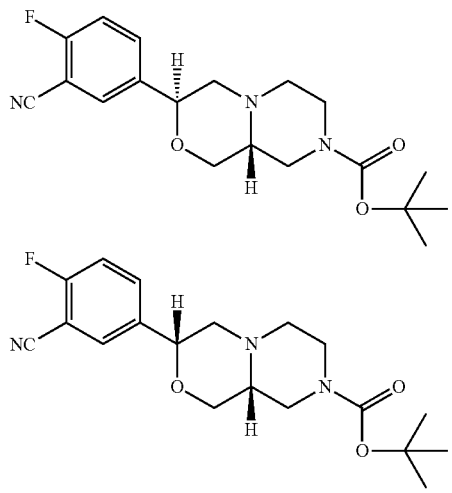

tert-butyl (3S,9aR)-3-(3-cyano-4-fluorophenyl) hexahydropyrazino[2,1-c][1,4]oxazine-8(1H)-carboxylate and tert-butyl (3R,9aR)-3-(3-cyano-4-fluorophenyl)hexahydropyrazino[2,1-c][1,4]oxazine-8 (1H)-carboxylate Step A:
3-bromo-4-fluoro-N-methoxy-N-methylbenzamide A solution of 3-bromo-4-fluorobenzoic acid (100 g, 0.456 mol) and CDI (77.2 g, 0.547 mol) in 1 L of dry DCM was stirred at r.t. for 30 min and then O,N-dimethyl-hydroxylamine (53.4 g, 0.547 mol) was added. The resulted mixture was stirred overnight. The solvents were removed under vacuum and the residue was purified via column chromatograph to afford the title compound.

Step B: 1-(3-bromo-4-fluorophenyl)ethanone

A solution of 3-bromo-4-fluoro-N-methoxy-N-methylbenzamide (50 g, 0.19 mol) in 500 mL of THF was cooled to 0° C. in ice bath, and then the mixture was added MeMgCl (27.3 g, 0.21 mol) dropwise. The reaction mixture was stirred under $N_2$ for 1 h. The reaction mixture was quenched with sat. $NH_4Cl$ and extracted with EtOAc. The combined organic layers were washed with brine, dried over $Na_2SO_4$ and concentrated in vacuum. The residue was purified with silica gel column chromatography to give 1-(3-bromo-4-fluorophenyl)ethanone.

Step C: 5-acetyl-2-fluorobenzonitrile

A solution of 1-(3-bromo-4-fluorophenyl)ethanone (81.3 g, 0.344 mol) in 300 mL of DMF was added CuCN (67.4 g, 0.749 mol) and the mixture was heated to reflux, and stirred under $N_2$ for 10 h. The reaction mixture was quenched with water and extracted with ether. The organic layer was washed with brine dried over $Na_2SO_4$ and concentrated in vacuum. The residue was purified with silica gel column chromatography to give the product 5-acetyl-2-fluorobenzonitrile.

Step D: 5-(bromoacetyl)-2-fluorobenzonitrile

A solution of 5-acetyl-2-fluorobenzonitrile (20.0 g, 0.123 mol) in 500 mL of DCM was heated to reflux for 2 h, and then a solution of bromine in 300 mL DCM was added dropwise into the boiling mixture. The reaction mixture was heated to reflux and stirred under $N_2$ protection overnight. The reaction mixture was washed with water and extracted with DCM. The organic layer was washed with brine, dried over $Na_2SO_4$ and concentrated in vacuum. The residue was purified via silica gel column chromatography to give 5-(bromoacetyl)-2-fluorobenzonitrile.

Step D: tert-butyl (3R)-4-[2-(3-cyano-4-fluorophenyl)-2-oxoethyl]-3-(hydroxymethyl)piperazine-1-carboxylate To a solution of 5-(bromoacetyl)-2-fluorobenzonitrile (13.1 g, 0.054 mol) in DMF (160 mL) was added tert-butyl (3R)-3-(hydroxymethyl)piperazine-1-carboxylate (13.1 g, 0.065 mol) and $K_2CO_3$ (11.77 g, 0.075 mol), and the mixture was stirred at r.t for 3 h. The mixture was washed with water, and extracted with EtOAc. The organic layer was washed with brine dried over $Na_2SO_4$ and concentrated in vacuum to give the desired product, which can be used for next step without further purification.

Step E: tert-butyl (3R)-4-[2-(3-cyano-4-fluorophenyl)-2-hydroxyethyl]-3-(hydroxymethyl)piperazine-1-carboxylate To a solution of tert-butyl (3R)-4-[2-(3-cyano-4-fluorophenyl)-2-oxoethyl]-3-(hydroxymethyl)piperazine-1-carboxylate (20 g, 0.053 mol) in MeOH (400 mL) was added partionwise $NaBH_4$ (15.6 g, 0.424 mol) at 0° C. and the mixture was stirred at r.t overnight. The reaction mixture was added water, extracted with EtOAc. The organic layer was combined, washed with brine, dried over $Na_2SO_4$ and concentrated in vacuum. The residue was purified with silica gel column chromatography to give the title compound.

Step F: tert-butyl (9aR)-3-(3-cyano-4-fluorophenyl)hexahydropyrazino[2,1-c][1,4]oxazine-8(1H)-carboxylate A solution of tert-butyl (3R)-4-[2-(3-cyano-4-fluorophenyl)-2-hydroxyethyl]-3-(hydroxymethyl)piperazine-1-carboxylate (5.0 g, 13.2 mmol) in 100 mL of THF was stirred at 0° C. for 10 min, and then NaH (60%) (1.32 g, 33.0 mmol) was added at 0° C. The resulting white suspension was stirred vigorously at 0° C. for 5 min, then at r.t for 1 h. The reaction suspension was then recooled to 0° C., N-Tosylimidazole was added and the resulting solution was stirred for a further 10 min at 0° C. before being warmed again to r.t and stirred for 1 h. The reaction solution was then cooled once more to 0° C., and excess sodium hydride was carefully quenched by the slow addition of sat. $NH_4Cl$ solution. The resulting biphasic solution was partitioned between sat. $NH_4Cl$ and EtOAc. The organic layer was washed with water and brine, dried over $Na_2SO_4$ and concentrated in vacuum. The residue was purified with silica gel column chromatography to give the title compound: $^1$H-NMR (300 MHz, $CDCl_3$) δ 7.76~7.79 (m, 1H), 7.49~7.58 (m, 1H), 7.11~7.15 (m, 1H), 7.16~7.12 (m, 1H), 3.86~4.06 (m, 2H), 3.33~3.48 (m, 1H), 3.08~3.17 (m, 1H), 2.80~2.94 (m, 2H), 2.64~2.74 (m, 2H), 2.29~2.46 (m, 2H), 2.09~2.20 (m, 1H), 1.40 (d, J=3.0 Hz, 9H);

Step G: tert-butyl (3S,9aR)-3-(3-cyano-4-fluorophenyl)hexahydropyrazino[2,1-c][1,4]oxazine-8(1H)-carboxylate and tert-butyl (3R,9aR)-3-(3-cyano-4-fluorophenyl)hexahydropyrazino[2,1-c][1,4]oxazine-8(1H)-carboxylate The single isomers the title compound were prepared by preparative HPLC separation of the mixture of isomers prepared as described immediately above.

Intermediates 17A and 17B (Method 1)

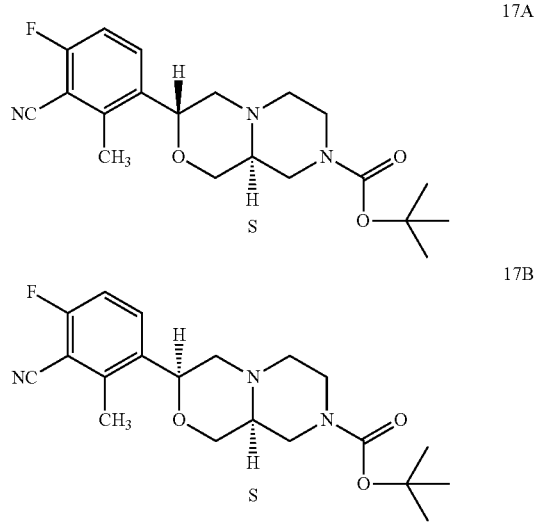

17A: tert-butyl(3R,9aS)-3-(3-cyano-4-fluoro-2-methylphenyl)hexahydropyrazino[2,1-c][1,4]oxazine-8(1H)-carboxylate 17B: tert-butyl(3S,9aS)-3-(3-cyano-4-fluoro-2-methylphenyl)hexahydropyrazino[2,1-c][1,4]oxazine-8(1H)-carboxylate

Step A: 3-bromo-6-fluoro-2-methylbenzonitrile (Method A)

Commercially available 2-fluoro-6-methylbenzonitrile (Apollo Scientific, 15.0 g, 111 mmol) was dissolved in triflic acid (75 mL) at 0° C. then NBS (20.7 g, 117 mmol) was added. The reaction mixture was stirred at RT for 1 h then poured into ice water and extracted twice with DCM. The organic layer was washed with brine, dried over Na$_2$SO$_4$, then filtered and evaporated to dryness to yield 3-bromo-6-fluoro-2-methylbenzonitrile: LC-MS: M+1=216.

Alternate Step A (Method B):

To a 3 L 3 Neck RB equipped with overhead stirrer was charged 2-Fluoro-6-methyl-benzonitrile (191.8 g., 1419 mmol) and MsOH (563 mL, 8516 mmol). NBS (265 g., 1490 mmol) was added portionwise to this stirred solution over 30 minutes, and the mixture was stirred at 50° C. for 33 hours. By this time, HPLC shows the reaction to be mostly complete, so the reaction was poured into 1 L of ice (exotherm noted), diluted with 700 mL 30% EtOAc/Hexanes, and agitated. The aqueous layer was cut, and the organics washed 2× with 1N NaOH and with water. The aqueous cuts were observed to be significantly enriched with impurities. The organics were dried over MgSO$_4$, concentrated, then stored in a −10° C. freezer overnight. Precipitate formed over this time, and was filtered and washed with 5% EtOAc/Hexanes. A second crop of precipitate was combined with the first crop to provide 3-bromo-6-fluoro-2-methyl-benzonitrile.

Step B: 3-ethenyl-6-fluoro-2-methylbenzonitrile

3-Bromo-6-fluoro-2-methylbenzonitrile (23.6 g, 110 mmol), potassium vinyl trifluoroborate (29.5 g, 221 mmol), PdCl$_2$(dppf)-CH$_2$Cl$_2$ Adduct (4.03 g, 5.51 mmol), and TEA (30.7 mL, 221 mmol) were added to 250 mL of ethanol. The reaction mixture was degassed then stirred at reflux for 4 h. LC-MS confirmed the presence of product. The reaction mixture was diluted with ethyl acetate, washed twice with brine, dried, and evaporated to dryness. The crude material was then purified by MPLC chromatography using a 330 g Redi-sep column and eluting with a 10% EtOAc/Hexane solvent system to yield 3-ethenyl-6-fluoro-2-methylbenzonitrile.

Step C:
6-fluoro-2-methyl-3-(oxiran-2-yl)benzonitrile

3-Ethenyl-6-fluoro-2-methylbenzonitrile (14.9 g, 92.0 mmol) was added to DCM (400 mL) at 0° C. then mCPBA (47.85 g, 277.5 mmol) was added and the mixture was stirred at RT for 72 h. The reaction mixture was washed with saturated aqueous Na$_2$S$_2$O$_3$, then with 1N NaOH, and brine. The organic layer was separated, dried over Na$_2$SO$_4$, filtered, and evaporated to dryness. The crude product was purified by chromatography through a 330 g Redi-sep column, eluting with 0-100% hexane/DCM solvent system to afford 6-fluoro-2-methyl-3-(oxiran-2-yl)benzonitrile. LC-MS: M+1=178.

Step D: tert-butyl (3S)-4-[2-(3-cyano-4-fluoro-2-methylphenyl)-2-hydroxyethyl]-3-(hydroxymethyl) piperazine-1-carboxylate 6-Fluoro-2-methyl-3-(oxiran-2-yl)benzonitrile (12.0 g, 67.7 mmol) and (S)-4-N—BOC-2-hydroxymethylpiperazine (22.0 g. 102 mmol) were suspended in ethanol (100 mL) then heated in a microwave apparatus for 30 minutes at 150° C. The reaction mixture was cooled and evaporated dryness. The residue was purified by MPLC chromatography through a 330 g Redi-sep column eluting with 5% MeOH/95% EtOAc solvent system to yield the title compound. LC-MS: M+1=394.

Step E: tert-butyl (9aS)-3-(3-cyano-4-fluoro-2-methylphenyl)hexahydropyrazino[2,1-c][1,4]oxazine-8 (1H)-carboxylate tert-Butyl (3S)-4-[2-(3-cyano-4-fluoro-2-methylphenyl)-2-hydroxyethyl]-3-(hydroxymethyl)piperazine-1-carboxylate (18.5 g, 47.0 mmol) and cyanomethylenetri-n-butylphosphorane (20.4 g, 85.0 mmol) were dissolved in 180 mL of benzene. The reaction mixture was degassed and heated to 100° C. for 16 h. LC-MS analysis indicated product peak (M+1=376). The reaction was cooled and evaporated to dryness. The residue was purified by chromatography through a 330 g Redi-sep column, eluting with a 20% acetone/80% hexane mixture to yield a cis-trans mixture of the title compound.

Step F: tert-butyl(3R,9aS)-3-(3-cyano-4-fluoro-2-methylphenyl)hexahydropyrazino[2,1-c][1,4]oxazine-8(1H)-carboxylate and tert-butyl(3S,9aS)-3-(3-cyano-4-fluoro-2-methylphenyl)hexahydropyrazino [2,1-c][1,4]oxazine-8(1H)-carboxylate The cis-trans isomers of the product of Step E were separated using a Chiralpak AD 4.6×250 mm 10 μcolumn with 20% IPA/80% heptane solvent system: 17A (trans-isomer eluted first): $^1$H-NMR (500 MHz, CDCl$_3$): δ ppm 7.74 (dd, J=6, 8.5 Hz, 1H), 7.095 (t, J=8.5 Hz, 1H), 4.838 (d, J=10 Hz, 1H), 3.98 (dd, J=3, 11.5 Hz, 1H), 3.84-4.21 (b, 2H), 3.50 (t, J=11 Hz, 1H), 2.98-3.18 (b, 1H), 2.85 (dd, J=2, 11.5 Hz, 1H), 2.75 (d, J=10 Hz, 1H), 2.6 ppm (s, 3H), 2.45-2.68 (b, 1H), 2.24-2.31 (m, 2H), 2.16 (t, J=11 Hz, 1H), 1.50 ppm (s, 9H); LC-MS: M+1=376; 17B (cis-isomer eluted second): $^1$H-NMR (500 MHz, CDCl$_3$): δ ppm 8.20 (t, J=6.95 Hz, 1H), 7.06 (t, J=8.5 Hz, 1H), 4.91 (t, J=3.5 Hz, 1H), 3.70-4.07 (b, 2H), 3.55 (d, J=11 Hz, 1H), 3.26 (t, J=9 Hz, 1H), 3.15 (dd, J=3, 12 Hz, 1H), 2.98-3.11 (b, 1H), 2.82 (dd, J=4, 12 Hz, 2H), 2.63 (s, 3H), 2.59-2.7 (b, 1H), 2.44-2.49 (m, 2H), 1.50 (s, 9H); LC-MS: M+1=376.

Intermediate 17B (Method 2)

Step A: 2-Fluoro-6-methyl-benzonitrile

A 10 L round bottom flask equipped with adapter, thermocouple and stir bar was charged with DMA (6 L) and degassed under vacuum and purged with N$_2$ three times. To the mixture was added Palladium Tetrakis triphenylphosphine (87.5 g, 72.0 mmol) and the mixture was degassed under vacuum and purged with N$_2$ three times. The reaction was heated to 80° C. for 30 min. 3-Fluoro-2-iodotoluene (575 g, 2.4 mol) and Zinc Cyanide (171.7 g, 1.46 mol) were added and the mixture was degassed under vacuum and purged with N$_2$ three times. The reaction mixture was heated to 80° C. for 16 h and then allowed to cool to RT. The solution was added to a 2.0 L aqueous solution of 1N NH$_4$OH and extracted three times with 1.5 L EtOAc. The extracts were washed with 2 L brine, dried over Na$_2$SO$_4$, filtered and concentrated. The crude product was treated with mCPBA in cooled DCM and then purified by chromatography (PE/EA=10:1) to get the title compound.

Step B: 3-Bromo-6-fluoro-2-methyl-benzonitrile

To a 3 L 3 Neck round bottomed flask equipped with overhead stirrer was charged 2-Fluoro-6-methyl-benzonitrile (191.8 g., 1419 mmol) and MsOH (563 mL, 8516 mmol). NBS (265 g., 1490 mmol) was added portionwise to this stirred solution over 30 minutes, and the mixture was stirred at 50° C. for 33 hours. By that time, HPLC showed the reaction to be mostly complete, so the reaction was poured into 1 L of ice (exotherm noted), diluted with 700 mL 30% EtOAc/Hexanes, and agitated. The aqueous layer was cut, and the organics washed 2× with 1N NaOH and with water. The aqueous cuts were observed to be significantly enriched with impurities. The organics were dried over $MgSO_4$, concentrated, then stored in a −10° C. freezer overnight. Precipitate formed over this time, and was filtered and washed with 5% EtOAc/Hexanes, providing a first crop of product. A second crop of precipitate provided further 3-Bromo-6-fluoro-2-methyl-benzonitrile.

Step C:
3-(2-Bromo-acetyl)-6-fluoro-2-methyl-benzonitrile

Degassed tributyl(1-ethoxyvinyl)tin (200 mL, 591 mmol) was added to a stirred, room temperature mixture of 3-Bromo-6-fluoro-2-methyl-benzonitrile (115 g, 537 mmol) and cis-$PdCl_2(PPh_3)_2$ (18.9 g, 26.9 mmol) in degassed Dioxane (1149 mL) and the mixture was stirred at 100° C. for 22 hours. By this time HPLC showed complete conversion of starting material (requires at least 12 hours), completion of the reaction can be seen by plating of palladium metal onto the side of the flask. At this time the reaction was cooled to 0° C. and THF (575 mL) and Water (230 mL) were added followed by NBS (110 g, 618 mmol) (added portionwise over 15 min, maintaining internal temperature <5° C.). After 30 minutes, HPLC showed full consumption of the intermediate enol ether. The solution was diluted with MTBE (1000 mL) and washed with 0.5% aqueous HBr (3×500 mL), then washed with water. The organics were dried over $MgSO_4$, filtered and concentrated. A precipitate was generated, and the solid was filtered and washed several times with hexanes. It was dried by nitrogen sweep, providing 3-(2-Bromo-acetyl)-6-fluoro-2-methyl-benzonitrile.

Step D: (3R,9aS)-3-(3-Cyano-4-fluoro-2-methyl-phenyl)-3-hydroxy-hexahydro-pyrazino[2,1-c][1,4]oxazine-8-carboxylic acid tert-butyl ester Diisopropylethylamine (44.0 mL, 252 mmol) was added to a stirred, room temperature mixture of 72 wt % 3-(2-Bromo-acetyl)-6-fluoro-2-methyl-benzonitrile (69 g, 194 mmol) and (S)-4-N-Boc-2-hydroxymethyl-piperazine (42.0 g, 194 mmol) in THF (1000 mL) and the mixture was stirred at room temperature for 18 h. The reaction was diluted with 1 L EtOAc, washed 2× with 500 mL 10% w/w $NaHCO_3$ aqueous solution, dried over $MgSO_4$, filtered and concentrated. The residue was purified by column chromatography on silica gel (40-80% EtOAc/Hexanes, linear gradient), to give the title compound.

Step E: (S)-3-(3-Cyano-4-fluoro-2-methyl-phenyl)-6,7,9,9a-tetrahydro-1H-pyrazino[2,1-c][1,4]oxazine-8-carboxylic acid tert-butyl ester Mesyl-Cl (17.2 mL, 221 mmol) was added dropwise to a stirred, <5° C. internal temperature mixture of (3R,9aS)-3-(3-Cyano-4-fluoro-2-methyl-phenyl)-3-hydroxy-hexahydro-pyrazino[2,1-c][1,4]oxazine-8-carboxylic acid tert-butyl ester (66.6 g, 170 mmol) and triethylamine (71.1 mL, 510 mmol) in $CH_2Cl_2$ (1000 mL) (exotherm occurs, so must keep addition slow), and the reaction was allowed to warm to room temperature for 30 minutes, by which time reaction was complete. The solution was washed with 500 mL 10% w/w $NaHCO_3$ aqueous solution. The organics were dried over $MgSO_4$, filtered and concentrated. The resulting material was taken up in a minimal amount of EtOAc (125 mL) with some heating (solution kept <50° C.) until all solids dissolved. The solution was allowed to cool with stirring, then dropwise overnight 350 mL hexanes was added. By the next morning the solution had clarified and there was considerable powder. The solids were collected by filtration and washed with 20% EtOAc/Hexanes, providing product. The mother liquors were concentrated until precipitate appeared, which was filtered to give additional (S)-3-(3-Cyano-4-fluoro-2-methyl-phenyl)-6,7,9,9a-tetrahydro-1H-pyrazino[2,1-c][1,4]oxazine-8-carboxylic acid tert-butyl ester.

Step F: (3S,9aS)-3-(3-Cyano-4-fluoro-2-methyl-phenyl)-hexahydro-pyrazino[2,1-c][1,4]oxazine-8-carboxylic acid tert-butyl ester To a 1 L 3 neck RB was charged 5% $Pd/CaCO_3$ (10.0 g., 4.02 mmol), MeOH (405 mL), and (S)-3-(3-Cyano-4-fluoro-2-methyl-phenyl)-6,7,9,9a-tetrahydro-1H-pyrazino[2,1-c][1,4]oxazine-8-carboxylic acid tert-butyl ester (15.0 g., 40.2 mmol). The solution was sparged with $N_2$ for 5 min, then put under an atmosphere of hydrogen with balloon pressure and warmed to 40° C. with stirring. After 38 h, HPLC shows full conversion of the olefin, with a 5:1 cis:trans ratio of diastereomers. The suspension was cooled to room temperature, filtered through a pad of Celite and concentrated. The residue was purified via column chromatography (60-100% EtOAc/Hexanes, linear gradient), to provide the title compound. $^1$H NMR (400 MHz, $CDCl_3$): δ 8.18 (m, 1H), 7.03 (t, J=7.9 Hz, 1H), 4.87 (s, 1H), 4.10-3.60 (m, 2H), 3.56 (d, J=10.5 Hz, 1H), 3.25-2.88 (m, 3H), 2.80-2.35 (m, 8H), 1.50 (s, 9H).

Intermediate 17A (Method 2)

A three-necked, round-bottomed flask equipped with a nitrogen inlet adapter, thermocouple, and a septum was charged with (3R,9aS)-3-(3-Cyano-4-fluoro-2-methyl-phenyl)-3-hydroxy-hexahydro-pyrazino[2,1-c][1,4]oxazine-8-carboxylic acid tert-butyl ester (330 g, 840 mmol), TFA (1.65 L, 21 mol), and 3300 mL of DCM. $Et_3SiH$ (292 g, 2.52 mol, 3 equiv) was added in one portion and the reaction mixture stirred at room temperature for 24 h. The reaction mixture was concentrated and azeotroped with toluene (100 mL) to remove the TFA. The resulting material was dissolved in DCM (1.7 L) and carefully charged with 2.5 M $Na_2CO_3$ (pH should be basic). $Boc_2O$ (218 g, 1.2 equiv) was added in one portion and the reaction mixture was stirred at room temperature for 2 h. The organic layer was separated, concentrated, and purified via column chromatography (0-30% acetone-hexanes) to give a mixture of product cis/trans isomers. Chiral SFC purification (Berger MultiGram™ SFC, Mettler Toledo Co, LTD, AD 250 mm*50 mm, 5 um column, A: supercritical $CO_2$, B: methanol, A:B=85:15 at 150 mL/min) afforded the major trans diastereomer 17A as well as the cis diastereomer 17B.

Intermediates 17C and 17D (Method 1)

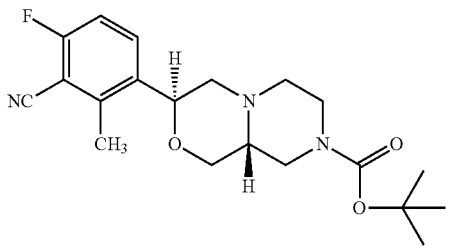

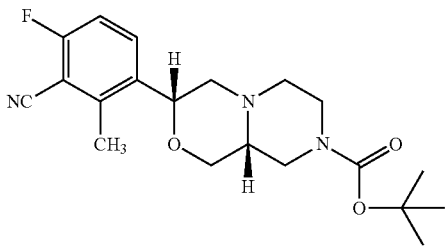

17C: tert-butyl(3S,9aR)-3-(3-cyano-4-fluoro-2-methylphenyl)hexahydropyrazino[2,1-c][1,4]oxazine-8(1H)-carboxylate 17D: tert-butyl(3R,9aR)-3-(3-cyano-4-fluoro-2-methylphenyl)hexahydropyrazino[2,1-c][1,4]oxazine-8(1H)-carboxylate Step A: tert-butyl (3R)-4-[2-(3-cyano-4-fluoro-2-methylphenyl)-2-hydroxyethyl]-3-(hydroxymethyl)piperazine-1-carboxylate 6-Fluoro-2-methyl-3-(2-oxiranyl)benzonitrile (prepared as described above, 4.80 g, 27.1 mmol) and (R)-4-N—BOC-2-hydroxymethyl-piperazine (8.79 g. 40.6 mmol) were suspended in EtOH (30 mL) and heated in a microwave apparatus at 150° C. for 1 h. The reaction mixture was cooled and evaporated to dryness. The residue was purified by chromatography through a 330 g ISCO Redi-sep column eluting with ethyl acetate to 5% MeOH/ethyl acetate to yield the title compound. LC-MS: M+1=394;

Step B: tert-butyl(3S,9aR)-3-(3-cyano-4-fluoro-2-methylphenyl)hexahydropyrazino[2,1-c][1,4]oxazine-8(1H)-carboxylate and tert-butyl(3R,9aR)-3-(3-cyano-4-fluoro-2-methylphenyl)hexahydropyrazino[2,1-c][1,4]oxazine-8(1H)-carboxylate tert-Butyl (3R)-4-[2-(3-cyano-4-fluoro-2-methylphenyl)-2-hydroxyethyl]-3-(hydroxymethyl)piperazine-1-carboxylate (7.14 g, 18.2 mmol) and cyanomethylene tributylphosphorane (7.88 g, 32.7 mmol) were dissolved in benzene (60.0 mL) then heated at 100° C. overnight. The reaction mixture was cooled and evaporated to dryness. The residue was purified by chromatography through a 330 g ISCO Redi-sep column eluting with 10% acetone/DCM to 20% acetone DCM to yield trans-cis mixture. The isomers were resolved by chiral HPLC (70 mL/min of 15% 2:1 MeOH:MeCN:CO$_2$ on a 30×250 mm Chiralpak IC column (Diacel Chemical Industries, LTD.) at 100 bar and 35° C., 230 nM). Isomer 17C (faster eluting): $^1$H-NMR (500 MHz, CDCl$_3$): δ ppm 7.73 (dd, J=9.0, 6.0 Hz, 1H), 7.09 (t, J=8.4 Hz, 1H), 4.83 (d, J=9.3 Hz, 1 Hz, 1H), 4.05 (b, 2H), 3.98 (dd, J=11.25, 2.7, 1H), 3.49 (t, J=10.5 Hz, 1H), 3.031 (b, 1H), 2.84 (d, J=11, 6 Hz, 1H), 2.74 (d, J=11.5 Hz, 1H), 2.59 (s, 3H), 2.54 (b, 1H), 2.22-2.30 (m, 2H), 2.146 (t, J=11.0 Hz, 1H), 1.5 (s, 9H): Isomer 17D (slower eluting): $^1$H-NMR (500 MHz, CDCl$_3$): δ ppm 8.19 (b, 1H), 7.05 (t, J=8.5 Hz, 1H), 4.90 (s, 1H), 3.98 (b, 3H), 3.54 (d, J=12.5 Hz, 1H), 3.24 (b, 1H), 3.14 (dd, J=12, 2.5 Hz, 1H), 3.05 (b, 1H), 2.80 (dd, J=11.25, 2.5 Hz, 2H), 2.68 (b, 1H), 2.63 (s, 3H), 2.46 (b, 1H), 1.5 (s, 9H).

Intermediate 17C and 17D (Method 2)

Step A: 2-Fluoro-6-methyl-benzonitrile

A 10 L round bottom flask equipped with adapter, thermocouple and stir bar was charged with DMA (6 L) and degassed under vacuum and purged with N$_2$ three times. To the mixture was added palladium tetrakis triphenylphosphine (87.5 g, 72.0 mmol) and the mixture was degassed under vacuum and purged with N$_2$ three times. The reaction was heated to 80° C. for 30 min. 3-Fluoro-2-iodotoluene (575 g, 2.4 mol) and zinc cyanide (171.7 g, 1.46 mol) were added and the mixture was degassed under vacuum and purged with N$_2$ three times. The reaction mixture was heated to 80° C. for 16 h and then allowed to cool to RT. The solution was added to a 2.0 L aqueous solution of 1N NH$_4$OH, which was extracted three times with 1.5 L EtOAc, washed with 2 L brine, dried over Na$_2$SO$_4$, filtered and concentrated. The crude product was treated with mCPBA in cooled DCM and then purified by chromatography (PE/EA=10:1) to get the title compound.

Step B: 3-Bromo-6-fluoro-2-methyl-benzonitrile

To a 3 L 3 Neck round bottomed flask equipped with overhead stirrer was charged 2-fluoro-6-methyl-benzonitrile (191.8 g., 1419 mmol) and MsOH (563 mL, 8516 mmol). NBS (265 g., 1490 mmol) was added portionwise to this stirred solution over 30 minutes, and the mixture was stirred at 50° C. for 33 hours. The reaction was poured into 1 L of ice, diluted with 700 mL 30% EtOAc/Hexanes, and agitated. The aqueous layer was cut, and the organics washed 2× with 1N NaOH and with water. The organics were dried over MgSO$_4$, concentrated, then stored in a –10° C. freezer overnight. Precipitate formed over this time, and was filtered and washed with 5% EtOAc/Hexanes, providing a first crop of product. A second crop of precipitate provided additional 3-Bromo-6-fluoro-2-methyl-benzonitrile.

Step C: 3-(2-Bromo-acetyl)-6-fluoro-2-methyl-benzonitrile

Degassed tributyl(1-ethoxyvinyl)tin (200 mL, 591 mmol) was added to a stirred, room temperature mixture of 3-bromo-6-fluoro-2-methyl-benzonitrile (115 g, 537 mmol) and cis-PdCl$_2$(PPh$_3$)$_2$(18.9 g, 26.9 mmol) in degassed dioxane (1149 mL) and the mixture was stirred at 100° C. for 22 hours. Completion of the reaction could be seen by plating of palladium metal onto the side of the flask. The reaction was cooled to 0° C. and THF (575 mL) and Water (230 mL) were added followed by NBS (110 g, 618 mmol) (added portionwise over 15 min, maintaining internal temperature <5° C.). After 30 minutes, HPLC showed full consumption of the intermediate enol ether. The solution was diluted with MTBE (1000 mL) and washed with 0.5% aqueous HBr (3×500 mL), then washed with water. The organics were dried over MgSO$_4$, filtered and concentrated. A precipitate was generated, and the solid was filtered and washed several times with hexanes. It was dried by nitrogen sweep, providing 3-(2-Bromo-acetyl)-6-fluoro-2-methyl-benzonitrile.

Step D: (3S,9aR)-3-(3-Cyano-4-fluoro-2-methylphenyl)-3-hydroxy-hexahydro-pyrazino[2,1-c][1,4]oxazine-8-carboxylic acid tert-butyl ester Diisopropylethylamine (156 mL, 894 mmol) was added to a stirred, room temperature mixture of 3-(2-Bromo-acetyl)-6-fluoro-2-methyl-benzonitrile (176 g, 688 mmol) and (R)-4-N-Boc-2-hydroxymethyl-piperazine (149 g, 688 mmol) in THF (3500 mL) and the mixture was stirred at room temperature for 18 h. The reaction was diluted with 3 L EtOAc, washed 2× with 1500 mL 10% w/w $NaHCO_3$ aqueous solution, dried over $MgSO_4$, filtered and concentrated. The residue was purified by column chromatography on silica gel (40-80% EtOAc/Hexanes, linear gradient), to provide the title compound.

Step E: 17C and 17D

A 5000-mL, three-necked, round-bottomed flask equipped with a nitrogen inlet adapter, thermocouple, and a septum was charged with the product of Step D (273 g, 696.2 mmol), TFA (1340 mL, 17.45 mol, 25 equiv), and 1300 mL of DCM. $Et_3SiH$ (333 mL, 2.1 mol, 3 equiv) was added in one portion and the reaction mixture was stirred at room temperature for 12 h. The reaction mixture was concentrated to remove the TFA. The resulting material was dissolved in DCM (600 mL) and carefully charged with 2.5 M $Na_2CO_3$ (1400 mL, 3.5 mol, 5 equiv) (pH should be basic). $Boc_2O$ (243 mL, 1.05 mol, 1.5 equiv) was added in one portion and the reaction mixture was stirred at room temperature for 2 h. The organic layer was separated, concentrated, and purified via column chromatography (0-30% acetone-hexanes) to give the product (ca. 2:1 trans:cis), which was separated by Chiral SFC to give both single isomers: Chrial SFC HPLC separation conditions: Instrument: Berger MultiGram SFC, Mettler Toledo Co, Ltd.; Column: Chiralpak AD column (Diacel Chemical Industries, LTD.) 250 mm×50 mm, 5 um.; Mobile phase: A: Supercritical $CO_2$, B: MeOH, A:B=85:15 at 150 mL/min.; Column Temp: 38° C.; Nozzle Pressure: 100 Bar; Nozzle Temp: 60° C.; Evaporator Temp: 20° C.; Trimmer Temp: 25° C.; Wavelength: 235 nm. 17C trans isomer $^1H$ NMR 400 MHz, $CDCl_3$ δ: 7.720-7.683 (dd, J=9, 6 Hz, 1H), 7.056 (t, J=8 Hz, 1H), 4.811-4.787 (d, J=9 Hz, 1H), 3.962-3.928 (dd, J=9, 6 Hz, 3H), 3.465 (t, J=10 Hz 1H), 3.002 (s, 1H), 2.826-2.797 (d, J=11 Hz, 1H), 2.719 (s, 1H), 2.638-2.559 (m, 4H), 2.091-2.253 (m, 3H), 1.469 (s, 9H); 17D cis isomer $^1H$ NMR 400 MHz, $CDCl_3$ δ: 8.182-8.146 (t, J=7 Hz, 1H), 7.019 (t, J=9 Hz, 1H), 4.873 (s, 1H), 3.952-3.711 (m, 2H), 3.530-3.503 (d, J=11 Hz, 1H), 3.215-3.020 (m, 3H), 2.801-2.761 (d, J=16 Hz, 1H), 2.593 (s, 4H), 2.452-2.430 (m, 3H), 1.463 (s, 9H).

Intermediate 18A

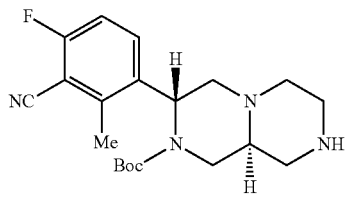 [SMILES: Cc1c([C@@H]2CN3CCNC[C@H]3CN2C(=O)OC(C)(C)C)ccc(F)c1C#N]

(3R,9aS)-tert-butyl 3-(3-cyano-4-fluoro-2-methylphenyl)hexahydro-1H-pyrazino[1,2-a]pyrazine-2(6H)-carboxylate Step A: (3S)-tert-butyl 4-(2-(3-cyano-4-fluoro-2-methylphenyl)-2-hydroxyethyl)-3-(hydroxymethyl)piperazine-1-carboxylate A mixture of 6-fluoro-2-methyl-3-(oxiran-2-yl)benzonitrile (785 mg, 4.43 mmol) and (S)-tert-butyl 3-(hydroxymethyl)piperazine-1-carboxylate (1340 mg, 6.2 mmol) in ethanol (10 mL) was heated in microwave at 150° C. for 3 h. The volatile was evaporated and the residue was purified on Biotage using 40-100% ethyl acetate/hexane to give the title compound: LC/MS: $(M+1)^+$: 394.19.

Step B: (3S)-benzyl 4-(2-(3-cyano-4-fluoro-2-methylphenyl)-2-hydroxyethyl)-3-(hydroxymethyl)piperazine-1-carboxylate To a solution of (3S)-tert-butyl 4-(2-(3-cyano-4-fluoro-2-methylphenyl)-2-hydroxyethyl)-3-(hydroxymethyl)piperazine-1-carboxylate (2.87 g, 7.32 mmol) in methylene chloride (20 mL) was added trifluoroacetic acid (20 mL) at rt, and the resulting solution was stirred at rt for 1 h. After removing the volatile solvents, the residue was dissolved in methylene chloride (50 mL). To the above solution was added triethylamine (6.12 mL, 43.9 mmol) and benzyl chloroformate (1.1 mL, 7.3 mmol) dropwise at 0° C. The reaction solution was stirred at 0° C. for 1 h before quenching with saturated sodium bicarbonate solution (200 mL). The mixture was then extracted with methylene chloride (3×100 mL). The combined organic phase was dried over sodium sulphate and concentrated to give the title compound. LC/MS: $(M+1)^+$: 428.18.

Step C: (7R,9aR)-benzyl 8-allyl-7-(3-cyano-4-fluoro-2-methylphenyl)hexahydro-1H-pyrazino[1,2-a]pyrazine-2(6H)-carboxylate and (7S,9aR)-benzyl 8-allyl-7-(3-cyano-4-fluoro-2-methylphenyl)hexahydro-1H-pyrazino[1,2-a]pyrazine-2(6H)-carboxylate A solution of (3S)-benzyl 4-(2-(3-cyano-4-fluoro-2-methylphenyl)-2-hydroxyethyl)-3-(hydroxymethyl)piperazine-1-carboxylate (1.68 g, 3.93 mmol) in sulfonyl chloride (14.0 g, 118 mmol) was heated at 90° C. for 1 h. After removing the volatile, the residue was dissolved in DMF (16 mL), treated with allylamine (1.726 mL, 23.58 mmol) and sodium iodide (0.059 g, 0.39 mmol) in a sealed tube at 0° C. and the resulting mixture was heated at 90° C. for 1 h. The mixture was diluted in ethyl acetate (300 mL), was washed with saturated sodium bicarbonate (3×200 mL), dried over sodium sulphate, concentrated, and the residue was purified on Biotage using 40-80% ethyl acetate/hexane to give the title compound (more polar on TLC). LC/MS: $(M+1)^+$: 449.24.

Step D: (3R,9aS)-8-benzyl 2-tert-butyl 3-(3-cyano-4-fluoro-2-methylphenyl)tetrahydro-1H-pyrazino[1,2-a]pyrazine-2,8(9H,9aH)-dicarboxylate A mixture of (7R,9aR)-benzyl 8-allyl-7-(3-cyano-4-fluoro-2-methylphenyl)hexahydro-1H-pyrazino[1,2-a]pyrazine-2(6H)-carboxylate (1260 mg, 2.81 mmol), 1,3-dimethylpyrimidine-2,4,6(1H,3H,5H)-trione (1316 mg, 8.430 mmol) and tetrakis(triphenylphosphine)palladium(0) (162 mg, 0.140 mmol) in methylene chloride (10 mL) was heated at 35° C. for 4 h. After cooling to rt, di-tert-butyl dicarbonate (736 mg, 3.37 mmol) and triethylamine (1579 μL, 11.24 mmol) were added and the resulting solution was stirred at rt overnight. After concentration, the residue was purified on Biotage using 40% EtOAc/hexane to give the title compound. LC/MS: $(M+1)^+$: 509.32.

Step E: (3R,9aS)-tert-butyl 3-(3-cyano-4-fluoro-2-methylphenyl)hexahydro-1H-pyrazino[1,2-a]pyrazine-2(6H)-carboxylate To a solution of (3R,9aS)-8-benzyl 2-tert-butyl 3-(3-cyano-4-fluoro-2-methylphenyl)tetrahydro-1H-pyrazino[1,2-a]pyrazine-2,8(9H,9aH)-dicarboxylate (600 mg, 1.180 mmol) in MeOH (100 mL) was added Palladium on carbon (10%,126 mg, 0.118 mmol) and the resulting mixture was subjected to hydrogenation at rt overnight. The reaction mixture was filtered through Celite, washed with mixture of methanol and methylene chloride (1:1) and the filtrate was concentrated to give the title compound: LC/MS: (M+1)$^+$: 375.28.

Intermediate 18B

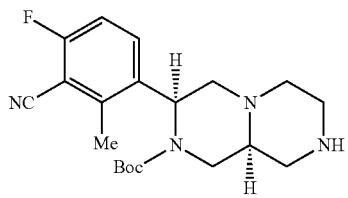 [SMILES: Cc1c([C@H]2CN3CCNC[C@H]3CN2C(=O)OC(C)(C)C)ccc(F)c1C#N]

(3S,9aS)-tert-butyl 3-(3-cyano-4-fluoro-2-methylphenyl)hexahydro-1H-pyrazino[1,2-a]pyrazine-2(6H)-carboxylate

Step A: (3S,9aS)-8-benzyl 2-tert-butyl 3-(3-cyano-4-fluoro-2-methylphenyl)tetrahydro-1H-pyrazino[1,2-a]pyrazine-2,8(9H,9Ah)-dicarboxylate A mixture of (7S,9aR)-benzyl 8-allyl-7-(3-cyano-4-fluoro-2-methylphenyl)hexahydro-1H-pyrazino[1,2-a]pyrazine-2(6H)-carboxylate (518 mg, 1.155 mmol), 1,3-dimethylpyrimidine-2,4,6(1H,3H,5H)-trione (518 mg, 1.16 mmol) and tetrakis(triphenylphosphine)palladium(0) (66.7 mg, 0.058 mmol) in methylene chloride (10 mL) was heated at 35° C. for 4 h. After cooling to rt, di-tert-butyl dicarbonate (302 mg, 1.39 mmol) and triethylamine (649 µL, 4.62 mmol) was added and the resulting solution was stirred at rt overnight. After concentration, the residue was purified on Biotage using 40% EtOAc/hexane to give the title compound: LC/MS: (M+1)$^+$: 509.26.

Step B: (3S,9aS)-tert-butyl 3-(3-cyano-4-fluoro-2-methylphenyl)hexahydro-1H-pyrazino[1,2-a]pyrazine-2(6H)-carboxylate To a solution of (3S,9aS)-8-benzyl 2-tert-butyl 3-(3-cyano-4-fluoro-2-methylphenyl)tetrahydro-1H-pyrazino[1,2-a]pyrazine-2,8(9H,9Ah)-dicarboxylate (0.78 g, 1.534 mmol) in MeOH (100 Ml) was added palladium on carbon (10%,0.163 g, 0.153 mmol) and the resulting mixture was subjected to hydrogenation at rt overnight. The reaction mixture was filtered through Celite, washed with mixture of methanol and methylene chloride (1:1) and the filtrate was concentrated to give the title compound: LC/MS: (M+1)$^+$: 375.28.

Intermediate 19A and 19B

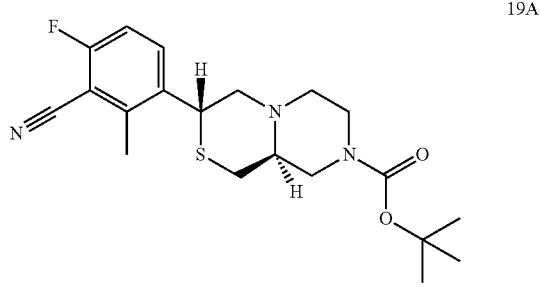

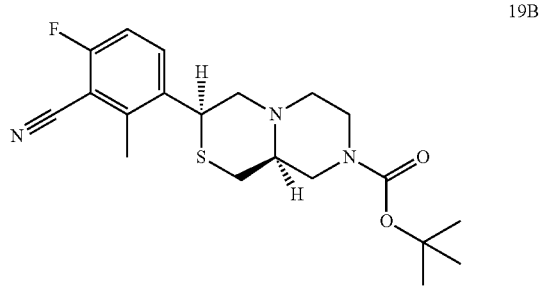

(3S,9aS)-tert-butyl 3-(3-cyano-4-fluoro-2-methylphenyl)hexahydropyrazino[2,1-c][1,4]thiazine-8(1H)-carboxylate and (3R,9aS)-tert-butyl 3-(3-cyano-4-fluoro-2-methylphenyl)hexahydropyrazino[2,1-c][1,4]thiazine-8(1H)-carboxylate

Step A: (3S)-tert-butyl 3-(acetylthiomethyl)-4-(2-(3-cyano-4-fluoro-2-methylphenyl)-2-hydroxyethyl)piperazine-1-carboxylate (3S)-tert-butyl 4-(2-(3-cyano-4-fluoro-2-methylphenyl)-2-hydroxyethyl)-3-(hydroxymethyl)piperazine-1-carboxylate (synthesis described above, 0.090 g, 0.23 mmol) was dissolved in THF (2.3 mL) and cooled to 0° C. Triethylamine (0.038 mL, 0.274 mmol) was added followed by addition of Ms-Cl (0.020 mL, 0.252 mmol), and DMAP (2.79 mg, 0.023 mmol). The ice bath was removed and stirring was continued for 2 hours. The reaction mixture was then concentrated under reduced pressure. The resulting material was re-dissolved in DMSO (2 mL) and treated with potassium thioacetate (0.035 g, 0.306 mmol). The reaction mixture was stirred at room temperature under nitrogen overnight and then heated at 45° C. for 2 h. The mixture was diluted with ethyl acetate and washed with water (3 times) and brine, dried (Na$_2$SO$_4$), filtered and concentrated. The crude product was purified by column chromatography (100% hexane to 80% EtOAc/Hexane) to give the desired product LC/MS: M+1=452.3.

Step B: (3S)-tert-butyl 3-(acetylthiomethyl)-4-(2-chloro-2-(3-cyano-4-fluoro-2-methylphenyl)ethyl)piperazine-1-carboxylate To a solution of (3S)-tert-butyl 3-(acetylthiomethyl)-4-(2-(3-cyano-4-fluoro-2-methylphenyl)-2-hydroxyethyl)piperazine-1-carboxylate (30.8 mg, 0.0680 mmol) in toluene (0.62 mL) was added thionyl chloride (14.9 µL, 0.205 mmol). The mixture was cooled with an ice bath and then pyridine (22.1 µL, 0.273 mmol) was added dropwise. The reaction mixture was stirred at 0° C. for 20 min, and then allowed to warm to room temperature over an hour and finally heated at 70° C. for 30 min. The reaction mixture was concentrated and the residue was diluted with ethyl acetate, washed with a minimum amount of saturated sodium bicarbonate aqueous solution, and then brine. The organic layer was separated, filtered through a pad of anhydrous sodium sulfate and concentrated. Used directly in the next step.

Step C: (3S,9aS)-tert-butyl 3-(3-cyano-4-fluoro-2-methylphenyl)hexahydropyrazino[2,1-c][1,4]thiazine-8(1H)-carboxylate and (3R,9aS)-tert-butyl 3-(3-cyano-4-fluoro-2-methylphenyl)hexahydropyrazino[2,1-c][1,4]thiazine-8(1H)-carboxylate (3S)-tert-Butyl 3-(acetylthiomethyl)-4-(2-chloro-2-(3-cyano-4-fluoro-2-methylphenyl)ethyl)piperazine-1-carboxylate (320 mg, 0.681 mmol) in THF (34 mL) was treated with sodium methoxide (441 mg, 2.04 mmol). The mixture was stirred at room temperature under $N_2$ for 3 h. LC-MS showed the formation of the desired product as a pair of diastereomers. The reaction mixture was concentrated and partitioned between ethyl acetate and water. The organic layer was separated and washed with brine, dried and evaporated to dryness. The crude product was purified by column chromatography (100% hexane for 2 CV, 100% hexane to 35% EtOAc/Hexane for 4 CV, then kept at 35% for 4 CV, then increased to 80% EtOAc/hexane through 4 CV. (CV=column volume) to give the title compound. $^1$H-NMR for 19B (500 MHz, CD$_3$OD) δ ppm 8.76 (q, J=6.5 Hz, 9.0 Hz, 1H), 7.13 (t, J=8.5 Hz, 1H), 4.05 (bs, 1H), 3.90-4.00 (q, 2H), 3.35 (q, J=2.5 Hz, 13.0 Hz, 1H), 3.06 (m, 1H), 2.95 (m, 1H), 2.64-2.77 (m, 2H), 2.54 (s, 3H), 2.43 (m, 1H), 2.31 (m, 2H), 2.20 (m, 1H), 1.47 (s, 9H). LC-MS: M+1=392.4; $^1$H-NMR for 19A (500 MHz, CD$_3$OD) δ ppm 7.72 (q, J=6.0 Hz, 9.0 Hz, 1H), 7.23 (t, J=9.0 Hz, 1H), 4.49 (broad doublet, J=10.5 Hz, 1H), 4.14 (m, 2H), 3.46 (m, 1H), 3.14-3.23 (m, 3H), 2.83-2.98 (m, 5H), 2.66 (s, 3H), 1.48 (s, 9H); LC-MS: M+1=392.4.

Intermediate 20

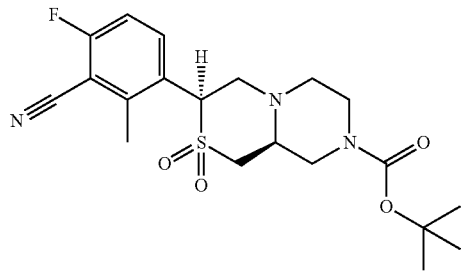 [SMILES: Cc1c([C@H]2CN3CCN(C(=O)OC(C)(C)C)C[C@H]3CS2(=O)=O)ccc(F)c1C#N]

tert-butyl (3S,9aS)-3-(3-cyano-4-fluoro-2-methylphenyl)hexahydropyrazino[2,1-c][1,4]thiazine-8(1H)-carboxylate 2,2-dioxide Step A: tert-butyl (3S,9aS)-3-(3-cyano-4-fluoro-2-methylphenyl)hexahydropyrazino[2,1-c][1,4]thiazine-8(1H)-carboxylate 2,2,5-trioxide (3S,9aS)-tert-butyl 3-(3-cyano-4-fluoro-2-methylphenyl)hexahydropyrazino[2,1-c][1,4]thiazine-8(1H)-carboxylate (20 mg, 0.051 mmol) was dissolved in acetonitrile (0.5 mL) and water (0.2 ml) and cooled to 0° C. OXONE (86.1 mg, 0.140 mmol) was added. The ice bath was removed and the reaction mixture was stirred at room temperature overnight. LC-MS showed the completion of the reaction. The reaction mixture was diluted with dichloromethane and water. The organic layer was separated and the aqueous layer was extracted with DCM again. The organic layers were combined and washed with brine, dried (Na$_2$SO$_4$) and concentrated: LC-MS: M+1=440, M+41=481.

Step B: tert-butyl (3S,9aS)-3-(3-cyano-4-fluoro-2-methylphenyl)hexahydropyrazino[2,1-c][1,4]thiazine-8(1H)-carboxylate 2,2-dioxide The above compound from step A (23 mg, 0.052 mmol) was combined with TRIPHENYLPHOSPHINE (24.71 mg, 0.094 mmol) in DMF (0.4 M) and warmed to 80° C. for 20 minutes. LC-Ms showed the completion of the reaction. The reaction mixture was diluted with methanol and purified with mass-directed reverse phase HPLC eluting with 10% acetonitrile/water with 0.1% TFA to 100% acetonitrile with 0.1% TFA to yield the title compound: $^1$H-NMR (500 MHz, CD$_3$OD): δ ppm 9.05 (m, 1H), 7.24 (m, 1H), 4.63 (bs, 1H), 4.03 (m, 2H), 3.32-3.45 (m, 2H), 3.05 (m, 3H), 2.92 (m, 1H), 2.75 (m, 2H), 2.63 (S, 3H), 2.25 (m, 1H), 1.48 (s, 9H); LC-MS: M+1=424.

Intermediates 21A and 21B

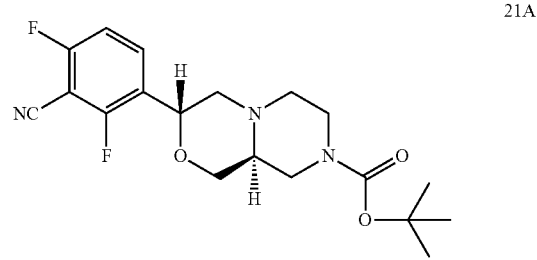

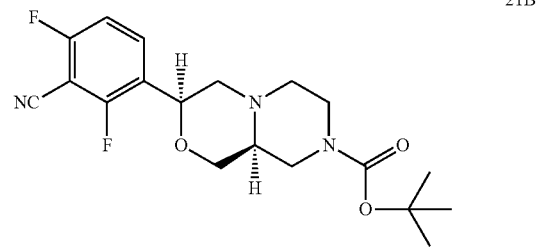

21A: tert-butyl (3R,9aS)-3-(3-cyano-2,4-difluorophenyl)hexahydropyrazino[2,1-c][1,4]oxazine-8(1H)-carboxylate: 21B: tert-butyl (3S,9aS)-3-(3-cyano-2,4-difluorophenyl)hexahydropyrazino[2,1-c][1,4]oxazine-8(1H)-carboxylate Step A: 2,6-difluoro-3-hydroxybenzonitrile 2,6-difluoro-3-methoxybenzonitrile (4.42 g, 26.1 mmol) was dissolved in DCM (10 mL) at 0° C. then 1 M BBr3 (52.2 mL, 52.2 mmol) was added. The reaction mixture was warmed up to RT and stirred overnight. The reaction mixture was poured into ice water and extracted with more DCM. The organic layer was separated, dried over Na$_2$SO$_4$, filtered, and evaporated to dryness to yield 2,6-difluoro-3-hydroxybenzonitrile: LC-MS: M+1=156.

Step B: 3-cyano-2,4-difluorophenyl trifluoromethanesulfonate 2,6-Difluoro-3-hydroxybenzonitrile (3.50 g, 22.6 mmol) was dissolved in DCM (50 mL), cooled to 0° C., and TEA was added (7.87 mL, 56.4 mmol) followed by triflic anhydride (7.63 mL, 45.1 mmol). The reaction mixture was stirred for 1 hour, then was poured into ice water and extracted with more DCM. The organic layer was separated and washed with sat'd aqueous NaHCO$_3$, then brine, then was dried over MgSO$_4$, filtered, and evaporated to dryness. The crude material was purified by MPLC chromatography through a 330 g Redi-sep column eluting with 0-80% EtOAc/hexane to yield 3-cyano-2,4-difluorophenyl trifluoromethanesulfonate.

Step C: 3-ethenyl-2,6-difluorobenzonitrile

3-Cyano-2,4-difluorophenyl trifluoromethanesulfonate (5.20 g, 18.1 mmol), potassium vinyl trifluoroborate (4.85 g, 36.2 mmol), PdCl$_2$(dppf)-CH$_2$Cl$_2$ Adduct (0.662 g, 0.905 mmol), and TEA (5.05 mL, 36.2 mmol) were added to 75 mL of ethanol. The reaction mixture was degassed then heated at reflux for 4 h. LC-MS analysis confirmed product peak. The reaction mixture was diluted with ethyl acetate, washed twice with brine, dried, and evaporated to dryness. The crude material was then purified by MPLC chromatography through a 330 g Redi-sep column eluting with 10% EtOAc/Hexane solvent system to yield 3-ethenyl-2,6-difluorobenzonitrile.

Step D: 2,6-difluoro-3-(oxiran-2-yl)benzonitrile

3-Ethenyl-2,6-difluorobenzonitrile (1.70 g, 10.3 mmol) was added to DCM (10 mL) at 0° C. Then mCPBA (5.33 g, 30.9 mmol) was added and the mixture was stirred at RT for 48 h. The reaction mixture was washed with saturated aqueous Na$_2$S$_2$O$_3$, then with 1N NaOH, and brine. The organic layer was separated and dried over Na$_2$SO$_4$, filtered, and evaporated to dryness. The crude product was purified by MPLC chromatography through a 120 g Redi-sep column, eluting with a 0-100% EtOAc/hexane solvent system. 2,6-Difluoro-3-(oxiran-2-yl)benzonitrile was isolated.

Step E: tert-butyl (3S)-4-[2-(3-cyano-2,4-difluorophenyl)-2-hydroxyethyl]-3-(hydroxymethyl)piperazine-1-carboxylate 2,6-Difluoro-3-(oxiran-2-yl)benzonitrile (1.50 g, 8.28 mmol) and (S)-4-N—BOC-2-hydroxymethylpiperazine (2.40 g, 11.1 mmol) were suspended in ethanol (15 mL) then heated in a microwave apparatus for 30 min at 150° C. The reaction mixture was cooled and evaporated dryness. The residue was purified by chromatography through a 120 g Redi-sep column eluting with 5% MeOH/95% EtOAc to yield the title compound LC-MS: M+1=398.

Step F: tert-butyl(9aS)-3-(3-cyano-2,4-difluorophenyl)hexahydropyrazino[2,1-c][1,4]oxazine-8(1H)-carboxylate tert-Butyl (3S)-4-[2-(3-cyano-2,4-difluorophenyl)-2-hydroxyethyl]-3-(hydroxymethyl)piperazine-1-carboxylate (1.2 g, 3.0 mmol) and cyanomethylenetri-n-butylphosphorane (1.31 g, 5.44 mmol) were dissolved in 5 mL of benzene. The reaction mixture was degassed and heated to 100° C. for 16 h. LC-MS analysis showed product peak at 2.07 min (M+1=380). The reaction was cooled and evaporated to dryness. The residue was purified by MPLC chromatography through an 80 g Redi-sep column eluting with a 40% EtOAc/60% hexane mixture to yield a cis-trans mixture of the title compound.

Step G: Isomers 20A and 20B

The isomers of the product of Step F were separated by chiral HPLC using a Chirapak AD 4.6×250 mm 10 µcolumn and eluting with 25% IPA/75% heptane. The (3R,9aS) trans-isomer 21A eluted first and the (3S,9aS) cis-isomer 21B eluted second:

21A: $^1$H-NMR (500 MHz, CDCl$_3$): δ ppm 7.79-7.84 (q, 1H), 7.08 (t, J=8 Hz, 1H), 4.94 (d, J=10.5 Hz, 1H), 4.0 (b, 2H), 3.96 (d, J=11 Hz, 1H), 3.48 (t, J=10.5 Hz, 1H), 3.02 (b, 1H), 2.97 (d, J=11 Hz, 1H), 2.75 (d, J=10.5 Hz, 1H), 2.53 (b, 1H), 2.25-2.29 (q, 2H), 2.13 (t, J=11 Hz, 1H), 1.51 (s, 9H): LC-MS: M+1=380. 21B: $^1$H-NMR (500 MHz, CDCl$_3$): δ ppm 8.29 (d, J=5.5 Hz, 1H), 7.08 (t, J=8.5 Hz, 1H), 5.0 (s, 1H), 3.70-4.10 ppm (b, 2H), 3.61 (d, J=11 Hz, 1H), 3.34 (b, 1H), 3.12 (d, J=12.5 Hz, 1H), 3.03 (b, 1H), 2.84 (d, J=12 Hz, 1H), 2.79 (d, J=11.5 Hz, 1H) 2.68 (b, 1H), 2.44-2.5 (m, 2H), 1.50 (s, 9H): LC-MS: M+1=380.

Intermediates 21C and 21D

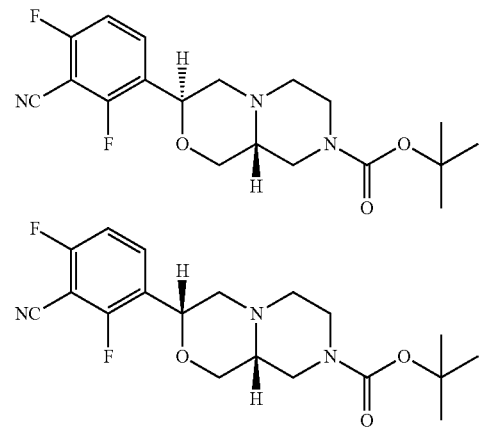

21C: (3S,9aR)-tert-butyl 3-(3-cyano-2,4-difluorophenyl)hexahydropyrazino[2,1-c][1,4]oxazine-8(1H)-carboxylate and 21D: (3R,9aR)-tert-butyl 3-(3-cyano-2,4-difluorophenyl)hexahydropyrazino[2,1-c][1,4]oxazine-8(1H)-carboxylate

Step A: (3R)-tert-butyl 4-(2-(3-cyano-2,4-difluorophenyl)-2-hydroxyethyl)-3-(hydroxymethyl)piperazine-1-carboxylate 2,6-difluoro-3-(oxiran-2-yl)benzonitrile (3.70 g, 20.4 mmol) and (R)-tert-butyl 3-(hydroxymethyl)piperazine-1-carboxylate (6.63 g, 30.6 mmol) were dissolved in ethanol (36.0 mL) then placed in 3-20 mL sealed tubes and microwaved at 140° C. for 1 h. The solvents were evaporated and the combined residue was purified by chromatography through a 120 g ISCO Redi-sep column with 50% to 100% ethyl acetate/hexane solvent system to yield the title compound LC-MS (IE, m/z): 398 [M+1]$^+$.

Step B: (9aR)-tert-butyl 3-(3-cyano-2,4-difluorophenyl)hexahydropyrazino[2,1-c][1,4]oxazine-8(1H)-carboxylate and (3S,9aR)-tert-butyl 3-(3-cyano-2,4-difluorophenyl)hexahydropyrazino[2,1-c][1,4]oxazine-8(1H)-carboxylate (3R)-tert-Butyl 4-(2-(3-cyano-2,4-difluorophenyl)-2-hydroxyethyl)-3-(hydroxymethyl)piperazine-1-carboxylate (7.30 g, 18.4 mmol) was dissolved in benzene (90 mL) and added cyanomethylene tributyl phosphorane (7.98 g, 33.1 mmol). The mixture was placed into five separate 20 mL microwave tubes, degassed and heated at 100° C. overnight. LC-MS showed product peak. Combined all reaction mixtures and concentrated. The crude product was purified by chromatography using a 330 g ISCO Redi-Sep column with 10% acetone/hexane solvent system to yield the title compound. The diastereomers were resolved by prep SFC using the following condition: 15% MeOH with 0.2% DEA)/$CO_2$ on Chiral OJ 21×250 mm column, 50 ml/min, 191 mg/mL in hot MeOH/MeCN, 35° C., 220 nm. 21C: $^1$H-NMR (600 MHz, CDCl3) δ ppm 7.788 (t, J=7.9 Hz, 0.5H), 7.777 (t, J=7.9 Hz, 0.5H), 7.066 (t, J=8.35 Hz, 1H), 4.93 (d, J=9.1 Hz, 1H), 3.943 (dd, J=9.25, 3.15 Hz, 1H), 4.097-3.80 (b, 2H), 3.469 (t, J=10.7 Hz, 1H), 3.01 (b, 1H),), 2.94 (dd, J=10, 1.7 Hz, 1H), 2.733 (d, J=9.9 Hz, 1H), 2.51-2.52 (b, 1H), 2.202-2.264 (m, 2H),), 2.115 (t, J=10.9 Hz, 1H), 1.476 (s, 9H). 21D: $^1$H-NMR (600 MHz, CDCl3) δ ppm 8.259 (d, J=6.1 Hz, 1H), 7.045 (t, J=8.3 Hz, 1H), 5.031 (s, 1H), 3.64-4.04 (b, 2H), 3.589 (dd, J=11.4, 2.8 Hz, 1H), 3.30 (b, 1H), 3.085 (dd, J=12, 3.1 Hz, 1H), 3.001 (b, 1H),), 2.802 (dd, J=12, 4.15 Hz, 1H), 2.757 (d, J=10.7 Hz, 1H), 2.638 (b, 1H), 2.401-2.46 (m, 2H), 1.476 (s, 9H).

Intermediates 22A and 22B

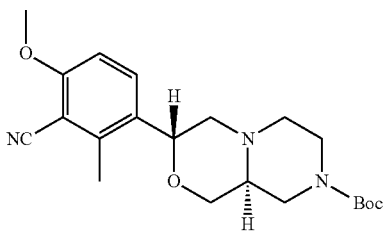

22A

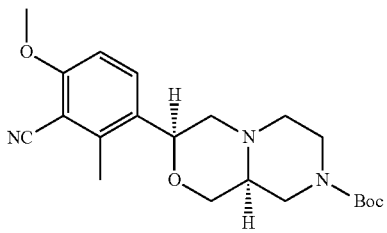

22B

22A: tert-butyl (3R,9aS)-3-(3-cyano-4-methoxy-2-methylphenyl)hexahydropyrazino[2,1-c][1,4]oxazine-8(1H)-carboxylate; 22B: tert-butyl (3S,9aS)-3-(3-cyano-4-methoxy-2-methylphenyl)hexahydropyrazino[2,1-c][1,4]oxazine-8(1H)-carboxylate

Step A: 3-bromo-6-methoxy-2-methylbenzonitrile

To a solution of 2-bromo-3-methylphenol (10.0 g, 53.5 mmol) in DMF (60 ml) was added sodium hydride (2.78 g, 69.5 mmol) in small portions at 0° C., which was followed by addition of MeI (6.69 mL, 107 mmol). TLC showed formation of a slightly less polar spot right away. The reaction was diluted with EtOAc (400 mL), washed with water 3 times, dried over $Na_2SO_4$, and concentrated. The crude product was used in the next step without further purification. To the flask charged with the above material and a stir bar was added CuCN (9.9 g, 109 mmol) and DMF (100 mL). The mixture was purged three times with nitrogen, and heated to 150° C. for 24 hours. TLC showed formation of a more polar spot. The reaction was cooled to RT, diluted with DCM (400 mL), and filtered through a pad of celite to remove the solids. The filtrate was washed with saturated $NH_4Oac$ and brine, dried over sodium sulfate, concentrated to afford a brownish solid (4.8 g, 60% yield). The resulting nitrile was used in the following step without further purification. To a flask charged with the nitrile and a stir bar was added NBS (6.4 g, 36 mmol) and TFA (60 mL). The reaction was allowed to stir at RT for 16 hours. TLC showed clean formation of a slightly more polar spot. The solvent was removed under vacuum, and the residue was purified by silica gel flash chromatography. After removal of solvent, 3-bromo-6-methoxy-2-methylbenzonitrile was collected.

Step B: 3-(bromoacetyl)-6-methoxy-2-methylbenzonitrile

To a flask charged with 3-bromo-6-methoxy-2-methylbenzonitrile (0.98 g, 4.33 mmol) and a stir bar was added BIS (TRIPHENYLPHOSPHINE)PALLADIUM(II) CHLORIDE (0.152 g, 0.217 mmol), tributyl(1-ethoxyethenyl)stannane (2.35 g, 6.50 mmol), and dioxane (20 mL). The mixture was fitted with a condenser and purged three times with nitrogen, and heated to 100° C. for 3 hours. The reaction was cooled, and to the solution was added THF (16 mL) and water (8 mL). After cooling the solution to 0° C. with an ice bath, NBS (1.543 g, 8.67 mmol) was added into the reaction. The dark solution turned brownish orange within 5 minutes. TLC showed a more polar spot. The reaction was diluted with EtOAc (100 mL), washed with brine, dried over sodium sulfate, and purified by flash chromatography to afford the title compound.

Step C: tert-butyl (3S)-4-[2-(3-cyano-4-methoxy-2-methylphenyl)-2-oxoethyl]-3-(hydroxymethyl)piperazine-1-carboxylate To a solution of the 3-(bromoacetyl)-6-methoxy-2-methylbenzonitrile (2.25 g, 8.40 mmol) in THF was added tert-butyl (3S)-3-(hydroxymethyl)piperazine-1-carboxylate (2.18 g, 10.8 mmol) and Hunig's Base (2.93 mL, 16.8 mmol). The reaction was allowed to stir at RT for 16 hours. TLC showed good reaction at that point. The crude reaction was adsorbed onto silica gel, and purified by silica gel flash chromatography to afford the title compound.

Step D: tert-butyl (3R,9aS)-3-(3-cyano-4-methoxy-2-methylphenyl)hexahydropyrazino[2,1-c][1,4]oxazine-8(1H)-carboxylate and tert-butyl (3S,9aS)-3-(3-cyano-4-methoxy-2-methylphenyl)hexahydropyrazino[2,1-c][1,4]oxazine-8(1H)-carboxylate To a solution of tert-butyl (3S)-4-[2-(3-cyano-4-methoxy-2-methylphenyl)-2-oxoethyl]-3-(hydroxymethyl)piperazine-1-carboxylate (800 mg, 1.983 mmol) and triethylsilane (1.58 mL, 9.91 mmol) in DCM (10 mL) was dropped TFA (5 mL) slowly. The reaction was allowed to stir at RT for 72 hours. LC showed quite clean reaction. The volatiles were removed under vacuum, and the residue was redissolved in DCM. To this solution was added Boc anhydride (1.08 g, 4.96 mmol) and saturated sodium carbonate (5 mL). TLC showed complete protection within 30 minutes. The reaction was diluted with water, extracted with DCM, dried over sodium sulfate, and purified by silica gel flash chromatography to afford a colorless oil (220 mg, 29% yield). NMR analysis suggested that it was a mixture of the trans, and cis-isomers in the ratio of about 3:1. The isomers were separated by chiral preparative HPLC (Chiralpak AD-SFC conditions) to give the trans-isomer 22A and the cis-isomer 22B: $^1$H-NMR (500 MHz, CDCl$_3$) δ ppm 22A: 7.61 (d, J=9.0 Hz, 1H), 6.81 (d, J=9.0 Hz, 1H), 4.77 (d, J=10 Hz, 1H), 4.05 (m, 2H), 3.93 (d, J=11.5 Hz, 1H), 3.90 (s, 3H), 3.46 (t, J=11 Hz, 1H), 3.01 (d, J=17.5 Hz, 1H), 3.00 (broad, 1H), 2.80 (d, J=11.5 Hz, 1H), 2.71 (d, J=9.0 Hz, 1H), 2.52 (s, 3H), 2.50 (m, 1H), 2.23 (q, J=12 Hz, 1H), 2.14 (t, J=11.5 Hz, 1H), 1.47 (s, 9H); 22B: 8.06 (d, J=9.0 Hz, 1H), 6.77 (d, J=9.0 Hz, 1H), 4.84 (s, 1H), 3.91 (s, 3H), 3.50 (d, J=11.5 Hz, 1H), 3.26 (m, 1H), 3.11 (d, J=1.5 Hz, 1H), 3.01 (s, 1H), 2.75 (m, 2H), 2.66 (m, 1H), 2.54 (s, 3H), 2.44 (m, 2H), 1.46 (s, 9H).

Intermediates 23A and 23B

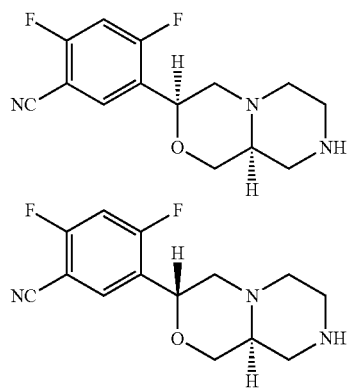

2,4-difluoro-5-[(3R,9aS)-octahydropyrazino[2,1-c][1,4]oxazin-3-yl]benzonitrile and 2,4-difluoro-5-[(3S,9aS)-octahydropyrazino[2,1-c][1,4]oxazin-3-yl]benzonitrile Step A: 5-cyano-2,4-difluorobenzoic acid To a solution of 5-bromo-2,4-difluorobenzonitrile (6.00 g, 27.5 mmol) in 80 mL of THF and 20 mL of water was added TEA (3.00 g, 29.7 mmol) and Pd(dppf)$_2$Cl$_2$ (0.8 g). The reaction was heated to 100° C. at 2 MPa of CO for 18 hours. After cooling to room temperature, the reaction was poured into 500 mL of water. The brown solid precipitated out was filtered. The filtrate cake was washed with water and then purified by silica gel column to give 5-cyano-2,4-difluorobenzoic acid.

Step B: 5-(bromoacetyl)-2,4-difluorobenzonitrile

Oxalyl chloride (5 mL) was added dropwise at 0° C. to a suspension of 5-cyano-2,4-difluorobenzoic acid (2.00 g, 10.9 mmol) in 30 mL of DCM with 0.5 mL of DMF. The mixture was stirred at 25° C. for 45 minutes and the clear solution was concentrated to dryness under reduced pressure. This acid chloride was taken up in 70 mL of THF and cooled to 0° C. with ice/water. CH$_2$N$_2$ solution (70 mmol in ~150 mL of ether) was added dropwise and stirred at 0° C. for 2 hours before 15 mL of concentrated (47%) HBr was added. The mixture was stirred at 0° C. for 20 minutes then diluted with 600 mL of EtOAc. Then the mixture was washed subsequently with water (30 mL), saturated NaHCO$_3$ (30 mL) and brine (30 mL). The EtOAc layer was dried over anhydrous Na$_2$SO$_4$ and concentrated to give 5-(bromoacetyl)-2,4-difluorobenzonitrile.

Step C: tert-butyl(3S)-4-[2-(5-cyano-2,4-difluorophenyl)-2-oxoethyl]-3-(hydroxymethyl)piperazine-1-carboxylate A suspension of 5-(bromoacetyl)-2,4-difluorobenzonitrile (2.5 g, 9.6 mmol), tert-butyl (3S)-3-(hydroxymethyl)piperazine-1-carboxylate (2.1 g, 9.6 mmol) and DIEA (1.90 g, 14.4 mmol) in 50 mL of THF was stirred at 20° C. for 10 hours. The reaction mixture was poured into ice water and extracted with EtOAc (3×200 mL). The combined organic layers were washed with water and brine, dried and concentrated. The residue was purified by column chromatography eluting with 5% MeOH in DCM to afford the title compound.

Step D: 21B: 2,4-difluoro-5-[(3R,9aS)-octahydropyrazino[2,1-c][1,4]oxazin-3-yl]benzonitrile and 21A: 2,4-difluoro-5-[(3S,9aS)-octahydropyrazino[2,1-c][1,4]oxazin-3-yl]benzonitrile To a solution of tert-butyl (3S)-4-[2-(5-cyano-2,4-difluorophenyl)-2-oxoethyl]-3-(hydroxymethyl)piperazine-1-carboxylate (3.1 g, 7.8 mmol) in 50 mL of TFA was added Et$_3$SiH (10.4 g, 89.0 mmol). The mixture was stirred at 50° C. for 90 minutes and concentrated to dryness under reduced pressure. The residue was washed with ether and the resulting oil was purified and the isomers separated by SFC (Column: Chiralpak AD-H 100×4.6 mm I.D., 5 um; Mobile phase: methanol (0.05% DEA) in CO$_2$ from 5% to 40%; Flow rate: 4.5 mL/min; Wavelength: 220 nm; Temp: 40. Gradient: 0 min 5%, 0.5 min 5%, 2.25 min 40%, 3.65 min 40%, 4.0 min 5%, 5.0 min 5%) to give the title compounds: Isomer 23A $^1$H-NMR (MeOD, 400 MHz) δ 8.24-8.28 (m, 1H), 7.27-7.32 (m, 1H), 5.03 (brs, 1H), 3.66-3.68 (m, 1H), 3.48-3.50 (m, 3H), 3.34-3.37 (m, 1H), 3.14-3.17 (m, 3H), 2.84-2.88 (m, 3H); MS m/z 280 (M+1)$^+$;

Isomer 23B $^1$H-NMR (MeOD, 400 MHz) δ 7.87-7.91 (m, 1H), 7.26-7.31 (m, 1H), 4.91 (s, 1H), 4.02-4.04 (m, 1H), 3.49-3.51 (m, 1H), 3.37-3.42 (m, 1H), 3.14-3.28 (m, 5H), 3.00-3.07 (m, 2H), 2.78-2.82 (m, 1H), 2.61-2.67 (m, 1H), 2.49-2.56 (m, 1H), 2.24-2.51 (m, 1H); MS m/z 280 (M+1)$^+$.

Intermediates 24A and 24B

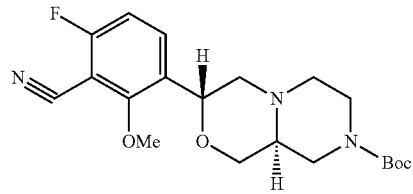

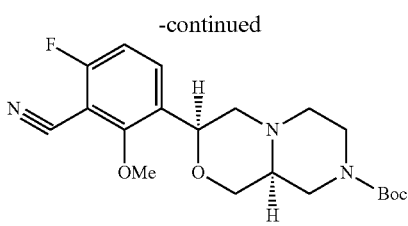

tert-butyl (3R,9aS)-3-(3-cyano-4-fluoro-2-methoxyphenyl)hexahydropyrazino[2,1-c][1,4]oxazine-8(1H)-carboxylate and tert-butyl (3S,9aS)-3-(3-cyano-4-fluoro-2-methoxyphenyl)hexahydropyrazino[2,1-c][1,4]oxazine-8(1H)-carboxylate Step A: 3-bromo-6-fluoro-2-methoxybenzonitrile 2-Fluoro-6-methoxybenzonitrile (8.30 g, 54.9 mmol) was dissolved in Triflic acid (75 mL) at 0° C. then NBS (10.3 g, 57.7 mmol) was added. The reaction mixture was stirred at RT for 1 h. LC-MS showed no starting material peak. The reaction mixture was poured into ice and extracted twice with DCM. The combined organic layers were washed with brine, dried over Na2SO4, filtered, and evaporated to dryness. The residue was purified by chromatography through a 330 g Redi-Sep column and eluted with 10% to 50% EtOAc/hexane solvent system to yield the title compound.

Step B: 3-ethenyl-6-fluoro-2-methoxybenzonitrile 3-bromo-6-fluoro-2-methoxybenzonitrile (4.40 g, 19.1 mmol), potassium vinyl trifluoroborate (5.12 g, 38.3 mmol), PdCl2(dppf)-CH$_2$Cl$_2$ Adduct (0.7 g, 1 mmol) and TEA (5.33 mL, 38.3 mmol) were added to 80 mL ethanol in a 200 mL flask. The reaction mixture was degassed and heated to reflux for 4 h. The reaction mixture was cooled and then most of the ETOH was removed. The residue was diluted with ethyl acetate. The mixture was washed with brine twice. The organic layer was separated and dried over Na2SO4, filtered, and evaporated to dryness. The residue was purified thru a 330 g RediSep column and eluted with 10% ETOAc/hexane solvent system to yield the title compound.

Step C: 6-fluoro-2-methoxy-3-(oxiran-2-yl)benzonitrile

3-Ethenyl-6-fluoro-2-methoxybenzonitrile (1.67 g, 9.43 mmol) was added to DCM (50 mL) at 0° C. then mCPBA (4.88 g, 28.3 mmol) was added and the reaction mixture was stirred at RT for 16 h. The reaction mixture was washed with saturated aqueous Na$_2$S$_2$O$_3$, then with 1N NaOH followed by brine. The organic layer was separated and dried over Na$_2$SO$_4$, filtered, and evaporated to dryness. The crude product was purified by chromatography through a 120 g. Redi-sep column and eluting with a 0-100% EtOAc/hexane solvent system. Isolated pure 6-fluoro-2-methoxy-3-(oxiran-2-yl)benzonitrile.

Step D-E: tert-butyl (3R,9aS)-3-(3-cyano-4-fluoro-2-methoxyphenyl)hexahydropyrazino[2,1-c][1,4]oxazine-8(1H)-carboxylate and tert-butyl (3S,9aS)-3-(3-cyano-4-fluoro-2-methoxyphenyl)hexahydropyrazino[2,1-c][1,4]oxazine-8(1H)-carboxylate The title compounds were prepared in an analogous fashion as described for tert-butyl(3S,9aR)-3-(3-cyano-4-fluoro-2-methylphenyl)hexahydropyrazino[2,1-c][1,4]oxazine-8(1H)-carboxylate and tert-butyl(3R,9aR)-3-(3-cyano-4-fluoro-2-methylphenyl)hexahydropyrazino[2,1-c][1,4]oxazine-8(1H)-carboxylate (Method 1) starting from 6-fluoro-2-methoxy-3-(oxiran-2-yl)benzonitrile. The isomers were separated by Chirapak AD-H 250 mm×30 mm I.D. column with 85% SFC CO2 and 15% EtOH. The trans-isomer eluted first, then the cis-isomer.

Isomer 1 $^1$H-NMR (500 MHz, CDCl$_3$): δ ppm 7.72 ppm (t, J=8 Hz, 1H), 6.96 (t, J=8 Hz, 1H), 4.92 (d, J=9.5 Hz, 1H), 4.17 (s, 3H), 4.03 (b, 2H), 3.96 (d, J=11 Hz, 1H), 3.49 (t, J=10.5 Hz, 1H), 3.05 (b, 1H), 2.95 (d, J=10.5 Hz, 1H), 2.74 (s, 1H), 2.54 (b, 1H), 2.24 (d, J=10.5 Hz, 2H), 2.07 (t, J=10.5 Hz, 1H), 1.50 (s, 9H); LC-MS: M+1=392;

Isomer 2 $^1$H-NMR (500 MHz, CDCl$_3$): δ ppm 8.28 (b, 1H), 6.96 (t, J=8.5 Hz, 1H), 5.06 (s, 1H), 4.16 (s, 3H), 3.80-4.05 ppm (b, 2H), 3.80 (s, 1H), 3.74 (s, 1H), 3.423 (b, 1H), 3.04 (d, J=10.5 Hz, 1H), 2.81 (b, 3H), 2.56 (b, 2H) 2.68, 1.50 (s, 9H); LC-MS: M+1=392.

Alternatively, the 3-bromo-6-fluoro-2-methoxybenzonitrile intermediate could be prepared in four steps as follows:

Step A: 1-bromo-4-fluoro-2-methoxybenzene

A solution of 2-bromo-5-fluorophenol (15 g, 79 mmol) in 125 mL of anhydrous DMF was added K$_2$CO$_3$ (17.0 g, 138 mmol) and MeI (14.0 g, 102 mmol) under cooling, then the reaction was stirred at room temperature for 3 hours. The mixture was poured to water, extracted with diethyl ether, washed with water and brine, dried over anhydrous Na$_2$SO$_4$ and concentrated to give 1-bromo-4-fluoro-2-methoxybenzene.

Step B: 3-bromo-6-fluoro-2-methoxybenzoic acid

A solution of dry diisopropylamine (10 g, 99 mmol) in dry THF under nitrogen was cooled with a −78° C. bath, n-butyl lithium (2.50 M in hexane, 40 mL, 99 mmol) was added and the solution was stirred at −78° C. for 20 minutes. 1-Bromo-4-fluoro-2-methoxybenzene (17.0 g, 82.5 mmol) was added. After stirring at −78° C. for 2 hours, the solution was bubbled with CO$_2$ and then warmed to 0° C. Then 1 N HCl was added until pH=3-4 and the mixture was extracted with AcOEt. The combined organic layers were washed with brine, dried over anhydrous sodium sulphate and concentrated to afford 3-bromo-6-fluoro-2-methoxybenzoic acid.

Step C: 3-bromo-6-fluoro-2-methoxybenzamide

Oxalyl chloride (15 mL) was added dropwise at 0° C. to a suspension of 3-bromo-6-fluoro-2-methoxybenzoic acid (15 g, 60 mmol) in 100 mL of DCM with 0.5 mL of DMF. The mixture was stirred at 25° C. for 2 hours and the clear solution was concentrated to dryness under reduced pressure. The residue dissolved in 60 mL of anhydrous acetonitrile was added to 600 mL of aqueous NH$_3$.H$_2$O at 0° C. and stirred for 2 hours, then filtered to give 3-bromo-6-fluoro-2-methoxybenzamide.

Step D: 3-bromo-6-fluoro-2-methoxybenzonitrile

A solution of 3-bromo-6-fluoro-2-methoxybenzamide (14 g, 61 mmol) in 100 mL of DMF was added 2,4,6-trichloro-

[1,3,5]triazine (12.3 g, 67.0 mmol) portionwise at 0° C. and stirred for 2 hours before poured to ice/water. The white solid was collected by filtration and was washed with water, dissolved in DCM, dried over anhydrous $Na_2SO_4$ and concentrated to afford 3-bromo-6-fluoro-2-methoxybenzonitrile.

$^1$H-NMR (400 MHz, $CDCl_3$) δ ppm 7.71~7.74 (m, 1H), 6.84~6.88 (m, 1H), 4.09 (s, 3H);

Intermediates 25A and 25B

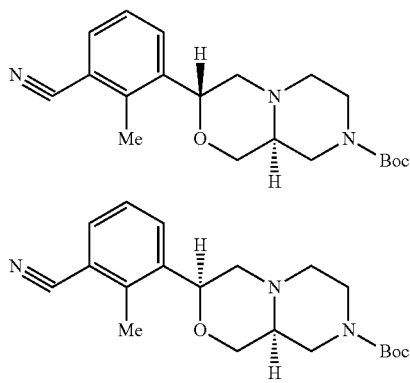

tert-butyl (3R,9aS)-3-(3-cyano-2-methylphenyl)hexahydropyrazino[2,1-c][1,4]oxazine-8(1H)-carboxylate and tert-butyl (3S,9aS)-3-(3-cyano-2-methylphenyl)hexahydropyrazino[2,1-c][1,4]oxazine-8 (1H)-carboxylate Part A:

3-bromo-2-methylbenzonitrile was prepared starting from commercially available 3-bromo-2-methylbenzoic acid using an analogous sequence to that described in Method 2, Steps C and D, for making 3-bromo-6-fluoro-2-methoxybenzonitrile.

Part B:

The preparation of the title compounds was accomplished in an analogous fashion as that described for making Intermediates 17A and 17B (Method 1) starting with 3-bromo-2-methylbenzonitrile in place of 3-bromo-6-fluoro-2-methylbenzonitrile. The trans and cis were separated with AD-H column, 30×250 mm, 25% IPA (0.2% DEA)/$CO_2$, 70 mL/min, 100 bar, 50 in MeOH, 35C, 220 nm. S-trans isomer (eluted first)-$^1$H-NMR (500 MHz, $CDCl_3$): δ ppm 7.74 (d, J=7.5 Hz, 1H), 7.57 (d, J=7.5 Hz, 1H), 7.34-7.32 (m, 1H), 4.87 (d, J=10 Hz, 1H), 4.07-4.02 (m, 2H), 3.98-3.96 (m, 2H), 3.52-3.48 (m, 1H), 2.86 (d, J=10 Hz, 1H), 2.75-2.73 (m, 1H), 2.59 (s, 3H), 2.29-2.24 (m, 2H), 2.19-2.15 (m, 2H), 1.49-1.48 (m, 9H); LC/MS: [(M+1)]$^+$=358: S-cis isomer (eluted second)-$^1$H-NMR (500 MHz, $CDCl_3$): δ ppm 8.14 (d, J=7 Hz, 1H), 7.59 (d, J=8 Hz, 1H), 7.32-7.31 (m, 1H), 4.93 (s, 1H), 4.08-4.03 (m, 2H), 3.59-3.56 (m, 2H), 3.31 (s, 1H), 3.18-3.15 (m, 2H), 2.82-2.87 (m, 2H), 2.65 (s, 3H), 2.53-2.49 (m, 2H), 1.49 (s, 9H); LC/MS: [(M+1)]$^+$=358

Intermediates 25C and 25D

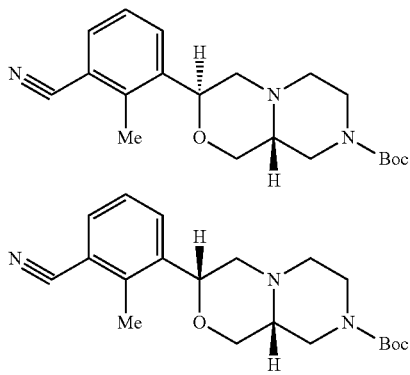

tert-butyl (3S,9aR)-3-(3-cyano-2-methylphenyl)hexahydropyrazino[2,1-c][1,4]oxazine-8(1)-carboxylate and tert-butyl(3R,9aR)-3-(3-cyano-2-methylphenyl)hexahydropyrazino[2,1-c][1,4]oxazine-8(1H)-carboxylate Step A: 3-(2-Chloroacetyl)-2-methylbenzonitrile To a solution of 3-iodo-2-methylbenzonitrile (7.71 g, 31.7 mmol) and 2-chloro-N-methoxy-N-methylacetamide (6.55 g, 47.6 mmol) in THF (100 mL) at −78° C. was added n-butyllithium (2.5 M in hexanes, 14.0 mL, 34.9 mmol) dropwise. After complete addition, the mixture was stirred 15 min. at −78° C., then quenched with the dropwise addition of 1 N HCl. The mixture was partitioned between EtOAc/water and the layers separated. The aqueous was extracted with EtOAc (2×) and the combined organic layers were washed with brine, dried (magnesium sulfate), filtered and concentrated. Recrystallization of the resulting residue from hexanes provided 3-(2-chloroacetyl)-2-methylbenzonitrile: $^1$H NMR (500 MHz, $CDCl_3$), δ 7.76 (m, 2H), 7.41 (m, 1H), 4.55 (s, 2H), 2.68 (s, 3H).

Step B: tert-butyl (3R)-4-[2-(3-cyano-2-methylphenyl)-2-oxoethyl]-3-(hydroxymethyl)piperazine-1-carboxylate To a solution of 3-(chloroacetyl)-2-methylbenzonitrile (1.7 g, 8.8 mmol) in THF (17.6 mL) was added (R)-4-N-boc-2-hydroxymethyl-piperazine (2.279 g, 10.54 mmol) and DIPEA (3.07 mL, 17.56 mmol) at rt. The reaction mixture was stirred at rt over the weekend. After concentration, the residue was partitioned between EtOAc and aqueous $NaHCO_3$ (saturated). The aqueous layer was extracted with EtOAc (2×). The combined organic phase was washed with brine, dried over anhydrous $MgSO_4$, and filtered. Concentration was followed by purification by prep TLC (silica gel; 10% MeOH/DCM) to give the title compound: LC/MS (M+1)$^+$=374.14

Step C: 2-methyl-3-[(3S,9aR)-octahydropyrazino[2,1-c][1,4]oxazin-3-yl]benzonitrile and 2-methyl-3-[(3R,9aR)-octahydropyrazino[2,1-c][1,4]oxazin-3-yl]benzonitrile To a solution of tert-butyl (3R)-4-[2-(3-cyano-2-methylphenyl)-2-oxoethyl]-3-(hydroxymethyl)piperazine-1-carboxylate (2.38 g, 6.37 mmol) in DCM (21.24 mL) and TRI-ETHYLSILANE (5.09 mL, 31.9 mmol) was added TFA (10.62 mL) drop-wise at room temperature. The reaction mixture was stirred at rt for 5 h. After concentration, the residue was partitioned between DCM and aqueous NaHCO$_3$ saturated. The aqueous layer was extracted with DCM (2×). The combined organic phase was washed with brine, dried over anhydrous MgSO$_4$, and filtered. After concentration, the residue was redissolved in 20 mL of DCM, and BOC$_2$O (3.70 mL, 15.9 mmol) was added at rt. The mixture was left to stir at rt for 2 h. After concentration, the residue was partitioned between EtOAc and aqueous NaHCO$_3$ saturated. The aqueous layer was extracted with EtOAc (2×). The combined organic phase was washed with brine, dried over anhydrous MgSO$_4$, and filtered. After concentration, the mixture was purified by prep TLC (silica gel; 10% MeOH/DCM) to give a mixture of cis and trans products. The mixture was resolved by prep SFC with 15% MeOH:MeCN at 35° C. on OD-H column to give two single diastereomers.

Intermediates 26A and 26B

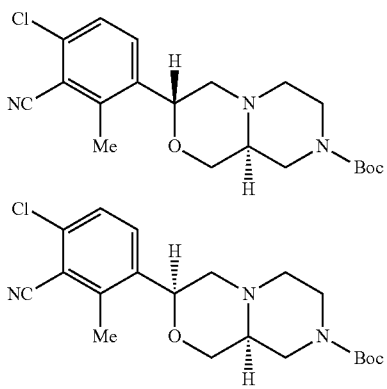

tert-butyl(3R,9aS)-3-(4-chloro-3-cyano-2-methylphenyl)hexahydropyrazino[2,1-c][,4]oxazine-8(1H)-carboxylate and tert-butyl(3S,9aS)-3-(4-chloro-3-cyano-2-methylphenyl)hexahydropyrazino[2,1-c][1,4]oxazine-8(1H)-carboxylate The title compounds were prepared by an analogous method to that described for the synthesis of tert-butyl(3R,9aS)-3-(3-cyano-4-fluoro-2-methylphenyl)hexahydropyrazino[2,1-c][1,4]oxazine-8(1H)-carboxylate and tert-butyl (3S,9aS)-3-(3-cyano-4-fluoro-2-methylphenyl) hexahydropyrazino[2,1-c][1,4]oxazine-8(1H)-carboxylate above (Method 1) starting from 2-chloro-6-methylbenzonitrile. The isomers were separated by Chiralcel OD, 20×250 mm, 50 mL/min, 100 bar, 30% MeOH/CO$_2$, 35 C, ~50 mg/mL in MeOH/DCM, 220 nm. The trans isomer eluted out first while the cis isomer eluted second: Trans $^1$H-NMR (500 MHz, CDCl$_3$): δ ppm 7.67 (d, J=8.5 Hz, 1H), 7.39 (d, J=8 Hz, 1H), 4.88 (d, J=9 Hz, 1H), 4.06-3.99 (m, 3H), 3.58-3.50 (m, 3H), 2.93-2.81 (m, 2H), 2.61 (s, 3H), 2.37-2.29 (m, 3H), 2.20-2.16 (m, 2H), 1.51 (s, 9H); LC/MS: [(M+1)]$^+$=392; Cis $^1$H-NMR (500 MHz, CDCl$_3$): δ ppm 8.11 (d, J=3 Hz, 1H), 4.92 (s, 2H), 4.05-3.52 (m, 2H), 3.27-3.22 (m, 2H), 3.16-3.05 (m, 3H), 2.83-2.82 (m, 2H), 2.652 (s, 3H), 2.52-2.39 (m, 2H), 1.50 (s, 9H); LC/MS: [(M+1)]$^+$=392.

Intermediates 27A and 27B

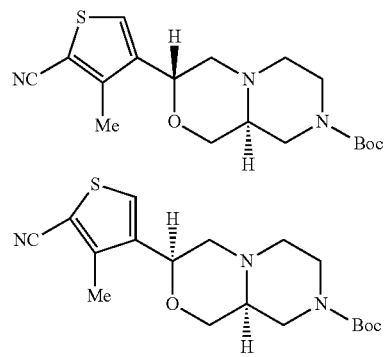

tert-butyl(3R,9aS)-3-(5-cyano-4-methylthiophen-3-yl)hexahydropyrazino[2,1-c][1,4]oxazine-8(1H)-carboxylate and tert-butyl(3S,9aS)-3-(5-cyano-4-methylthiophen-3-yl)hexahydropyrazino[2,1-c][1,4]oxazine-8(1H)-carboxylate Step A: 2,4-dibromo-3-methylthiophene To a solution of 2,3,5-tribromo-4-methylthiophene (46.2 g, 138 mmol) in 500 mL of THF was added dropwise n-BuLi (55.2 mL, 138.0 mmol) at −70° C. The mixture was stirred at −70° C. for 15 minutes and 50 mL of water was added slowly. The resulting mixture was allowed to warm to room temperature and stirred for 10 minutes and extracted with EtOAc. The organic layers were washed with water and brine, dried over anhydrous Na$_2$SO$_4$ and concentrated to give crude 2,4-dibromo-3-methylthiophene.

Step B: 4-bromo-3-methylthiophene-2-carbonitrile

A mixture of 2,4-dibromo-3-methylthiophene (20.0 g, 78.1 mmol) and CuCN (6.30 g, 70.3 mmol) in 150 mL of DMF was stirred at reflux for 4 hours before cooling down. The reaction mixture was poured into 1 L of ether with stirring and the precipitate was removed by filtration. The filtrate was washed with water (100 mL×3), brine (100 mL), dried over anhydrous Na$_2$SO$_4$ and concentrated. The residue was purified by silica column chromatography (petrol ether:EtOAc=50:1) to afford 4-bromo-3-methylthiophene-2-carbonitrile.

Step C: 4-ethenyl-3-methylthiophene-2-carbonitrile

A mixture of 4-bromo-3-methylthiophene-2-carbonitrile (3.00 g, 14.8 mmol), potassium vinyltrifluoroborate (2.40 g, 17.8 mmol) and Pd (dppf)$_2$Cl$_2$ (0.5 g) in 30 mL of EtOH and 30 mL of TEA was refluxed under Ar for 4 hours. The reaction mixture was concentrated, and the residue was purified by column chromatography (petrol ether:EtOAc=50:1) to afford 4-ethenyl-3-methylthiophene-2-carbonitrile.

Step D: 3-methyl-4-(oxiran-2-yl)thiophene-2-carbonitrile

A suspension of 4-ethenyl-3-methylthiophene-2-carbonitrile (1.70 g, 11.4 mmol) in 30 mL of t-Bu-OH and 60 mL of water was added NBS (2.40 g, 13.7 mmol) portionwise. The mixture was stirred at 90° C. for 1 hour then cooled down to 10° C. Then a solution of NaOH (0.7 g in 10 mL of water, 17.5 mmol) was added dropwise and stirred for 15 minutes. The reaction mixture was extracted with EtOAc twice and concentrated. The residue was purified by silica column chromatography (petrol ether: EtOAc=20:1) to afford 3-methyl-4-(oxiran-2-yl)thiophene-2-carbonitrile.

Step E: tert-butyl(3S)-4-[2-(5-cyano-4-methylthiophen-3-yl)-2-hydroxyethyl]-3-(hydroxymethyl)piperazine-1-carboxylate A mixture of 3-methyl-4-(oxiran-2-yl)thiophene-2-carbonitrile (1.3 g, 7.9 mmol) and tert-butyl (3S)-3-(hydroxymethyl)piperazine-1-carboxylate (2.0 g, 9.5 mmol) in 5 mL of EtOH was heated in a microwave apparatus at 140° C. for 90 minutes and then cooled down. The reaction mixture was concentrated, and the residue was purified by column chromatography (DCM: MeOH=10:1) to afford the title compound.

Step F: tert-butyl(3R,9aS)-3-(5-cyano-4-methylthiophen-3-yl)hexahydropyrazino[2,1-c][1,4]oxazine-8(1H)-carboxylate and tert-butyl(3S,9aS)-3-(5-cyano-4-methylthiophen-3-yl)hexahydropyrazino[2,1-c][1,4]oxazine-8(1H)-carboxylate tert-Butyl (3S)-4-[2-(5-cyano-4-methylthiophen-3-yl)-2-hydroxyethyl]-3-(hydroxymethyl)piperazine-1-carboxylate (1.40 g, 3.67 mmol) and cyanomethylene tributylphosphorane (1.59 g, 6.61 mmol) were dissolved in benzene (15 mL) in a microwave tube then sealed, degassed and heated to 100° C. overnight. The reaction mixture was cooled and the benzene was evaporated off. The residue was then purified by chromatography through a 80 g Redi-sep column eluting with acetone:DCM (5:95). The cis-isomer tert-butyl (3S,9aS) eluted first; the trans-isomer (3R,9aS) eluted second:Isomer 1:1 H-NMR (500 MHz, CDCl₃): δ ppm 8.06 (s, 1H), 4.76 (s, 1H), 4.00 (b, 1H), 3.79 (d, J=11 Hz, 0.5H), 3.70 (d, J=10 Hz, 0.5H), 3.42 (d, J=11.5 Hz, 1H), 3.15 (t, J=10.5 Hz, 1H), 3.10 (s, 0.5H), 3.08 (s, 0.5H), 2.99 (b, 1H), 2.75 (t, J=13.0 Hz, 2H), 2.46 (b, 1H), 2.41 (s, 3H), 2.24-2.40 (m, 2H), 1.45 (s, 9H); LC-MS: M+1=264; Isomer 2: ¹H-NMR (500 MHz, CDCl₃): δ ppm 7.50 (s, 1H), 4.66 (d, J=10 Hz, 1H), 3.80-4.15 (m, 3H), 3.45 (t, J=10 Hz, 1H), 3.02 (b, 1H), 2.89 (d, J=11.5 Hz, 1H), 2.75 (d, J=9.5 Hz, 1H), 2.53 (b, 1H), 2.43 (s, 3H), 2.27 (t, J=10.5 Hz, 3H), 1.49 (s, 9H); LC-MS: M+1=264.

Intermediates 28A and 28B

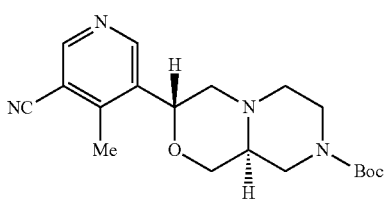

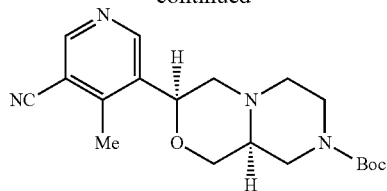

tert-butyl (3R,9aS)-3-(5-cyano-4-methylpyridin-3-yl)hexahydropyrazino[2,1-c][1,4]oxazine-8(1H)-carboxylate and tert-butyl (3S,9aS)-3-(5-cyano-4-methylpyridin-3-yl)hexahydropyrazino[2,1-c][1,4]oxazine-8(1H)-carboxylate Step A: 3,5-dibromo-4-methylpyridine A solution of dry diisopropylamine (11.0 g, 108 mmol) in dry THF under nitrogen was cooled with a −78° C. bath, and n-butyl lithium (2.50 M in hexane, 39 mL) was added. The reactant solution was warmed to ambient temperature, and then cooled to −78° C. again. A solution of 3,5-dibromopyridine (22 g, 93 mmol) in dry THF was added. After stirring at −78° C. for 30 min, CH₃I (17 g, 120 mmol) was added, the mixture was warmed to ambient temperature and stirred over night. The reaction was quenched with water, extracted with EtOAc, the organic layer was washed with brine, dried over anhydrous sodium sulphate and concentrated. The residue was purified by column chromatography to afford 3,5-dibromo-4-methylpyridine: ¹H-NMR (400 MHz, CDCl₃) ppm 8.55 (s, 2H), 2.55 (s, 3H);

Step B: 5-bromo-4-methylpyridine-3-carbonitrile

A mixture of 3,5-dibromo-4-methylpyridine (16 g, 64 mmol) and CuCN (6.2 g, 69 mmol) in 150 mL of DMF was refluxed for 4 hours before cooled down. The reaction mixture was poured to 1 L of EtOAc with stirring and the precipitate was removed by filtration. The filtrate was washed with water, brine, dried over anhydrous Na₂SO₄ and concentrated. The residue was purified by column chromatography to afford 5-bromo-4-methylpyridine-3-carbonitrile.

Step C: 5-ethenyl-4-methylpyridine-3-carbonitrile

A mixture of 5-bromo-4-methylpyridine-3-carbonitrile (4.40 g, 22.3 mmol), potassium vinyltrifluoroborate (3.70 g, 27.9 mmol) and Pd (dppf)₂Cl₂ (0.4 g) in 30 mL of EtOH and 30 mL of TEA was refluxed under Ar for 4 hours. Concentrated, the residue was purified by column chromatography (petrol ether: EtOAc=50:1) to afford 5-ethenyl-4-methylpyridine-3-carbonitrile.

Step D: 4-methyl-5-(oxiran-2-yl)pyridine-3-carbonitrile

A suspension of 5-ethenyl-4-methylpyridine-3-carbonitrile (3.00 g, 20.8 mmol) in 30 mL of Bu'OH and 60 mL of water was added NBS (4.6 g, 26 mmol) portionwise. The mixture was stirred at 40° C. for 2.5 hour then cooled down to 10° C. NaOH solution (2.5 g in 70 mL of water, 62.4 mmol) was added dropwise and stirred for 15 minutes. The reaction mixture was extracted with EtOAc twice and condensed. The residue was purified by column chromatography (petrol ether: EtOAc=20:1) to afford 4-methyl-5-(oxiran-2-yl)pyridine-3-carbonitrile.

Step E-F: tert-butyl (3R,9aS)-3-(5-cyano-4-methylpyridin-3-yl)hexahydropyrazino[2,1-c][1,4]oxazine-8(1H)-carboxylate and tert-butyl (3S,9aS)-3-(5-cyano-4-methylpyridin-3-yl)hexahydropyrazino[2,1-c][1,4]oxazine-8(1H)-carboxylate The title compounds were prepared from 4-methyl-5-(oxiran-2-yl)pyridine-3-carbonitrile in an analagous fashion to that described for Intermediates 17A and 17B (Method 1). The product isomer mixture was purified by chromatography through a 120 g ISCO Redi-sep column and eluting with a 20% acetone/DCM solvent system to yield tert-butyl (3S, 9aS)-3-(5-cyano-4-methylpyridin-3-yl) hexahydro-pyrazino[2,1-c][1,4]oxazine-8(1H)-carboxylate and tert-butyl (3R, 9aS)-3-(5-cyano-4-methylpyridin-3-yl) hexahydro-pyrazino[2,1-c][1,4]oxazine-8(1H)-carboxylate: cis isomer $^1$H-NMR (500 MHz, CDCl$_3$): δ ppm 9.29 (s, 1H), 8.77 ppm (s, 1H), 4.997 (s, 1H), 3.75-4.09 (m, 2H), 3.54 (d, J=11 Hz, 1H), 3.25 (d, J=10.2 Hz, 1H), 3.15 (t, J=9.7 Hz, 1H), 3.05 (b, 1H), 2.88 (dd, J=12.5, 4 Hz, 1H), 2.82 (d, J=10.5 Hz, 1H), 2.70 (s, 3H) 2.57 (b, 1H), 2.517 (b, 1H), 2.47 (b, 1H), 1.50 (s, 9H); LC-MS: M+1=359; trans isomer $^1$H-NMR (500 MHz, CDCl$_3$): δ ppm 8.83 (s, 1H), 8.75 (s, 1H), 4.89 (d, J=10 Hz, 1H), 4.0 (dd, J=11.25, 2.5 Hz, 2H), 3.48 (t, J=11 Hz, 1H), 3.018 (b, 1H), 2.87 (d, J=11.5 Hz, 1H), 2.74 (d, J=10 Hz, 1H), 2.6 (s, 3H), 2.51 (b, 1H), 2.24-2.34 (m, 3H) 1.49 (s, 9H); LC-MS: M+1=359.

Intermediates 29A and 29B

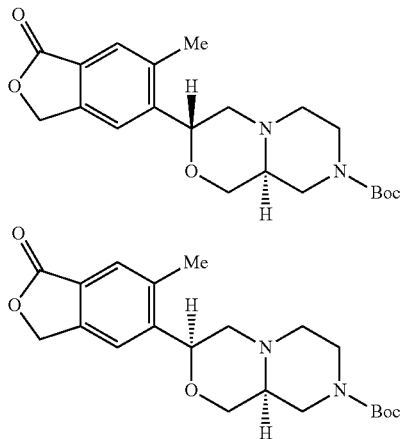

tert-butyl(3R,9aS)-3-(6-methyl-1-oxo-1,3-dihydro-2-benzofuran-5-yl)hexahydropyrazino[2,1-c][1,4]oxazine-8(1H)-carboxylate and tert-butyl(3S,9aS)-3-(6-methyl-1-oxo-1,3-dihydro-2-benzofuran-5-yl)hexahydropyrazino[2,1-c][1,4]oxazine-8(1H)-carboxylate Step A: 5-(prop-2-en-1-yl)-2-benzofuran-1(3H)-one A mixture of 5-bromo-2-benzofuran-1(3H)-one (15.0 g, 70.4 mmol), allyl-tributyl-stannane (25.6 g, 77.5 mmol), LiCl (11.8 g, 282 mmol) and Pd(PPh$_3$)$_4$(1.2 g, 1 mmol) in 100 mL toluene was heated under N$_2$ at 90-100° C. overnight. After cooling to r.t., the mixture was diluted with 250 mL EtOAc and filtered. The filtrate was washed with water and brine, dried over anhydrous Na$_2$SO$_4$ and concentrated to dryness. The residue was purified via silica column chromatography (DCM/Petrol Ether=1:5) to give 5-(prop-2-en-1-yl)-2-benzofuran-1(3H)-one.

Step B: 5-(2-hydroxyethyl)-2-benzofuran-1(3H)-one

To a solution of 5-(prop-2-en-1-yl)-2-benzofuran-1(3H)-one (13.5 g, 45.2 mmol) in 200 mL DCM/MeOH (V/V=1:1) was bubbled O$_3$ at −78° C. for 30 min, and N$_2$ was bubbled for another 15 min at −78° C. Then 20 mL of Me$_2$S were added, and the mixture was stirred at r.t. overnight before concentrating to dryness. The residue was dissolved in MeOH (100 mL) and then cooled to 0° C. NaBH$_4$ (5.90 g, 155 mmol) was added in portions. The resulting mixture was stirred at 0° C. for 1 hr, then quenched with citric acid (aq.) and extracted with EtOAc (3×500 mL). The combined organic layers were washed with NaHCO$_3$ (aq.) and brine, dried over anhydrous Na$_2$SO$_4$ and concentrated to dryness. The residue was purified via silica column chromatography (EtOAc/Petrol Ether=1:5) to give 5-(2-hydroxyethyl)-2-benzofuran-1(3H)-one.

Step C: 5-(2-hydroxyethyl)-6-iodo-2-benzofuran-1(3H)-one

To a cooled (0° C.) solution of 5-(2-hydroxyethyl)-2-benzofuran-1(3H)-one (9.00 g, 50.6 mmol) in 100 mL of TfOH was added NIS (12.5 g, 55.6 mmol), then the mixture was stirred at 0° C. for 2 hrs and then poured into ice-water (500 mL). The solution was extracted with EtOAc (3×500 mL) and the combined organic layers were washed with saturated NaHCO$_3$ solution and brine, and dried over anhydrous sodium sulfate, filtered and concentrated. The residue was purified by silica column chromatography (EtOAc/Petrol Ether=1:5) to give 5-(2-hydroxyethyl)-6-iodo-2-benzofuran-1(3H)-one and its separated regioisomer.

Step D: 5-(2-hydroxyethyl)-6-methyl-2-benzofuran-1(3H)-one

To a flask charged with 5-(2-hydroxyethyl)-6-iodo-2-benzofuran-1(3H)-one (6.00 g, 19.7 mmol) and a stir bar was added Pd$_2$(dba)$_3$ (452 mg, 0.493 mmol), PPh$_3$ (1.00 g, 3.95 mmol) and NMP (50 mL). The mixture was purged with N$_2$ and heated to 50° C. for 10 min, followed by addition of CuI (375 mg, 1.97 mmol). Then the mixture was heated for another 10 min, after which Sn(CH$_3$)$_4$(5.30 g, 29.6 mmol) was added into the reaction, and it was heated to 120° C. for 2 h. After cooling to room temperature, the mixture was diluted with saturated NH$_4$Cl (200 mL) and extracted with EtOAc (3×200 mL). The combined organic layers were washed with water and brine, dried over anhydrous sodium sulfate, filtered and concentrated. The residue was purified by preparative HPLC to give 5-(2-hydroxyethyl)-6-methyl-2-benzofuran-1(3H)-one.

Step E: 2-(6-methyl-1-oxo-1,3-dihydro-2-benzofuran-5-yl)ethyl methanesulfonate

To a solution of 5-(2-hydroxyethyl)-6-methyl-2-benzofuran-1(3H)-one (1.20 g, 6.25 mmol) and TEA (2.5 g, 25 mmol) in DCM (100 mL) was added MsCl (1.40 g, 12.5 mmol) at 0° C. The mixture was stirred at ambient temperature overnight, then was washed with water and brine. The organic layer was dried and concentrated to dryness. The resulting 2-(6-methyl-1-oxo-1,3-dihydro-2-benzofuran-5-yl)ethyl methanesulfonate was used for the next step without any purification.

Step F: 5-ethenyl-6-methyl-2-benzofuran-1(3H)-one

To a mixture of 2-(6-methyl-1-oxo-1,3-dihydro-2-benzofuran-5-yl)ethyl methanesulfonate (2.0 g, 7.4 mmol) and TEA (5 mL) in DCM (50 mL) was added DBU (5 mL) slowly at 0° C. The mixture was stirred at r.t. overnight, and then diluted with 50 mL of DCM, washed with 2 N HCl in three times and brine. The organic layer was dried and concentrated to dryness. The residue was purified by prep-TLC to give 5-ethenyl-6-methyl-2-benzofuran-1(3H)-one.

Step G: 6-methyl-5-(oxiran-2-yl)-2-benzofuran-1(3H)-one

A solution of 5-ethenyl-6-methyl-2-benzofuran-1(3H)-one (1.00 g, 5.75 mmol) in 50 mL of DCM was slowly added mCPBA (3.50 g, 17.4 mmol) in 50 mL of DCM at 0° C. Warmed to room temperature, the mixture was stirred for 2 days. The mixture was washed with aqueous $Na_2SO_3$ until the KI paper didn't change color. The organic layers was washed with brine and then concentrated. The residue was purified via column chromatography to give the product 6-methyl-5-(oxiran-2-yl)-2-benzofuran-1(3H)-one.

Step H: tert-butyl(3S)-3-(hydroxymethyl)-4-[2-hydroxy-2-(6-methyl-1-oxo-1,3-dihydro-2-benzofuran-5-yl)ethyl]piperazine-1-carboxylate A mixture of 6-methyl-5-(oxiran-2-yl)-2-benzofuran-1(3H)-one (750 mg, 3.95 mmol) and tert-butyl (3S)-3-(hydroxymethyl)piperazine-1-carboxylate (1.02 g, 4.74 mmol) in EtOH (5 mL) was reacted under microwave condition (140° C.) for 90 min. After cooling to r.t., the mixture was concentrated to dryness. The residue was purified by prep-TLC to give tert-butyl (3S)-3-(hydroxymethyl)-4-[2-hydroxy-2-(6-methyl-1-oxo-1,3-dihydro-2-benzofuran-5-yl)ethyl]piperazine-1-carboxylate.

Step I: tert-butyl(3R,9aS)-3-(6-methyl-1-oxo-1,3-dihydro-2-benzofuran-5-yl)hexahydropyrazino[2,1-c][1,4]oxazine-8(1H)-carboxylate and tert-butyl(3S,9aS)-3-(6-methyl-1-oxo-1,3-dihydro-2-benzofuran-5-yl)hexahydropyrazino[2,1-c][1,4]oxazine-8(1H)-carboxylate The synthesis of the title compounds was achieved in an analogous fashion to that previously described for isomers tert-butyl(3R,9aS)-3-(4-methyl-1-oxo-1,3-dihydro-2-benzofuran-5-yl)hexahydropyrazino[2,1-c][1,4]oxazine-8(1H)-carboxylate and tert-butyl(3S,9aS)-3-(4-methyl-1-oxo-1,3-dihydro-2-benzofuran-5-yl)hexahydropyrazino[2,1-c][1,4]oxazine-8(1H)-carboxylate (Steps B-C) starting from tert-butyl (3S)-3-(hydroxymethyl)-4-[2-hydroxy-2-(6-methyl-1-oxo-1,3-dihydro-2-benzofuran-5-yl)ethyl]piperazine-1-carboxylate. The isomers were separated by Chiralcel OD-H, 4.6×250, 20% IPA/$CO_2$, 2.1 mL/min, 100 bar, 40 C. The trans isomer eluted first, while the cis isomer eluted second. trans-$^1$H-NMR (500 MHz, $CDCl_3$): δ ppm 7.72 (s, 1H), 7.68 (s, 1H), 5.31 (s, 2H), 4.95 (d, J=10 Hz, 1H), 4.07-3.99 (m, 3H), 3.56-3.52 (m, 1H), 2.77-2.493 (m, 5H), 2.32-2.14 (m, 2H), 1.63 (s, 3H), 1.54-1.49 (m, 9H); LC/MS: [(M+1)]$^+$=389; cis-LC/MS: [(M+1)]$^+$=389.

Intermediate 30A

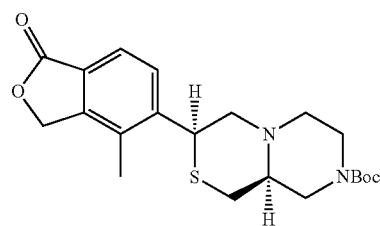 [SMILES: Cc1c([C@H]2CN3CCN(C(=O)OC(C)(C)C)C[C@H]3CS2)ccc2c1COC2=O]

(3S,9aS)-tert-butyl 3-(4-methyl-1-oxo-1,3-dihydroisobenzofuran-5-yl)hexahydropyrazino[2,1-c][1,4]thiazine-8(1H)-carboxylate Step A: (S)-tert-butyl 4-((R)-2-hydroxy-2-(4-methyl-1-oxo-1,3-dihydroisobenzofuran-5-yl)ethyl)-3-(hydroxymethyl)piperazine-1-carboxylate (S)-tert-Butyl 4-((R)-2-hydroxy-2-(4-methyl-1-oxo-1,3-dihydroisobenzofuran-5-yl)ethyl)-3-(hydroxymethyl)piperazine-1-carboxylate was prepared starting from 4-methyl-5-[(2R)-oxiran-2-yl]-2-benzofuran-1(3H)-one in an analogous fashion to that described above for the synthesis of (S)-tert-butyl 4-(2-hydroxy-2-(4-methyl-1-oxo-1,3-dihydroisobenzofuran-5-yl)ethyl)-3-(hydroxymethyl)piperazine-1-carboxylate.

Step B: (S)-tert-butyl 3-(acetylthiomethyl)-4-((R)-2-hydroxy-2-(4-methyl-1-oxo-1,3-dihydroisobenzofuran-5-yl)ethyl)piperazine-1-carboxylate To the solution of (S)-tert-butyl 4-((R)-2-hydroxy-2-(4-methyl-1-oxo-1,3-dihydroisobenzofuran-5-yl)ethyl)-3-(hydroxymethyl)piperazine-1-carboxylate (817 mg, 2.01 mmol) in anhydrous THF (20 mL) under nitrogen atmosphere at 0° C. was added anhydrous triethylamine (0.560 mL, 4.02 mmol), followed by addition of methanesulfonyl chloride (0.234 mL, 3.01 mmol) and 4-dimethylaminopyridine (24.6 mg, 0.201 mmol). The ice bath removed and reaction mixture was stirred for 2 hours. Resulting mixture was then concentrated under reduced pressure. Resulting oil was redissolved in anhydrous DMSO (13 mL) and treated with potassium thioacetate (1235 mg, 10.81 mmol). The reaction mixture was stirred at room temperature under nitrogen for 2 hours. The mixture was diluted with ethyl acetate, washed with water (3 times), brine, and dried ($MgSO_4$), filtered and concentrated. The crude product was purified on Biotage SP1 (40+M equilibrated), eluting with 20-80% ethyl acetate/hexanes, 20 CV (CV stands for column volume). LC/MS: [(M+1)]$^+$=465.2;

Step C: (3S)-tert-butyl 3-(acetylthiomethyl)-4-(2-chloro-2-(4-methyl-1-oxo-1,3-dihydroisobenzofuran-5-yl)ethyl)piperazine-1-carboxylate To a cooled with an ice bath solution of (S)-tert-butyl 3-(acetylthiomethyl)-4-((R)-2-hydroxy-2-(4-methyl-1-oxo-1,3-dihydroisobenzofuran-5-yl)ethyl)piperazine-1-carboxylate (573 mg, 1.23 mmol) in anhydrous toluene (12.3 mL) was added thionyl chloride (0.268 mL, 3.70 mmol). Then, anhydrous pyridine (0.399 mL, 4.93 mmol) was added dropwise. The reaction mixture was kept at 0° C. for 20 min, then warmed to room temperature and stirred for 3 hours. TLC showed the consumption of the starting material. The reaction was concentrated under reduced pressure and dried on high vacuum overnight. Used directly in the next step.

Step D: (3S,9aS)-tert-butyl 3-(4-methyl-1-oxo-1,3-dihydroisobenzofuran-5-yl)hexahydropyrazino[2,1-c][1,4]thiazine-8(1H)-carboxylate A solution of (3S)-tert-butyl 3-(acetylthiomethyl)-4-(2-chloro-2-(4-methyl-1-oxo-1,3-dihydroisobenzofuran-5-yl) ethyl)piperazine-1-carboxylate (596 mg, 1.234 mmol) in anhydrous THF (20 mL) was treated dropwise with sodium methoxide, 25% solution in methanol (0.846 mL, 3.70 mmol). The reaction mixture was stirred for 2 hours under nitrogen at room temperature. LCMS showed formation of the desired product. Solvent was removed under reduced pressure. Residue was redissolved in dichloromethane and washed with brine. Organic layer was dried over MgSO$_4$, filtered and concentrated. Residue was purified on Biotage SP 1, eluting with 20-80% ethyl acetate/hexanes, 16 CV (CV stands for column volume): $^1$H NMR (500 MHz, CDCl$_3$) δ 8.64 (d, J=8.0 Hz, 1H), 7.77 (d, J=8.0 Hz, 1H), 5.29 (s, 2H), 3.81-4.20 (m, 3H), 3.38 (dd, J=2.3, 12.6 Hz), 3.00-3.22 (m, 2H), 2.57-2.82 (m, 2H), 2.24-2.56 (m, 7H), 1.51 (s, 9H).

Intermediate 30B

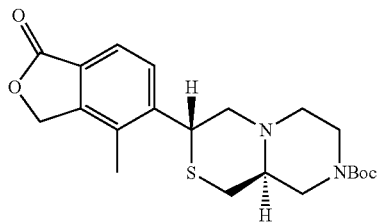 [SMILES: Cc1c([C@@H]2CN3CCN(C(=O)OC(C)(C)C)C[C@H]3CS2)ccc2c1COC2=O]

(3R,9aS)-tert-butyl 3-(4-methyl-1-oxo-1,3-dihydroisobenzofuran-5-yl)hexahydropyrazino[2,1-c][1,4]thiazine-8(1H)-carboxylate Step A: (S)-tert-butyl 3-(acetylthiomethyl)-4-((S)-2-hydroxy-2-(4-methyl-1-oxo-1,3-dihydroisobenzofuran-5-yl)ethyl)piperazine-1-carboxylate Synthesis is analogous to that for (S)-tert-butyl 3-(acetylthiomethyl)-4-((R)-2-hydroxy-2-(4-methyl-1-oxo-1,3-dihydroisobenzofuran-5-yl)ethyl)piperazine-1-carboxylate starting from 4-methyl-5-[(2S)-oxiran-2-yl]-2-benzofuran-1(3H)-one: LC/MS: [(M+1)]$^+$=465.3;

Step B: (3R,9aS)-tert-butyl 3-(4-methyl-1-oxo-1,3-dihydroisobenzofuran-5-yl)hexahydropyrazino[2,1-c][1,4]thiazine-8(1H)-carboxylate Synthesis from (S)-tert-butyl 3-(acetylthiomethyl)-4-((S)-2-hydroxy-2-(4-methyl-1-oxo-1,3-dihydroisobenzofuran-5-yl)ethyl)piperazine-1-carboxylate is analagous to that for the synthesis of (3S,9aS)-tert-butyl 3-(4-methyl-1-oxo-1,3-dihydroisobenzofuran-5-yl)hexahydropyrazino[2,1-c][1,4]thiazine-8(1H)-carboxylate: $^1$H NMR (500 MHz, CDCl$_3$) δ 7.78 (d, J=8.0 Hz, 1H), 7.61 (d, J=8.0 Hz, 1H), 5.28 (s, 2H), 4.41 (dd, J=2.2, 10.9 Hz, 1H), 4.04 (bm, 2H), 2.93-3.15 (m, 2H), 2.53-2.88 (m, 5H), 2.33-2.45 (m, 5H), 1.51 (s, 9H); LC/MS: [(M+1)]$^+$=405.2.

Intermediates 31A and 31B

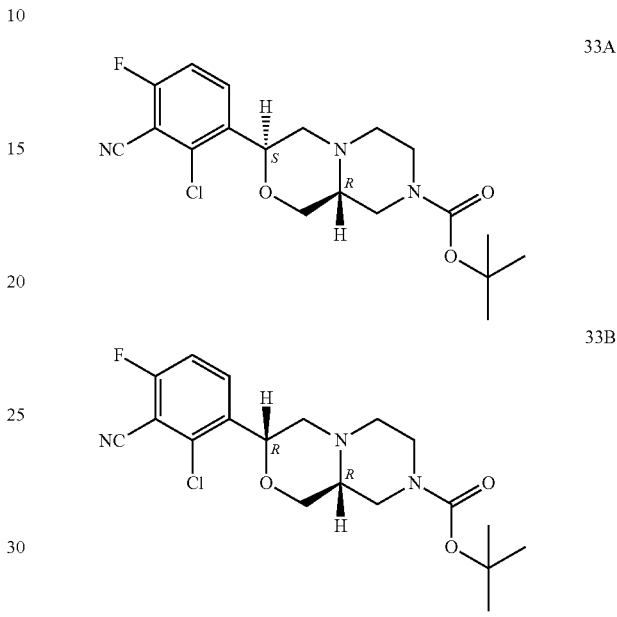

33A: tert-butyl (3S,9aR)-3-(2-chloro-3-cyano-4-fluorophenyl)hexahydropyrazino[2,1-c][1,4]oxazine-8(1H)-carboxylate and 33B: tert-butyl (3R,9aR)-3-(2-chloro-3-cyano-4-fluorophenyl) hexahydro-pyrazino[2,1-c][1,4]oxazine-8(1H)-carboxylate Step A: 3-bromo-2-chloro-6-fluorobenzonitrile 2-Chloro-6-fluorobenzonitrile (15.6 g, 100 mmol) was dissolved in triflic acid (75 mL) at 0° C., then NBS (17.8 g, 100 mmol) was added. The reaction was warmed up to room temperature and stirred overnight. The reaction mixture was poured into ice and extracted with DCM (2×). DCM layers were washed with NaHCO$_3$ and brine. The DCM was dried over Na$_2$SO$_4$ then filtered and concentrated. The product was purified by chromatography through a 330 g ISCO Redi-Sep column with 10-20% ethyl acetate/hexane solvent system to yield 3-bromo-2-chloro-6-fluorobenzonitrile.

Step B: 2-chloro-6-fluoro-3-vinylbenzonitrile

3-Bromo-2-chloro-6-fluorobenzonitrile (15.4 g, 65.6 mmol), potassium vinyl trifluoroborate (17.6 g, 131 mmol), triethylamine (18.3 mL, 131 mmol) and PdCl$_2$(dppf)-CH$_2$Cl$_2$ adduct (2.68 g, 3.28 mmol) were added to ethanol (75 mL) then degassed and heated at reflux for 3 h. The reaction was diluted with ethyl acetate and washed with brine, dried and evaporated to dryness. The product was purified by chromatography through a 330 g ISCO Redi-Sep column with 10% ethyl acetate/hexane solvent system to yield 2-chloro-6-fluoro-3-vinylbenzonitrile.

Step C: 2-chloro-6-fluoro-3-(oxiran-2-yl)benzonitrile 2-chloro-6-fluoro-3-vinylbenzonitrile dissolved in CHCl₃ (300 mL) then added mCPBA (29.4 g, 171 mmol) and stirred at RT for 16 h. When TLC showed starting materials were consumed, the mixture was washed with Na₂S₂O₃ (1×), 1N NaOH (1×), brine (2×), then dried over Na₂SO₄. Filtered and concentrated then purified by MPLC chromatography using 330 g ISCO Redi-sep column and eluted with 20% ethyl acetate/hexane solvent system to yield 2-chloro-6-fluoro-3-(oxiran-2-yl)benzonitrile.

Step D: (3R)-tert-butyl 4-(2-(2-chloro-3-cyano-4-fluorophenyl)-2-hydroxyethyl)-3-(hydroxymethyl)piperazine-1-carboxylate 2-Chloro-6-fluoro-3-(oxiran-2-yl)benzonitrile (9.1 g, 46 mmol) and (R)-tert-butyl 3-(hydroxymethyl)piperazine-1-carboxylate (14.9 g, 69.1 mmol) were dissolved in ethanol (105 mL) and dispensed into 9 sealed tubes then microwaved at 140° C. for 1 h. The combined reaction mixture was concentrated and purified through a 330 g ISCO Redi-sep column with 50%-100 ethyl acetate/hexane solvent system to yield the title compound.

Step E: (9aR)-tert-butyl 3-(2-chloro-3-cyano-4-fluorophenyl)hexahydropyrazino[2,1-c][1,4]oxazine-8(1H)-carboxylate (3R)-tert-butyl 4-(2-(2-chloro-3-cyano-4-fluorophenyl)-2-hydroxyethyl)-3-(hydroxymethyl)piperazine-1-carboxylate (15.6 g, 37.3 mmol) and cyanomethylene tri-n-butyl phosphorane (16.4 g, 67.8 mmol) were dissolved in benzene (90 mL), degassed and heated at 100° C. for 16 h. The reaction mixture was concentrated and chromatographed through a 330 g ISCO Redi-sep column and eluted with 35% EtOAc/hexane to yield the title compound (cis-trans diastereomers mixture). LC-MS (IE, m/z): 396 [M+1]⁺; The cis-trans diastereomers were separated by SFC-HPLC using the following condition: Chiralpak AD 21×250 mm, 20% IPA, 50 ml/min, ~85 mg/mL in 1:1 MeOH/MeCN, 100 bar, 220 nm, 35° C. 31A: ¹H-NMR (600 MHz, CDCl3) δ ppm 7.826 (dd, J=8.7, 6.5 Hz, 1H), 7.184 (t, J=8.4 Hz, 1H), 4.975 (dd, J=9.6, 1.9 Hz, 1H), 3.989 (b, 2H), 3.953 (dd, J=5.7, 3.2 Hz, 1H) 3.484 (t, J=10.85 Hz, 1H), 3.015 (dd, J=11.4, 2.2 Hz, 2H), 2.733 (d, J=10.3 Hz, 1H), 2.52 (b, 1H), 2.18-2.26 (m, 2H), 1.981 (t, J=10.85 Hz, 1H), 1.474 (s, 9H). 31B: ¹H-NMR (600 MHz, CDCl3) δ ppm 8.331 (s, 1H), 7.163 (t, J=8.35 Hz, 1H), 5.038 (t, J=3.7 Hz, 1H), 3.738-3.947 (b, 2H), 3.649 (d, J=10.9 Hz, 1H) 3.371 (s, 1H), 3.02 (dd, J=12, 4.1 Hz, 2H), 2.843 (dd, J=12, 3.8 Hz, 1H), 2.784 (d, J=9.4 Hz, 2H), 2.556 (b, 2H), 1.471 (s, 9H).

Intermediates 31C and 31D

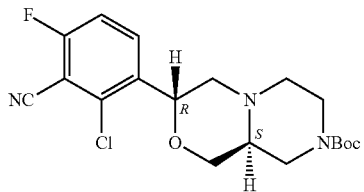

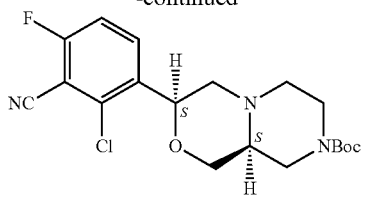

tert-butyl (3R,9aS)-3-(2-chloro-3-cyano-4-fluorophenyl)hexahydropyrazino[2,1-c][1,4]oxazine-8(1H)-carboxylate and tert-butyl (3S,9aS)-3-(2-chloro-3-cyano-4-fluorophenyl)hexahydro-pyrazino[2,1-c][1,4]oxazine-8(1H)-carboxylate tert-butyl (3R,9aS)-3-(2-chloro-3-cyano-4-fluorophenyl)hexahydropyrazino[2,1-c][1,4]oxazine-8(1H)-carboxylate and tert-butyl (3S,9aS)-3-(2-chloro-3-cyano-4-fluorophenyl)hexahydro-pyrazino[2,1-c][1,4]oxazine-8(1H)-carboxylate was prepared in an analogous fashion to that described for the isomers tert-butyl (3S,9aR)-3-(2-chloro-3-cyano-4-fluorophenyl)hexahydropyrazino[2,1-c][1,4]oxazine-8(1H)-carboxylate and tert-butyl (3R,9aR)-3-(2-chloro-3-cyano-4-fluorophenyl)hexahydro-pyrazino[2,1-c][1, 4]oxazine-8(1H)-carboxylate above with a minor change in the last step as described below:

Step E: tert-butyl (3R,9aS)-3-(2-chloro-3-cyano-4-fluorophenyl)hexahydropyrazino[2,1-c][1, 4]oxazine-8(1H)-carboxylate and tert-butyl (3S,9aS)-3-(2-chloro-3-cyano-4-fluorophenyl)hexahydropyrazino[2,1-c][1,4]oxazine-8(1H)-carboxylate tert-Butyl (3S)-4-[2-(2-chloro-3-cyano-4-fluorophenyl)-2-hydroxyethyl]-3-(hydroxymethyl)piperazine-1-carboxylate (4.00 g, 9.66 mmol) and cyanomethylene tri-n-butylphosphorane (4.20 g, 517 mmol) were dissolved in 60 mL benzene. The reaction mixture was degassed and heated to 100° C. for 3 h. The reaction was cooled and evaporated to dryness. The residue was purified by chromatography through a 330 g Redi-sep column, eluting with 33% EtOAc/67% hexane. The trans-isomer 31C eluted out first and then the cis-isomer 31D: Compound 31C-trans-¹H-NMR (500 MHz, CDCl₃): δ ppm. 7.86 (t, J=6.5 Hz, 1H), 7.21 (t, J=7.5 Hz, 1H), 5.01 (d, J=10.5 Hz, 1H), 4.04 (b, 2H), 3.99 (d, J=11.5 Hz, 2H) 3.52 (t, J=10 Hz, 1H), 3.05 (d, J=11.5 Hz, 2H), 2.77 (d, J=10.5 Hz, 1H), 2.57 (b, 1H), 2.21-2.29 (m, 2H), 2.02 (t, J=11.5 Hz, 1H), 1.51 (s, 9H); LC-MS: M+1=396: Compound 31D-cis: ¹H-NMR (500 MHz, CDCl₃): δ ppm 8.36 (s, 1H), 7.19 ppm (t, J=8.5 Hz, 1H), 5.07 ppm (s, 1H), 3.91 (b, 2H), 3.68 (d, J=11.5 Hz, 1H), 3.40 (s, 1H), 3.06 (d, J=12 Hz, 2H), 2.87 (s, 1H), 2.86 (s, 1H), 2.815 (d, J=10.5 Hz, 1H) 2.60 (d, J=10 Hz, 2H); 1.50 (s, 9H); LC-MS: M+1=396.

Intermediate 32

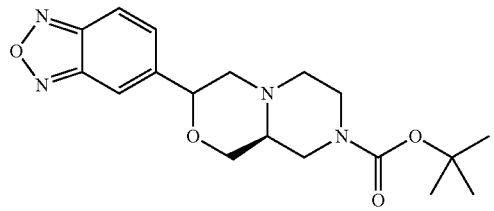

tert-butyl (9aS)-3-(2,1,3-benzoxadiazol-5-yl)hexahydropyrazino[2,1-c][1,4]oxazine-8(1H)-carboxylate

Step A: 5-ethenyl-2,1,3-benzoxadiazole 5-bromo-2,1,3-benzoxadiazole (4.0 g, 20 mmol), potassium vinyltrifluoroborate (5.40 g, 40.2 mmol) and Pd(dppf)

Cl$_2$ (1.6 g, 2 mmol) in TEA (5.2 mL) and EtOH (15 mL) were added to a flask containing a stir bar, and the flask was then heated at 80° C. for 12 h. The organic residue was dissolved in EtOAc (500 mL) and the solution was washed with brine, dried over sodium sulfate, filtered and concentrated. The resulting organic residue was subjected to purification over silica gel to give the title compound.

Step B: 5-(oxiran-2-yl)-2,1,3-benzoxadiazole

To a solution of 5-ethenyl-2,1,3-benzoxadiazole (1.80 g, 12.3 mmol) in DCM (20 mL) was slowly added m-CPBA (3.8 g, 22 mmol) at 0° C. The flask was warmed to room temperature; the mixture was then stirred for 12 hours. TLC as well as LC indicated that reaction had gone to completion. The mixture was washed with aqueous Na$_2$S$_2$O$_3$, NaHCO$_3$, and water. The organic layers was washed with brine and then concentrated. The residue was purified over silica gel to afford the title compound.

Step C: tert-butyl (3S)-4-[2-(2,1,3-benzoxadiazol-5-yl)-2-hydroxyethyl]-3-(hydroxymethyl)piperazine-1-carboxylate To a microwave tube containing a stir bar was added 5-(oxiran-2-yl)-2,1,3-benzoxadiazole (1.2 g, 7.4 mmol), Boc-piperizine alcohol (2.8 g, 13.3 mmol); the resulting mixture was dissolved in anhydrous toluene (15 mL), purged with N$_2$ and the tube was heated in a microwave reactor for 1 h at 150° C. TLC analysis of the rectrion mix. showed the completion of the reaction. The solution was concentrated to dryness and absorbed into silica gel and was subjected for purification over a silica column to give the title compound.

Step D: tert-butyl (9aS)-3-(2,1,3-benzoxadiazol-5-yl)hexahydropyrazino[2,1-c][1,4]oxazine-8(1H)-carboxylate To a 20 mL size microwave tube containing a stir bar was added tert-butyl (3S)-4-[2-(2,1,3-benzoxadiazol-5-yl)-2-hydroxyethyl]-3-(hydroxymethyl)piperazine-1-carboxylate (0.80 g, 2.1 mmol), cyanomethylene tri-n-Butylphosphorane (0.92 g, 3.8 mmol) and anhydrous toluene (15 mL). The tube was degassed and purged with N$_2$ followed by heating at 100° C. for 12 h. The solution was concentrated to dryness and the organic residue was then purified over silica gel with the solvent systems of 30% Acetone in DCM to furnish the title compound: $^1$H-NMR (CDCl3, 500 MHz), δ 7.854-7.832 (m, 2H), 7.428 (d, J=9 Hz, 1H), 4.754 (d, J=10.5 Hz, 1H), 4.041-4.015 (m, 3H), 3.774-3.733 (m, 2H), 3.517 (t, J=11 Hz, 1H), 3.011 (d, J=11.5 Hz, 1H), 2.782 (d, J=9.5 Hz, 1H), 2.335-2.240 (m, 3H), 1.510 (s, 9H).

Intermediates 33A and 33B

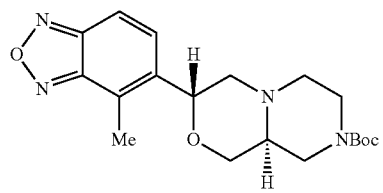

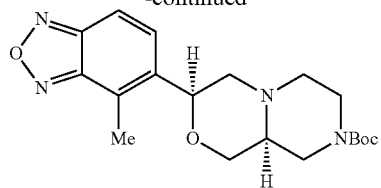

tert-butyl(3R,9aS)-3-(4-methyl-2,1,3-benzoxadiazol-5-yl)hexahydropyrazino[2,1-c][1,4]oxazine-8(1H)-carboxylate and tert-butyl(3S,9aS)-3-(4-methyl-2,1,3-benzoxadiazol-5-yl)hexahydropyrazino[2,1-c][1,4]oxazine-8(1H)-carboxylate Step A: 1-methoxy-2-methyl-3,4-dinitrobenzene To cooled (0° C.) fuming nitric acid (100 mL) was added slowly 2-methyl-3-nitroanisole (13.0 g, 77.8 mmol) in ten times. After the addition, the mixture was warmed to r.t. and stirred for 4 h, then poured into ice-water (500 g). The resulting mixture was extracted with EtOAc (3×500 mL). The combined organic layers were washed with water, saturated NaHCO$_3$, brine, dried over Na$_2$SO$_4$, and concentrated to dryness. The residue was purified by silica column chromatography (petroleum ether/EtOAc=20:1) to obtain the pure product 1-methoxy-2-methyl-3,4-dinitrobenzene.

Step B: 2-azido-4-methoxy-3-methyl-1-nitrobenzene

To a solution of 1-methoxy-2-methyl-3,4-dinitrobenzene (3.4 g, 16 mmol) in 60 mL of DMSO was added NaN$_3$ (2.1 g, 32 mmol) at one portion and the reaction was stirred for 72 hours at room temperature. Then the reaction was poured into 500 mL of ice water, and then was extracted with DCM (100 mL×3). The combined organic layers were washed with water, dried and concentrated to about 100 mL of solvent. Then 100 mL of toluene was added and the residual DCM was removed under reduced pressure, the toluene solution of 2-azido-4-methoxy-3-methyl-1-nitrobenzene was used directly the next step.

Step C: 6-methoxy-7-methyl-2,1,3-benzoxadiazole 1-oxide

The toluene solution of 2-azido-4-methoxy-3-methyl-1-nitrobenzene was refluxed for 96 hours under Ar, then the solvent was removed under reduced pressure and the residue was purified by silica gel column to give 6-methoxy-7-methyl-2,1,3-benzoxadiazole 1-oxide.

Step D: 5-methoxy-4-methyl-2,1,3-benzoxadiazole

To a solution of 6-methoxy-7-methyl-2,1,3-benzoxadiazole 1-oxide (6.80 g, 37.7 mmol) in 150 mL of toluene was added PPh$_3$ at one portion and the mixture was refluxed for 3 hours under Ar. Then the solvent was removed under reduced pressure and the residue was purified by silica gel column to give the title compound.

Step E: 4-methyl-2,1,3-benzoxadiazol-5-ol

To a solution of 5-methoxy-4-methyl-2,1,3-benzoxadiazole (3.00 g, 18.2 mmol) in 120 mL of DCE was added 17.6 mL of BBr₃ at one portion and the mixture was stirred at reflux for 12 hours under Ar, then the solvent was removed under reduced pressure and the residue was purified by silica gel column to give 4-methyl-2,1,3-benzoxadiazol-5-ol.

Step F: 4-methyl-2,1,3-benzoxadiazol-5-yl trifluoromethanesulfonate

To a solution of 4-methyl-2,1,3-benzoxadiazol-5-ol (2.10 g, 17.9 mmol) in 40 mL of dry DCM was added Tf₂O (7.61 g, 26.9 mmol) dropwise at −78° C. under Ar and stirred for 5 minutes, then Et₃N (2.73 g, 26.9 mmol) was added dropwise to the mixture and the reaction was stirred at 0° C. for 4 hours. Then the reaction was poured into 200 mL of ice water and extracted with DCM (50 mL×3). The combined organic layers were washed with brine, dried and concentrated, the residue was purified by silica gel column to give the title compound.

Step G: 5-ethenyl-4-methyl-2,1,3-benzoxadiazole

The mixture of 4-methyl-2,1,3-benzoxadiazol-5-yl trifluoromethanesulfonate (3.90 g, 13.8 mmol), potassium vinyltrifluoroborate (2.22 g, 16.6 mmol) and Pd (dppf)₂Cl₂ (0.5 g) in 50 mL of EtOH and 15 mL of TEA was refluxed under Ar for 4 hours. Concentrated, the residue was purified by silica column chromatography (PE:EtOAc=20:1) to afford 5-ethenyl-4-methyl-2,1,3-benzoxadiazole.

Step H: 4-methyl-5-(oxiran-2-yl)-2,1,3-benzoxadiazole

A mixture of 5-ethenyl-4-methyl-2,1,3-benzoxadiazole (1.4 g, 8.4 mmol) and mCPBA (85%, 2.57 g, 12.6 mmol) in 200 mL of DCM was stirred at room temperature for 96 hours. The reaction mixture was cooled to 0° C. and was washed subsequently with saturated NaHCO₃ (50 mL), saturated Na₂SO₃ (50 mL), 5% NaOH (50 mL×2) and brine (50 mL), dried over anhydrous Na₂SO₄ and concentrated. The residue was purified by silica column chromatography (PE:EtOAc=5:1) to afford the title compound.

Step I-J: tert-butyl(3R,9aS)-3-(4-methyl-2,1,3-benzoxadiazol-5-yl)hexahydropyrazino[2,1-c][1,4]oxazine-8(1H)-carboxylate and tert-butyl(3S,9aS)-3-(4-methyl-2,1,3-benzoxadiazol-5-yl)hexahydropyrazino[2,1-c][1,4]oxazine-8(1H)-carboxylate The title compound was prepared from 4-methyl-5-(oxiran-2-yl)-2,1,3-benzoxadiazole in a similar fashion to that described for: Intermediates 17A and 17B (Method 1). The isomers were separated by Chiralcel OD-H, 4.6×250, 20% MeOH/CO₂, 2.4 mL/min, 100 bar, 40 C. The trans-isomer eluted first, while the cis-isomer eluted second: trans-¹H-NMR (500 MHz, CDCl₃): δ ppm 7.69-7.42 (m, 2H), 5.03 (d, J=5.2 Hz, 1H), 4.11-3.99 (m, 3H), 3.56-3.53 (m, 2H), 3.11-3.03 (m, 2H), 2.84-2.74 (m, 4H), 1.62 (s, 3H), 1.56-1.52 (m, 9H); cis-¹H-NMR (500 MHz, CDCl₃): δ ppm 8.01 (d, J=2.8 Hz, 1H) 7.72 (d, J=3.4 Hz, 1H), 5.02 (s, 1H), 4.01-3.52 (m, 4H), 3.20-2.72 (m, 7H), 1.61 (s, 3H), 1.55 (s, 9H).

Intermediate 34

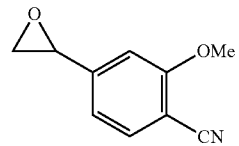 [SMILES: COc1cc(C2CO2)ccc1C#N]

2-Methoxy-4-(oxiran-2-yl)benzonitrile

Step A: 4-Formyl-2-methoxyphenyl trifluoromethanesulfonate

To a solution of vanillin (20 g, 131 mmol) in DMF (200 mL) at room temperature was added potassium carbonate (36.30 g, 263 mmol) and 4-nitrophenyl trifluoromethanesulfonate (53.5 g, 197 mmol) and the reaction mixture was stirred for 8 hr. EtOAc (600 mL) was added to the reaction mixture and the organic layer was washed three times with water, dried, filtered, and concentrated. The crude compound was then purified by flash chromatography (ethylacetate/hexanes 1:9→3:7) to provide sulfonate.

Step B: 4-Formyl-2-methoxybenzonitrile

A mixture of the sulfonate (37.0 g, 130 mmol), zinc cyanide (61.1 g, 521 mmol) and tetrakis triphenylphosphine palladium (0) (22.57 g, 19.53 mmol) in DMF (300 mL) were stirred at 110° C. for 8 hr. EtOAc was added to the reaction mixture and the organic layer was washed two times with water, dried, filtered and concentrated. The crude product was then purified by column chromatography (silica gel, ethylacetate/hexanes 3:7) which afforded the title compound: LC/MS: (IE, m/z) [M+1]⁺=162.34.

Step C: 2-Methoxy-4-(oxiran-2-yl)benzonitrile

To a cool solution of NaH (0.16 g, 3.9 mmol) in THF (40 mL) was added dropwise a solution of trimethylsulfonium iodide (0.91 g, 4.5 mmol) in DMSO (20 mL). The resulting mixture was stirred at 0° C. under N2 for 20 min. A solution of 4-formyl-2-methoxybenzonitrile (0.60 g, 3.72 mmol) in THF (20 mL) was added. The resulting reaction mixture was stirred at 0° C. under N₂ for 1 hr, and then it was warmed gradually to room temperature and stirred at that temperature for 12 hr. The starting material was consumed as indicated by TLC (25% ethyl acetate/hexanes). The reaction mixture was cooled to 0° C. and quenched with dropwise addition of water. The mixture was extracted with ethyl acetate (2×70 mL). The combined organic layers were washed with water, brine, then dried (MgSO₄) and filtered. The filtrate was concentrated in vacuo. The residue was purified via column chromatography (silica gel, 10-30% EtOAc-hexanes) to afford 2-methoxy-4-(oxiran-2-yl)benzonitrile: ¹H NMR (CDCl₃, 500 MHz) δ 7.57 (d, J=8 Hz, 1H), 6.99 (dd, J=1.1 Hz, J=1.2 Hz, 1H), 6.89

(s, 1H), 3.97 (s, 3H), 3.94-3.92 (m, 1H), 3.22 (dd, J=5.2, Hz, J=4.1 Hz, 1H), 2.77 (d, J=2.5 Hz, 1H); LC/MS: (IE, m/z) [M+1]⁺=176.33.

Intermediates 35A and 35B (Mixture of Cis/Trans) and Separated Cis and Trans Isomers

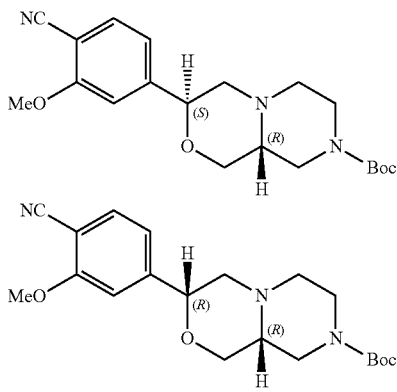

tert-Butyl (3S,9aR)-3-(4-cyano-3-methoxyphenyl) hexahydropyrazino[2,1-c][1,4]oxazine-8(1H)-carboxylate and tert-Butyl (3R,9aR)-3-(4-cyano-3-methoxyphenyl)hexahydropyrazino[2,1-c][1,4] oxazine-8(1H)-carboxylate Step A: tert-Butyl (3R)-4-[2-(4-cyano-3-methoxyphenyl)-2-hydroxyethyl]-3 (hydroxymethyl)piperazine1-carboxylate A Pyrex vessel was charged with magnetic stirring bar, (2.0 g, 11.42 mmol) of 2-methoxy-4-(oxiran-2-yl)benzonitrile, (3.70 g, 17.12 mmol) of tert-butyl (3R)-3-(hydroxymethyl) piperazine-1-carboxylate, and 6 mL of EtOH. Then it was introduced in the microwave reactor and irradiated at 150° C. for 3 h. The mixture was cooled to room temperature and the solvent was evaporated and the resulting residue was purified by column chromatography (silica gel, 1-20% dichloromethane/MeOH) which afforded the product as a mixture of two diastereomers (1:1) LC/MS: (IE, m/z) [(M+1)-t-Bu]⁺=336.41

Step B: tert-Butyl (9aR)-3-(4-cyano-3-methoxyphenyl)hexahydropyrazino[2,1-c][1,4]oxazine-8(1H)-carboxylate The isomeric mixture of the prior step (3.48 g, 8.89 mmol, 1:1) in benzene was treated with (tributyl-λ⁵-phosphanylidene) acetonitrile (3.22 g, 13.3 mmol). The reaction mixture was microwaved for 3 hr at 135° C. in a Biotage apparatus. Then the mixture was cooled to room temperature, and solvent removal gave crude product. The crude product was chromatographed (silica gel, hexanes/EtOAc 9:1→3:7, as eluent) to give an isomeric mixture of the bicyclic title compound.

Step C: tert-Butyl(3S,9aR)-3-(4-cyano-3-methoxyphenyl)hexahydropyrazino[2,1-c][1, 4]oxazine-8 (1H)-carboxylate and tert-Butyl(3R,9aR)-3-(4-cyano-3-methoxyphenyl)hexahydropyrazino[2,1-c][1, 4]oxazine-8(1H)-carboxylate The isomeric mixture was further separated into its enantiomers using a 21×250 mm ChiralCel OJ-H, column, eluting with 15% MeOH/CO₂ with a flow rate of 50 mL/min, 100 bar, 59 mg/mL in MeOH, 35 C, 220 nm, Thr=200: trans-¹H NMR (CDCl₃, (trans) isomer, 500 MHz) δ 7.54 (d, J=7.9 Hz, 1H), 7.05 (s, 1H), 6.97 (d, J=7.9 Hz, 1H), 4.72 (d, J=8.9 Hz, 1H), 4.12-4.0 (m, 2H), 3.98 (s, 3H), 3.49 (t, J=9.4 Hz, J=9.0 Hz, 1H), 3.03 (bs, 1H), 2.94 (d, J=11.2 Hz, 1H), 2.76 (d, J=9 Hz, 1H), 2.56 (bs, 1H), 2.29-2.192 (m, 3H), 1.69 (bs, 1H), 1.50 (s, 9H); LC/MS: (IE, m/z) [(M+1)-t-Bu]⁺=318.40; cis-¹H NMR (CDCl₃, (cis) isomer, 500 MHz) δ 7.58 (d, J=7.9 Hz, 1H), 7.21 (s, 1H), 7.17 (d, J=7.8 Hz, 1H), 4.82 (bs, 1H), 4.06-3.99 (m, 2H), 3.98 (s, 3H), 3.64 (bs, 1H), 3.43 (bs, 1H), 3.23 (d, J=11.6 Hz, 1H), 3.05 (bs, 1H), 2.81 (bs, 2H), 2.72-2.42 (m, 3H), 1.50 (s, 9H); LC/MS: (IE, m/z) [(M+1)-t-Bu]⁺=318.35.

Intermediates 35 C and 35D (Mixture of Cis/Trans) and Separated Cis and Trans Isomers

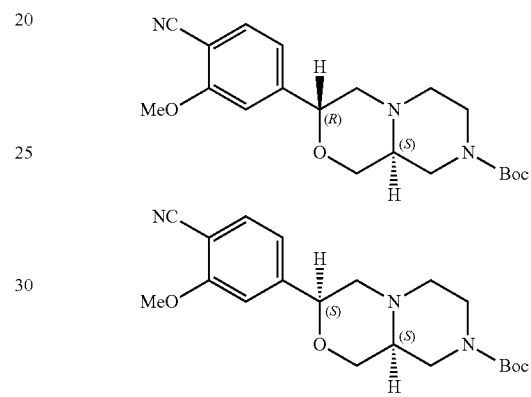

tert-Butyl (3R,9aS)-3-(4-cyano-3-methoxyphenyl) hexahydropyrazino[2,1-c][1,4]oxazine-8(1H)-carboxylate and tert-Butyl (3S,9aS)-3-(4-cyano-3-methoxyphenyl)hexahydropyrazino[2,1-c][1,4]oxazine-8 (1H)-carboxylate Step A: tert-Butyl (3S)-4-[2-(4-cyano-3-methoxyphenyl)-2-hydroxyethyl]-3-(hydroxymethyl)piperazine-1-carboxylate A Pyrex vessel was charged with magnetic stirring bar, (0.350 g, 2.00 mmol) of 2-methoxy-4-(oxiran-2-yl)benzonitrile, (0.457 g, 2.20 mmol) of tert-butyl (3S)-3-(hydroxymethyl)piperazine-1-carboxylate, and 6 mL of EtOH. Then it was introduced in the microwave reactor and irradiated at 150° C. for 3 h. Then the mixture was cooled to RT and the solvent was evaporated and the resulting residue was purified by column chromatography (silica gel, 1-20% dichloromethane/MeOH) which afforded the title compound as a mixture of two diastereomers (1:1). LC/MS: (IE, m/z) [(M+1)-t-Bu]⁺=336.1.

Step B: tert-Butyl (9aS)-3-(4-cyano-3-methoxyphenyl)hexahydropyrazino[2,1-c][1,4]oxazine-8(1H)-carboxylate The isomeric mixture of the prior step (0.55 g, 1.40 mmol, 1:1) in benzene was treated with (tributyl-λ⁵-phosphanylidene) acetonitrile (0.678 g, 2.81 mmol). The reaction mixture was microwaved for 3 hr at 135° C. in a Biotage apparatus. Then the mixture was cooled to room temperature, and solvent removal gave crude product. The crude product was chromatographed (silica gel, hexanes/EtOAc 9:1→3:7, as eluent) to give an isomeric mixture of the bicyclic title compound LC/MS: (IE, m/z) [(M+1)-t-Bu]$^+$=318.06.

Step C: 29C: and 29D tert-Butyl (9aS)-3-(4-cyano-3-methoxyphenyl)hexahydropyrazino[2,1-c][1,4]oxazine-8(1H)-carboxylate was further separated into its enantiomers using a 21×250 mm ChiralCel OJ-H, column, eluting with 15% MeOH/CO$_2$ with a flow rate of 50 mL/min, 100 bar, 59 mg/mL in MeOH, 35 C, 220 nm, Thr=200: trans-$^1$H NMR (CDCl$_3$, (trans) isomer, 500 MHz) δ 7.55 (d, J=8.0 Hz, 1H), 7.06 (s, 1H), 6.97 (d, J=8.0 Hz, 1H), 4.71 (d, J=9.4 Hz, 1H), 4.12-4.0 (m, 2H), 3.98 (s, 3H), 3.48 (t, J=9.4 Hz, J=10.3 Hz, 1H), 3.03 (bs, 1H), 2.94 (d, J=11.0 Hz, 1H), 2.76 (d, J=7.8 Hz, 1H), 2.54 (bs, 1H), 2.29-2.192 (m, 3H), 1.51 (s, 9H); LC/MS: (IE, m/z) [(M+1)-t-Bu]$^+$=318.17; cis-$^1$H NMR (CDCl$_3$, (cis) isomer, 500 MHz) δ 7.58 (d, J=8.0 Hz, 1H), 7.22 (s, 1H), 7.17 (d, J=7.8 Hz, 1H), 4.82 (bs, 1H), 4.06-3.99 (m, 2H), 3.98 (s, 3H), 3.64 (bs, 1H), 3.43 (bs, 1H), 3.23 (dd, J=3.6 Hz, J=3.7 Hz, 1H), 3.01 (bs, 1H), 2.80 (bs, 2H), 2.72-2.42 (m, 3H), 1.50 (s, 9H); LC/MS: (IE, m/z) [(M+1)-t-Bu]$^+$=318.35.

Intermediate 36

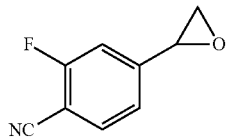 [SMILES: N#Cc1ccc(C2CO2)cc1F]

2-fluoro-4-oxiran-2-ylbenzonitrile

Step A: (4-cyano-3-fluorophenyl)acetic acid

A solution of dry diisopropylamine (16.5 g, 163 mmol) in dry THF (150 mL) under nitrogen was cooled with a −78° C. dry ice/acetone bath, and n-butyl lithium (2.50 M in hexane, 65.2 mL) was added slowly. The resulting solution was warmed to ambient temperature for 10 min and then cooled to −78° C. again. HMPA (30.0 mL, 168 mmol) was added, followed by a solution of 2-fluoro-4-methylbenzonitrile (20.0 g, 148 mmol) in 50 mL of dry THF. After stirring at −78° C. for 2 hours, CO$_2$ was bubbled through the solution for 20 min, and then the mixture was warmed slowly to 0° C. Then 1 N HCl was added until pH=2 and the mixture was extracted with EtOAc. The organic layers were washed with brine and dried over anhydrous sodium sulphate and concentrated to afford title compound.

Step B: 2-fluoro-4-(2-hydroxyethyl)benzonitrile

To a solution of (4-cyano-3-fluorophenyl)acetic acid (25.6 g, 143 mmol) in 150 mL of dry THF was cooled by ice/water, and then BH3/Me2S (10 M, 15.7 mL, 157 mmol) was added slowly. The reaction was warmed to ambient temperature and stirred overnight. The mixture was quenched with MeOH and concentrated to dryness. The residue was partitioned between water and EtOAc. The organic layers were washed with brine, dried over anhydrous sodium sulfate and concentrated to afford 2-fluoro-4-(2-hydroxyethyl)benzonitrile.

Step C: 2-(4-cyano-3-fluorophenyl)ethyl methanesulfonate

A solution of 2-fluoro-4-(2-hydroxyethyl)benzonitrile (22.5 g, 136 mmol) and MsCl (23.3 g, 205 mmol) in 200 mL of dry DCM was added dropwise TEA (27.5 g, 273 mmol) at 0° C. The resulting mixture was stirred at room temperature overnight before concentrating to dryness. The residue was dissolved in 300 mL of EtOAc and washed with 1 N HCl and brine, dried over anhydrous Na2SO4 and concentrated to afford crude title compound: LC-MS m/z 244 (M+1)$^+$;

Step D: 4-ethenyl-2-fluorobenzonitrile

A solution of 2-(4-cyano-3-fluorophenyl)ethyl methanesulfonate (35.0 g, 144 mmol) and triethylamine (50 mL) in DCM (200 mL) was added DBU (50 mL) dropwise to at 0° C. After stirring at room temperature overnight, the solution was diluted with DCM, washed with 1 N HCl and brine, and dried over anhydrous sodium sulphate and concentrated. The residue was purified by column chromatography to give title compound.

Step E: 2-fluoro-4-oxiran-2-ylbenzonitrile

To a solution of 4-ethenyl-2-fluorobenzonitrile (18.0 g, 122 mmol) in 200 mL of DCM was slowly added mCPBA (74.8 g, 367.347 mmol) in portions at 0° C. The mixture was warmed to room temperature and stirred overnight. The solution was washed with aqueous Na$_2$SO$_3$ until KI paper didn't change color. The organic layers was washed with brine and then concentrated. The residue was purified via column chromatography to give 2-fluoro-4-oxiran-2-ylbenzonitrile: $^1$H-NMR (400 MHz, CDCl$_3$) δ ppm 7.59~7.62 (m, 1H), 7.12~7.22 (m, 2H), 3.89~3.91 (m, 1H), 3.20~3.22 (m, 1H), 2.72~2.74 (m, 1H).

Intermediate 37

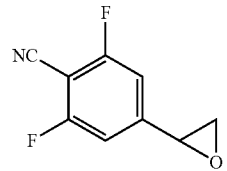 [SMILES: N#Cc1c(F)cc(C2CO2)cc1F]

2,6-difluoro-4-(oxiran-2-yl)benzonitrile

Step A: 2,6-difluoro-4-vinylbenzonitrile 2,6-Difluoro-4-vinylbenzonitrile was prepared from 4-bromo-2,6-difluorobenzonitrile using potassium vinyl trifluoroborate and PdCl2(dppf)2 in an analagous fashion as described for 4-ethenyl-3-methyl-2-(methyloxy)benzonitrile above.

Step B: 2,6-difluoro-4-(oxiran-2-yl)benzonitrile 2,6-Difluoro-4-(oxiran-2-yl)benzonitrile was prepared from 2,6-Difluoro-4-vinylbenzonitrile using m-CPBA in an analagous fashion to that described for 5-fluoro-2-methoxy-4-(oxiran-2-yl)benzonitrile (Step H) above: $^1$H NMR (500

MHz, CDCl₃) δ 7.02 (d, J=8.0 Hz, 2H), 3.92 (dd, J=3.6, 2.4 Hz, 1H), 3.24 (dd, J=5.4, 4.0 Hz, 1H), 2.74 (dd, J=5.4, 2.4 Hz, 1H).

Intermediate 38

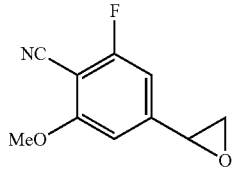 [SMILES: COc1cc(C2CO2)cc(F)c1C#N]

2-fluoro-6-methoxy-4-(oxiran-2-yl)benzonitrile

Step A: 4-bromo-2-fluoro-6-methoxybenzonitrile

To methanol (0.28 mL, 6.9 mmol) and 4-bromo-2,6-difluorobenzonitrile (1500 mg, 6.88 mmol) in THF (34 mL) was added NaHMDS (6.88 mL, 1.0 M in THF, 6.88 mmol) at 0° C. The reaction mixture was stirred at rt overnight, and diluted with brine, extracted with EtOAc. The organic layer was dried, and evaporated. The crude product was purified by column chromatography (0-30% EtOAc/Hex) to give 4-bromo-2-fluoro-6-methoxybenzonitrile.

Step B: 2-fluoro-6-methoxy-4-vinvylbenzonitrile

The title compound was prepared from 4-bromo-2-fluoro-6-methoxybenzonitrile using potassium vinyl trifluoroborate and PdCl2(dppf)2 in an analagous fashion as described for 4-ethenyl-3-methyl-2-(methyloxy)benzonitrile above.

Step C: 2-fluoro-6-methoxy-4-(oxiran-2-yl)benzonitrile

The title compound was prepared from 2-fluoro-6-methoxy-4-vinylbenzonitrile using m-CPBA in an analagous fashion to that described for 5-fluoro-2-methoxy-4-(oxiran-2-yl)benzonitrile (Step H) above: ¹H NMR (500 MHz, CDCl₃) δ 6.75 (dd, J=9.1, 0.9 Hz, 1H), 6.71 (d, J=0.9 Hz, 1H), 3.97 (s, 3H), 3.90 (dd, J=4.0, 2.5 Hz, 1H), 3.21 (dd, J=5.5, 4.0 Hz, 1H), 2.73 (dd, J=5.5, 2.5 Hz, 1H).

Intermediate 39

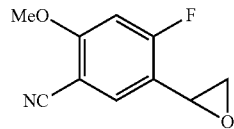 [SMILES: COc1cc(F)c(C2CO2)cc1C#N]

4-fluoro-2-methoxy-5-(oxiran-2-yl)benzonitrile

Step A: 5-bromo-4-fluoro-2-methoxybenzonitrile

To a 500 mL flask was added 4-fluoro-2-methoxybenzonitrile (9.00 g, 59.5 mmol), NBS (12.7 g, 71.5 mmol) and TFA (40 mL); the resulting mixture was stirred for 4 h at 65° C. Analysis of the reaction by LC indicated completion of the reaction. The reaction mixture was concentrated to dryness, treated with EtOAc (200 mL) and washed with brine and water, dried (Na₂SO₄), filtered and concentrated to dryness. The resulting organic residue was purified by MPLC with the solvent systems of hexanes/EtOAc=1/1 to furnish the desired product: LC/MS: [(M+2)]⁺=232;

Step B: 5-ethenyl-4-fluoro-2-methoxybenzonitrile

5-Ethenyl-4-fluoro-2-methoxybenzonitrile was prepared from 4-bromo-2-fluoro-6-methoxybenzonitrile using potassium vinyl trifluoroborate and PdCl2(dppf)2 in an analagous fashion as described for 4-ethenyl-3-methyl-2-(methyloxy)benzonitrile above: LC/MS: [(M+1)]⁺=178

Step C: 4-fluoro-2-methoxy-5-(oxiran-2-yl)benzonitrile

4-Fluoro-2-methoxy-5-(oxiran-2-yl)benzonitrile was prepared from 2-fluoro-6-methoxy-4-vinylbenzonitrile using m-CPBA in an analagous fashion to that described for 5-fluoro-2-methoxy-4-(oxiran-2-yl)benzonitrile (Step H) above: LC/MS: [(M+1)]⁺=194

The Boc-piperazine intermediates described in Table 1 were prepared from the indicated epoxides (prepared as described above) and (S)-4-N—BOC-2-hydroxymethylpiperazine or (R)-4-N—BOC-2-hydroxymethylpiperazine in an analagous fashion to that described for tert-butyl (3S,9aR)-3-(4-cyano-3-methoxyphenyl)hexahydropyrazino[2,1-c][1,4] oxazine-8(1H)-carboxylate and its diastereomer tert-Butyl (3R,9aR)-3-(4-cyano-3-methoxyphenyl)hexahydropyrazino [2,1-c][1,4]oxazine-8(1H)-carboxylate above.

TABLE 1

| INTER-MEDIATE | Epoxide starting intermediate | INTERMEDIATE structure Characterization or separation notes |
|---|---|---|
| 40A | ![epoxide] | ![structure] Prep SFC with 10% IPA/CO₂ on OD column; LC/MS: (IE, m/z) [(M + 1) − t-Bu]⁺ = 305.99. |

| INTER-MEDIATE | Epoxide starting intermediate | INTERMEDIATE structure Characterization or separation notes |
|---|---|---|
| 40B | 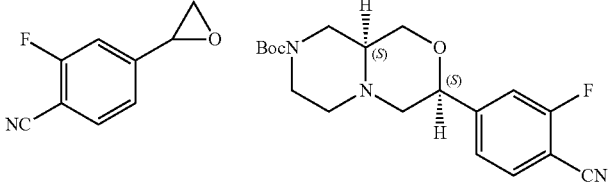 | |

Prep SFC with 10% IPA/CO$_2$ on OD column; LC/MS: (IE, m/z) [(M + 1) − t-Bu]$^+$ = 305.98.

| 41A | 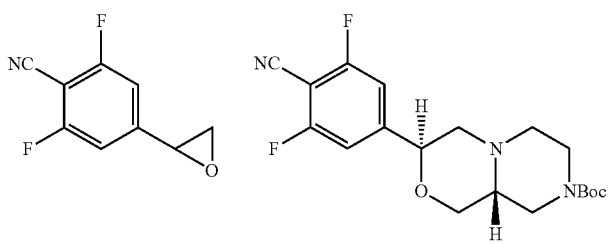 | |

Trans and cis isomers were separated by prep SFC with 15% (2:1 MeOH:MeCN)/CO$_2$ on IA column; $^1$H NMR (500 MHz, CDCl$_3$) δ 7.05 (d, J = 8.4 Hz, 2H), 4.66 (dd, J = 10.4, 2.1 Hz, 1H), 4.12-3.92 (m, 3H), 3.42 (t, J = 10.8 Hz, 1H), 3.00-2.87 (m, 2H), 2.72 (d, J = 11.1 Hz, 1H), 2.48 (br s, 1H), 2.25-2.20 (m, 2H), 2.11 (t, J = 11.0 Hz, 1H), 1.46 (s, 9H).

| 41B | 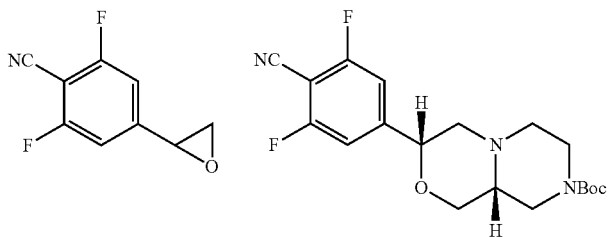 | |

Trans and cis isomers were separated by prep SFC with 15% (2:1 MeOH:MeCN)/CO$_2$ on IA column; $^1$H NMR (500 MHz, CDCl$_3$) δ 7.25 (d, J = 8.8 Hz, 2H), 4.79 (br s, 1H), 4.02-3.64 (m, 2H), 3.59 (dd, J = 11.6, 2.8 Hz, 1H), 3.28-3.22 (m, 1H), 3.17 (dd, J = 12.4, 2.6 Hz, 1H), 2.96 (br s, 1H), 2.81-2.76 (m, 2H), 2.52-2.36 (m, 3H), 1.47 (s, 9H).

| 41C | 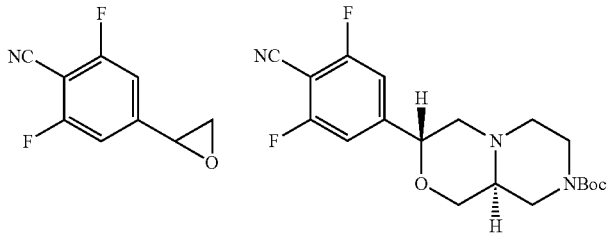 | |

Trans and cis isomers were separated by prep SFC with 15% (2:1 MeOH:MeCN)/CO$_2$ on IA column; $^1$H NMR (500 MHz, CDCl$_3$) δ 7.08 (d, J = 8.4 Hz, 2H), 4.69 (dd, J = 10.4, 2.1 Hz, 1H), 4.12-3.92 (m, 3H), 3.46 (t, J = 10.8 Hz, 1H), 3.00-2.87 (m, 2H), 2.72 (d, J = 11.1 Hz, 1H), 2.48 (br s, 1H), 2.25-2.20 (m, 2H), 2.14 (t, J = 11.0 Hz, 1H), 1.49 (s, 9H).

TABLE 1-continued

| INTER-MEDIATE | Epoxide starting intermediate | INTERMEDIATE structure Characterization or separation notes |
|---|---|---|
| 41D | 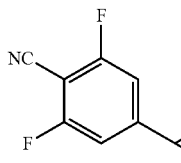 | 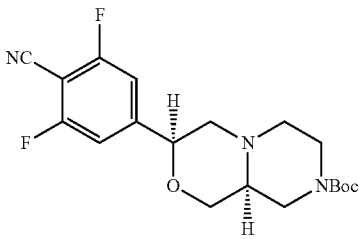 [SMILES: CC(C)(C)OC(=O)N1CCN2C[C@H](c3cc(F)c(C#N)c(F)c3)OC[C@@H]2C1] |

Trans and cis isomers were separated by prep SFC with 15% (2:1 MeOH:MeCN)/CO$_2$ on IA column; $^1$H NMR (500 MHz, CDCl$_3$) δ 7.24 (d, J = 8.8 Hz, 2H), 4.79 (br s, 1H), 4.02-3.64 (m, 2H), 3.59 (dd, J = 11.6, 2.8 Hz, 1H), 3.28-3.22 (m, 1H), 3.17 (dd, J = 12.4, 2.6 Hz, 1H), 2.96 (br s, 1H), 2.81-2.76 (m, 2H), 2.52-2.36 (m, 3H), 1.47 (s, 9H).

| 42A | 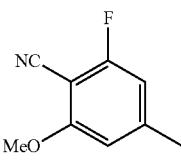 | 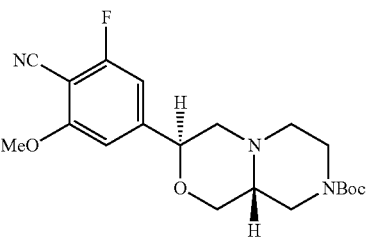 [SMILES: COc1cc([C@H]2CN3CCN(C(=O)OC(C)(C)C)C[C@@H]3CO2)cc(F)c1C#N] |

Trans and cis isomers were separated by prep SFC with 15% (2:1 MeOH:MeCN)/CO$_2$ on IA column; $^1$H NMR (500 MHz, CDCl$_3$) δ 6.80 (s, 1H), 6.75 (d, J = 9.1 Hz, 1H), 4.65 (dd, J = 10.4, 2.1 Hz, 1H), 4.12-3.92 (m, 6H), 3.43 (t, J = 10.6 Hz, 1H), 3.02-2.87 (m, 2H), 2.73 (d, J = 11.0 Hz, 1H), 2.50 (br s, 1H), 2.28-2.18 (m, 2H), 2.15 (t, J = 11.0 Hz, 1H), 1.47 (s, 9H).

| 42B | 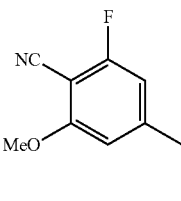 | 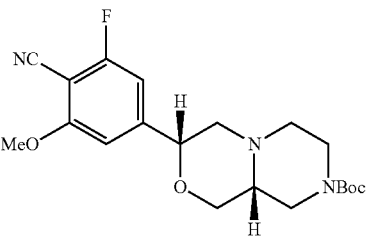 [SMILES: COc1cc([C@@H]2CN3CCN(C(=O)OC(C)(C)C)C[C@@H]3CO2)cc(F)c1C#N] |

Trans and cis isomers were separated by prep SFC with 15% (2:1 MeOH:MeCN)/CO$_2$ on IA column; $^1$H NMR (500 MHz, CDCl$_3$) δ 6.98 (d, J = 9.6 Hz, 1H), 6.96 (s, 1H), 4.79 (s, 1H), 4.02-3.92 (m, 5H), 3.65 (d, J = 10.9 Hz, 1H), 3.40-3.36 (m, 1H), 3.18 (dd, J = 12.2, 3.5 Hz, 1H), 3.00 (br s, 1H), 2.81-2.76 (m, 2H), 2.63-2.45 (m, 3H), 1.47 (s, 9H).

| 42C | 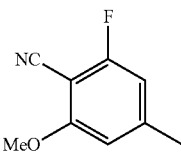 | 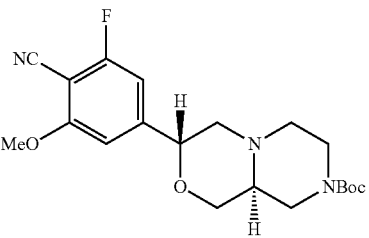 [SMILES: COc1cc([C@@H]2CN3CCN(C(=O)OC(C)(C)C)C[C@H]3CO2)cc(F)c1C#N] |

Trans and cis isomers were separated by prep SFC with 15% (2:1 MeOH:MeCN)/CO$_2$ on IA column. Trans isomer eluted first; $^1$H NMR (500 MHz, CDCl$_3$) δ 6.81 (s, 1H), 6.76 (d, J = 9.1 Hz, 1H), 4.66 (dd, J = 10.4, 2.1 Hz, 1H), 4.12-3.92 (m, 6H), 3.45 (t, J = 10.6 Hz, 1H), 3.02-2.87 (m, 2H), 2.73 (d, J = 11.0 Hz, 1H), 2.50 (br s, 1H), 2.28-2.18 (m, 2H), 2.16 (t, J = 11.0 Hz, 1H), 1.48 (s, 9H).

TABLE 1-continued

| INTER-MEDIATE | Epoxide starting intermediate | INTERMEDIATE structure Characterization or separation notes |
|---|---|---|
| 42D | | 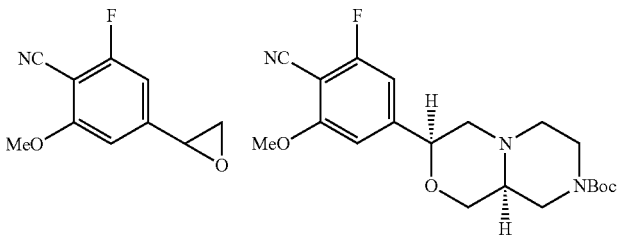 |

Trans and cis isomers were separated by prep SFC with 15% (2:1 MeOH:MeCN)/$CO_2$ on IA column. Trans isomer eluted first; $^1$H NMR (500 MHz, $CDCl_3$) δ 6.98 (d, J = 9.6 Hz, 1H), 6.96 (s, 1H), 4.79 (s, 1H), 4.02-3.92 (m, 5H), 3.65 (d, J = 10.9 Hz, 1H), 3.40-3.36 (m, 1H), 3.18 (dd, J = 12.2, 3.5 Hz, 1H), 3.00 (br s, 1H), 2.81-2.76 (m, 2H), 2.63-2.45 (m, 3H), 1.48 (s, 9H).

| | | |
|---|---|---|
| 43B | | 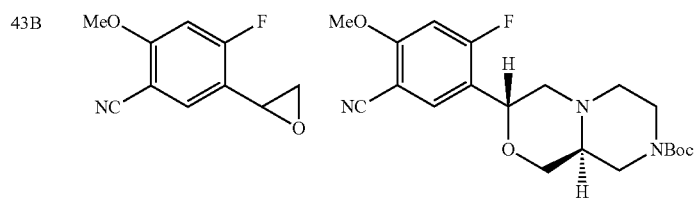 |

Trans and cis were resolved by AD column, 30 × 250 mm, 20% 2:1 MeOH:MeCN/CO2, 70 ml/min, 100 bar, 250 mg/ml in MeOH/MeCN, 35° C., 230 nm;
$^1$H-NMR (500 MHz, $CDCl_3$) δ ppm 7.75 (d, J = 7.5 Hz, 1H), 6.67 (d, J = 11.5 Hz, 1H), 4.88 (d, J = 10 Hz, 1H), 3.94 (s, 3H), 3.49-3.45 (m, 2H), 2.94-2.91 (m, 2H), 2.75-2.73 (m, 1H), 2.28-2.23 (m, 4H), 2.17-2.13 (m, 2H), 1.5 (s, 9H).

Intermediate 44A (R,S)

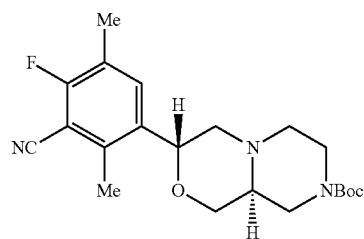 [SMILES: Cc1cc([C@@H]2CN3CCN(C(=O)OC(C)(C)C)C[C@H]3CO2)c(C)c(C#N)c1F]

(3R,9aS)-tert-butyl 3-(3-cyano-4-fluoro-2,5-dimethylphenyl)hexahydropyrazino[2,1-c][1,4]oxazine-8(1H)-carboxylate

Step A: 2-fluoro-3-iodo-6-methyl-5-((3R,9aS)-octahydropyrazino[2,1-c][1,4]oxazin-3-yl)benzonitrile 6-fluoro-2-methyl-3-((3R,9aS)-octahydropyrazino[2,1-c][1,4]oxazin-3-yl)benzonitrile (600 mg, 2.18 mmol) was dissolved in triflic acid (5.80 mL, 65.4 mmol), and NIS (1226 mg, 5.45 mmol) was added at 0° C. The reaction mixture was stirred at rt overnight and quenched into ice water and basified with 5 N NaOH. The aqueous layer was extracted with DCM. The organic layer was washed with aqueous $NaS_2O_3$, $NaHCO_3$, brine, dried and evaporated to give crude title compound, which was used without further purification. LC/MS: $[(M+1)]^+$=402.1;

Step B: (3R,9aS)-tert-butyl 3-(3-cyano-4-fluoro-5-iodo-2-methylphenyl)hexahydropyrazino[2,1-c][1,4]oxazine-8(1H)-carboxylate To 2-fluoro-3-iodo-6-methyl-5-((3R,9aS)-octahydropyrazino[2,1-c][1,4]oxazin-3-yl)benzonitrile (340 mg, 0.847 mmol) in DCM (5.6 mL) was added Hunig's Base (0.30 mL, 1.7 mmol) and $(Boc)_2O$ (0.24 mL, 1.02 mmol). After 30 min, the reaction mixture was concentrated, and the crude product was purified by column chromatography (0-10% MeOH/DCM) to give title compound.

Step C: (3R,9aS)-tert-butyl 3-(3-cyano-4-fluoro-2,5-dimethylphenyl)hexahydropyrazino[2,1-c][1,4]oxazine-8(1H)-carboxylate To a vial was charged with (3R,9aS)-tert-butyl 3-(3-cyano-4-fluoro-5-iodo-2-methylphenyl)hexahydropyrazino[2,1-c][1,4]oxazine-8(1H)-carboxylate (50 mg, 0.10 mmol), $MeBF_3K$ (24 mg, 0.20 mmol), $Pd(OAc)_2$ (2.2 mg, 0.01 mmol), Ru-Phos (9.3 mg, 0.02 mmol), and $Cs_2CO_3$ (97 mg, 0.3 mmol). The vial was sealed, vacuumed, and refilled with $N_2$. $PhMe/H_2O$ (0.5/0.05 mL) was added, and the reaction mixture was heated at 80° C. overnight. The reaction mixture was diluted with water, extracted with EtOAc, washed with brined and dried. The crude product was purified with prep-TLC (5% MeOH/DCM) to give title compound: LC/MS: $[(M+1-56)]^+$=334.3.

Intermediate 44C(S,R)

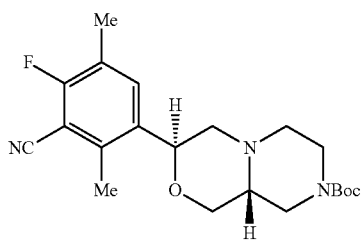 [SMILES: Cc1cc([C@H]2CN3CCN(C(=O)OC(C)(C)C)C[C@@H]3CO2)c(C)c(C#N)c1F]

(3S,9aR)-tert-butyl 3-(3-cyano-4-fluoro-2,5-dimethylphenyl)hexahydropyrazino[2,1-c][1,4]oxazine-8(1H)-carboxylate The title compound was prepared in an analogous fashion to that described for the synthesis of (3R,9aS)-tert-butyl 3-(3-cyano-4-fluoro-2,5-dimethylphenyl)hexahydropyrazino[2,1-c][1,4]oxazine-8(1H)-carboxylate starting from 6-fluoro-2-methyl-3-((3S,9aR)-octahydropyrazino[2,1-c][1,4]oxazin-3-yl)benzonitrile.

LC/MS: [(M+1-56)]⁺=334.3.

Intermediate 44D (R,R)

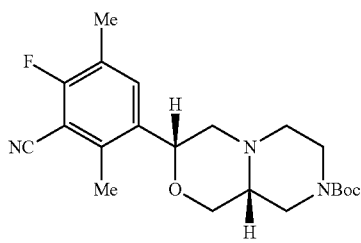 [SMILES: Cc1cc([C@@H]2CN3CCN(C(=O)OC(C)(C)C)C[C@@H]3CO2)c(C)c(C#N)c1F]

(3R,9aR)-tert-butyl 3-(3-cyano-4-fluoro-2,5-dimethylphenyl)hexahydropyrazino[2,1-c][1,4]oxazine-8(1H)-carboxylate (3R,9aR)-tert-Butyl 3-(3-cyano-4-fluoro-2,5-dimethylphenyl)hexahydropyrazino[2,1-c][1,4]oxazine-8(1H)-carboxylate was prepared in an analogous fashion to that described for the synthesis of (3R,9aS)-tert-butyl 3-(3-cyano-4-fluoro-2,5-dimethylphenyl)hexahydropyrazino[2,1-c][1,4]oxazine-8(1H)-carboxylate starting from 6-fluoro-2-methyl-3-((3R,9aR)-octahydropyrazino[2,1-c][1,4]oxazin-3-yl)benzonitrile.

LC/MS: [(M+1-56)]⁺=334.3.

Intermediate 45A (Trans)

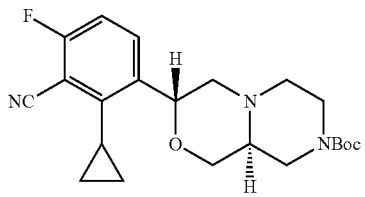 [SMILES: CC(C)(C)OC(=O)N1CCN2C[C@@H](c3ccc(F)c(C#N)c3C3CC3)OC[C@@H]2C1]

(3R,9aS)-tert-butyl 3-(3-cyano-2-cyclopropyl-4-fluorophenyl)hexahydropyrazino[2,1-c][1,4]oxazine-8(1H)-carboxylate To a microwave vial was charged with (3R,9aS)-tert-butyl 3-(2-chloro-3-cyano-4-fluorophenyl)hexahydropyrazino[2,1-c][1,4]oxazine-8(1H)-carboxylate (30 mg, 0.076 mmol), potassium cyclopropyltrifluoroborate (16.8 mg, 0.114 mmol), Pd(OAc)₂ (1.7 mg, 7.58 μmol), X-Phos (7.2 mg, 0.015 mmol), and potassium carbonate (31.4 mg, 0.227 mmol). CPME (0.4 mL) and Water (40 μL) were added, and the reaction mixture was degassed with N₂ and heated at 100° C. for 24 h. The reaction mixture was filtered to give the crude product, which was purified by prep-TLC (1000 μm, 5% MeOH/DCM) to give the title compound: LC/MS: [(M+1-56)]⁺=346.3.

Intermediate 45B (Cis)

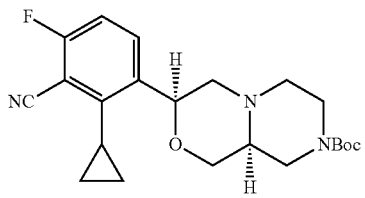 [SMILES: CC(C)(C)OC(=O)N1CCN2C[C@H](c3ccc(F)c(C#N)c3C3CC3)OC[C@@H]2C1]

(3S,9aS)-tert-butyl 3-(3-cyano-2-cyclopropyl-4-fluorophenyl)hexahydropyrazino[2,1-c][1,4]oxazine-8(1H)-carboxylate The title compound was prepared in an analogous fashion to Intermediate 52A starting from (3S,9aS)-tert-butyl 3-(2-chloro-3-cyano-4-fluorophenyl)hexahydropyrazino[2,1-c][1,4]oxazine-8(1H)-carboxylate: LC/MS: [(M+1-56)]= 346.3.

Intermediates 46 (Mixture of Four Isomers, Separated to Mixture of Two Cis and Two Trans Isomers and Further Separated to Two Single Cis and Two Single Trans Isomers)

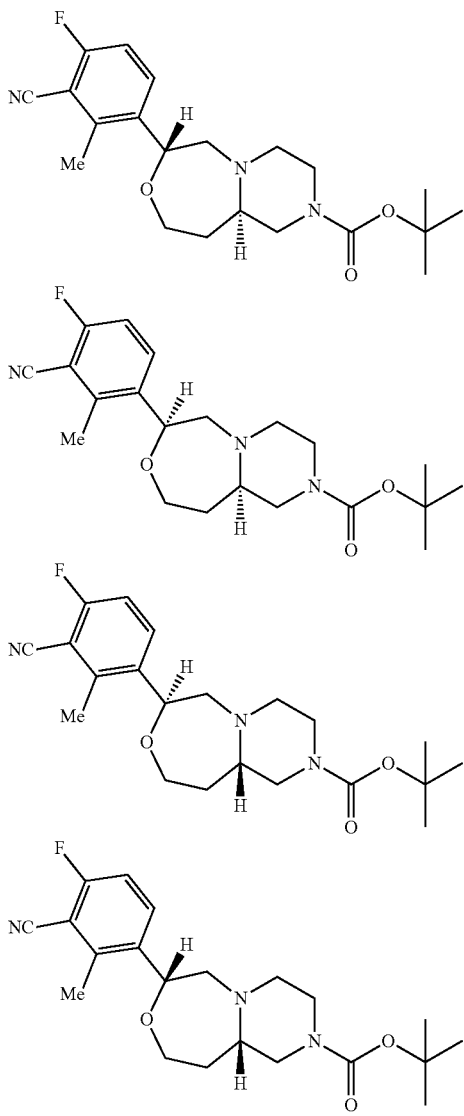 [SMILES: Cc1c([C@@H]2CN3CCN(C(=O)OC(C)(C)C)C[C@H]3CCO2)ccc(F)c1C#N ; Cc1c([C@H]2CN3CCN(C(=O)OC(C)(C)C)C[C@H]3CCO2)ccc(F)c1C#N ; Cc1c([C@H]2CN3CCN(C(=O)OC(C)(C)C)C[C@@H]3CCO2)ccc(F)c1C#N ; Cc1c([C@@H]2CN3CCN(C(=O)OC(C)(C)C)C[C@@H]3CCO2)ccc(F)c1C#N]

tert-butyl (7R,10aR)-7-(3-cyano-4-fluoro-2-methylphenyl)octahydro-2H-pyrazino[1,2-d][1,4]oxazepine-2-carboxylate, tert-butyl (7S,10aR)-7-(3-cyano-4-fluoro-2-methylphenyl)octahydro-2H-pyrazino[1,2-d][1,4]oxazepine-2-carboxylate, tert-butyl (7S,10aS)-7-(3-cyano-4-fluoro-2-methylphenyl)octahydro-2H-pyrazino[1,2-d][1,4]oxazepine-2-carboxylate, and tert-butyl (7R,10aS)-7-(3-cyano-4-fluoro-2-methylphenyl)octahydro-2H-pyrazino[1,2-d][1,4]oxazepine-2-carboxylate

Step A: tert-butyl 4-(2-(3-cyano-4-fluoro-2-methylphenyl)-2-oxoethyl)-3-(2-hydroxyethyl)piperazine-1-carboxylate 3-(2-Bromoacetyl)-6-fluoro-2-methylbenzonitrile (prepared as described above, 5.11 g, 20.0 mmol) was dissolved in THF (100 mL), then known, commercially available compound tert-butyl 3-(2-hydroxyethyl)piperazine-1-carboxylate (4.60 g, 20.0 mmol) was added, followed by Hunig's base (6.96 mL, 39.9 mmol) and the mixture was stirred overnight. The reaction mixed was poured into brine and extracted with ethyl acetate (twice), dried over Na$_2$SO$_4$, filtered and concentrated. The product was purified by MPLC chromatography using a 330 g ISCO Redi Sep column and 5% MeOH/DCM solvent system-to yield tert-butyl 4-(2-(3-cyano-4-fluoro-2-methylphenyl)-2-oxoethyl)-3-(2-hydroxyethyl)piperazine-1-carboxylate: LC-MS (IE, m/z): 406 [M+1]$^+$;

Step B: tert-butyl 4-(2-(3-cyano-4-fluoro-2-methylphenyl)-2-hydroxyethyl)-3-(2-hydroxyethyl)piperazine-1-carboxylate tert-Butyl 4-(2-(3-cyano-4-fluoro-2-methylphenyl)-2-oxoethyl)-3-(2-hydroxyethyl)piperazine-1-carboxylate (3.81 g, 9.40 mmol) and dissolved in EtOH (60 mL) then NaBH$_4$ (1.42 g, 37.6 mmol) was added and the mixture was stirred for 3 h. The ethanol was evaporated and brine was added then extracted with ethyl acetate twice. The organic layer was dried over sodium sulfate, filtered and concentrated. The crude product was purified by MPLC chromatography using a 330 g ISCO Redi-sep column with 5% MeOH/DCM solvent system to yield tert-butyl 4-(2-(3-cyano-4-fluoro-2-methylphenyl)-2-hydroxyethyl)-3-(2-hydroxyethyl)piperazine-1-carboxylate: LC-MS (IE, m/z): 408 [M+1]$^+$;

Step C: tert-butyl 7-(3-cyano-4-fluoro-2-methylphenyl)-hexahydro-1H-pyrazino[1,2-d][1,4]oxazepine-2 (9H)-carboxylate tert-Butyl 4-(2-(3-cyano-4-fluoro-2-methylphenyl)-2-hydroxyethyl)-3-(2-hydroxyethyl)piperazine-1-carboxylate (2.61 g, 6.41 mmol) and dissolved in benzene (60 mL) and added cyanomethylene tributyl phosphorane (2.78 g, 11.5 mmol). The mixture was placed into four separate 20 mL microwave tubes then heated at 100° C. overnight. The reaction mixtures were combined, concentrated then purified by MPLC chromatography using a 330 g ISCO Redi-Sep column and 5% acetone-95% DCM solvent system. Under these purification conditions was separated tert-butyl 7-(3-cyano-4-fluoro-2-methylphenyl)-hexahydro-1H-pyrazino[1,2-d][1,4]oxazepine-2(9H)-carboxylate cis diastereomers from the trans diastereomers LC-MS (IE, m/z): 334 [(M-56)+1]$^+$; The cis-diastereomers were further separated to S,R and R,S diastereomers using the following conditions: Chiral IC column: 30×250 mm, 20% MeOH:/CO2, 70 mL/min, 100 bar, 50 mg/ml in MeOH, 35° C., 330 nm: cis-diastereomer A: $^1$H-NMR (600 MHz, CDCl3) δ ppm 7.88 (dd, J=8.7, 6.2 Hz, 1H), 7.04 (t, J=8.6 Hz, 1H), 4.83 (s, 1H), 4.03 (d, J=12.9 Hz, 1H), 3.86 (t, J=11.3 Hz, 1H), 3.79-3.96 (b, 2H), 2.93 (q, 2H), 2.83 (b, 1H), 2.56-2.63 (m, 4H), 2.53 (s, 3H), 1.78-1.87 (m, 2H), 1.49 (s, 9H).

LC-MS (IE, m/z): 334 [(M-56)+1]$^+$; cis-diastereomer B: $^1$H-NMR (600 MHz, CDCl3) δ ppm 7.88 (dd, J=8.7, 6.1 Hz, 1H), 7.04 (t, J=8.45 Hz, 1H), 4.83 (t, J=3.55 Hz, 1H), 4.04 (t, J=3.3 Hz, 0.5H), 4.02 (t, J=3.3 Hz, 0.5H), 3.81-3.95 (b, 2H), 3.86 (t, J=11.45 Hz, 1H), 2.93 (q, 2H), 2.82 (b, 1H), 2.54-2.63 (m, 4H), 2.53 (s, 3H), 1.78-1.87 (m, 2H), 1.46 (s, 9H). The trans diastereomers were further separated to the S,S and R,R diastereomers using the following conditions: Chiralcel OD-H, 21×250 mm, 7% MeOH+0.2% DEA/CO$_2$, 50 mL/min, 50 mg/ml in 1:1 MeOH/DCM, 220 mm, 40° C. trans-diastereomer A: $^1$H-NMR (600 MHz, CDCl3) δ ppm 7.63-7.67 (m, 1H), 6.98-7.02 (m, 1H), 4.94 (b, 1H), 4.00-4.04 (m, 1H), 3.93-3.96 (m, 1H), 3.75-3.93 (b, 2H), 2.96 (b, 1H), 2.60-2.76 (m, 3H), 2.56 (s, 0.5H), 2.53 (b, 0.5H), 2.52 (s, 3H), 2.36 (b, 2H), 1.95-1.98 (m, 1H), 1.86-1.89 (m, 1H), 1.46 (s, 9H): LC-MS (IE, m/z): 334 [(M-100)+1]$^+$; trans-diastereomer 5B: $^1$H-NMR (600 MHz, CDCl3) δ ppm 7.67 (dd, J=9.6 Hz, 1H), 7.02 (t, J=8.55 Hz, 1H), 4.96 (d, J=8.8 Hz, 1H), 4.02-4.06 (m, 1H), 3.95-3.99 (m, 1H), 3.76-3.90 (b, 2H), 2.98 (b, 1H), 2.73 (dd, J=14.4, 9.05 Hz, 2H), 2.65-2.70 (m, 1H), 2.57 (d, J=14.3 Hz, 1H), 2.55 (s, 3H), 2.36-2.40 (m, 2H), 1.96-2.01 (m, 1H), 1.87-1.92 (m, 1H), 1.46 (s, 9H): LC-MS (IE, m/z): 334 [(M-100)+1]$^+$.

Intermediate 47

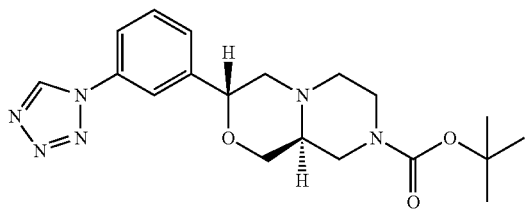 [SMILES: CC(C)(C)OC(=O)N1CCN2C[C@@H](c3cccc(-n4cnnn4)c3)OC[C@@H]2C1]

tert-butyl (3R,9aS)-3-[3-(1H-tetrazol-1-yl)phenyl] hexahydropyrazino[2,1-c][1,4]oxazine-8(1H)-carboxylate Step A: (S)-tert-butyl 3-(hydroxymethyl)-4-(2-(3-nitrophenyl)-2-oxoethyl)piperazine-1-carboxylate 2-Bromo-1-(3-nitrophenyl)ethanone (1.01 g, 4.14 mmol) was dissolved in THF (20 mL) and added (S)-tert-butyl 3-(hydroxymethyl)piperazine-1-carboxylate (1.074 g, 4.97 mmol) followed by Hunig's base (1.45 mL, 8.28 mmol) then stirred at room temperature overnight. The reaction was poured into water and extracted with ETOAC (2×). The organic layer was separated, dried over Na$_2$SO$_4$, filtered and concentrated. The product was purified by chromatography through a 120 g ISCO Redi-sep column eluting with 0-70% ethyl acetate/hexane to yield the title compound.

Step B: (9aS)-tert-butyl 3-(3-nitrophenyl)hexahydropyrazino[2,1-c][1,4]oxazine-8(1H)-carboxylate (S)-tert-butyl 3-(hydroxymethyl)-4-(2-(3-nitrophenyl)-2-oxoethyl)piperazine-1-carboxylate (1.5 g, 3.95 mmol) was dissolved in mixture of DCM (10 mL)/TFA (5 ml) then added triethylsilane (3.16 mL, 19.8 mmol) and stirred at room temperature overnight. The reaction mixture was concentrated. The residue was dissolved in DCM (15 mL) with saturated aqueous NaHCO3 (15 ml) and di-tert-butyl dicarbonate (2.157 g, 9.88 mmol) was added then stirred for 2 hrs. The reaction was extracted with DCM (2×). The combined DCM was washed with brine, dried over Na2SO4, filtered and evaporated to dryness. The product was chromatographed through 120 g ISCO Redi-sep column and eluted with 10-70% ethyl acetate/hexane to yield the title compound; the product was almost exclusively the trans isomer.
LC-MS (IE, m/z): 364 [M+1]$^+$ Step C: (9aS)-tert-butyl 3-(3-aminophenyl)hexahydropyrazino[2,1-c][1,4]oxazine-8(1H)-carboxylate (9aS)-tert-Butyl 3-(3-nitrophenyl)hexahydropyrazino[2,1-c][1,4]oxazine-8(1H)-carboxylate (1.37 g, 3.77 mmol, mostly trans isomer) was dissolved in ethyl acetate (30 mL) then added 10% Pd/C (0.1 g, 0.940 mmol). The mixture was stirred under a balloon of hydrogen overnight. The reaction mixture was filtered and concentrated to yield (9aS)-tert-butyl 3-aminophenyl)hexahydropyrazino[2,1-c][1,4]oxazine-8(1H)-carboxylate (trans isomer).

Step D: tert-butyl (3R,9aS)-3-[3-(1H-tetrazol-1-yl) phenyl]hexahydropyrazino[2,1-c][1,4]oxazine-8 (1H)-carboxylate (9aS)-tert-Butyl 3-(3-aminophenyl) hexahydropyrazino[2,1-c][1,4]oxazine-8(1H)-carboxylate (1.27 g, 3.81 mmol, trans isomer), sodium azide (0.446 g, 6.86 mmol) and triethyl orthoformate (1.27 mL, 7.62 mmol) were stirred in acetic acid (15 mL) then refluxed for 3 hrs. The reaction was concentrated and taken up with ethyl acetate then washed with NaHCO3, dried over Na2SO4, filtered and concentrated. The product was purified by chromatography through a 120 g ISCO Redi-sep column eluting with 2.5% MeOH/DCM to yield the title compound: LC-MS (IE, m/z): 387 [M+1]; $^1$H-NMR (600 MHz, CDCl3) δ ppm 9.008 (s, 1H), 7.752 (s, 1H), 7.653 (d, J=8 Hz, 1H), 7.566 (t, J=7.8 Hz, 1H), 7.488 (d, J=7.70 Hz, 1H), 4.768 (dd, J=10.8, 1.8 Hz, 1H), 4.009 (b, 1H), 3.982 (dd, J=11.1, 3.2 Hz, 2H), 3.488 (t, J=10.8 Hz, 1H), 3.013 (b, 1H), 2.971 (dd, J=11.7, 2.2 Hz, 1H), 2.748 (d, J=10.1 Hz, 1H), 2.529 (b, 1H), 2.297-2.231 (m, 3H), 1.481 (s, 9H).

Intermediates 48A and 48B

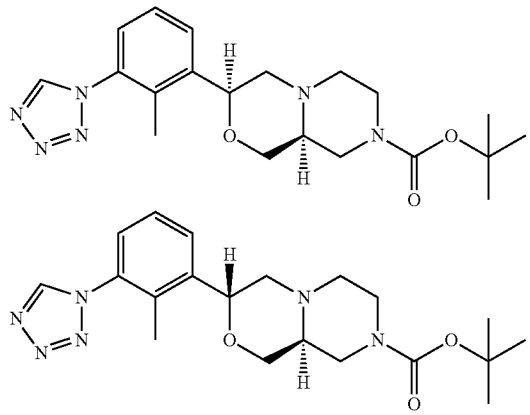

(3S,9aS)-tert-butyl 3-(2-methyl-3-(1H-tetrazol-1-yl) phenyl)hexahydropyrazino[2,1-c][1,4]oxazine-8 (1H)-carboxylate and (3R,9aS)-tert-butyl 3-(2-methyl-3-(1H-tetrazol-1-yl)phenyl)hexahydropyrazino [2,1-c][1,4]oxazine-8(1H)-carboxylate Step A: 2-methyl-1-nitro-3-vinylbenzene 1-Bromo-2-methyl-3-nitrobenzene (5.00 g, 23.1 mmol), potassium trifluoro(vinyl)borate (5.00 g, 37.3 mmol)), TEA (6.45 mL, 46.3 mmol) and PdCl2(dppf)-CH2Cl2Adduct (0.945 g, 1.157 mmol) were added to ethanol (75 mL). The mixture was degassed and then reflux for 3 hrs. The reaction was poured into brine and extracted with ETOAc. The organic layer was separated, dried over Na2SO4, filtered then concentrated. The residue was purified by chromatography on a 330 g ISCO Redi-Sep column using ethyl acetate/hexane solvent system to yield 2-methyl-1-nitro-3-vinylbenzene.

Step B: 2-(2-methyl-3-nitrophenyl)oxirane

2-Methyl-1-nitro-3-vinylbenzene (2 g, 12.26 mmol) was dissolved in DCM (50 ml) then cooled to 0° C. and added mCPBA (3.17 g, 14.14 mmol) then stirred at room temperature for 16 hrs. When TLC showed starting materials, more mCPBA (1.58 g, 7.07 mmol) was added. The reaction was stirred for another 16 hrs. The reaction was washed with saturated aqueous Na2S2O3, NaHCO3, brine; then dried over Na2SO4, filtered and concentrated. The residue was purified by chromatography through a 120 g ISCO Redi-Sep column eluting with 0-20% ETOAc/hexane to yield the title compound.

Step C: (3S)-tert-butyl 4-(2-hydroxy-2-(2-methyl-3-nitrophenyl)ethyl)-3-(hydroxymethyl)piperazine-1-carboxylate 2-(2-Methyl-3-nitrophenyl)oxirane (1.47 g, 8.20 mmol) was dissolved in EtOH (10 mL) then added (S)-4N—BOC-2-hydroxymethyl-piperazine (3.19 g, 14.77 mmol) and microwaved at 140° C. for 1 hr. Solvent was evaporated and the residue was purified by chromatography through a 120 g ISCO Redi-Sep column eluting with 0-20% ethyl acetate: hexane to yield the title compound: LC-MS (IE, m/z): 396 [M+1];

Step D: (9aS)-tert-butyl 3-(2-methyl-3-nitrophenyl) hexahydropyrazino[2,1-c][1,4]oxazine-8(1H)-carboxylate (3S)-tert-Butyl 4-(2-hydroxy-2-(2-methyl-3-nitrophenyl) ethyl)-3-(hydroxymethyl)piperazine-1-carboxylate (2.15 g, 5.44 mmol) was dissolved in benzene (30 mL) then added cyanomethylenetribuylphosphorane (2.362 g, 9.79 mmol). The mixture was degassed then heated to 100° C. overnight. After cooling, the benzene was evaporated off and the residue was purified by chromatography through a 330 g ISCO Redi-sep column eluting with 5-10% acetone: methylene chloride to yield the title compound: LC-MS (IE, m/z): 378 [M+1]$^+$ Step E: (9aS)-tert-butyl 3-(3-amino-2-methylphenyl) hexahydropyrazino[2,1-c][1,4]oxazine-8(1H)-carboxylate 9aS)-tert-Butyl 3-(2-methyl-3-nitrophenyl)hexahydropyrazino[2,1-c][1,4]oxazine-8(1H)-carboxylate (1.45 g, 3.84 mmol) was dissolved in EtOAc (30 ml) then added 10% Pd/C (0.409 g) and stirred under a balloon of hydrogen overnight. The catalyst was filtered off and solvent evaporated to yield the title compound. LC-MS (IE, m/z): 348 [M+1]$^+$ Step F: (9aS)-tert-butyl 3-(2-methyl-3-(1H-tetrazol-1-yl)phenyl)hexahydropyrazino[2,1-c][1,4]oxazine-8 (1H)-carboxylate (9aS)-tert-Butyl 3-(3-amino-2-methylphenyl) hexahydropyrazino[2,1-c][1,4]oxazine-8(1H)-carboxylate (1.12 g, 3.22 mmol) in acetic acid (15 ml) was added sodium azide (0.377 g, 5.80 mmol) and triethyl orthoformate (1.07 mL, 6.45 mmol) then refluxed for 3 h. The reaction was concentrated and taken up with EtOAc then washed with sat; d NaHCO3. The organic layer was dried over Na2SO4, filtered and evaporated to dryness to yield diastereomer mixture of the title compound. LC-MS (IE, m/z): 401 [M+1]$^+$ Step G: (3S,9aS)-tert-butyl 3-(2-methyl-3-(1H-tetrazol-1-yl)phenyl)hexahydropyrazino[2,1-c][1,4]oxazine-8(1H)-carboxylate and (3R,9aS)-tert-butyl 3-(2-methyl-3-(1H-tetrazol-1-yl)phenyl)hexahydropyrazino[2,1-c][1,4]oxazine-8(1H)-carboxylate The diastereomers were separated by SFC-HPLC on a Chiralpak AD column (20×250 mm, 25% MeOH at 50 ml/min, 100 mg/ml in MeOH, UV=220 nm, 35° C.) to yield the separated cis and trans isomers: (3S,9aS)-tert-butyl 3-(2-methyl-3-(1H-tetrazol-1-yl)phenyl)hexahydropyrazino[2,1-c][1,4]oxazine-8(1H)-carboxylate: $^1$H-NMR (500 MHz, CDCl3) δ ppm 8.783 (s, 1H), 8.297 (d, J=7.80 Hz, 1H), 7.407 (t, J=7.80 Hz, 1H), 7.265 (d, J=7.60 Hz, 1H), 4.973 (t, J=3.65 Hz, 1H), 3.955 (b, 2H), 3.592 (dd, J=11.1, 2.5 Hz, 1H), 3.377 (t, J=8.1 Hz, 1H), 3.232 (dd, J=12.0, 3.5 Hz, 1H), 3.081 (b, 1H), 2.803 (dd, J=12.25, 4.0 Hz, 2H), 2.755 (b, 1H), 2.516 (m, 2H), 2.137 (s, 3H), 1.49 (s, 9H);

(3R,9aS)-tert-butyl 3-(2-methyl-3-(1H-tetrazol-1-yl) phenyl)hexahydropyrazino[2,1-c][1,4]oxazine-8 (1H)-carboxylate $^1$H-NMR (500 MHz, CDCl3) δ ppm 8.764 (s, 1H), 7.77 (d, J=7.90 Hz, 1H), 7.432 (t, J=7.80 Hz, 1H), 7.246 (d, J=7.80 Hz, 1H), 4.910 (d, J=9.0 Hz, 1H), 4.099 (b, 2H), 3.995 (dd, J=11.25, 3.1 Hz, 1H), 3.513 (t, J=10.2 Hz, 1H), 3.027 (b, 1H), 2.916 (dd J=11.75, 1.6 Hz, 1H), 2.745 (d, J=10.7 Hz, 1H), 2.54 (b, 1H), 2.223-2.333 (m, 3H), 2.109 (s, 3H), 1.49 (s, 9H).

Intermediate 49A

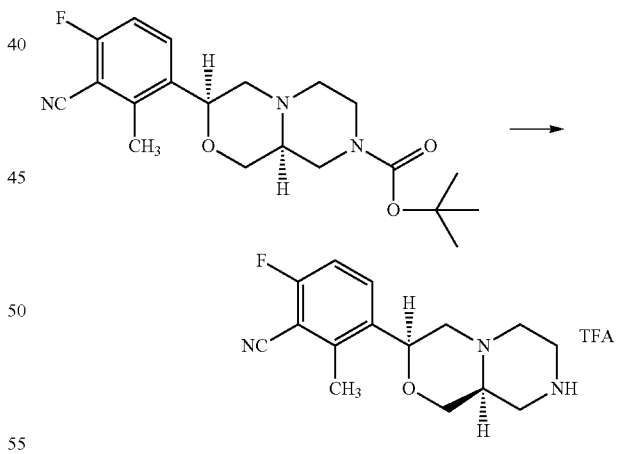

6-fluoro-2-methyl-3-[(3S,9aS)-octahydropyrazino[2, 1-c][1,4]oxazin-3-yl]benzonitrile 2,2,2-trifluoroacetate tert-Butyl (3S,9aS)-3-(3-cyano-4-fluoro-2-methylphenyl) hexahydropyrazino[2,1-c][1,4]oxazine-8(1H)-carboxylate (1.88 g, 5.01 mmol) was treated with 10 mL TFA at RT for 1 h. The TFA was then removed under reduced pressure to yield the title compound. LC-MS: M+1=276: $^1$H-NMR (600 MHz, DMSO) δ ppm 7.954 (dd, J=8.7, 6.25 Hz, 1H), 7.412 (t, J=8.85 Hz, 1H), 4.939 (dd, J=8.4, 2.75 Hz, 1H), 3.848 (d, J=11.8 Hz, 1H), 3.762 (b, 1H), 3.189-3.536 (m, 8H), 3.072 (d, J=12 Hz, 1H), 2.485 (s, 3H).

Hz, 1H), 2.984-3.089 (m, 3H), 2.715 (t, J=11.37 Hz, 1H), 2.639 (t, J=10 Hz, 1H), 2.50 (s, 3H), 2.46 (b, 1H), 2.337 (t. J=10.9 Hz, 1H).

Intermediate 49B

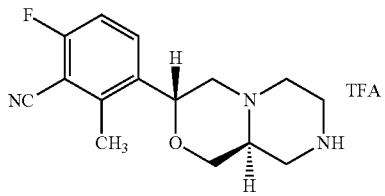 [SMILES: Cc1c([C@@H]2CN3CCNC[C@H]3CO2)ccc(F)c1C#N]

6-fluoro-2-methyl-3-[(3R,9aS)-octahydropyrazino[2,1-c][1,4]oxazin-3-yl]benzonitrile 2,2,2-trifluoroacetate tert-Butyl (3R,9aS)-3-(3-cyano-4-fluoro-2-methylphenyl)hexahydropyrazino[2,1-c][1,4]oxazine-8(1H)-carboxylate (1.73 g, 4.61 mmol) was treated with 10 mL TFA at RT for 1 h. The trifluoroacetic acid was then removed under reduced pressure to yield the title compound. LC-MS: M+1=276: $^1$H-NMR (600 MHz, DMSO) δ ppm 7.724 (dd, J=9.0, 6.2 Hz, 1H), 7.353 (t, J=8.85 Hz, 1H), 4.738 (d, J=10.3 Hz, 1H), 3.924 (d, J=11.10 Hz, 1H), 3.386 (t, J=11.65 Hz, 1H), 3.285 (d, J=12.3 Hz, 1H), 3.20 (d, J=11.8 Hz, 1H), 3.01 (b, 1H), 2.934 (d, J=111.6 Hz, 1H), 2.884 (d, J=11.0 Hz, 1H), 2.642 (b, 1H), 2.476 (s, 3H), 2.47 (b, 1H), 2.329-2.367 (m, 1H), 2.054-2.089 (m, 1H).

Intermediate 49C-1 (Method 1)

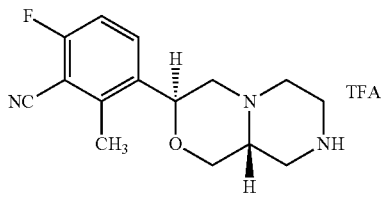 [SMILES: Cc1c([C@H]2CN3CCNC[C@@H]3CO2)ccc(F)c1C#N]

6-fluoro-2-methyl-3-[(3S,9aS)-octahydropyrazino[2,1-c][1,4]oxazin-3-yl]benzonitrile 2,2,2-trifluoroacetate (3S,9aR)-tert-Butyl 3-(3-cyano-4-fluoro-2-methylphenyl)hexahydropyrazino[2,1-c][1,4]oxazine-8(1H)-carboxylate (3.00 g, 7.99 mmol) was dissolved in TFA (10 mL) and stirred for 1 hr. The trifluoroacetic acid was removed under reduced pressure and azeotroped with dichloroethane (3×) then was dried over high vacuum to yield the title compound: LC-MS (IE, m/z): 276 [M+1]$^+$; $^1$H-NMR (500 MHz, DMSO) δ ppm 7.755 (dd, J=8.75, 6.2 Hz, 1H), 7.38 (t, J=8.85 Hz, 1H), 4.80 (d, J=10.1 Hz, 1H), 3.98 (dd, J=11.25, 2.5 Hz, 1H), 3.456 (t, J=10.7 Hz, 1H), 3.354 (d, J=12.6 Hz, 1H), 3.273 (d, J=11.8

Intermediate 49C-2 (Method 2)

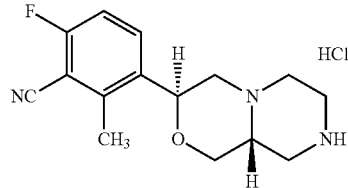

6-fluoro-2-methyl-3-[(3S,9aR)-octahydropyrazino[2,1-c][1,4]oxazin-3-yl]benzonitrile hydrochloride (3S,9aR)-tert-Butyl 3-(3-cyano-4-fluoro-2-methylphenyl)hexahydropyrazino[2,1-c][1,4]oxazine-8(1H)-carboxylate (158.8 g, 423.0 mmol) was suspended with 318 mL of 2-propanol. The resulting slurry was treated with HCl solution in 2-propanol (5.5 M, 1000 mL, 5499 mmol), and the mixture was heated to 50° C. for 2 hours. The mixture was concentrated to remove approximately 400 mL of 2-propanol, then was cooled to rt and agitated overnight. The mixture was filtered to collect the solid product and the wet cake was washed with 50 mL of 2-propanol. The filter cake was dried under vacuum for two days at 40° C. with nitrogen bleed to afford the title compound.

Intermediate 49D

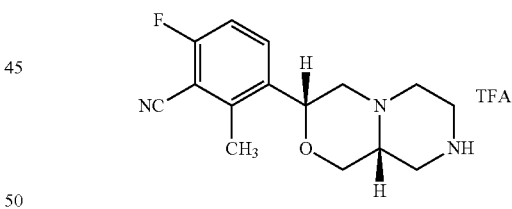

6-fluoro-2-methyl-3-[(3R,9aR)-octahydropyrazino[2,1-c][1,4]oxazin-3-yl]benzonitrile 2,2,2-trifluoroacetate (3R,9aR)-tert-Butyl 3-(3-cyano-4-fluoro-2-methylphenyl)hexahydropyrazino[2,1-c][1,4]oxazine-8(1H)-carboxylate (1.09 g, 2.90 mmol) was stirred in trifluoroacetic acid (10 mL) for 1 h then concentrated and azeotroped with dichloroethane (3×) to yield the title compound. LC-MS (IE, m/z): 276 [M+1]$^+$; $^1$H-NMR (500 MHz, DMSO) δ ppm 7.989 (t, J=6.4 Hz, 1H), 7.416 (t, J=8.85 Hz, 1H), 4.959 (dd, J=7.75, 2.35 Hz, 1H), 3.855 (d, J=11.9 Hz, 1H), 3.755 (b, 1H), 3.236-3.54 (m, 8H), 3.066 (d, J=11.5 Hz, 1H), 2.50 (s, 3H).

Intermediate 50A

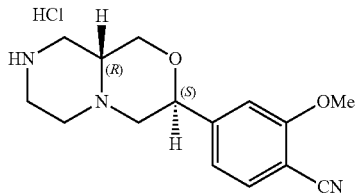

2-Methoxy-4-[(3S,9aR)-octahydropyrazino[2,1-c][1,4]oxazin-3-yl]benzonitrile hydrochloride tert-Butyl (3S,9aR)-3-(4-cyano-3-methoxyphenyl)hexahydropyrazino[2,1-c][1,4]oxazine-8(1H)-carboxylate (520 mg, 1.39 mmol) was dissolved in 10 Ml of 4 M HCl in dioxane and stirred at room temperature for 8 h. The mixture was concentrated to ¼ the original volume and diluted with 10 Ml of diethyl ether. The precipitate was filtered and dried under high vacuum to offer the title amine HCl salt: $^1$H NMR (DMSO-$d_6$, E (trans) isomer, 500 MHz) δ 7.76 (d, J=8.0 Hz, 1H), 7.25 (s, 1H), 7.11 (d, J=7.9 Hz, 1H), 5.0 (bs, 1H), 4.17 (bs, 1H), 3.94 (s, 3H), 3.85-3.60 (bs, 2H), 3.62-3.34 (m, 6H), 1.69 (bs, 2H); LC/MS: (IE, m/z) [M+1]$^+$=274.

Intermediate 50B

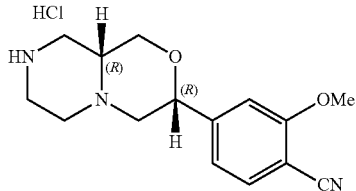

2-Methoxy-4-[(3R,9aR)-octahydropyrazino[2,1-c][1,4]oxazin-3-yl]benzonitrile hydrochloride tert-Butyl (3R,9aR)-3-(4-cyano-3-methoxyphenyl)hexahydropyrazino[2,1-c][1,4]oxazine-8(1H)-carboxylate (120 mg, 0.321 mmol) was dissolved in 10 Ml of 4 M HCl in dioxane and stirred at room temperature for 8 h. The mixture was concentrated to ¼ the original volume and diluted with 10 Ml of diethyl ether. The precipitate was filtered and dried under high vacuum to offer amine HCl salt: NMR (DMSO-$d_6$, Z (cis) isomer, 500 MHz) δ 7.77 (d, J=7.9 Hz, 1H), 7.32 (s, 1H), 7.19 (d, J=7.9 Hz, 1H), 4.95 (bs, 1H), 4.08 (bs, 2H), 3.96 (s, 3H), 3.85-3.60 (bs, 3H), 3.58-3.34 (m, 6H); LC/MS: (IE, m/z) [M+1]$^+$=274.

Intermediate 50C

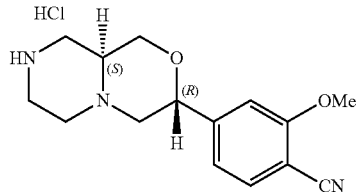

2-Methoxy-4-[(3R,9aS)-octahydropyrazino[2,1-c][1,4]oxazin-3-yl]benzonitrile hydrochloride tert-Butyl (3R,9aS)-3-(4-cyano-3-methoxyphenyl)hexahydropyrazino[2,1-c][1,4]oxazine-8(1H)-carboxylate (90.0 mg, 0.241 mmol) was dissolved in 5 mL of 4 M HCl in dioxane and stirred at room temperature for 8 h. The mixture was concentrated to ¼ the original volume and diluted with 10 mL of diethyl ether. The precipitate was filtered and dried under high vacuum to offer amine HCl salt: $^1$H NMR (DMSO-$d_6$, E (trans) isomer, 500 MHz) δ 7.68 (d, J=8.0 Hz, 1H), 7.19 (s, 1H), 7.07 (d, J=8.0 Hz, 1H), 4.65 (dd, J=1.8 Hz, J=1.6 Hz, 1H), 3.91 (s, 3H), 3.82 (dd, J=3.0 Hz, 1H), 3.32-3.27 (m, 2H), 2.87-2.62 (m, 5H), 2.24-1.98 (m, 3H); LC/MS: (IE, m/z) [M+1]$^+$=274.

Intermediate 50D

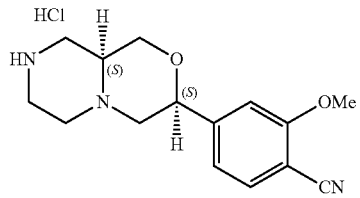

2-Methoxy-4-[(3S,9aS)-octahydropyrazino[2,1-c][1,4]oxazin-3-yl]benzonitrile hydrochloride tert-Butyl (3S,9aS)-3-(4-cyano-3-methoxyphenyl)hexahydropyrazino[2,1-c][1,4]oxazine-8(1H)-carboxylate (38.0 mg, 0.102 mmol) was dissolved in 10 mL of 4 M HCl in dioxane and stirred at room temperature for 8 h. The mixture was concentrated to ¼ the original volume and diluted with 5 mL of diethyl ether. The precipitate was filtered and dried under high vacuum to offer amine HCl salt: $^1$H NMR (DMSO-$d_6$, Z (cis) isomer, 500 MHz) δ 7.77 (d, J=7.9 Hz, 1H), 7.32 (s, 1H), 7.19 (d, J=7.9 Hz, 1H), 4.95 (bs, 1H), 4.08 (bs, 2H), 3.96 (s, 3H), 3.85-3.60 (bs, 3H), 3.58-3.34 (m, 6H); LC/MS: (IE, m/z) [M+1]$^+$=274.

The intermediates shown in Table 2 below were prepared in an analogous fashion to that described for the syntheses of Intermediates 49A: 6-fluoro-2-methyl-3-[(3S,9aS)-octahydropyrazino[2,1-c][1,4]oxazin-3-yl]benzonitrile 2,2,2-trifluoroacetate, and 50D: 2-methoxy-4-[(3S,9aS)-octahydropyrazino[2,1-c][1,4]oxazin-3-yl]benzonitrile hydrochloride, using either HCl or TFA to remove the Boc protective group present in the corresponding Boc-piperazine precursor (the acid used in the reaction and the mass spec data are provided below each structure in Table 2). It is understood that the resulting intermediates may be TFA or HCl salts, or they may be obtained as free base amines by routine partitioning of the product with an organic solvent and a basic aqueous solution such as saturated sodium bicarbonate solution and concentration of the resulting organic solution.

TABLE 2

| INTERMEDIATE #, conditions | Structure of INTERMEDIATE and MS characterization |
|---|---|
| 51A TFA | MS (M + H)+ 275 |
| 52B TFA | MS (M + H)+ 275 |
| 53A TFA | MS (M + H)+ 289 |
| 53B TFA | MS (M + H)+ 289 |
| 53C TFA | MS (M + H)+ 289 |
| 53D TFA | MS (M + H)+ 289 |
| 54A HCl | MS (M + H)+ 303 |
| 54B HCl | MS (M + H)+ 303 |
| 54C HCl | |
| 54D HCl | |

TABLE 2-continued

| INTERMEDIATE #, conditions | Structure of INTERMEDIATE and MS characterization |
|---|---|
| 54E HCl | |
| 54F HCl | |
| 54G HCl | MS (M + H)+ 303 |
| 54H HCl | MS (M + H)+ 303 |
| 55B TFA | MS (M + H)+ 353, 355 |
| 55A TFA | MS (M + H)+ 309 |
| 55B TFA | MS (M + H)+ 309 |
| 56A TFA | |
| 56B HCl | |
| 56B2 HCl | |

TABLE 2-continued

| INTERMEDIATE #, conditions | Structure of INTERMEDIATE and MS characterization |
|---|---|
| 57A TFA | 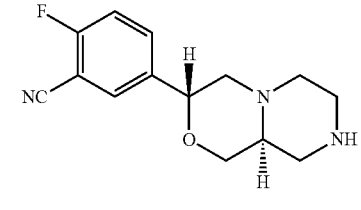 [SMILES: N#Cc1cc([C@@H]2CN3CCNC[C@H]3CO2)ccc1F]  MS (M + H)⁺ 303 |
| 57B TFA | MS (M + H)⁺ 303 |
| 57C TFA | MS (M + H)⁺ 303 |
| 57D TFA | MS (M + H)⁺ 303 |

TABLE 2-continued

| INTERMEDIATE #, conditions | Structure of INTERMEDIATE and MS characterization |
|---|---|
| 58A TFA | 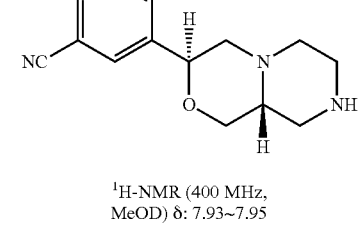  MS (M + H)⁺ 262 |
| 58C HCl | ¹H-NMR (400 MHz, MeOD) δ: 7.93~7.95 (m, 1H), 7.84~7.87 (m, 1H), 7.42 (t, J = 8.0 Hz, 1H), 4.95~4.99 (m, 1H), 4.06~4.15 (m, 2H), 3.75~3.80 (m, 3H), 3.51~3.62 (m, 5H), 3.41 (d, J = 6.0 Hz, 1H). |
| 58D, HCl | ¹H-NMR (400 MHz, MeOD) δ: 7.84~7.86 (m, 1H), 7.77~7.81 (m, 1H), 7.40 (t, J = 8.0 Hz, 1H), 5.02~5.07 (m, 1H), 4.20~4.23 (m, 1H), 3.89~3.93 (m, 1H), 3.55~3.63 (m, 6H), 3.33~3.34 (m, 1H), 3.19~3.24 (m, 1H), 3.01~3.12 (m, 1H). |
| 59B TFA | LC/MS: [(M + 1)]⁺ = 292 |

TABLE 2-continued
| INTER-MEDIATE #, conditions | Structure of INTERMEDIATE and MS characterization |
|---|---|
| 60 TFA | 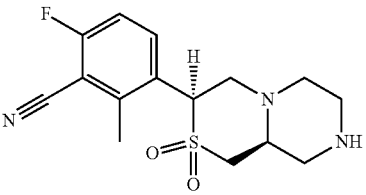 [SMILES: Cc1c([C@H]2CN3CCNC[C@H]3CS2(=O)=O)ccc(F)c1C#N] LC/MS: [(M + 1)]⁺ = 324 |
| 61A TFA | 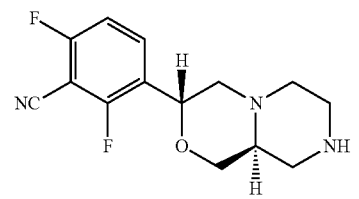 [SMILES: N#Cc1c(F)ccc([C@@H]2CN3CCNC[C@H]3CO2)c1F] LC/MS: [(M + 1)]⁺ = 280 |
| 61B TFA | 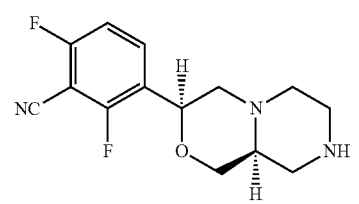 [SMILES: N#Cc1c(F)ccc([C@H]2CN3CCNC[C@H]3CO2)c1F] LC/MS: [(M + 1)]⁺ = 280 |
| 61C TFA | 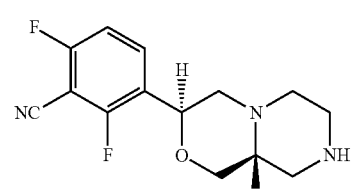 LC/MS: [(M + 1)]⁺ = 280 |
| 61D TFA | 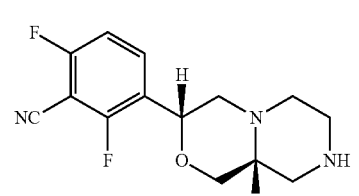 LC/MS: [(M + 1)]⁺ = 280 |
| 62A HCl | 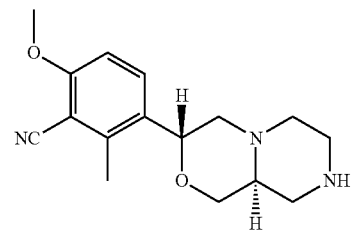 [SMILES: COc1ccc([C@@H]2CN3CCNC[C@H]3CO2)c(C)c1C#N] LC/MS: [(M + 1)]⁺ = 288 |
| 62B HCl | 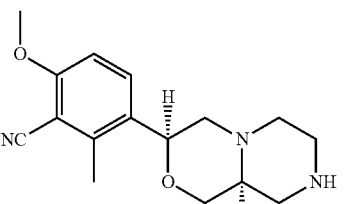 LC/MS: [(M + 1)]⁺ = 288 |
| 63B TFA | 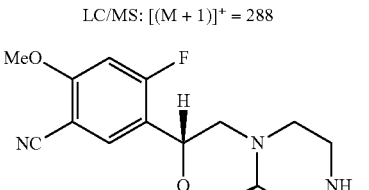 LC/MS: [(M + 1)]⁺ = 292 |
| 63C TFA | 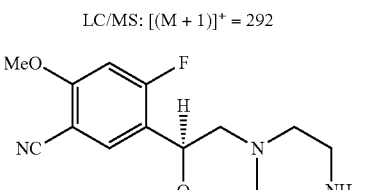 LC/MS: [(M + 1)]⁺ = 292 |
| 64A TFA | 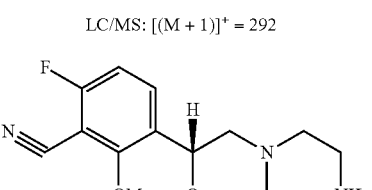 LC/MS: [(M + 1)]⁺ = 292 |
| 64B TFA | 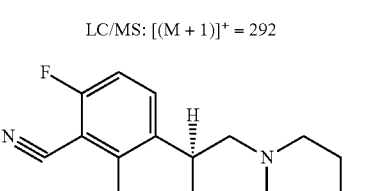 LC/MS: [(M + 1)]⁺ = 292 |
| 65A TFA | 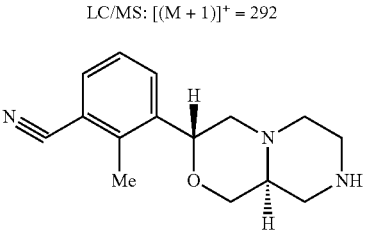 LC/MS: [(M + 1)]⁺ = 258 |

TABLE 2-continued
| INTERMEDIATE #, conditions | Structure of INTERMEDIATE and MS characterization |
|---|---|
| 66B TFA | 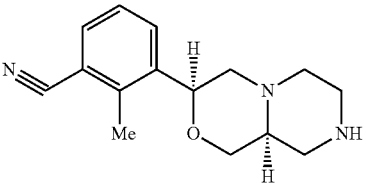 [SMILES: Cc1c(C#N)cccc1[C@H]1CN2CCNC[C@H]2CO1] LC/MS: [(M + 1)]⁺ = 258 |
| 66D HCl | 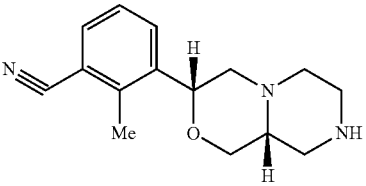 [SMILES: Cc1c(C#N)cccc1[C@@H]1CN2CCNC[C@@H]2CO1] LC/MS: [(M + 1)]⁺ = 258 |
| 67A TFA | 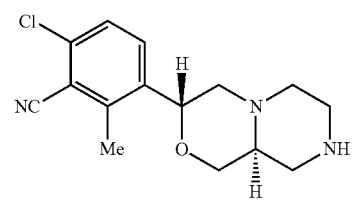 [SMILES: Cc1c([C@@H]2CN3CCNC[C@H]3CO2)ccc(Cl)c1C#N] LC/MS: [(M + 1)]⁺ = 292 |
| 67B TFA | 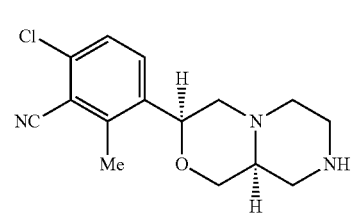 [SMILES: Cc1c([C@H]2CN3CCNC[C@H]3CO2)ccc(Cl)c1C#N] LC/MS: [(M + 1)]⁺ = 292 |
| 68A TFA | 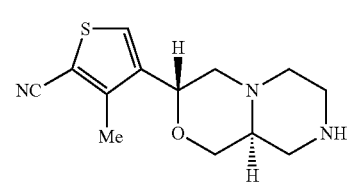 [SMILES: Cc1c([C@@H]2CN3CCNC[C@H]3CO2)csc1C#N] LC/MS: [(M + 1)]⁺ = 264 |
| 68B TFA | 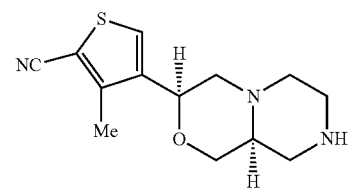 [SMILES: Cc1c([C@H]2CN3CCNC[C@H]3CO2)csc1C#N] LC/MS: [(M + 1)]⁺ = 264 |
| 69A TFA | 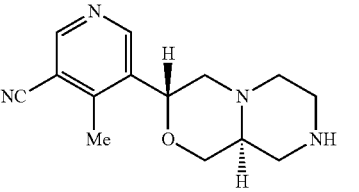 [SMILES: Cc1c(C#N)cncc1[C@@H]1CN2CCNC[C@H]2CO1] LC/MS: [(M + 1)]⁺ = 259 |
| 70A TFA | 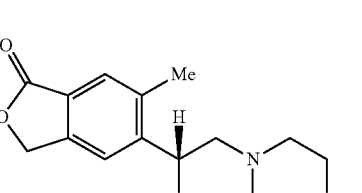 LC/MS: [(M + 1)]⁺ = 289 |
| 70B | 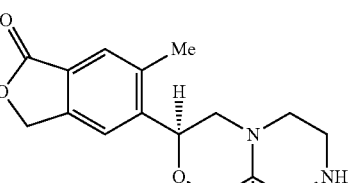 LC/MS: [(M + 1)]⁺ = 289 |
| 71A TFA | 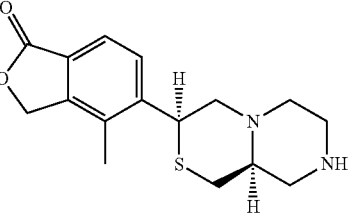 LC/MS: [(M + 1)]⁺ = 305 |
| 71B TFA | 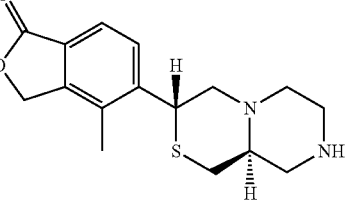 LC/MS: [(M + 1)]⁺ = 305 |

TABLE 2-continued
| INTERMEDIATE #, conditions | Structure of INTERMEDIATE and MS characterization |
|---|---|
| 72A TFA | 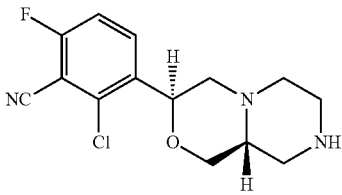 [SMILES: N#Cc1c(F)ccc([C@H]2CN3CCNC[C@H]3CO2)c1Cl]<br>LC/MS: [(M + 1)]⁺ = 296 |
| 72B TFA | 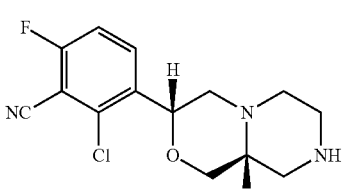<br>LC/MS: [(M + 1)]⁺ = 296 |
| 72C TFA | 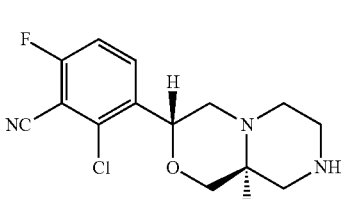<br>LC/MS: [(M + 1)]⁺ = 296 |
| 72D TFA | 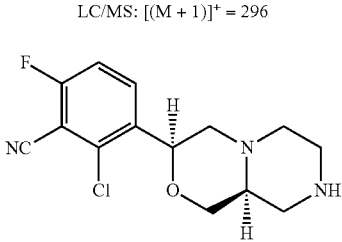<br>LC/MS: [(M + 1)]⁺ = 296 |
| 73 TFA | 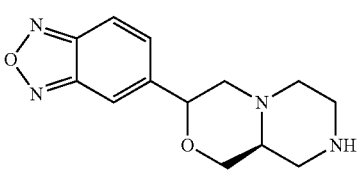<br>LC/MS: [(M + 1)]⁺ = 261 |
| 74A TFA | 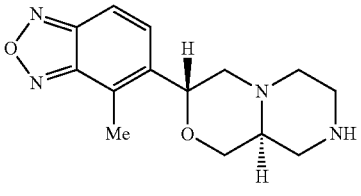 [SMILES: Cc1c([C@@H]2CN3CCNC[C@H]3CO2)ccc2nonc12]<br>LC/MS: [(M + 1)]⁺ = 275 |
| 74B TFA | 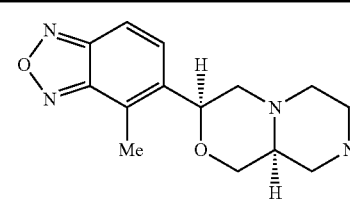<br>LC/MS: [(M + 1)]⁺ = 275 |
| 75A TFA | 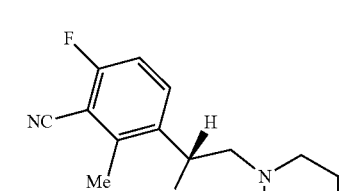<br>LC/MS: [(M + 1)]⁺ = 290 |
| 75B TFA | 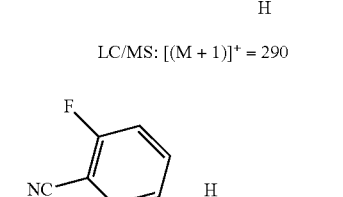<br>LC/MS: [(M + 1)]⁺ = 290 |
| 75C TFA | 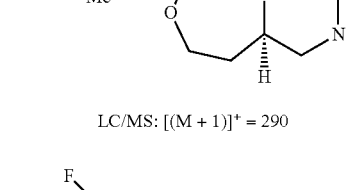<br>LC/MS: [(M + 1)]⁺ = 290 |
| 75D TFA | 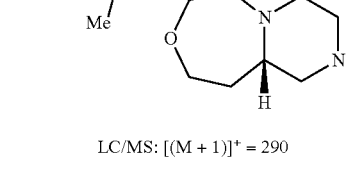<br>LC/MS: [(M + 1)]⁺ = 290 |

TABLE 2-continued
| INTERMEDIATE #, conditions | Structure of INTERMEDIATE and MS characterization |
|---|---|
| 76A TFA | 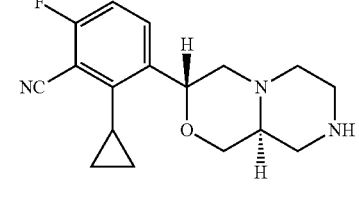 LC/MS: [(M + 1)]⁺ = 302.4 |
| 76B TFA | LC/MS: [(M + 1)]⁺ = 302.4 |
| 77A HCl | LC/MS: [(M + 1)]⁺ = 276 |
| 78A HCl | LC/MS: [(M + 1)]⁺ = 262 |
| 78B HCl | LC/MS: [(M + 1)]⁺ = 262 |
| 79A TFA | LC/MS: [(M + 1)]⁺ = 280 |
| 79B TFA | LC/MS: [(M + 1)]⁺ = 280 |
| 79C TFA | LC/MS: [(M + 1)]⁺ = 280 |
| 79D TFA | LC/MS: [(M + 1)]⁺ = 280 |
| 80A TFA | LC/MS: [(M + 1)]⁺ = 292 |
| 80B TFA | LC/MS: [(M + 1)]⁺ = 292 |

TABLE 2-continued

| INTERMEDIATE #, conditions | Structure of INTERMEDIATE and MS characterization |
|---|---|
| 80C TFA | 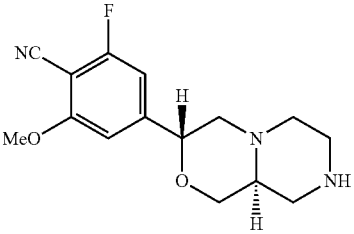 [SMILES: COc1cc([C@@H]2CN3CCNC[C@H]3CO2)cc(F)c1C#N]<br>LC/MS: [(M + 1)]⁺ = 292 |
| 80D TFA | 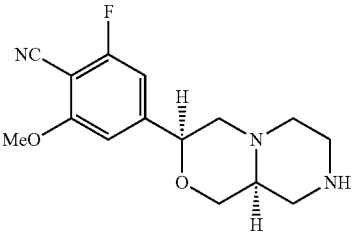 [SMILES: COc1cc([C@H]2CN3CCNC[C@H]3CO2)cc(F)c1C#N]<br>LC/MS: [(M + 1)]⁺ = 292 |
| 81A TFA | 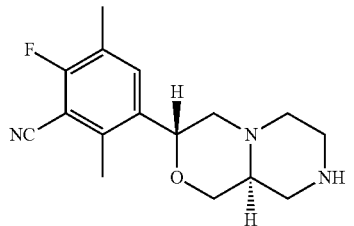 [SMILES: Cc1cc([C@@H]2CN3CCNC[C@H]3CO2)c(C)c(C#N)c1F]<br>LC/MS: [(M + 1)]⁺ = 290 |
| 81C TFA | 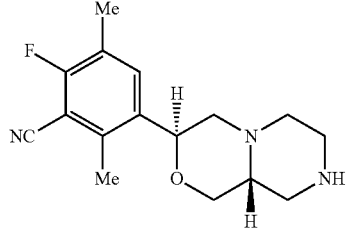 [SMILES: Cc1cc([C@H]2CN3CCNC[C@@H]3CO2)c(C)c(C#N)c1F]<br>LC/MS: [(M + 1)]⁺ = 290 |
| 81D TFA | 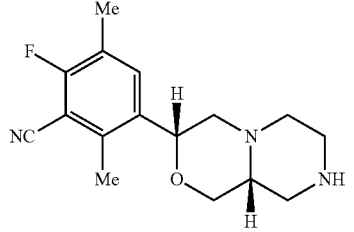 [SMILES: Cc1cc([C@@H]2CN3CCNC[C@@H]3CO2)c(C)c(C#N)c1F]<br>LC/MS: [(M + 1)]⁺ = 290 |

TABLE 2-continued

| INTERMEDIATE #, conditions | Structure of INTERMEDIATE and MS characterization |
|---|---|
| 82 TFA | 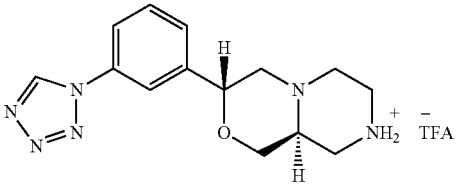<br>LC-MS: 287 [M + 1]⁺ |
| 83B TFA | 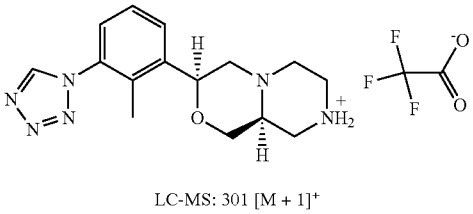<br>LC-MS: 301 [M + 1]⁺ |
| 83A TFA | 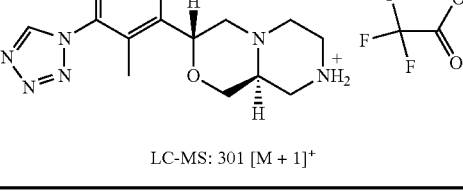<br>LC-MS: 301 [M + 1]⁺ |

Intermediate 84A

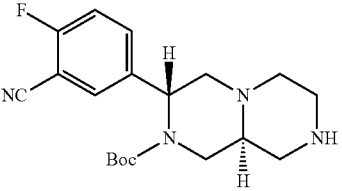 [SMILES: CC(C)(C)OC(=O)N1C[C@@H]2CNCCN2C[C@H]1c1ccc(F)c(C#N)c1]

(3R,9aS)-tert-butyl 3-(3-cyano-4-fluorophenyl) hexahydro-1H-pyrazino[1,2-a]pyrazine-2(6H)-carboxylate (3R,9aS)-tert-butyl 3-(3-cyano-4-fluorophenyl)hexahydro-1H-pyrazino[1,2-a]pyrazine-2(6H)-carboxylate was synthesized following the procedure of (3R,9aS)-tert-butyl 3-((R)-3-methyl-1-oxoisochroman-6-yl)hexahydro-1H-pyrazino[1,2-a]pyrazine-2(6H)-carboxylate starting from 5-bromo-2-fluorobenzonitrile: LC/MS: (M+1)⁺: 361.17.

Intermediate 85

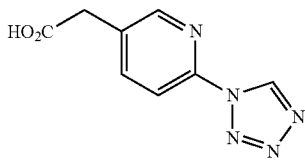 [SMILES: O=C(O)Cc1ccc(-n2cnnn2)nc1]

[6-(1H-tetrazol-1-yl)pyridin-3-yl]acetic acid

Step A: 5-chloro-2-nitropyridine

To concentrated $H_2SO_4$ (50 mL) was added 30% $H_2O_2$ (25 mL) at 0° C. and a solution of 5-chloropyridin-2-amine (5.0 g, 39 mmol) in concentrated $H_2SO_4$ (20 mL) was added at 0° C. The mixture was stirred for 20 hours at room temperature. The mixture was poured into ice water under vigorously stirring and the resulting solid was filtered. The solid was recrystallized from ethanol to give 5-chloro-2-nitropyridine: MS m/z 159 (M+1)$^+$.

Step B: tert-butyl ethyl (6-nitropyridin-3-yl)propanedioate

To a suspension of NaH (60% in oil, 0.650 g, 16.4 mmol) in DMF (40 mL) was added tert-butyl ethyl propanedioate (2.8 g, 15.1 mmol) at room temperature. The mixture was stirred for 30 min. A solution of 5-chloro-2-nitropyridine (2.00 g, 12.6 mmol) in DMF (10 mL) was added. The mixture was heated to 80° C. and stirred for 4 hours. The solvent was removed under reduce pressure. Water was added and the mixture was extracted with EtOAc. The combined organic layer was washed with brine, dried over anhydrous $Na_2SO_4$, concentrated and the residue was purified by column chromatography with silica gel to give tert-butyl ethyl (6-nitropyridin-3-yl)propanedioate.

Step C: ethyl (6-nitropyridin-3-yl)acetate

A mixture of tert-butyl ethyl (6-nitropyridin-3-yl)propanedioate (1.4 g, 4.5 mmol) in a mixed solution of TFA/DCM (10 mL/10 mL) was stirred for 5 hours at room temperature. The mixture was concentrated under reduce pressure. The residue was dissolved with DCM, washed with sat. $NaHCO_3$, dried over anhydrous $Na_2SO_4$ and concentrated to give ethyl (6-nitropyridin-3-yl)acetate.

Step D: ethyl (6-aminopyridin-3-yl)acetate

A mixture of ethyl (6-nitropyridin-3-yl)acetate (0.9 g, 4.28 mmol), Pd/C (10%, 0.1 g) in MeOH (50 mL) was stirred for 2 hours under $H_2$ atmosphere at room temperature. The mixture was filtered and concentrated to give ethyl (6-aminopyridin-3-yl)acetate.

Step E: ethyl[6-(1H-tetrazol-1-yl)pyridin-3-yl]acetate

To a mixture of ethyl (6-aminopyridin-3-yl)acetate (0.55 g, 3.05 mmol), CH(OEt)$_3$ (1.35 g, 9.15 mmol) in AcOH (20 mL) was added NaN$_3$ (0.24 g, 3.7 mmol) at room temperature. The mixture was heated to 80° C. and stirred for 3 hours. The mixture was concentrated under reduce pressure. Water was added, and the mixture was extracted with EtOAc. The combined organic layer was washed with brine, dried over anhydrous $Na_2SO_4$, concentrated and the residue was purified by column chromatography via silica gel to give ethyl[6-(1H-tetrazol-1-yl)pyridin-3-yl]acetate.

Step F: [6-(1H-tetrazol-1-yl)pyridin-3-yl]acetic acid

To a mixture ethyl[6-(1H-tetrazol-1-yl)pyridin-3-yl]acetate (0.42 g, 1.8 mmol) in THF (3 mL) was added 1.4 M LiOH (aq.) (5 mL) at room temperature. The mixture was stirred 3 hours at room temperature. The reaction was acidified with citric acid until Ph about 3~4. The mixture was extracted with EtOAc. The combined organic layer was washed with brine, dried over anhydrous $Na_2SO_4$, concentrated to give [6-(1H-tetrazol-1-yl)pyridin-3-yl]acetic acid: $^1$H-NMR (400 MHz, DMSO) δ 12.62 (s, 1H), 10.16 (s, 1H), 8.54 (s, 1H), 8.01~8.09 (m, 2H), 3.80 (s, 2H).

Intermediate 86

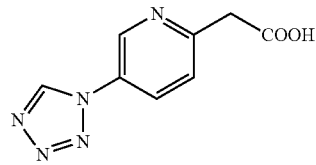 [SMILES: O=C(O)Cc1ccc(-n2cnnn2)cn1]

[5-(1H-tetrazol-1-yl)pyridin-2-yl]acetic acid

Step A: tert-butyl ethyl (5-nitropyridin-2-yl)propanedioate

To a suspension of NaH (60% in oil, 1.89 g, 47 mmol) in 20 mL of DMF was added tert-butyl ethyl propanedioate (6.5 g, 34.7 mmol) at room temperature. The mixture was stirred for 30 min. A solution of 2-chloro-5-nitropyridine (5.0 g, 31.5 mmol) in 10 mL of DMF was added. The mixture was stirred at r.t. overnight. The solvent was removed under reduce pressure. Water was added and the mixture was extracted with EtOAc. The combined organic layer was washed with brine, dried over anhydrous $Na_2SO_4$, concentrated and the residue was purified by column chromatography with silica gel to give tert-butyl ethyl (5-nitropyridin-2-yl)propanedioate: $^1$H-NMR (400 MHz, CDCl3) δ 9.39 (s, 1H), 8.51 (d, J=8.8 Hz, 1H), 7.76 (d, J=8.8 Hz, 1H), 5.00 (s, 1H), 4.28 (q, J=7.2 Hz, 2H), 1.49 (s, 9H), 1.31 (t, J=7.2 Hz, 3H).

Step B: ethyl (5-nitropyridin-2-yl)acetate

A mixture of tert-butyl ethyl (5-nitropyridin-2-yl)propanedioate (4.10 g, 13.2 mmol) in a mixed solution of TFA/DCM (4 mL/20 mL) was stirred for 5 hours at room temperature. The mixture was concentrated under reduce pressure. The residue was dissolved with DCM, washed with sat. $NaHCO_3$, dried over anhydrous $Na_2SO_4$ and concentrated to give title compound. $^1$H-NMR (400 MHz, CDCl$_3$) δ 9.41 (s, 1H), 8.58 (d, J=8.4 Hz, 1H), 7.64 (d, J=8.4 Hz, 1H), 4.16 (q, J=7.2 Hz, 2H), 4.02 (s, 2H), 1.22 (t, J=7.2 Hz, 3H).

Step C: ethyl (5-aminopyridin-2-yl)acetate

A mixture of ethyl (5-nitropyridin-2-yl)acetate (2.40 g, 11.4 mmol), Raney-Ni (50 mg) in 100 mL of MeOH was stirred at room temperature overnight. The mixture was filtered and concentrated to give ethyl (5-aminopyridin-2-yl)acetate.

$^1$H-NMR (400 MHz, CDCl$_3$) δ 8.03 (s, 1H), 7.06 (dd, J=8.4 Hz, 1H), 6.95 (d, J=8.4 Hz, 1H), 4.15 (q, J=7.2 Hz, 2H), 3.71 (s, 2H), 3.65 (br, 2H), 1.24 (t, J=7.2 Hz, 3H).

Step D: ethyl[5-(1H-tetrazol-1-yl)pyridin-2-yl]acetate

To a mixture of ethyl (5-aminopyridin-2-yl)acetate (1.0 g, 5.5 mmol), CH(OEt)$_3$ (1.31 g, 8.80 mmol) in AcOH (10 mL) was added NaN$_3$ (0.54 g, 8.3 mmol) at room temperature. The mixture was heated to 80° C. and stirred for 3 hours. The mixture was concentrated under reduce pressure. Water was added, and the mixture was extracted with EtOAc. The combined organic layer was washed with brine, dried over anhydrous Na$_2$SO$_4$, concentrated and the residue was purified by silica column chromatography to give title compound:
$^1$H-NMR (400 MHz, CDCl$_3$) δ 9.03 (s, 1H), 8.90 (s, 1H), 8.06 (d, J=8.4 Hz, 1H), 7.58 (d, J=8.4 Hz, 1H), 4.21 (q, J=7.2 Hz, 2H), 3.96 (s, 2H), 1.29 (t, J=7.2 Hz, 3H).

Step E: [5-(1H-tetrazol-1-yl)pyridin-2-yl]acetic acid

To a mixture ethyl[5-(1H-tetrazol-1-yl)pyridin-2-yl]acetate (0.19 g, 0.81 mmol) in THF (4 mL) was added 1.4 M LiOH (aq.) (2.9 mL) at room temperature. The mixture was stirred 3 hours at room temperature. The reaction was acidified with citric acid until pH about 3~4. The mixture was extracted with EtOAc. The combined organic layer was washed with brine, dried over anhydrous Na$_2$SO$_4$, concentrated to give [5-(1H-tetrazol-1-yl)pyridin-2-yl]acetic acid:
$^1$H-NMR (400 MHz, MeOD) δ 9.83 (s, 1H), 9.02 (s, 1H), 8.28 (d, J=8.8 Hz, 1H), 7.68 (d, J=8.8 Hz, 1H), 3.95 (s, 2H).

Intermediate 87

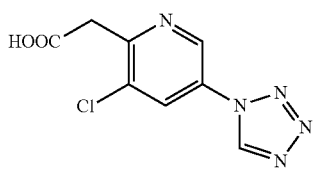 [SMILES: O=C(O)Cc1ncc(-n2cnnn2)cc1Cl]

2-(3-chloro-5-(1H-tetrazol-1-yl)pyridin-2-yl)acetic acid

The title compound was prepared in an analagous fashion to that described for the syntheses of [6-(1H-tetrazol-1-yl)pyridin-3-yl]acetic acid (Steps B-F) and [5-(1H-tetrazol-1-yl)pyridin-2-yl]acetic acid (Steps A-E) starting from 2,3-dichloro-5-nitropyridine. LC/MS: [(M+1-28)]$^+$=212.5.

Intermediate 88

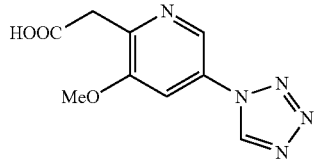 [SMILES: COc1cc(-n2cnnn2)cnc1CC(=O)O]

2-(3-methoxy-5-(1H-tetrazol-1-yl)pyridin-2-yl)acetic acid

The title compound was prepared in an analagous fashion to that described for the syntheses of [6-(1H-tetrazol-1-yl)pyridin-3-yl]acetic acid (Method 1, Steps B-F and [5-(1H-tetrazol-1-yl)pyridin-2-yl]acetic acid (Steps A-E) starting from 2-chloro-3-methoxy-5-nitropyridine. LC/MS: [(M+1-28)]$^+$=208.2.

Intermediate 89

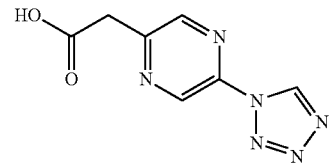 [SMILES: O=C(O)Cc1cnc(-n2cnnn2)cn1]

[5-(1H-tetrazol-1-yl)pyrazin-2-yl]acetic acid

Step A: 5-bromopyrazin-2-amine

To a solution of pyrazin-2-amine (20 g, 210 mmol) in 1.5 L of DCM was added NBS (37.4 g, 210 mmol) at 0° C. The resulting mixture was stirred for 3 hours at 0° C. then filtrated through celite. The filtrate was washed with saturated Na$_2$CO$_3$ and brine, dried over Na$_2$SO$_4$ and evaporated to afford a brown solid. The crude material was purified on silica gel (eluting with 20-40 percent ethyl acetate in hexane) to give 5-bromopyrazin-2-amine.

Step B: 2-bromo-5-[(dimethyl-λ$^4$-sulfanylidene)amino]pyrazine

To a solution of DMSO (11 g, 138 mmol) in 100 mL of DCM was added Tf$_2$O (42 g, 149 mmol) at −70° C. The resulting mixture was stirred at −70° C. for 15 minutes then a solution of 5-bromopyrazin-2-amine (20 g, 115 mmol, in 100 mL of DCM and 50 mL of DMSO) was added dropwise. The mixture was stirred at −60° C. for 3 hours and diluted with 500 mL of DCM and washed with water. The water layer was basified to pH=1 with aq. Na$_2$CO$_3$ and extracted with DCM twice. The combined DCM layer was washed with brine, dried over Na$_2$SO$_4$ and evaporated to afford title compound.

Step C: 2-bromo-5-nitropyrazine

To a solution of mCPBA (85%, 37.4 g, 184.2 mmol) in 1 L of DCM was added a solution of 2-bromo-5-[(dimethyl-λ$^4$- sulfanylidene)amino]pyrazine (26.7 g, 114 mmol) in 800 mL of DCM at 0° C. The resulting mixture was stirred at 0° C. for 45 minutes and 30 mL of DMSO was added. Ozone was bubbled through the mixture for 45 minutes then diluted with 2 L of DCM, washed subsequently with water, aq. $Na_2CO_3$ and brine, dried over $Na_2SO_4$ and evaporated. The crude material was purified on silica gel (eluting with 20 percent ethyl acetate in hexane) to give 2-bromo-5-nitropyrazine.

Step D: tert-butyl ethyl (5-nitropyrazine-2-yl)propanedioate

A suspension of NaH (60%, 3.0 g, 75 mmol) in 100 mL of DMF was added tert-butyl ethyl propanedioate (14.1 g, 75 mmol) dropwise at 25° C. The mixture was stirred at 40° C. for 30 minutes and 2-bromo-5-nitropyrazine (10.2 g, 50 mmol) in 50 mL of DMF was added dropwise. The resulting suspension was stirred at 50° C. for 2 hours and diluted with 500 mL of EtOAc. The mixture was washed with water (100 mL*3), brine, dried over anhydrous $Na_2SO_4$ and concentrated. The residue was purified by column chromatography (petrol ether: EtOAc=5:1) to afford title compound.

Step E: ethyl (5-nitropyrazine-2-yl)acetate

A mixture of tert-butyl ethyl (5-nitropyrazine-2-yl)propanedioate (10.7 g, 34.4 mmol) in 30 mL of TFA and 30 mL DCM was stirred at 35° C. for 3 hours before concentrated to dryness. The residue was dissolved in 200 mL of EtOAc and washed with water (25 mL) and brine (25 mL), dried over anhydrous $Na_2SO_4$ and concentrated to afford ethyl (5-nitropyrazine-2-yl)acetate.

Step F: ethyl[5-(hydroxyamino)pyrazin-2-yl]acetate

A mixture of ethyl (5-nitropyrazine-2-yl)acetate (6.7 g, 31.7 mmol) and Pd/C (1 g, 10%) in 300 mL of EtOAc was stirred at room temperature under hydrogen balloon for 6 hours before filtration. The filtrate was concentrated to afford ethyl[5-(hydroxyamino)pyrazin-2-yl]acetate (incomplete reduction).

Step G: ethyl (5-aminopyrazin-2-yl)acetate

A mixture of ethyl[5-(hydroxyamino)pyrazin-2-yl]acetate (2.8 g, 14.2 mmol) and $Pd(OH)_2$ (3 g, 10%) in 150 mL of methanol was stirred at room temperature under 50 psi of $H_2$ for 2 hours before filtration. The filtrate was concentrated to afford ethyl (5-aminopyrazin-2-yl)acetate.

Step H: ethyl[5-(1H-tetrazol-1-yl)pyrazin-2-yl]acetate

A solution of the ethyl (5-aminopyrazin-2-yl)acetate (2.0 g, 11.0 mmol) and triethyl orthoformate (4.9 g, 33.1 mmol) in 60 mL of HOAc was added sodium azide (0.9 g, 13.8 mmol) and heated to 100° C. for 1 hour. The reaction was completed which was checked by TLC. The reaction mixture was cooled to r.t. The solvent was removed under vacuum. The residue was dissolved in EtOAc, washed with water, dried over anhydrous sodium sulfate, and concentrated. The residue was purified by column chromatograph to afford the product ethyl[5-(1H-tetrazol-1-yl)pyrazin-2-yl]acetate.

Step I: [5-(1H-tetrazol-1-yl)pyrazin-2-yl]acetic acid

A mixture of ethyl[5-(1H-tetrazol-1-yl)pyrazin-2-yl]acetate (2.0 g, 8.5 mmol) in 60 mL of THF/MeOH/$H_2O$ (2:2:1) was added $LiOH.H_2O$ (540 mg, 12.8 mmol) portionwise and stirred for 30 minutes before diluting with 200 mL of water and washing with ether (30 mL×3). The water layer was acidified to pH=4 with diluted HCl and extracted with EtOAc (50 mL×5). The combined organic layer was washed with brine, dried over anhydrous $Na_2SO_4$ and concentrated to afford title compound: $^1$H-NMR (400 MHz, d6-DMSO) δ ppm 12.93 (brs, 1H), 10.22 (s, 1H), 9.25 (d, J=1.2 Hz, 1H), 8.71 (d, J=1.2 Hz, 1H), 3.98 (s, 2H).

Intermediate 90

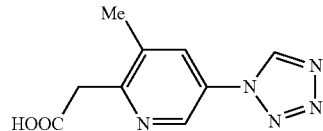 [SMILES: Cc1cc(-n2cnnn2)cnc1CC(=O)O]

[3-methyl-5-(1H-tetrazol-1-yl)pyridin-2-yl]acetic acid

The title compound was prepared in five steps starting from commercially available 2-chloro-3-methyl-5-nitropyridine in an analogous fashion as described for the synthesis of [6-(1H-tetrazol-1-yl)pyridin-3-yl]acetic acid (Method 1, Steps B-F). This compound was more stable stored as the Li salt: LC-MS (IE, m/z): 192 [M+1-N2]$^+$, small peak 220 [M+1]$^+$.

Intermediate 91

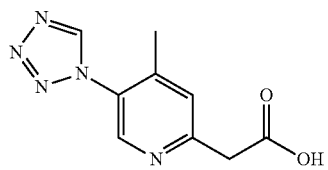 [SMILES: Cc1cc(CC(=O)O)ncc1-n1cnnn1]

2-(4-methyl-5-(1H-tetrazol-1-yl)pyridin-2-yl)acetic acid

Step A: N-(6-bromo-4-methylpyridin-3-yl)pivalamide

6-Bromo-4 methyl-3 pyridinamine (1.03 g, 5.51 mmol) was dissolved in DCM (20 ml) at 0° C. then added Hunig's Base (1.154 ml, 6.61 mmol) followed by pivaloyl chloride (0.745 ml, 6.06 mmol). After stirring for 1 hr, the reaction was not complete. Another equivalent of TEA and pivaloyl chloride were added then stirred for an hour. The reaction was poured into brine and extracted with DCM (2×). The organic layer was separated and dried over Na2SO4, filtered and concentrated. The residue was chromatographed thru a 200 g ISCO redisep column and eluted with 5% MeOH/DCM to yield title compound. LC-MS: M+2=273;

Step B: tert-butyl 2-(4-methyl-5-pivalamidopyridin-2-yl)acetate

N-(6-bromo-4-methylpyridin-3-yl) pivalamide (0.644 g, 2.375 mmol), 2-dicyclohexylphosphino-2',4',6'-triisopropyl-biphenyl X-Phos (0.068 g, 0.143 mmol) and tris(dibenzylideneacetone)dipalladium(0) (0.065 g, 0.071 mmol) were dissolved in tetrahydrofuran (30 ml) then added 2-(tert-butoxy)-2-oxoethylzinc chloride (14.25 ml, 7.13 mmol). The mixture was placed into three tubes and microwaved at 100° C. for 1.5 hr. The reactions were poured into NH4Cl/brine solution and extracted with ETOAc (2×), dried over Na2SO4, filtered and concentrated. The residue was chromatographed through an 80 g ISCO Redi-sep column and eluted with ethyl acetate/hexane 1:2 to yield tert-butyl 2-(4-methyl-5-pivalamidopyridin-2-yl)acetate: LC-MS: M+1=307, 251 (M-56)

Step C: methyl 2-(5-amino-4-methylpyridin-2-yl)acetate

Tert-butyl 2-(4-methyl-5-pivalamidopyridin-2-yl)acetate (0.200 g, 0.653 mmol) was refluxed in hydrochloric acid 6N (10 ml) overnight. The reaction was concentrated then redissolved in MeOH (10 ml) and cooled to 0° C. then added TMS-diazomethane (0.653 ml, 1.305 mmol). When no SM was observed by TLC, the reaction was quenched with glacial acetic acid and concentrated. The residue was taken up with ethyl acetate and washed with NaHCO3. The organic layer was dried over NaSO4, filtered and evaporated to dryness. The residue was purified by chromatography using 40 g ISCO Redisep column and 5% MeOH/DCM solvent system to yield title compound.

Step D: Methyl 2-(4-methyl-5-(1H-tetrazol-1-yl)pyridin-2-yl)acetate

Methyl 2-(5-amino-4-methylpyridin-2-yl)acetate (90 mg, 0.499 mmol) was stirred in acetic acid (3 ml) then added triethyl orthoformate (0.166 ml, 0.999 mmol) and sodium azide (58.4 mg, 0.899 mmol). The mixture was stirred at 80° C. for 3 hrs then diluted with brine and extracted with ethyl acetate. The organic layer was dried over Na2SO4, filtered and evaporated to dryness. The residue was chromatographed thru 40 g ISCO Redi-sep column and eluted with 5% MeOH/DCM to yield methyl 2-(4-methyl-5-(1H-tetrazol-1-yl)pyridin-2-yl)acetate: $^1$H-NMR (500 MHz, CDCl3) δ ppm 8.867 (s, 1H), 8.527 (s, 1H), 7.438 (s, 1H), 3.963 (s, 2H), 3.790 (s, 3H), 2.308 (s, 3H).

Step E: 2-(4-methyl-5-(1H-tetrazol-1-yl)pyridin-2-yl)acetic acid

Lithium hydroxide monohydrate (19.2 mg, 0.458 mmol) was dissolved in 5 mL water then added to a methyl 2-(4-methyl-5-(1H-tetrazol-1-yl)pyridin-2-yl)acetate in tetrahydrofuran (15 mL). The reaction was stirred for 1 h then acidified with 1 N HCl to pH ~3. The mixture was extracted with a mixture of THF/ethyl acetate (4×.). Dried over Na2SO4, filtered and evaporated concentrated to yield 2-(4-methyl-5-(1H-tetrazol-1-yl)pyridin-2-yl)acetic acid.

Intermediate 92

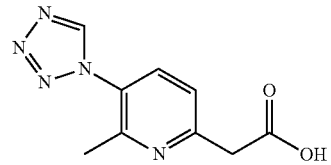 [SMILES: Cc1nc(CC(=O)O)ccc1-n1cnnn1]

2-(6-methyl-5-(1H-tetrazol-1-yl)pyridin-2-yl)acetic acid

Step A: Ethyl 2-(6-methyl-5-nitropyridin-2-yl)acetate tert-Butyl ethyl malonate (4.27 mL, 22.6 mmol) was dissolved in DMF (40 ml) then cooled to 0° C. and added sodium hydride (0.827 g, 20.68 mmol). The mixture was stirred at RT for ½ hr then added 2-bromo-5-nitro-6-picoline (4.08 g, 18.80 mmol) and stirred at 80° C. overnight. The reaction mixture was concentrated and added ice water then extracted with ETOAc (3×). The combined organic layer was washed with brine (2×), dried over NaSO4, filtered and concentrated to yield 1-tert-butyl 3-ethyl 2-(6-methyl-5-nitropyridin-2-yl) malonate. The crude 1-tert-butyl 3-ethyl 2-(6-methyl-5-nitropyridin-2-yl) malonate was stirred in a mixture of DCM (100 ml) and TFA (100 ml) overnight. The reaction mixture was concentrated then took up with DCM and washed with aqueous NaHCO3. The methylene chloride layer was dried over MgSO4, filtered and evaporated to dryness. The residue was purified by MPLC on a 330 g Redi-sep column with 30% ETOAc/hexane to yield ethyl 2-(6-methyl-5-nitropyridin-2-yl)acetate: LC-MS: M+1=225;

Step B: ethyl 2-(5-amino-6-methylpyridin-2-yl)acetate

Ethyl 2-(6-methyl-5-nitropyridin-2-yl)acetate (1.10 g, 4.91 mmol) was dissolved in ethyl acetate and added Pd/C (0.5 g) then stirred under a balloon of hydrogen for 2 hrs. Filtered over catalyst and concentrated to yield ethyl 2-(5-amino-6-methylpyridin-2-yl)acetate: LC-MS: M+1=195;

Step C: Ethyl 2-(6-methyl-5-(1H-tetrazol-1-yl)pyridin-2-yl)acetate

Trimethylsilyl trifluoroacetate (1.010 ml, 5.85 mmol) was added to a suspension of ethyl 2-(5-amino-6-methylpyridin-2-yl)acetate (710 mg, 3.66 mmol) in ethyl acetate (20 ml). The mixture was stirred for 5 mins then added triethyl orthoformate (1.096 ml, 6.58 mmol). Stirred for another 5 mins then added azidotrimethylsilane (0.817 ml, 6.21 mmol). The reaction was stirred overnight. The reaction was poured into brine and extracted with ethyl acetate. The ethyl acetate was separated, dried over Na2SO4, filtered and concentrated. The residue was purified by chromatography through 120 g ISCO Redi-Sep column and eluted with 5% MeOH/DCM to yield ethyl 2-(6-methyl-5-(1H-tetrazol-1-yl)pyridin-2-yl)acetate.

Step D: 2-(6-methyl-5-(1H-tetrazol-1-yl)pyridin-2-yl)acetic acid

Ethyl 2-(6-methyl-5-(1H-tetrazol-1-yl)pyridin-2-yl)acetate (310 mg, 1.25 mmol) was dissolved in THF (6 mL) and water (3 mL). Lithium hydroxide monohydrate (68.31 mg, 1.628 mmol) was added. A small amount of ethanol was also added to ensure the reaction mixture was homogeneous. After 1 hr, the reaction was acidified with 2N HCl to pH ~5-6 then extracted with a mixture of ethyl acetate/THF (2×). The combined organic layer was dried over Na2SO4, filtered and concentrated to yield title compound: $^1$H-NMR (600 MHz, CDCl3) δ ppm 8.975 (s, 1H), 7.738 (d, J=8.1 Hz, 1H), 7.396 (d, J=8.1 Hz, 1H), 3.907 (s, 2H), 2.009 (s, 3H): LC-MS: M+1=220

Intermediate 93

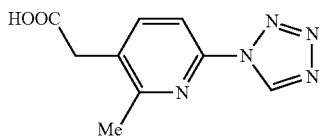 [SMILES: Cc1nc(-n2cnnn2)ccc1CC(=O)O]

[2-methyl-6-(1H-tetrazol-1-yl)pyridin-3-yl]acetic acid

Step A: 5-chloro-6-methylpyridin-2-amine

A solution of 6-methylpyridin-2-amine (10.80 g, 100 mmol) in 50 mL of dry DMF was added a solution of NCS (13.4 g, 100 mmol) in 60 mL of dry DMF dropwise at 0° C. over 20 min. The resulting brown yellow solution was stirred at 0° C. for 1 hour, and at room temperature for 3 hours, then poured to 300 mL of ice-water. The resulting mixture was extracted with EtOAc, washed with water and brine, dried over anhydrous sodium sulfate and concentrated. The residue was purified via column chromatograph to afford 5-chloro-6-methylpyridin-2-amine.

Subsequent steps: [2-methyl-6-(1H-tetrazol-1-yl)pyridin-3-yl]acetic acid

The title compound was prepared from 5-chloro-6-methylpyridin-2-amine in six steps in an analogous fashion to that described for the synthesis of [6-(1H-tetrazol-1-yl)pyridin-3-yl]acetic acid (Method 1, Steps A-F): LC-MS (IE, m/z): 192 [M+1-N2]$^+$, 220 [M+1]$^+$; $^1$H-NMR (400 MHz, CDCl$_3$) δ 9.88 (s, 1H), 7.9 (d, 1H), 7.85 (d, 1H), 3.79 (s, 2H), 2.59 (s, 3H).

Intermediate 94

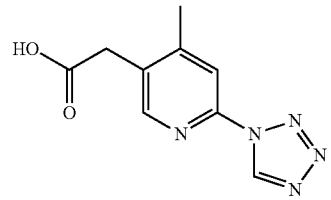 [SMILES: Cc1cc(-n2cnnn2)ncc1CC(=O)O]

[4-Methyl-6-(1H-tetrazol-1-yl)pyridin-3-yl]acetic Acid

Step A: tert-Butyl Ethyl (6-Nitro-4-methylpyridin-3-yl)propanedioate

A dry flask was charged with sodium hydride (60% suspension in mineral oil, 1.29 g, 32.3 mmol) and 100 ml of dry DMF, and cooled to 0° C. followed by dropwise addition of tert-butyl ethyl propanedioate (5.20 g, 27.6 mmol) via syringe. After 30 min at 0° C., a solution of 3-chloro-2,4-difluorobenzonitrile (5.00 g, 23.0 mmol) in DMF (10 ml) was added over a period of 15 minutes. The ice bath was removed and the reaction mixture was subjected to heating at 80° C. in an oil bath for 12 hrs. The mixture was cooled to RT, quenched with saturated ammonium chloride, and partitioned between water and ethyl acetate. The organic layer was concentrated and the resulting title compound was used directly in the next step: LC-MS (IE, m/z): 295 [M+1]+.

Step B: Ethyl (4-Methyl-6-nitropyridin-3-yl)acetate tert-Butyl ethyl (6-nitro-4-methylpyridin-3-yl)propanedioate (7.4 g, 22.8 mmol) was dissolved in DCM (100 mL) and treated with trifluoromethanesulfonic acid (25 mL). The reaction mixture stirred 12 h, then was concentrated in vacuo and dried under high vacuum. The resulting residue purified by flash chromatography (eluted with 2->10% hexanes/ethyl acetate) to provide title compound.

Step C: Ethyl (4-Methyl-6-aminopyridin-3-yl)acetate

A mixture of ethyl (4-methyl-6-nitropyridin-3-yl)acetate (1.65 g, 7.36 mmol) and palladium on carbon (10%, 1.57 g, 1.47 mmol) in Ethanol (10 mL) was evacuated and refilled with nitrogen (3×), then stirred under an atmosphere of hydrogen for 2 h. The reaction mixture was filtered through celite and concentrated in vacuoto provide title compound which was used directly in the next reaction without further purification: LC-MS (IE, m/z): 195 [M+1]$^+$.

Step D: Ethyl[4-Methyl-6-(1H-tetrazol-1-yl)pyridin-3-yl]acetate

Sodium azide (0.712 g, 11.0 mmol) was added to a stirred mixture of triethyl orthoformate (1.95 ml, 11.7 mmol) and ethyl (4-methyl-6-aminopyridin-3-yl)acetate (1.42 g, 7.30 mmol) in acetic acid (10 ml) and the mixture was stirred at 80° C. for 24 h. The reaction mixture was cooled, diluted with water, and extracted with EtOAc (2×). The combined organic layers were washed with brine, dried (Na$_2$SO$_4$), filtered, and concentrated to provide title compound. LC-MS (IE, m/z): 248 [M+1]$^+$.

Step E: [4-Methyl-6-(1H-tetrazol-1-yl)pyridin-3-yl]acetic Acid

A solution of lithium hydroxide (1 N, 4.75 ml) was added to a stirred mixture of [4-methyl-6-(1H-tetrazol-1-yl)pyridin-3-yl]acetate (1.00 g, 4.29 mmol) in THF (10 ml) and the mixture was stirred at room temperature for 2 h. The reaction mixture was acidified to pH ~3-4 and extracted with EtOAc (3×). The combined organic layers were washed with brine, dried (Na$_2$SO$_4$), filtered and concentrated to provide title compound which was used directly: LC-MS (IE, m/z): 206 [M+1]$^+$.

Intermediate 95

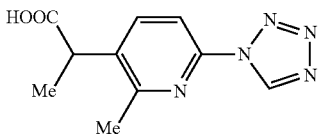 [SMILES: Cc1nc(-n2cnnn2)ccc1C(C)C(=O)O]

2-[2-methyl-6-(1H-tetrazol-1-yl)pyridin-3-yl]propanoic acid

Step A: 3-chloro-2-methyl-6-nitropyridine

A flask containing 100 mL of conc. H$_2$SO$_4$ was added 30% H$_2$O$_2$(50 mL) at 0° C. and then a solution of 5-chloro-6-methylpyridin-2-amine (10.0 g, 70 mmol) in 50 mL of conc.H$_2$SO$_4$ was added at 0° C. The mixture was stirred for 20 hours at room temperature. The mixture was poured into ice water under vigorously stirring. The resulting solid was filtered. The solid was recrystallized with ethanol to give title compound.

Step B: tert-butyl ethyl (2-methyl-6-nitropyridin-3-yl)propanedioate

To a suspension of NaH (60% in oil, 1.4 g, 36 mmol)) in DMF (50 mL) was added tert-butyl ethyl propanedioate (6.8 g, 36 mmol) at room temperature. The mixture was stirred for 30 min. A solution of 3-chloro-2-methyl-6-nitropyridine (4.8 g, 28 mmol) in DMF (10 mL) was added. The mixture was heated to 80° C. and stirred for 5 h. Cooled to ambient temperature, poured to ice/water, extracted with EtOAc. The combined organic layer was washed with brine, dried over anhydrous Na$_2$SO$_4$, concentrated and the residue was purified by column chromatography to give title compound.

Step C: tert-butyl ethyl methyl(2-methyl-6-nitropyridin-3-yl)propanedioate

To a suspension of NaH (60% in oil, 0.8 g, 19 mmol) in DMF (50 mL) was added tert-butyl ethyl (2-methyl-6-nitropyridin-3-yl)propanedioate (4 g, 13 mmol) at room temperature. The mixture was stirred for 1 hour and CH$_3$I (3.7 g, 26 mmol) was added. The mixture was heated to 40° C. for 2 hours. Cooled to ambient temperature, the mixture was poured to ice/water, extracted with EtOAc. The combined organic layer was washed with brine, dried over anhydrous Na$_2$SO$_4$, concentrated and the residue was purified by column chromatograph silica gel to give title compound.

Step D: ethyl 2-(2-methyl-6-nitropyridin-3-yl)propanoate

A mixture of tert-butyl ethyl methyl(2-methyl-6-nitropyridin-3-yl)propanedioate (2.8 g, 8 mmol) in a mixed solution of TFA/DCM (30 mL/30 mL) was stirred over night at room temperature. The mixture was concentrated under reduce pressure to give ethyl 2-(2-methyl-6-nitropyridin-3-yl)propanoate.

Step E: ethyl 2-(6-amino-2-methylpyridin-3-yl)propanoate

A mixture of ethyl 2-(2-methyl-6-nitropyridin-3-yl)propanoate (1.6 g, 6.7 mmol), 10% Pd/C (0.1 g) and AcOH (3 mL) in MeOH (50 mL) was stirred over night under 1 atm of H$_2$ at room temperature. The mixture was filtered and concentrated to give the crude product ethyl 2-(6-amino-2-methylpyridin-3-yl)propanoate.

Step F: ethyl 2-[2-methyl-6-(1H-tetrazol-1-yl)pyridin-3-yl]propanoate

To a mixture of ethyl 2-(6-amino-2-methylpyridin-3-yl)propanoate (1.6 g, 7.6 mmol), CH(OEt)$_3$ (3.4 g, 22.8 mmol) in AcOH (50 mL) was added NaN$_3$ (0.6 g, 9.2 mmol) at room temperature. The mixture was heated to 90° C. and stirred for 50 min. The mixture was cooled to ambient temperature and stand over night. The mixture was concentrated under reduced pressure. Water was added, and the mixture was extracted with EtOAc. The combined organic layer was washed with brine, dried over anhydrous Na$_2$SO$_4$, concentrated and the residue was purified by column chromatography to give ethyl 2-[2-methyl-6-(1H-tetrazol-1-yl)pyridin-3-yl]propanoate.

Step G: 2-[2-methyl-6-(1H-tetrazol-1-yl)pyridin-3-yl]propanoic acid

A mixture of ethyl 2-[2-methyl-6-(1H-tetrazol-1-yl)pyridin-3-yl]propanoate (300 mg, 1.1 mmol) in 8 mL of MeOH/THF/H$_2$O (2:2:1) was added LiOH.H$_2$O (75 mg, 1.8 mmol) and stirred for 30 min at room temperature. The reaction was acidified with citric acid until pH about 3-4. Extracted with EtOAc, the combined organic layer was washed with brine, dried over anhydrous Na$_2$SO$_4$, concentrated to give title compound. $^1$H-NMR (400 MHz, CDCl$_3$) δ ppm 9.51 (s, 1H), 7.86-7.91 (m, 2H), 4.00-4.05 (m, 1H), 2.64 (s, 3H), 1.57 (d, J=7.8 Hz, 3H).

Intermediate 96

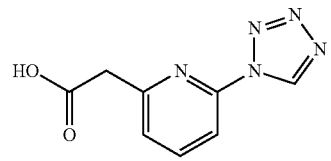 [SMILES: O=C(O)Cc1cccc(-n2cnnn2)n1]

[6-(1H-tetrazol-1-yl)pyridin-2-yl]acetic acid

Step A: methyl{6-[(diphenylmethylidene)amino]pyridin-2-yl}acetate

To a solution of Pd$_2$(dba)$_3$ (4.0 mg, 0.0040 mmol), BINAP (41 mg, 0.065 mmol), and potassium tert-butoxide (490 mg, 4.35 mmol) in toluene (10 mL) was added methyl (6-bromopyridin-2-yl)acetate (1 g, 4.35 mmol) and benzophenone imine (1.1 mL, 6.52 mmol). The reaction was degassed for 15 minutes and then heated at 100° C. for 15 hours in a sealed tube. The reaction was then cooled to room temperature and concentrated in vacuo. The crude residue was taken up in ethyl acetate (200 mL), filtered over celite, and washed with water. The organic layers were dried over sodium sulfate, filtered and concentrated in vacuo. The crude material was purified via MPLC (0-100% EtOAc/Hex gradient) to afford title compound. LC/MS (M+H)⁺ 331.

Step B: methyl (6-aminopyridin-2-yl)acetate

{6-[(diphenylmethylidene)amino]pyridin-2-yl}acetate (1.3 g, 3.93 mmol) was dissolved in 1:1 mixture of THF/water (20 mL) and treated with 4.5 mL of a 1N aqueous hydrochloric acid solution. The reaction was allowed to stir at ambient temperature for 30 minutes and then concentrated in vacuo. The crude residue was dissolved in DCM and washed with a saturated aqueous sodium bicarbonate solution. The organic layers were dried over sodium sulfate, filtered and concentrated to afford crude methyl (6-aminopyridin-2-yl)acetate which was used without further purification: LC/MS (M+H)⁺ 167.

Step C: methyl[6-(1H-tetrazol-1-yl)pyridin-2-yl]acetate

To a solution of (6-aminopyridin-2-yl)acetate (375 mg, 2.26 mmol) in glacial acetic acid (5 mL) was added triethyl orthoformate (1.13 mL, 6.77 mmol) and sodium azide (440 mg, 6.77 mmol). The reaction mixture was heated at 80° C. for 3 hours in a sealed vial and then cooled to ambient temperature. Once cooled, water (5 mL) and solid sodium bicarbonate were added until a Ph range of 6-7 was achieved. The aqueous layer was extracted with ethyl acetate (3×20 mL). The combined organic layers were then dried (sodium sulfate), filtered and concentrated in vacuo. The crude residue was purified via MPLC (0-100% EtOAc/Hex gradient) to afford title compound: LC-MS: (M+H-28)⁺192.

Step D: [6-(1H-tetrazol-1-yl)pyridin-2-yl]acetic acid

To a solution of methyl[6-(1H-tetrazol-1-yl)pyridin-2-yl]acetate (367 mg, 1.67 mmol) in THF (5 mL) was added 1.5 mL of 1N aqueous lithium hydroxide solution. The reaction mixture was allowed to stir at ambient temperature for 30 minutes and then concentrated in vacuo. The crude residue was dissolved in 4 mL of a 1N aqueous hydrochloric acid solution and extracted with DCM (3×20 mL). The combined organic layers were then dried over sodium sulfate, filtered and concentrated in vacuo to afford crude title compound which was used without further purification. LC/MS (M+H-28)⁺178.

Intermediate 97

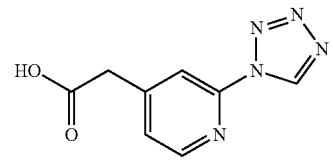 [SMILES: O=C(O)Cc1ccnc(-n2cnnn2)c1]

[2-(1H-tetrazol-1-yl)pyridin-4-yl]acetic acid

Step A: tert-butyl (2-bromopyridin-4-yl)acetate

A 2M solution of LDA (3.2 mL, 6.39 mmol) in THF (6 mL) cooled to −78° C. was treated with dropwise addition of 2-bromo-4-methylpyridine (1.00 g, 5.81 mmol) in THF (2 mL). After stirring at −78° C. for 1 hour, BOC anhydride (1.4 g, 6.39 mmol) was added and the reaction mixture was allowed to slowly warm to room temperature over a period of 2 hours. Once at ambient temperature, water is added and extracted with ethyl acetate (3×50 mL). The combined organic layers were washed with brine, dried over sodium sulfate, filtered and concentrated in vacuo. The crude residue was purified via prep TLC (30% EtOAc/Hex) to afford tert-butyl (2-bromopyridin-4-yl)acetate: LC-MS: (M+H)⁺273.

Step B: tert-butyl{2-[(diphenylmethylidene)amino]pyridin-4-yl}acetate

To a solution of Pd₂(dba)₃ (1.9 mg, 0.0001 mmol), BINAP (5 mg, 0.008 mmol), and potassium tert-butoxide (62 mg, 0.55 mmol) in toluene (3 mL) was added tert-butyl (2-bromopyridin-4-yl)acetate (150 mg, 0.55 mmol) and benzophenone imine (140 µL, 0.83 mmol). The reaction was degassed for 15 minutes and then heated at 100° C. for 15 hours in a sealed tube. The reaction was then cooled to ambient temperature and concentrated in vacuo. The crude residue was dissolved ethyl acetate (200 mL), filtered over celite, and washed with water. The organic layers were dried over sodium sulfate, filtered and concentrated in vacuo. The crude material was purified via MPLC (0-100% EtOAc/Hex gradient) to afford title compound. LC-MS: (M+H)⁺373.

Step C: tert-butyl (2-aminopyridin-4-yl)acetate tert-butyl{2-[(diphenylmethylidene)amino]-pyridin-4-yl}acetate (35 mg, 0.94 mmol) was dissolved in 1:1 mixture of THF/water (5 mL) and treated with 500 µL of a 1N aqueous hydrochloric acid solution. The reaction was allowed to stir at ambient temperature for 30 minutes and then concentrated in vacuo. The crude residue was dissolved in DCM and washed with a saturated aqueous sodium bicarbonate solution. The organic layers were dried over sodium sulfate, filtered and concentrated to afford crude title compound which was used without further purification: LC-MS: (M+H)⁺209.

Step D: tert-butyl[2-(1H-tetrazol-1-yl)pyridin-4-yl]acetate

To a solution of tert-butyl (2-aminopyridin-4-yl)acetate (18 mg, 0.087 mmol) in glacial acetic acid (1 mL) was added triethyl orthoformate (43 μL, 0.261 mmol) and sodium azide (17 mg, 0.261 mmol). The reaction mixture was heated at 80° C. for 3 hours in a sealed vial and then cooled to ambient temperature. Once cooled, water (1.5 mL) and solid sodium bicarbonate were added until a pH range of 6-7 was achieved. The aqueous layer was extracted with ethyl acetate (3×6 mL). The combined organic layers were then dried over sodium sulfate, filtered and concentrated in vacuo. The crude residue was purified via reverse phase reverse-phase HPLC (TMC Pro-Pac C18; 10-100% 0.1% trifluoroacetic acid in acetonitrile/0.1% trifluoroacetic acid in water gradient) to afford tert-butyl[2-(1H-tetrazol-1-yl)pyridin-4-yl]acetate: LC-MS: (M+H-28)$^+$234.

Step E: [2-(1H-tetrazol-1-yl)pyridin-4-yl]acetic acid

To a solution of tert-butyl[2-(1H-tetrazol-1-yl)pyridin-4-yl]acetate (50 mg, 0.192 mmol) in DCM (1.5 mL) was added trifluoroacetic acid (200 μL). The reaction mixture was heated at 40° C. for 45 minutes. The reaction mixture was then concentrated in vacuo to afford crude[2-(1H-tetrazol-1-yl)pyridin-4-yl]acetic acid (trifluoroacetic acid salt) which was used without further purification: LC-MS: (M+H-28)$^+$ 178.

Intermediate 98

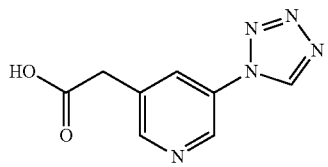 [SMILES: O=C(O)Cc1cncc(-n2cnnn2)c1]

[5-(1H-tetrazol-1-yl)pyridin-3-yl]acetic acid

Step A: methyl (5-bromopyridin-3-yl)acetate 5-bromopyridin-3-yl)acetic acid (1 g, 4.63 mmol) was dissolved in a 1:1 mixture of MeOH/Et$_2$O (10 mL) and cooled to 0° C. To this solution was added a 2M solution of trimethylsilyldiazomethane (7 mL, 13.89 mmol). The reaction was quenched by the addition of glacial acetic acid (7 mL) and concentrated in vacuo. The crude material was purified via MPLC (0-100% EtOAc/Hex gradient) to afford methyl (5-bromopyridin-3-yl)acetate: LC-MS: (M+H)$^+$232.

Steps B: [5-(1H-tetrazol-1-yl)pyridin-3-yl]acetic acid

[5-($^1$H-Tetrazol-1-yl)pyridin-3-yl]acetic acid was prepared from methyl (5-bromopyridin-3-yl)acetate according to the procedure outlined for the preparation of intermediate [2-(1H-tetrazol-1-yl)pyridin-4-yl]acetic acid, except that in the final step the ester was hydrolyzed under basic conditions rather than acid.

Intermediate 99

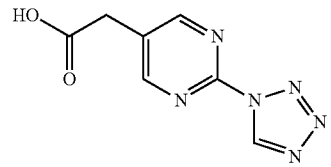 [SMILES: O=C(O)Cc1cnc(-n2cnnn2)nc1]

[2-(1H-tetrazol-1-yl)pyrimidin-5-yl]acetic acid

Step A: tert-butyl (2-aminopyrimidin-5-yl)acetate

A 1 L RB flask was charged with 2-amino-5-bromopyrimidine (8.75 g, 50.3 mmol). THF (262 ml) was added followed by tris(dibenzylideneacetone)dipalladium(0) (0.94 g, 1.027 mmol), X—PHOS (0.978 g, 2.05 mmol) and 2-(tert-butoxy)-2-oxoethylzinc chloride (262 mL, 131 mmol). It was heated at 60° C. (oil bath temperature) overnight. An additional tris(dibenzylideneacetone)dipalladium(0) (500 mg, 0.546 mmol) was added followed by X—PHOS (520 mg, 1.09 mmol). The reaction mixture was heated at reflux for 42 hours. The reaction mixture was then cooled to RT and quenched by addition of saturated NH$_4$Cl solution and the layers separated. The aqueous phase was extracted with EtOAc(2×200 mL). The organic extracts were combined, washed with brine, dried (MgSO4), filtered and the solvent evaporated. The crude product was purified by flash chromatography on silica using a gradient from EtOAc: Hex. 3:2 to EtOAc to afford the title compound.

Step B: tert-butyl[2-(1H-tetrazol-1-yl)pyrimidin-5-yl]acetate

Trimethylsilyl trifluoroacetate (0.14 mL, 0.81 mmol) was added to a suspension of tert-butyl (2-aminopyrimidin-5-yl)acetate (100 mg, 0.478 mmol) in Ethyl acetate (1.5 mL). The reaction mixture was stirred at RT for 5 minutes and triethyl orthoformate (0.14 mL, 0.84 mmol) was added. The reaction mixture was stirred at RT for 5 minutes and azidotrimethylsilane (0.1 mL, 0.760 mmol) was added. The reaction mixture was stirred at RT overnight. The reaction mixture was diluted with EtOAc and washed with water and brine, dried (MgSO4), filtered and the solvent evaporated to afford the title compound: LC/MS (M+1)+ at 263 and (M+1-N2-tBu)+ at 179.

Step C: [2-(1H-tetrazol-1-yl)pyrimidin-5-yl]acetic acid

Trifluoroacetic acid (36 mL, 467 mmol) was added slowly to a solution of tert-butyl[2-(1H-tetrazol-1-yl)pyrimidin-5-yl]acetate (9.80 g, 37.4 mmol) in dichloromethane (36 mL) at RT. The reaction mixture was stirred at RT overnight then evaporated. The residue was triturated with ether:hexane (1:1) (100 mL). The solid was triturated with acetonitrile to afford title compound: $^1$H NMR 600 MHz (CD$_3$OD) 10.01 (s, 1H); 8.94 (s, 2H); 3.88 (s, 2H); LC/MS (M+Na)+ at 229, (M+1)+ at 207, and (M+1-N2)+ at 179.

Intermediate 100

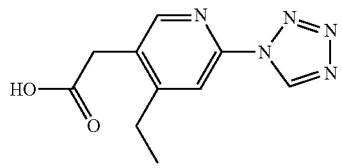 [SMILES: CCc1cc(-n2cnnn2)ncc1CC(=O)O]

[4-ethyl-6-(1H-tetrazol-1-yl)pyridin-3-yl]acetic acid

Step A: 4-ethyl-5-iodopyridin-2-amine

1-Iodopyrrolidine-2,5-dione (NIS, 3.87 g, 17.2 mmol) was added in portions to 4-ethylpyridin-2-amine (2.00 g, 16.4 mmol) in AcOH (60 m) during 30 min at 65° C. The mixture was heated at 65° C. for 36 hours, was concentrated. The residue was purified by silica gel column chromatography (ethyl acetate/hexane 25 to 40%) to provide 4-ethyl-5-iodopyridin-2-amine: LC-MS: $[(M+1)]^+=249.00$ Step B: tert-butyl (6-amino-4-ethylpyridin-3-yl)acetate To a solution of 4-ethyl-5-iodopyridin-2-amine (400 mg, 1.612 mmol) in THF were added $Pd_2(dba)_3$ (118 mg, 0.129 mmol), X-Phose (92 mg, 0.19 mmol). The reaction mixture was degassed and filled with nitrogen, followed by addition of 2-(tert-butoxy)-2-oxoethyzink chloride (8.06 ml, 4.03 mmol). The reaction mixture was heated at 60° C. overnight, cooled to RT, quenched with sat $NH_4Cl$, and extracted with EtOAc. The organic layer was washed with brine, dried over $Na_2SO_4$, and concentrated. The residue was purified with preparative TLC (1500 uM, hex/EA=2/1) to give tert-butyl (6-amino-4-ethylpyridin-3-yl)acetate: LC-MS: $[(M+1)]^+=237.24$, $[(M+1-56)]^+=181.29$ Step C: tert-butyl[4-ethyl-6-(1H-tetrazol-1-yl)pyridin-3-yl]acetate To a solution of tert-butyl (6-amino-4-ethylpyridin-3-yl) acetate (198 mg, 0.838 mmol) in EtOAc (4 mL) was added trimethylsilyl trifluoroacetate (0.246 ml, 1.424 mmol) at room temperature. After stirred 5 min, triethyl orthoformate (0.251 ml, 1.508 mmol) was added. After stirred another 5 min, azidotrimethylsilane (0.176 ml, 1.34 mmol) was added. The reaction mixture was stirred at RT for two days, then concentrated. The residue was purified prep TLC (hex/EA=1/1) to give title compound. LC-MS: $[(M+1)]^+=290.23$, $[(M+1-28)]^+=262.22$, $[(M+1-28-56)]^+=206.21$ Step D: [4-ethyl-6-(1H-tetrazol-1-yl)pyridin-3-yl]acetic acid To a solution of tert-butyl[4-ethyl-6-(1H-tetrazol-1-yl)pyridin-3-yl]acetate (165 mg, 0.570 mmol) in DCM containing thioanisole (0.405 ml, 3.42 mmol) was added TFA (0.879 ml, 11.41 mmol) at 0° C. The mixture was stirred at RT overnight, concentrated. The residue was triturated with ether:hexane (1:1) to give [4-ethyl-6-(1H-tetrazol-1-yl)pyridin-3-yl]acetic acid: LC-MS: $[(M+1)]^+=234.17$.

Intermediate 101

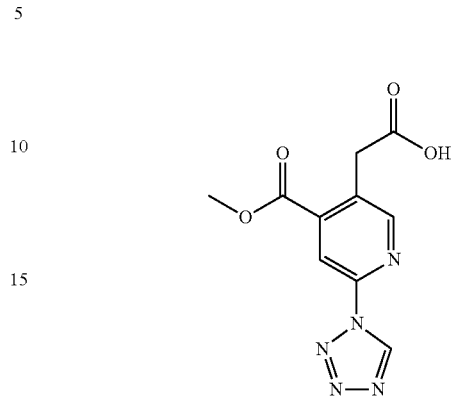

[4-(Methoxycarbonyl)-6-(1H-tetrazol-1-yl)pyridin-3-yl]acetic acid

The title compound was prepared according to the method described for the preparation of [4-ethyl-6-(1H-tetrazol-1-yl) pyridin-3-yl]acetic acid (Steps B-D) starting from methyl 2-amino-5-bromopyridine-4-carboxylate. LC-MS: $[(M+1)]^+=264.10$, $[(M+1-28)]^+=236.12$.

Intermediate 102

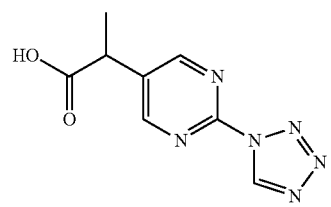 [SMILES: CC(C(=O)O)c1cnc(-n2cnnn2)nc1]

2-(2-(1H-tetrazol-1-yl)pyrimidin-5-yl)propanoic acid

Step A: Methyl 2-(2-(1H-tetrazol-1-yl)pyrimidin-5-yl)acetate

To a solution of 2-(2-(1H-tetrazol-1-yl)pyrimidin-5-yl) acetic acid (100 mg, 0.485 mmol) in methanol (30 mL) was added sulfuric acid (1 mL, 18.8 mmol). Stirred at room temperature and sonicated to dissolve all acid starting material. Reaction was complete within about 2-3 min. The reaction was concentrated under reduced pressure, neutralized with saturated aqueous sodium bicarbonate, extracted with DCM (2 times), washed organics with brine, dried over magnesium sulfate. Solvent was removed under reduced pressure and residue dried on high vacuum overnight. LC/MS: $[(M+1)]^+=221.0$;

Step B: Methyl 2-(2-(1H-tetrazol-1-yl)pyrimidin-5-yl)propanoate

To a suspension of sodium hydride (60% dispersion in mineral oil) (19.1 mg, 0.477 mmol) in anhydrous DMF (3.2 mL) was added solution of methyl 2-(2-(1H-tetrazol-1-yl)

pyrimidin-5-yl)acetate (100 mg, 0.454 mmol) in anhydrous DMF (1.4 mL) at room temperature. Stirred for 10 min, then added methyl iodide (42.6 µl, 0.681 mmol) dropwise. Stirred at room temperature for 1 h. Reaction mixture was diluted with ethyl acetate and washed with water (3 times). Organic layer was washed with brine, dried over anhydrous magnesium sulfate and concentrated. The residue was purified by MPLC, eluting with 20-100% ethyl acetate/hexanes, 26 column volumes. LC/MS: [(M+1)]+=235.2;

Step C: 2-(2-(1H-tetrazol-1-yl)pyrimidin-5-yl)propanoic acid

A solution of methyl 2-(2-(1H-tetrazol-1-yl)pyrimidin-5-yl)propanoate (70.2 mg, 0.300 mmol) in the mixture of THF (2.6 mL)/Water (0.4 mL) was treated with sodium hydroxide (1M, aqueous) (450 µl, 0.450 mmol) at room temperature under nitrogen for 1 h. The reaction was quenched with hydrochloric acid (450 µl, 0.450 mmol). Solvent was removed under reduced pressure and residue was freeze dried overnight. Product contains 1.5 equivalents of sodium chloride: LC/MS: [(M+1)]$^+$=220.9.

Intermediate 103

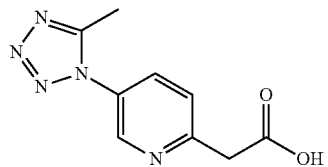 [SMILES: Cc1nnnn1-c1ccc(CC(=O)O)nc1]

2-(5-(5-methyl-1H-tetrazol-1-yl)pyridin-2-yl)acetic acid

Step A: Ethyl 2-(5-nitropyridin-2-yl)acetate tert-Butyl ethyl malonate (8.96 mL, 47.3 mmol) was dissolved in DMF (100 mL) and cooled to 0° C. then added sodium hydride (1.014 g, 25.3 mmol). The reaction mixture was stirred at RT for ½ hr and added 2-bromo-5-nitropyridine (8 g, 39.4 mmol) then stirred at 80° C. overnight. On cooling, the reaction mixture was poured into ice water and extracted with ethyl acetate/ether (3×). Combined organic layer was washed with brine (2×), dried over Na$_2$SO$_4$ filtered and evaporated to dryness to yield 1-tert-butyl 3-ethyl 2-(5-nitropyridin-2-yl) malonate. The crude 1-tert-butyl 3-ethyl 2-(5-nitropyridin-2-yl) malonate was stirred overnight in a mixture of DCM (100 ml) and TFA (100 ml). The reaction was concentrated and the residue was dissolved in ethyl acetate and washed with NaHCO3 (2×), brine (1×), dried over MgSO$_4$ then filtered and evaporated to dryness. The crude material was chromatographed thru 330 g ISCO Redi-sep column and eluted with 25% ethyl acetate/hexane to yield ethyl 2-(5-nitropyridin-2-yl)acetate: LC-MS: M+1=211

Step B: Ethyl 2-(5-aminopyridin-2-yl)acetate

Ethyl 2-(5-nitropyridin-2-yl)acetate (1.75 g, 8.33 mmol) was dissolved in ethyl acetate (20 ml) the added Pd/C (1.0 g, 9.4 mmol) and stirred under a balloon of hydrogen for 3 hrs. Filtered off the catalysts and concentrated to yield ethyl 2-(5-aminopyridin-2-yl)acetate: LC-MS: M+1=181

Step C: Ethyl 2-(5-(5-methyl-1H-tetrazol-1-yl)pyridin-2-yl)acetate

Ethyl 2-(5-aminopyridin-2-yl)acetate (1.314 g, 7.29 mmol) dissolved in acetic acid (24.31 ml) and added triethyl orthoacetate (2.69 ml, 14.58 mmol) and sodium azide (0.881 g, 13.55 mmol). The reaction was stirred at 80° C. for 3 hrs. When LC-MS showed reaction was not complete, added more triethyl orthoacetate (2.69 ml, 14.58 mmol) and sodium azide (0.881 g, 13.55 mmol) then continued heating at 80° C. overnight. Evaporated off acetic acid then diluted with ethyl acetate and washed with saturated NaHCO3 solution, brine, then dried over Na2SO4, filtered and concentrated. The crude material was purified by chromatography through an ISCO 40 g Redi-sep column and eluting with 5% MeOH/DCM to yield title compound: LC-MS: M+1=248

Step D: 2-(5-(5-methyl-1H-tetrazol-1-yl)pyridin-2-yl)acetic acid

Lithium hydroxide (161 mg, 3.84 mmol) dissolved in water (3 mL) was added to ethyl 2-(5-(5-methyl-1H-tetrazol-1-yl)pyridin-2-yl)acetate (776 mg, 3.14 mmol) in THF (10 ml) and stirred at room temperature. The reaction was followed by TLC. Evaporated off the organics without heating and cooled in ice bath then acidified with 1N HCL (3.84 ml, pH ~3). Extracted with EtOAc/THF (2×), washed with brine (1×), dried over Na2SO4, filtered and concentrated to yield 2-(5-(5-methyl-1H-tetrazol-1-yl)pyridin-2-yl)acetic acid: $^1$H-NMR (500 MHz, CD3OD) δ ppm 8.79 (d, J=2.4 Hz, 1H), 8.098 (dd, J=8.0, 2.5 Hz, 1H), 7.710 (d, J=8.3 Hz, 1H), 3.978 (s, 2H), 2.649 (s, 3H)

Intermediate 104

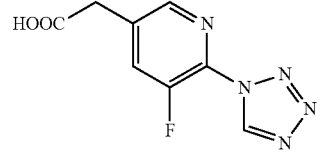 [SMILES: O=C(O)Cc1cnc(-n2cnnn2)c(F)c1]

2-(5-fluoro-6-(1H-tetrazol-1-yl)pyridin-3-yl)acetic acid

Step A: tert-butyl 2-(6-amino-5-fluoropyridin-3-yl)acetate

To 5-bromo-3-fluoropyridin-2-amine (300 mg, 2.0 mmol) in THF (10 mL) was added Pd$_2$(dba)$_3$ (94 mg, 0.10 mmol) and X—PHOS (98 mg, 0.20 mmol), followed by 2-(tert-butoxy)-2-oxoethylzinc chloride solution (10.6 mL, 0.5 M, 5.3 mmol). The reaction mixture was heated at 65° C. over night. The reaction mixture was quenched with NH$_4$Cl, and the aqueous layer was extracted with EtOAc. The organic extracts were washed with brine, dried, and evaporated to give the crude product, which was purified by column chromatography (0-100% EtOAc/hexanes) to give title compound: LC/MS: [(M+1-56)]$^+$=171.5;

Step B: tert-butyl 2-(5-fluoro-6-(1H-tetrazol-1-yl)pyridin-3-yl)acetate

To tert-butyl 2-(6-amino-5-fluoropyridin-3-yl)acetate (120 mg, 0.53 mmol) in EtOAc (2.6 mL) was added trimethylsilyl trifluoroacetate (156 μL, 0.90 mmol), triethyl orthoformate (156 μl, 0.94 mmol), and azidotrimethylsilane (112 μL, 0.85 mmol). The reaction mixture was stirred at rt overnight. The reaction mixture was concentrated to give the crude product, which was purified by column chromatography to give title compound: LC/MS: [(M+1-56-28)]⁺=196.4;

Step C: 2-(5-fluoro-6-(1H-tetrazol-1-yl)pyridin-3-yl) acetic acid

To tert-butyl 2-(5-fluoro-6-(1H-tetrazol-1-yl)pyridin-3-yl) acetate (70 mg, 0.25 mmol) in DCM (0.50 mL) was added thioanisole (163 μl, 1.38 mmol) and TFA (241 μl, 3.13 mmol) at 0° C. The reaction mixture was stirred at rt for 5 h. The reaction mixture was concentrated to give the crude product, which was used in the next step without further purification: LC/MS: [(M+1-28)]⁺=196.5.

Intermediate 105

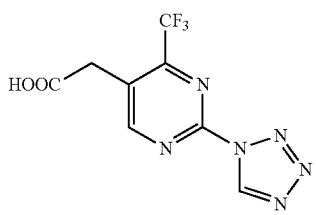 [SMILES: O=C(O)Cc1cnc(-n2cnnn2)nc1C(F)(F)F]

2-(2-(1H-tetrazol-1-yl)-4-(trifluoromethyl)pyrimidin-5-yl)acetic acid 2-(2-(¹H-Tetrazol-1-yl)-4-(trifluoromethyl)pyrimidin-5-yl)acetic acid was prepared in an analogous fashion to that described for the synthesis of 2-(5-fluoro-6-(1H-tetrazol-1-yl)pyridin-3-yl)acetic acid starting from 5-bromo-4-(trifluoromethyl)pyrimidin-2-amine. LC/MS: [(M+1-28)]⁺=247.4.

Intermediate 106

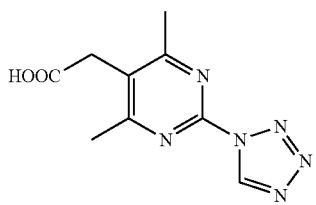 [SMILES: Cc1nc(-n2cnnn2)nc(C)c1CC(=O)O]

2-(4,6-dimethyl-2-(1H-tetrazol-1-yl)pyrimidin-5-yl) acetic acid 2-(4,6-Dimethyl-2-(1H-tetrazol-1-yl)pyrimidin-5-yl)acetic acid was prepared in an analagous fashion to that described for the synthesis of 2-(5-fluoro-6-(1H-tetrazol-1-yl)pyridin-3-yl)acetic acid starting from 5-bromo-4,6-dimethylpyrimidin-2-amine. LC/MS: [(M+1-28)]⁺=207.5.

Intermediate 107

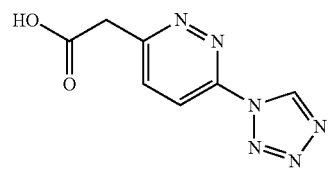 [SMILES: O=C(O)Cc1ccc(-n2cnnn2)nn1]

2-(6-(¹H-Tetrazol-1-yl)pyridazin-3-yl)acetic Acid

Step A: N-(6-Bromopyridazin-3-yl)pivalamide

Pivaloyl chloride (2.85 ml, 23.2 mmol) was added dropwise to a solution of 6-bromopyridazin-3-amine (2.00 g, 15.4 mmol) in pyridine (8 mL). The mixture stirred 12 h at room temperature, then was diluted with water and extracted with dichloromethane (3×). The combined organic layers were washed with water (2×) and brine, then dried (sodium sulfate), filtered and concentrated in vacuo. The resulting residue was purified by column chromatography (2–>20% EtOAc:Hex) to give title compound.

Step B: tert-Butyl 2-(6-Pivalamidopyridazin-3-yl)acetate

A mixture of N-(6-bromopyridazin-3-yl)pivalamide (2.00 g, 7.75 mmol), dicyclohexyl(2',4',6'-triisopropylbiphenyl-2-yl)phosphine (0.222 g, 0.465 mmol), and tris-dipalladium (dibenzylideneacetone) (0.213 g, 0.232 mmol) was flushed with nitrogen for 30 min. THF (20 mL) was added, followed by a 1.0 M solution of (2-tert-butoxy-2-oxoethyl)zinc(II) chloride in diethyl ether (38.7 mL, 19.4 mmol) and the reaction was sealed and stirred for 2 h at 50° C. An additional amount of (2-tert-butoxy-2-oxoethyl)zinc(II) chloride (15.5 ml, 7.75 mmol) was added and the mixture stirred for 2 h at 50 C. The resulting mixture was diluted with EtOAc and filtered, then washed with water and brine. The organic layer was dried (sodium sulfate), filtered and concentrated. MPLC (3–>30% EtOAc:Hex) provided title compound. LC-MS (IE, m/z): 294 [M+1]⁺.

Step C: Methyl 2-(6-Aminopyridazin-3-yl)acetate

A solution of 2-(6-pivalamidopyridazin-3-yl)acetate (740 mg, 2.52 mmol) in 6 N hydrochloric acid (24 mL) was heated to 105° C. for 12 h, then cooled and concentrated in vacuo. The resulting crude residue was redissolved in methanol (10 mL) and treated dropwise with a 2 N solution of trimethylsilyldiazomethane in diethylether (2.52 mL, 5.04 mmol). After 1 h, the mixture was diluted with water and extracted with EtOAc. The organic layer was washed with water and brine, dried (sodium sulfate), filtered and concentrated to provide title compound. LC-MS (IE, m/z): 168 [M+1]⁺.

Step D: 2-(6-(¹H-Tetrazol-1-yl)pyridazin-3-yl)acetic Acid

To a solution of methyl 2-(6-aminopyridazin-3-yl)acetate (418 mg, 2.50 mmol) in acetic acid (10 mL) was added triethyl orthoformate (0.667 ml, 4.00 mmol), followed by sodium azide (244 mg, 3.75 mmol). The mixture was heated at 80° C. for 1 h. After cooling, the mixture was diluted with water and EtOAc. The layers were separated and the aqueous was extracted with EtOAc (2×) and the combined organics washed with water, brine, dried (sodium sulfate) and concentrated to provide crude methyl 2-(6-(1H-tetrazol-1-yl)pyridazin-3-yl)acetate (LC-MS (IE, m/z): 193 [M+1-28]$^+$). The crude ester was dissolved in THF (5.0 mL) and treated with 1 N LiOH (3.75 mL) and the resulting mixture was stirred for 1 h. The resulting mixture was concentrated in vacuo and the resulting powder dried under high vacuum to provide title compound which was used directly in the next step without further purification. LC-MS (IE, m/z): 173 [M+1-28]$^+$.

Intermediate 108

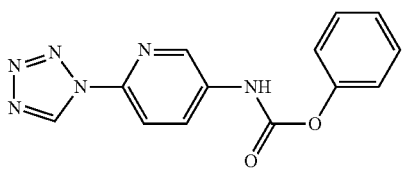 [SMILES: O=C(Nc1ccc(-n2cnnn2)nc1)Oc1ccccc1]

Phenyl[6-(1H-tetrazol-1-yl)pyridin-3-yl]carbamate

Step A: 5-nitro-2-(1H-tetrazol-1-yl)pyridine

To 5-nitropyridin-2-amine (1.00 g, 7.19 mmol) in AcOH was added trimethylsilyl trifluoroacetate (2.111 mL, 12.22 mmol). After stirring for 5 min, triethyl orthoformate (2.155 ml, 12.94 mmol) was added. Azidotrimethylsilane (1.513 mL, 11.50 mmol) was added after stirring for another 5 min. The reaction mixture was stirred at RT overnight, and was concentrated to give the crude solid. The solid was washed with DCM, and dried under vacuum to give title compound. LC/MS: [(M+1)]$^+$=193.19, [(M+1-28)]$^+$=165.19

Step B: 6-(1H-tetrazol-1-yl)pyridin-3-amine

5-Nitro-2-(1H-tetrazol-1-yl)pyridine (1020 mg, 5.31 mmol) was suspended in acetic acid (10 ml). Zinc (3472 mg, 53.1 mmol) was added slowly (exothermic reaction). The mixture was stirred at 50° C. for 1 hour, cooled, diluted with EtOAc. The mixture was filtered, rinsed with ethyl acetate. The filtrate was concentrated to dryness to give crude 6-(1H-tetrazol-1-yl)pyridin-3-amine: LC/MS: [(M+1-28)]$^+$=135.1.9.

Step C: phenyl[6-(1H-tetrazol-1-yl)pyridin-3-yl]carbamate 6-($^1$H-Tetrazol-1-yl)pyridin-3-amine (50 mg, 0.308 mmol) was dissolved in pyridine (1.5 mL), followed by addition of phenyl chloroformate (53.1 mg, 0.339 mmol). The mixture was stirred at RT overnight, and was concentrated to give crude title compound. LC/MS: [(M+1]$^+$=283.14, [(M+1-28)]$^+$=255.13.

Intermediate 109

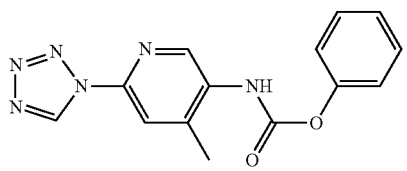 [SMILES: Cc1cc(-n2cnnn2)ncc1NC(=O)Oc1ccccc1]

Phenyl 4-methyl-6-(1H-tetrazol-1-yl)pyridin-3-ylcarbamate

The title compound was prepared according to the method described in the preparation of phenyl[6-(1H-tetrazol-1-yl)pyridin-3-yl]carbamate. LC/MS: [(M+1]$^+$=297.09, [(M+1-28)]$^+$=269.11.

Intermediate 110

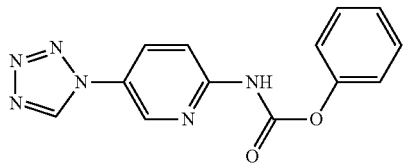 [SMILES: O=C(Nc1ccc(-n2cnnn2)cn1)Oc1ccccc1]

Phenyl 5-(1H-tetrazol-1-yl)pyridin-2-ylcarbamate

Step A: tert-butyl 5-nitropyridin-2-ylcarbamate

To a solution of 5-nitropyridin-2-amine (3.00 g, 21.6 mmol) in THF at 0° C. under N$_2$ was added NaHMDS (23.72 ml, 23.72 mmol) via syringe (dark yellow slurry was formed). The mixture was stirred at 0° C. for 15 min, followed by addition of di-tert-butyl dicarbonate (4.94 g, 22.64 mmol) in 10 mL THF via syringe. The mixture was stirred at RT for 3 hours, quenched with water, extracted with EtOAc. The organic layer was washed with brine, and concentrated. The residue was triturated with EtOAc, and filtered. Solid was washed with EtOAc, dried under vacuum to give tert-butyl 5-nitropyridin-2-ylcarbamate: LC/MS: [(M+1-56)]$^+$=184.13.

Step B: tert-butyl 5-aminopyridin-2-ylcarbamate tert-Butyl 5-nitropyridin-2-ylcarbamate (750 mg, 3.14 mmol) was suspended in AcOH at RT with vigorously stirring. Zinc (2051 mg, 31.4 mmol) was added slowly (exothermic reaction). The mixture was stirred at RT for 20 min, and filtered. The filter cake was washed with ethyl acetate. The filtrate was concentrated to give tert-butyl 5-aminopyridin-2-ylcarbamate: LC/MS: [(M+1-56)]$^+$=154.16.

Step C: tert-butyl 5-(1H-tetrazol-1-yl)pyridin-2-ylcarbamate tert-Butyl 5-(1H-tetrazol-1-yl)pyridin-2-ylcarbamate was prepared according to the method described in the preparation of 5-nitro-2-(1H-tetrazol-1-yl)pyridine (Step A): LC/MS: [(M+1-56-28)]⁺=179.16.

Step D: 5-(1H-tetrazol-1-yl)pyridin-2-amine hydrochloride tert-Butyl 5-(1H-tetrazol-1-yl)pyridin-2-ylcarbamate (300 mg, 1.14 mmol) was dissolved in DCM (2 mL), followed by addition of 4 M HCl in dioxane (2.86 mL, 11.4 mmol). The mixture was stirred at RT for 4 hours, then concentrated to give title compound. LC/MS: [(M+1)]⁺=163.20.

Step E: Phenyl 5-(1H-tetrazol-1-yl)pyridin-2-ylcarbamate

Phenyl 5-(1H-tetrazol-1-yl)pyridin-2-ylcarbamate was prepared according to the method described in the preparation of phenyl[6-(1H-tetrazol-1-yl)pyridin-3-yl]carbamate (Step C): LC/MS: [(M+1]⁺=283.11

Example 1

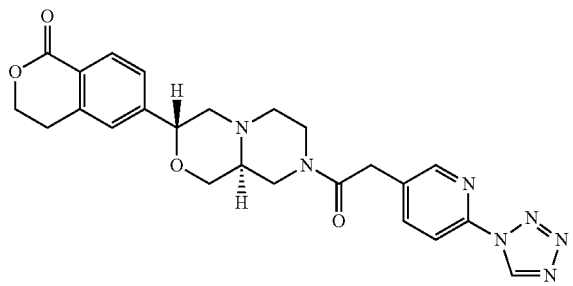 [SMILES: O=C1OCCc2cc([C@@H]3CN4CCN(C(=O)Cc5ccc(-n6cnnn6)nc5)C[C@H]4CO3)ccc21]

6-((3R,9aS)-8-{[4-(1H-tetrazol-1-yl)phenyl]acetyl}octahydropyrazino[2,1-c][1,4]oxazin-3-yl)-3,4-dihydro-1H-isochromen-1-one

[6-(¹H-Tetrazol-1-yl)pyridine-3-yl]acetic acid (82 mg, 0.40 mmol, 1.3 eq), N-[3-(dimethylamino)propyl]-N'-ethyl-carbodiimide hydrochloride (83 mg, 0.43 mmol, 1.4 eq) and ¹H-1,2,3-benzotriazol-1-ol hydrate (66 mg, 0.43 mmol, 1.4 eq) were dissolved in dichloromethane (3 mL) in a 16 mL reaction vial. The mixture was stirred at r.t. for 30 min under $N_2$. To the above mixture was added the dichloromethane solution (2 mL) of (3R,9aS)-3-(1-oxo-3,4-dihydro-1H-isochromen-6-yl)octahydropyrazino[2,1-c][1,4]oxazin-8-ium chloride (100 mg, 0.31 mmol, 1.0 eq) that was neutralized with N-methylmorpholine (34 μL, 0.31 mmol, 1.0 eq). The reaction was stirred at r.t. for 18 h, diluted with dichloromethane (10 mL), washed with saturated sodium bicarbonate solution (2×10 mL), brine (5 mL) and water (5 mL). The organic phase was dried over MgSO4, filtered and concentrated to give the crude product. The desired product was obtained after purification by flash column chromatography (0-10% MeOH/CH₂Cl₂) followed by preparative TLC (NH₄OH/MeOH/CHCl₃: 0.5:4.5:95): LC-MS (IE, m/z): [(M+1)-28]⁺=448.5, [(M+Na]⁺=498.4: ¹H NMR (500 MHz, CDCl₃, δ in ppm): 9.41 (1H, m), 7.99 (2H, m), 7.81 (1H, m), 7.28 (2H, m), 4.55-4.75 (1H, m), 4.45-4.55 (2H, m), 3.93 (1H, dd, J=3.2 Hz, J=11.2 Hz), 3.70-3.92 (3H, m), 3.40-3.55 (2H, m), 3.01 (2H, t, J=6.0 Hz), 2.80-3.00 (3H, m), 2.33 (1H, t, J=2.6 Hz,), 2.15-2.30 (3H, m).

Example 2 (R,S)

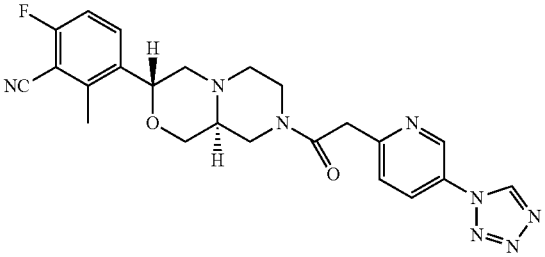 [SMILES: Cc1c([C@@H]2CN3CCN(C(=O)Cc4ccc(-n5cnnn5)cn4)C[C@H]3CO2)ccc(F)c1C#N]

3-((3R,9aS)-8-(2-(5-(1H-tetrazol-1-yl)pyridin-2-yl)acetyl)octahydropyrazino[2,1-c][1,4]oxazin-3-yl)-6-fluoro-2-methylbenzonitrile 6-Fluoro-2-methyl-3-((3R,9aS)-octahydropyrazino[2,1-c][1,4]oxazin-3-yl)benzonitrile 2,2,2-trifluoroacetate (1404 mg, 3.610 mmol) was suspended in DCM (20 mL) then TEA (2.011 ml, 14.43 mmol) was added. The mixture was stirred for 5 min, and then HOBT (828 mg, 5.41 mmol), 2-(5-(1H-tetrazol-1-yl)pyridin-2-yl)acetic acid (740 mg, 3.61 mmol), and EDC (1383 mg, 7.21 mmol) were added and the resulting mixture was stirred for 2 h. The reaction was poured into a brine/NaHCO3 mixture. The DCM layer was separated and dried over Na2SO4 then filtered and concentrated. The residue was purified by chromatography using 120 g ISCO Redisep column eluting with a 5% (NH₄OH: MeOH 1:9)/95% DCM solvent system to yield 3-((3R,9aS)-8-(2-(5-(1H-tetrazol-1-yl)pyridin-2-yl)acetyl)octahydropyrazino[2,1-c][1,4]oxazin-3-yl)-6-fluoro-2-methylbenzonitrile: LC-MS: M+1=463: ¹H-NMR (600 MHz, CDCl3) δ ppm 9.10 (s, 0.5H), 9.084 (s, 0.5H), 8.919 (dd, J=14.4, 2.5 Hz, 1H), 8.053 (m, 1H), 7.681 (m, 1H), 7.609 (t, J=8.25 Hz, 1H), 7.048 (t, J=8.5 Hz, 1H), 4.785 (d, J=10.1 Hz, 1H), 4.587 (d, J=13.2 Hz, 0.5H), 4.484 (d, J=12.8 Hz, 0.5H), 3.947-4.095 (m, 4H), 3.497 (t, J=11 Hz, 0.5H), 3.477 (t, J=11.1 Hz, 0.5H), 3.384 (t, J=12.6 Hz, 0.5H), 2.94-2.875 (m, 1H), 2.83-2.777 (m, 2H), 2.548 (s, 3H), 2.409 (t, J=11.2 Hz, 0.5H), 2.251-2.16 (m, 2H), 2.129-2.084 (m, 1H).

Example 3 (S,S)

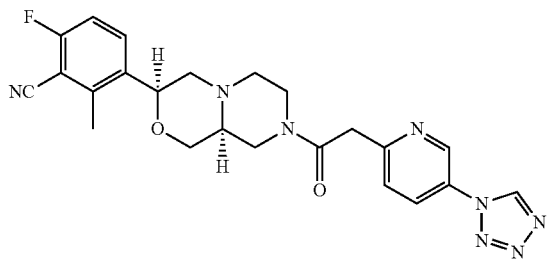 [SMILES: Cc1c([C@H]2CN3CCN(C(=O)Cc4ccc(-n5cnnn5)cn4)C[C@H]3CO2)ccc(F)c1C#N]

3-((3S,9aS)-8-(2-(5-(1H-tetrazol-1-yl)pyridin-2-yl)acetyl)octahydropyrazino[2,1-c][1,4]oxazin-3-yl)-6-fluoro-2-methylbenzonitrile 6-Fluoro-2-methyl-3-((3S,9aS)-octahydropyrazino[2,1-c][1,4]oxazin-3-yl)benzonitrile 2,2,2-trifluoroacetate (1.06 g, 2.71 mmol) was suspended in DCM (20 mL) and TEA (1.13 ml, 8.13 mmol) was added. The mixture was stirred for 5 min and then 2-(5-(1H-tetrazol-1-yl)pyridin-2-yl)acetic acid (0.555 g, 2.71 mmol), HOBT (0.623 g, 4.07 mmol) and EDC (1.039 g, 5.42 mmol) were added and the mixture was stirred for 4 h. The reaction mixture was poured into brine/NaHCO3 mixture. The DCM layer was separated and dried over Na2SO4, then was filtered and concentrated. The residue was purified by chromatography using a 120 g ISCO Redisep column eluting with a 5% (NH4OH: MeOH 1:9)/95% DCM solvent system to yield 3-((3S,9aS)-8-(2-(5-(1H-tetrazol-1-yl)pyridin-2-yl)acetyl)-octahydropyrazino[2,1-c][1,4]oxazin-3-yl)-6-fluoro-2-methylbenzonitrile: LC-MS: M+1=463.

$^1$H-NMR (500 MHz, CDCl3) δ ppm 9.127 (s, 1H), 8.943 (dd, J=7.5, 2.4 Hz, 1H), 8.165 (m, 1H), 8.084 (dd, J=8.5, 1.8 Hz, 1H), 7.644 (d, J=8.3 Hz, 1H), 7.052 (m, 1H), 4.915 (s, 1H), 4.57 (d, J=13.2 Hz, 0.5H), 4.3875 (d, J=12.8 Hz, 0.5H), 4.152-4.000 (m, 2.5H), 3.884 (d, J=12.5 Hz, 0.5H), 3.579 (d, J=11.4 Hz, 1H), 3.461 (t, J=12.9 Hz, 0.5H),), 3.284 (t, J=8.5 Hz, 1H), 3.19-3.152 (m, 1H), 3.077 (t, J=10.6 Hz, 0.5H), 2.979-2.85 (m, 1.5H), 2.825 (dd, J=12.25, 3.7 Hz, 1H), 2.62 (s, 3H), 2.581 (m, 0.5), 2.454 (b, 2H).

Example 4 (S,S)

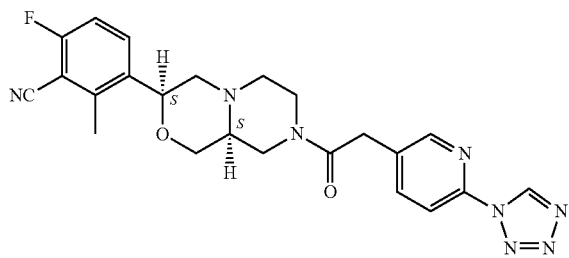

6-fluoro-2-methyl-3-[(3S,9aS)-8-{[6-(1H-tetrazol-1-yl)pyridin-3-yl]acetyl}octahydropyrazino[2,1-c][1,4]oxazin-3-yl]benzonitrile (3S,9aS)-3-(3-Cyano-4-fluoro-2-methylphenyl)octahydropyrazino[2,1-c][1,4]oxazin-8-ium trifluoroacetate (1.44 g, 3.70 mmol) and N-methylmorpholine (1.220 mL, 11.10 mmol) was added to DCM (25 mL). Then [6-(1H-tetrazol-1-yl)pyridin-3-yl]acetic acid (0.911 g, 4.44 mmol), HOBT (0.850 g, 5.55 mmol) and EDC (1.418 g, 7.40 mmol) were added in that order. The reaction mixture was stirred at RT for 4 h. The reaction mixture was washed with brine and saturated aq. NaHCO3 solution. The DCM layer was separated and dried over Na2SO4, filtered, and evaporated to dryness. The residue was purified by preparative TLC eluting with a 5% (10% NH4OH in Methanol): 95% chloroform solvent system to yield the title compound: $^1$H-NMR (500 MHz, DMSO): δ ppm 10.17 (s, 1H), 8.48 (s, 1H), 8.22 (t, J=7.35 Hz, 1H), 8.01 (s, 2H), 7.37 (s, 1H), 4.93 (s, 1H), 4.21 (dd, J=13.3, 60.75 Hz, 1H), 3.89-3.99 (m, 3H), 3.57 (dd, J=11, 23.5 Hz, 1H), 3.29 (s, 1H), 3.10-3.24 (m, 2H), 2.80-3.0 (m, 2H), 2.68 (d, J=11 Hz, 1H), 2.53 (s, 3H), 2.23-2.48 (2H).

LC-MS: M+1=463.

Example 5 (R,S)

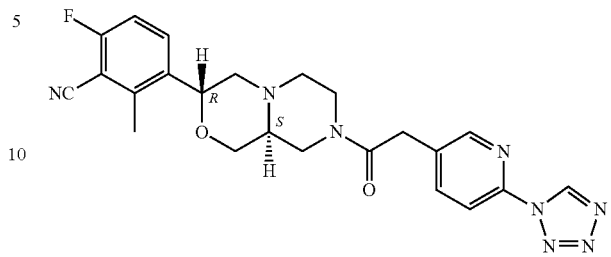

6-fluoro-2-methyl-3-[(3R,9aS)-8-{[6-(1H-tetrazol-1-yl)pyridin-3-yl]acetyl}octahydropyrazino[2,1-c][1,4]oxazin-3-yl]benzonitrile (3R,9aS)-3-(3-cyano-4-fluoro-2-methylphenyl)octahydropyrazino[2,1-c][1,4]oxazin-8-ium trifluoroacetate (0.025 g, 0.064 mmol) and TEA (0.027 mL, 0.193 mmol) was added to DCM (10 mL) then [6-(1H-tetrazol-1-yl)pyridin-3-yl]acetic acid (0.0171 g, 0.083 mmol) was added followed by EDC (0.0246 g, 0.128 mmol). The reaction mixture was stirred at room temperature for 16 h. The reaction mixture was washed with brine and saturated aqueous NaHCO3 solution. The DCM layer was separated, dried over Na2SO4, filtered, and evaporated to dryness. The residue was purified by mass directed reverse phase HPLC to afford the TFA salt of the title compound.

$^1$H-NMR (500 MHz, DMSO): δ ppm 10.17 (s, 1H), 8.49 (s, 1H), 8.05 (d, J=8.5 Hz, 1H), 8.01 (d, J=8.5 Hz, 1H), 7.76 (t, J=8.5 Hz, 1H), 7.40 (m, 1H), 5.01 (d, J=10.5 Hz, 1H), 4.5 (b, 1H), 4.25 (b, 2H), 3.87-4.0 (m, 3H), 3.65 (b, 1H), 3.40 (b, 1H), 3.24 (b, 1H), 3.15 (b, 1H), 2.92 (b, 1H), 2.7 (b, 1H), 2.54 (s, 3H).

Example 6 (S,S)

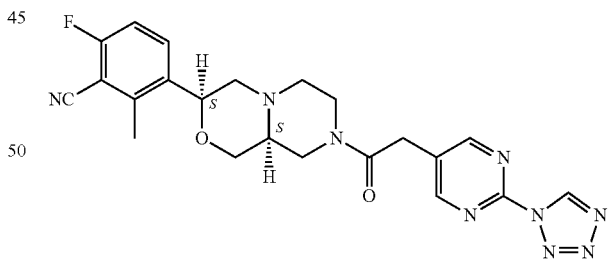

6-fluoro-2-methyl-3-[(3S,9aS)-8-{[2-(1H-tetrazol-1-yl)pyrimidin-5-yl]acetyl}octahydropyrazino[2,1-c][1,4]oxazin-3-yl]benzonitrile HATU (192 mg, 0.504 mmol) was added to a solution of (3S,9aS)-3-(3-cyano-4-fluoro-2-methylphenyl)octahydropyrazino[2,1-c][1,4]oxazin-8-ium trifluoroacetate (104 mg, 0.504 mmol) in DMF (1.5 mL). The reaction mixture was stirred at RT for 15 minutes and a solution of [2-(1H-tetrazol-1-yl)pyrimidin-5-yl]acetic acid (284 mg, 0.564 mmol) and triethylamine (0.37 ml, 2.65 mmol) in DMF (1 mL) was added. The flask was rinsed with DMF (0.5 mL). The solution was stirred at RT overnight then diluted with EtOAc and washed with dilute NaHCO3 solution, water (3×) and brine, dried (MgSO4), filtered and the solvent evaporated. The residue was purified by silica gel chromatography (24 g cartridge) using CH2Cl2 (A) and CH2Cl2:MeOH 90:10 (B) with gradient elution from 100% A to 100% B over 12 column volumes and holding at 60% A for 2 column volumes to afford the title compound: LC/MS: 505 (M+CH3CN+Na), 464 (M+H). The title compound was converted to its hydrochloride salt by dissolving in methylene chloride and adding 1 equivalent 1M HCl in ether. The suspension was stirred at RT for 30 minutes and the solvent evaporated: NMR 500 MHz (CD3OD(mixture amide rotamers) 10.03 (s, 1H); 8.87 (s, 1H); 8.86 (s, 1H); 7.94 (q, 1H); 7.31 (d t, 1H); 5.08-5.15 (m, 1H); 54.68 (d, 0.5H); 4.60 (d, 0.5H); 4.01-4.38 (m, 5.5H); 3.82 (t, 2H); 3.58-3.71 (m, 1.5H); 3.40-3.53 (m, 2.5H); 3-31-3.37 (m, 1.5H); 2.61 (br s, 3H); LC/MS 527 (M+Na+CH3CN), 505 (M+H+CH3CN), 486 (M+Na), 464 (M+H).

The following EXAMPLES in Table 3 were prepared in an analagous fashion to that described for the synthesis of EXAMPLES 1-6 above from the appropriate amine and carboxylic acid INTERMEDIATES (commercially available or prepared as described above) using one of the amide coupling agents EDC or HATU.

TABLE 3

| Example # | Structure | Name / Data |
|---|---|---|
| 7 (S,R) | | 6-fluoro-2-methyl-3-[(3S,9aR)-8-{[6-(1H-tetrazol-1-yl)pyridin-3-yl]acetyl}octahydropyrazino[2,1-c][1,4]oxazin-3-yl]benzonitrile<br>$^1$H-NMR (500 MHz, CDCl$_3$): δ ppm 9.52 (s, 1H), 8.40 (s, 1H), 8.05 (d, J = 6.5 Hz, 1H), 7.90 (d, J = 6.5 Hz, 1H), 7.66-7.71 (m, 1H), 4.80 (t, J = 6.5 Hz, 1H), 4.60 (d, J = 10.5 Hz, 0.5H), 4.50 (d, J = 10.5 Hz, 0.5H), 3.98 (dd, J = 2.5, 9.25 Hz, 1H), 3.74-3.90 (m, 3H), 3.41-3.54 (m, 3H), 2.98 (t, J = 10 Hz, 0.5 H), 2.90 (t, J = 10 Hz, 0.5H), 2.84 (t, J = 9 Hz, 1H), 2.55 (s, 3 H), 2.43 (t, J = 10 Hz, 1H), 2.22-2.29 (m, 2H), 2.10-2.17 (m, 1H). |
| 8 (R,R) | | 6-fluoro-2-methyl-3-[(3R,9aR)-8-{[6-(1H-tetrazol-1-yl)pyridin-3-yl]acetyl}octahydropyrazino[2,1-c][1,4]oxazin-3-yl]benzonitrile<br>$^1$H-NMR (500 MHz, CDCl$_3$): δ ppm 9.52 (s, 1H), 8.40 (d, J = 6.5 Hz, 1H), 8.11-8.15 (q, 1H), 8.05 (dd, J = 2.5, 7 Hz, 1H), 7.90 (t, J = 6.5 Hz, 1H), 7.00-: 7.04 (q, 1H), 4.89 (t, J = 2.5 Hz, 1H), 4.55 (d, J = 11.5 Hz, 0.5H), 4.36 (d, J = Hz, 0.5H), 3.75-3.85 (m, 3H), 3.61 (d, J = 11 Hz, 1H), 3.55 (d, J = 9.5 Hz, 1 H), 3.47 (t, J = 11, 1 H), 3.25 (t, J = 9 Hz, 1 H), 3.08 (t, J = 10.5 Hz, 0.5 H), 2.87-2.96 (m, 1.5 H), 2.80-2.84 (m, 1H), 2.59 (s, 3 H), 2.55 (t, J = 10.5, 1H), 2.40-2.50 (m, 2H). |
| 9 (S,R) | | 6-fluoro-2-methyl-3-[(3S,9aR)-8-{[2-(1H-tetrazol-1-yl)pyrimidin-5-yl]acetyl}octahydropyrazino[2,1-c][1,4]oxazin-3-yl]benzonitrile<br>HCl salt: LC/MS 486 (M + Na), 464 (M + H), 436 (M + H − N2). |
| 10 | | 2-chloro-6-fluoro-3-[(3S,9aS)-8-{[6-(1H-tetrazol-1-yl)pyridin-3-yl]acetyl}octahydropyrazino[2,1-c][1,4]oxazin-3-yl]benzonitrile<br>LC-MS: M + 1 = 483 |

TABLE 3-continued

| Example # | | |
|---|---|---|
| 11 | 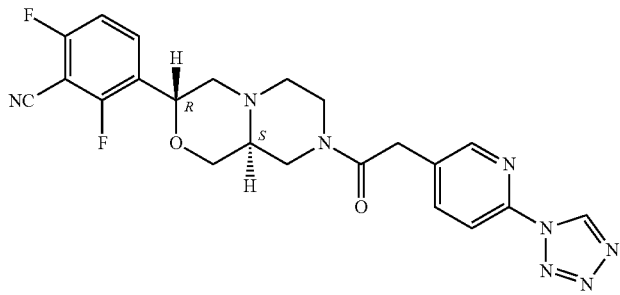 | 2,6-difluoro-3-[(3R,9aS)-8-{[6-(1H-tetrazol-1-yl)pyridin-3-yl]acetyl}octahydropyrazino[2,1-c][1,4]oxazin-3-yl]benzonitrile<br>LC-MS: M + 1 = 467. |
| 12 | 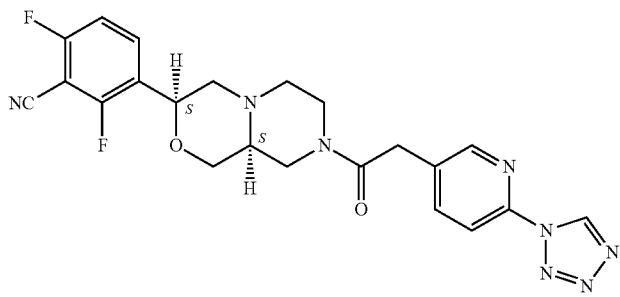 | 2,6-difluoro-3-[(3S,9aS)-8-{[6-(1H-tetrazol-1-yl)pyridin-3-yl]acetyl}octahydropyrazino[2,1-c][1,4]oxazin-3-yl]benzonitrile<br>LC-MS: M + 1 = 467 |
| 13 | 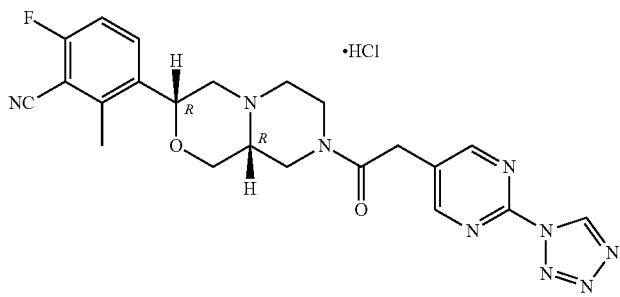 | 6-fluoro-2-methyl-3-[(3R,9aR)-8-{[2-(1H-tetrazol-1-yl)pyrimidin-5-yl]acetyl}octahydropyrazino[2,1-c][1,4]oxazin-3-yl]benzonitrile<br>LC/MS 436 (M + H − N2). |
| 14 | 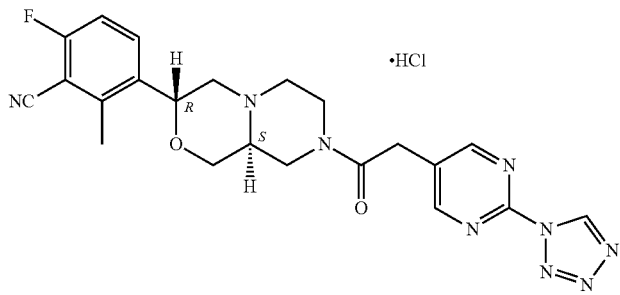 | 6-fluoro-2-methyl-3-[(3R,9aS)-8-{[2-(1H-tetrazol-1-yl)pyrimidin-5-yl]acetyl}octahydropyrazino[2,1-c][1,4]oxazin-3-yl]benzonitrile<br>LC/MS 436 (M + H − N2). |
| 15 | 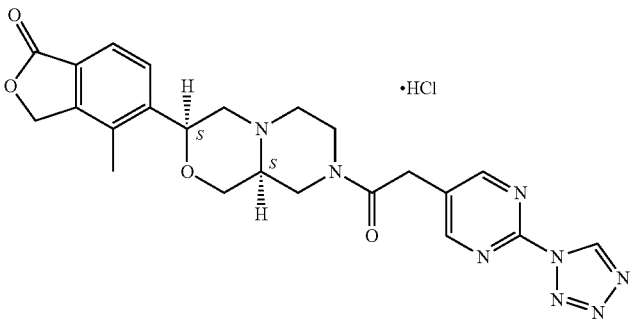 | 4-methyl-5-[(3S,9aS)-8-{[2-(1H-tetrazol-1-yl)pyrimidin-5-yl]acetyl}octahydropyrazino[2,1-c][1,4]oxazin-3-yl]-2-benzofuran-1(3H)-one;<br>LC/MS 499 (M + Na), 477 (M + H). |

TABLE 3-continued

| Example # | | |
|---|---|---|
| 16 | 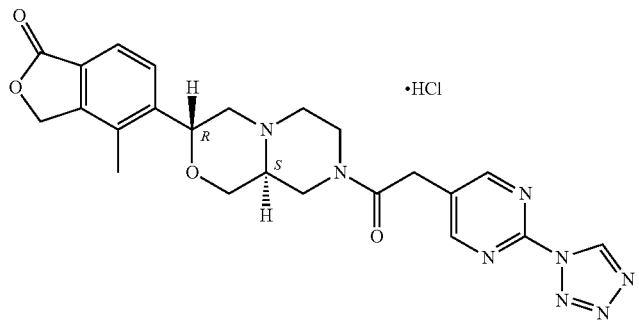 ·HCl | 4-methyl-5-[(3R,9aS)-8-{[2-(1H-tetrazol-1-yl)pyrimidin-5-yl]acetyl}octahydropyrazino[2,1-c][1,4]oxazin-3-yl]-2-benzofuran-1(3H)-one; LC/MS 499 (M + Na), 477 (M + H). |
| 17 | 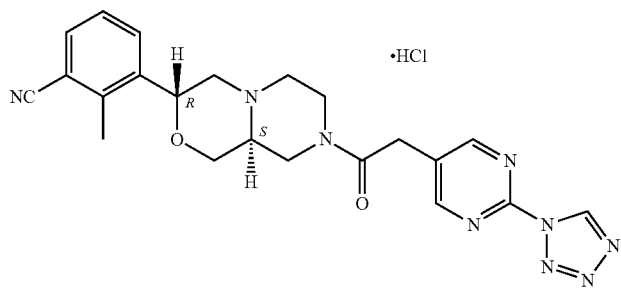 ·HCl | 2-methyl-3-[(3R,9aS)-8-{[2-(1H-tetrazol-1-yl)pyrimidin-5-yl]acetyl}octahydropyrazino[2,1-c][1,4]oxazin-3-yl]benzonitrile LC/MS 418 (M + H − N2). |
| 18 | 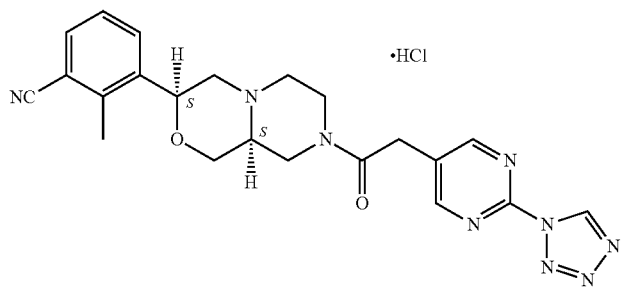 ·HCl | 2-methyl-3-[(3S,9aS)-8-{[2-(1H-tetrazol-1-yl)pyrimidin-5-yl]acetyl}octahydropyrazino[2,1-c][1,4]oxazin-3-yl]benzonitrile LC/MS 418 (M + H − N2). |
| 19 | 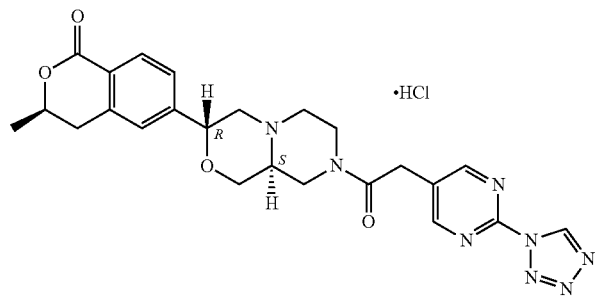 ·HCl | (3R)-3-methyl-6-[(3R,9aS)-8-{[2-(1H-tetrazol-1-yl)pyrimidin-5-yl]acetyl}octahydropyrazino[2,1-c][1,4]oxazin-3-yl]-3,4-dihydro-1H-isochromen-1-one; LC/MS 513 (M + Na), 491 (M + H). |
| 20 | 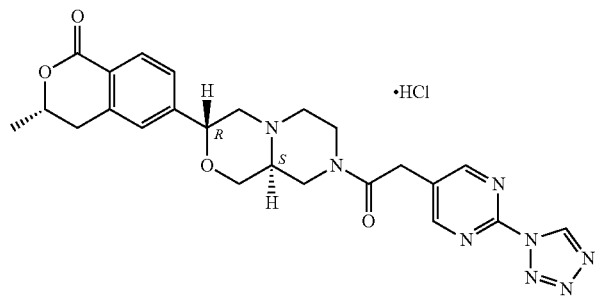 ·HCl | (3S)-3-methyl-6-[(3R,9aS)-8-{[2-(1H-tetrazol-1-yl)pyrimidin-5-yl]acetyl}octahydropyrazino[2,1-c][1,4]oxazin-3-yl]-3,4-dihydro-1H-isochromen-1-one; LC/MS 513 (M + Na). |

TABLE 3-continued

| Example # | | |
|---|---|---|
| 21 | 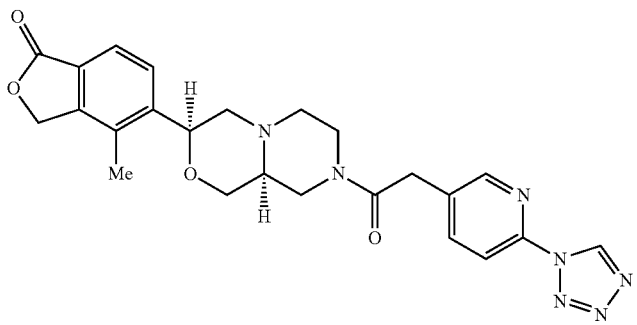 [SMILES: Cc1c([C@H]2CN3CCN(C(=O)Cc4ccc(-n5cnnn5)nc4)C[C@H]3CO2)ccc2c1COC2=O] | LC/MS (M + H) 476<br>4-methyl-5-[(3S,9aS)-8-{[6-(1H-tetrazol-1-yl)pyridin-3-yl]acetyl}octahydropyrazino[2,1-c][1,4]oxazin-3-yl]-2-benzofuran-1(3H)one |
| 22 | 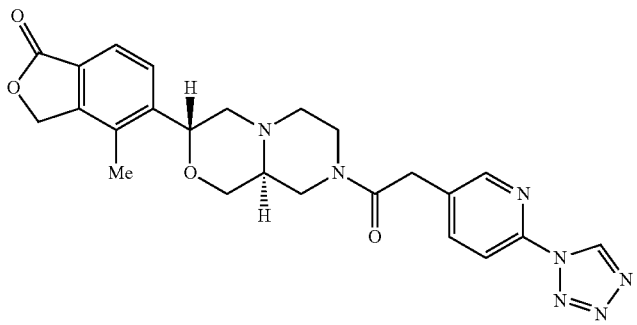 [SMILES: Cc1c([C@@H]2CN3CCN(C(=O)Cc4ccc(-n5cnnn5)nc4)C[C@H]3CO2)ccc2c1COC2=O] | LC/MS (M + H) 476<br>4-methyl-5-[(3R,9aS)-8-{[6-(1H-tetrazol-1-yl)pyridin-3-yl]acetyl}octahydropyrazino[2,1-c][1,4]oxazin-3-yl]-2-benzofuran-1(3H)-one |
| 23 | 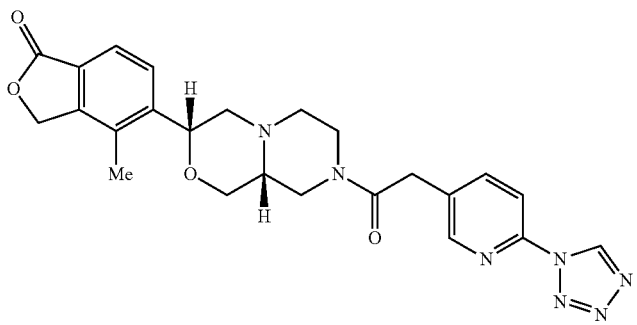 [SMILES: Cc1c([C@@H]2CN3CCN(C(=O)Cc4ccc(-n5cnnn5)nc4)C[C@@H]3CO2)ccc2c1COC2=O] | LC/MS (M + H) 476<br>4-methyl-5-[(3R,9aR)-8-{[6-(1H-tetrazol-1-yl)pyridin-3-yl]acetyl}octahydropyrazino[2,1-c][1,4]oxazin-3-yl]-2-benzofuran-1(3H)-one |
| 24 | 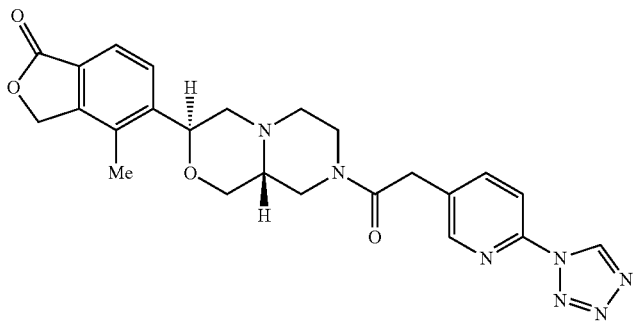 [SMILES: Cc1c([C@H]2CN3CCN(C(=O)Cc4ccc(-n5cnnn5)nc4)C[C@@H]3CO2)ccc2c1COC2=O] | LC/MS (M + H) 476<br>4-methyl-5-[(3S,9aR)-8-{[6-(1H-tetrazol-1-yl)pyridin-3-yl]acetyl}octahydropyrazino[2,1-c][1,4]oxazin-3-yl]-2-benzofuran-1(3H)-one |

TABLE 3-continued

| Example # | | |
|---|---|---|
| 25 | 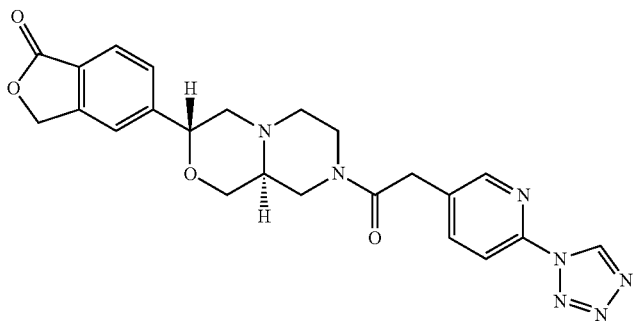 [SMILES: O=C1OCc2cc([C@@H]3CN4CCN(C(=O)Cc5ccc(-n6cnnn6)nc5)C[C@H]4CO3)ccc21] | LC/MS (M + H) 462<br>5-[(3R,9aS)-8-{[6-(1H-tetrazol-1-yl)pyridin-3-yl]acetyl}octahydropyrazino[2,1-c][1,4]oxazin-3-yl]-2-benzofuran-1(3H)-one |
| 26 | 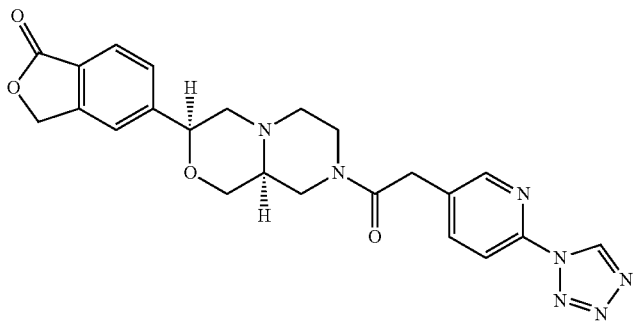 [SMILES: O=C1OCc2cc([C@H]3CN4CCN(C(=O)Cc5ccc(-n6cnnn6)nc5)C[C@H]4CO3)ccc21] | LC/MS (M + H) 462<br>5-[(3S,9aS)-8-{[6-(1H-tetrazol-1-yl)pyridin-3-yl]acetyl}octahydropyrazino[2,1-c][1,4]oxazin-3-yl]-2-benzofuran-1(3H)-one |
| 27 | 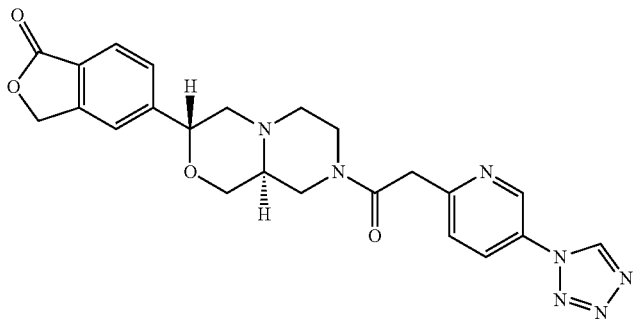 [SMILES: O=C1OCc2cc([C@@H]3CN4CCN(C(=O)Cc5ccc(-n6cnnn6)cn5)C[C@H]4CO3)ccc21] | LC/MS (M + H) 462<br>5-[(3R,9aS)-8-{[5-(1H-tetrazol-1-yl)pyridin-2-yl]acetyl}octahydropyrazino[2,1-c][1,4]oxazin-3-yl]-2-benzofuran-1(3H)-one |
| 28 | 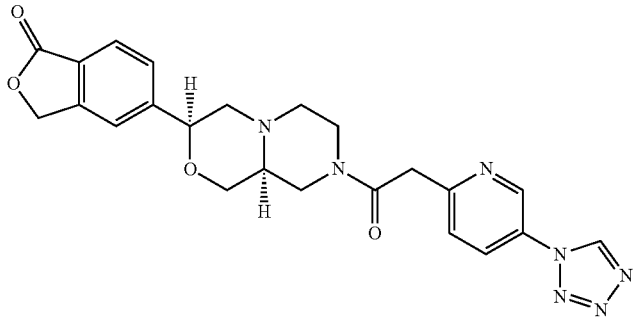 [SMILES: O=C1OCc2cc([C@H]3CN4CCN(C(=O)Cc5ccc(-n6cnnn6)cn5)C[C@H]4CO3)ccc21] | LC/MS (M + H) 462<br>5-[(3S,9aS)-8-{[5-(1H-tetrazol-1-yl)pyridin-2-yl]acetyl}octahydropyrazino[2,1-c][1,4]oxazin-3-yl]-2-benzofuran-1(3H)-one |

TABLE 3-continued

| Example # | | |
|---|---|---|
| 29 | | LC/MS (M + H) 476<br>4-methyl-5-[(3S,9aS)-8-{[5-(1H-tetrazol-1-yl)pyridin-2-yl]acetyl}octahydropyrazino[2,1-c][1,4]oxazin-3-yl]-2-benzofuran-1(3H)-one |
| 30 | | LC/MS (M + H) 490<br>6-[(3R,9aS)-8-{[2-methyl-6-(1H-tetrazol-1-yl)pyridin-3-yl]acetyl}octahydropyrazino[2,1-c][1,4]oxazin-3-yl]-3,4-dihydro-1H-isochromen-1-one |
| 31 | | LC/MS (M + H) 463<br>6-fluoro-2-methyl-3-[(3S,9aR)-8-{[5-(1H-tetrazol-1-yl)pyridin-2-yl]acetyl}octahydropyrazino[2,1-c][1,4]oxazin-3-yl]benzonitrile |
| 32 | | LC/MS (M + H) 463<br>6-fluoro-2-methyl-3-[(3R,9aR)-8-{[5-(1H-tetrazol-1-yl)pyridin-2-yl]acetyl}octahydropyrazino[2,1-c][1,4]oxazin-3-yl]benzonitrile |
| 33 | | LC/MS (M + H) 490<br>(3S)-3-methyl-6-[(3R,9aS)-8-{[6-(1H-tetrazol-1-yl)pyridin-3-yl]acetyl}octahydropyrazino[2,1-c][1,4]oxazin-3-yl]-3,4-dihydro-1H-isochromen-1-one |

TABLE 3-continued

| Example # | | |
|---|---|---|
| 34 | 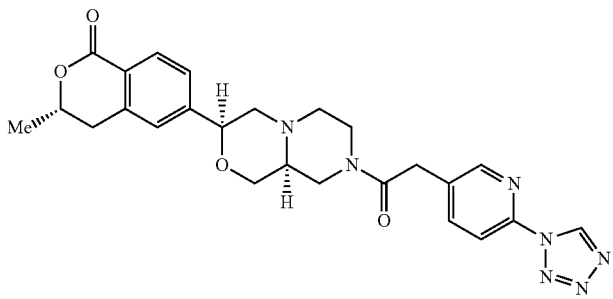 [SMILES: C[C@H]1Cc2cc([C@H]3CN4CCN(C(=O)Cc5ccc(-n6cnnn6)nc5)C[C@H]4CO3)ccc2C(=O)O1] | LC/MS (M + H) 490<br>(3S)-3-methyl-6-[(3S,9aS)-8-{[6-(1H-tetrazol-1-yl)pyridin-3-yl]acetyl}octahydropyrazino[2,1-c][1,4]oxazin-3-yl]-3,4-dihydro-1H-isochromen-1-one |
| 35 | 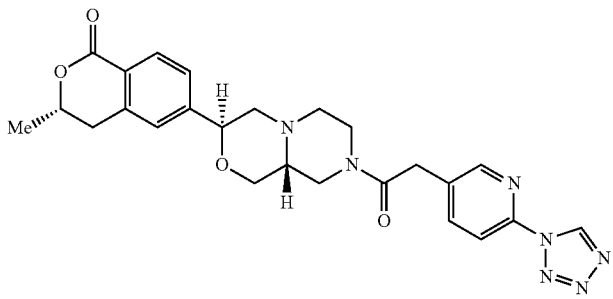 [SMILES: C[C@H]1Cc2cc([C@H]3CN4CCN(C(=O)Cc5ccc(-n6cnnn6)nc5)C[C@@H]4CO3)ccc2C(=O)O1] | LC/MS (M + H) 490<br>(3S)-3-methyl-6-[(3S,9aR)-8-{[6-(1H-tetrazol-1-yl)pyridin-3-yl]acetyl}octahydropyrazino[2,1-c][1,4]oxazin-3-yl]-3,4-dihydro-1H-isochromen-1-one |
| 36 | 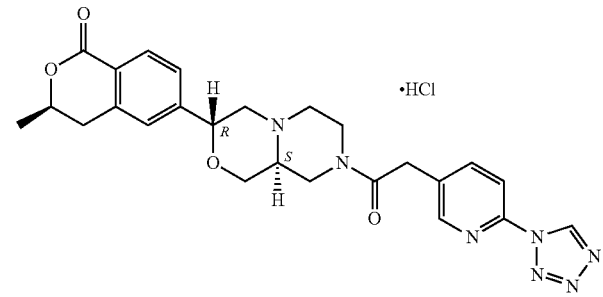 | LC/MS (M + H) 490<br>(3R)-3-methyl-6-[(3R,9aS)-8-{[6-(1H-tetrazol-1-yl)pyridin-3-yl]acetyl}octahydropyrazino[2,1-c][1,4]oxazin-3-yl]-3,4-dihydro-1H-isochromen-1-one |
| 37 | 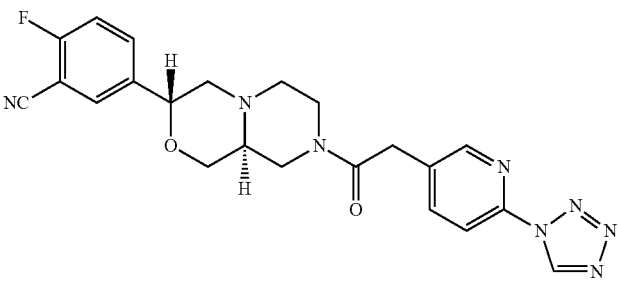 [SMILES: N#Cc1cc([C@@H]2CN3CCN(C(=O)Cc4ccc(-n5cnnn5)nc4)C[C@H]3CO2)ccc1F] | LC/MS (M + H) 449<br>2-fluoro-5-[(3R,9aS)-8-{[6-(1H-tetrazol-1-yl)pyridin-3-yl]acetyl}octahydropyrazino[2,1-c][1,4]oxazin-3-yl]benzonitrile |
| 38 | 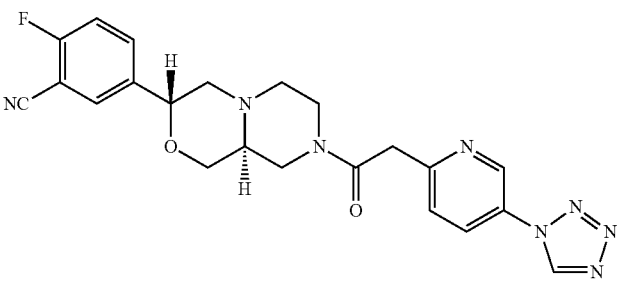 [SMILES: N#Cc1cc([C@@H]2CN3CCN(C(=O)Cc4ccc(-n5cnnn5)cn4)C[C@H]3CO2)ccc1F] | LC/MS (M + H) 449<br>2-fluoro-5-[(3R,9aS)-8-{[5-(1H-tetrazol-1-yl)pyridin-2-yl]acetyl}octahydropyrazino[2,1-c][1,4]oxazin-3-yl]benzonitrile |

TABLE 3-continued

| Example # | Structure | Description |
|---|---|---|
| 39 | 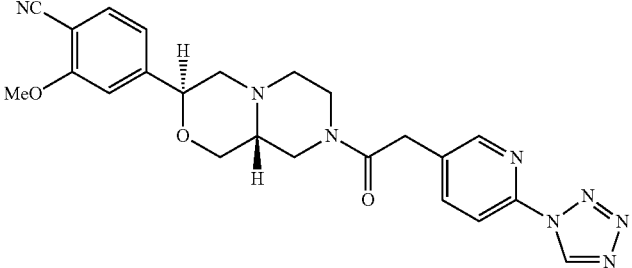 [SMILES: COc1cc([C@H]2CN3CCN(C(=O)Cc4ccc(-n5cnnn5)nc4)C[C@@H]3CO2)ccc1C#N] | LC/MS (M + H) 461<br>2-methoxy-4-[(3S,9aR)-8-{[6-(1H-tetrazol-1-yl)pyridin-3-yl]acetyl}octahydropyrazino[2,1-c][1,4]oxazin-3-yl]benzonitrile |
| 40 | 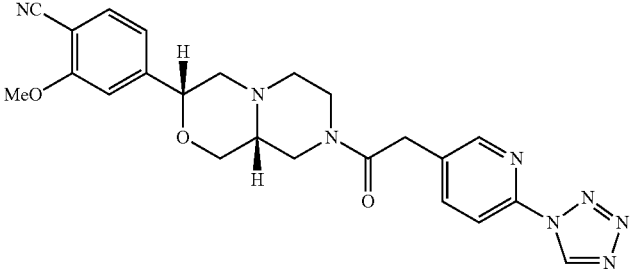 [SMILES: COc1cc([C@@H]2CN3CCN(C(=O)Cc4ccc(-n5cnnn5)nc4)C[C@@H]3CO2)ccc1C#N] | LC/MS (M + H) 461<br>2-methoxy-4-[(3R,9aR)-8-{[6-(1H-tetrazol-1-yl)pyridin-3-yl]acetyl}octahydropyrazino[2,1-c][1,4]oxazin-3-yl]benzonitrile |
| 41 | 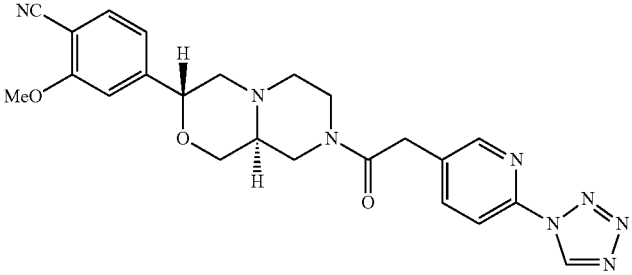 [SMILES: COc1cc([C@@H]2CN3CCN(C(=O)Cc4ccc(-n5cnnn5)nc4)C[C@H]3CO2)ccc1C#N] | LC/MS (M + H) 461<br>2-methoxy-4-[(3R,9aS)-8-{[6-(1H-tetrazol-1-yl)pyridin-3-yl]acetyl}octahydropyrazino[2,1-c][1,4]oxazin-3-yl]benzonitrile |
| 42 | 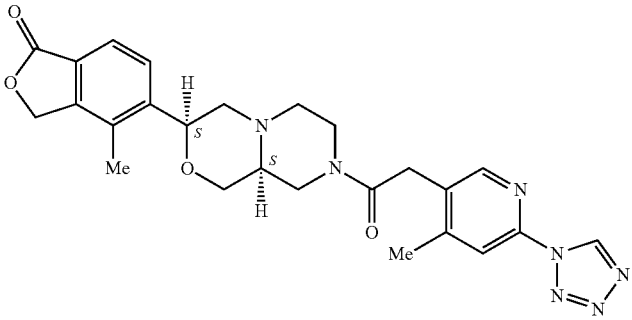 | LC/MS (M + H) 490<br>4-methyl-5-[(3S,9aS)-8-{[4-methyl-6-(1H-tetrazol-1-yl)pyridin-3-yl]acetyl}octahydropyrazino[2,1-c][1,4]oxazin-3-yl]-2-benzofuran-1(3H)-one |
| 43 | 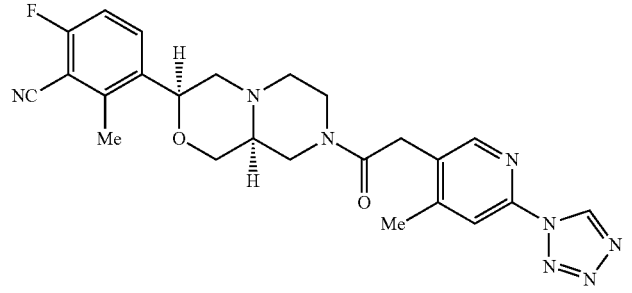 [SMILES: Cc1cc(-n2cnnn2)ncc1CC(=O)N1CCN2C[C@H](c3ccc(F)c(C#N)c3C)OC[C@@H]2C1] | LC/MS (M + H) 477<br>6-fluoro-2-methyl-3-[(3S,9aS)-8-{[4-methyl-6-(1H-tetrazol-1-yl)pyridin-3-yl]acetyl}octahydropyrazino[2,1-c][1,4]oxazin-3-yl]benzonitrile |

TABLE 3-continued

| Example # | | |
|---|---|---|
| 44 | 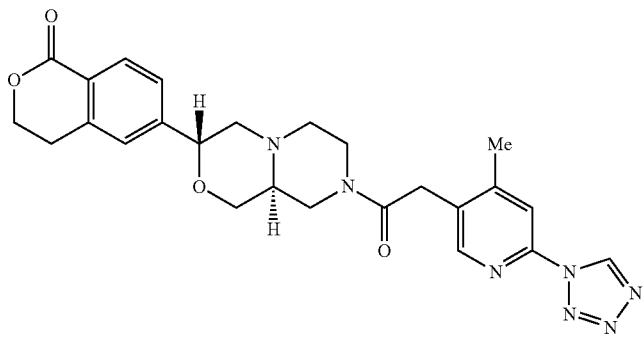 [SMILES: Cc1cc(-n2cnnn2)ncc1CC(=O)N1CCN2C[C@@H](c3ccc4c(c3)CCOC4=O)OC[C@@H]2C1] | LC/MS (M + H) 490<br>6-[(3R,9aS)-8-{[4-methyl-6-(1H-tetrazol-1-yl)pyridin-3-yl]acetyl}octahydropyrazino[2,1-c][1,4]oxazin-3-yl]-3,4-dihydro-1H-isochromen-1-one |
| 45 | 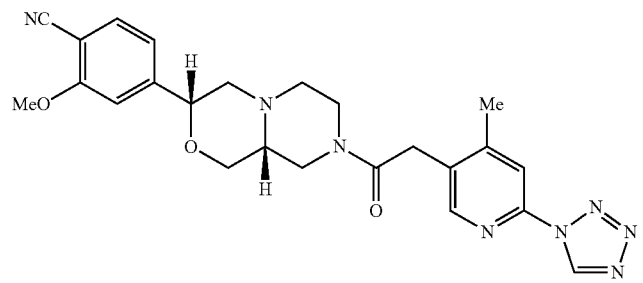 [SMILES: COc1cc([C@@H]2CN3CCN(C(=O)Cc4cnc(-n5cnnn5)cc4C)C[C@@H]3CO2)ccc1C#N] | LC/MS (M + H) 475<br>2-methoxy-4-[(3R,9aR)-8-{[4-methyl-6-(1H-tetrazol-1-yl)pyridin-3-yl]acetyl}octahydropyrazino[2,1-c][1,4]oxazin-3-yl]benzonitrile |
| 46 | 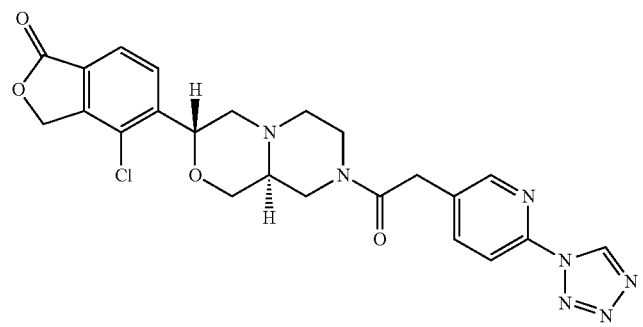 [SMILES: O=C1OCc2c1ccc([C@@H]1CN3CCN(C(=O)Cc4ccc(-n5cnnn5)nc4)C[C@H]3CO1)c2Cl] | LC/MS (M + H) 496<br>4-chloro-5-[(3R,9aS)-8-{[6-(1H-tetrazol-1-yl)pyridin-3-yl]acetyl}octahydropyrazino[2,1-c][1,4]oxazin-3-yl]-2-benzofuran-1(3H)-one |
| 47 | 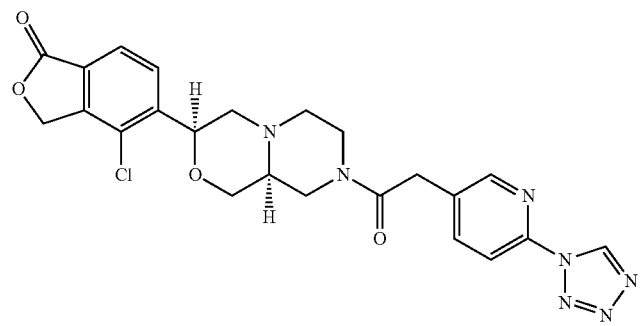 | LC/MS (M + H) 496<br>4-chloro-5-[(3S,9aS)-8-{[6-(1H-tetrazol-1-yl)pyridin-3-yl]acetyl}octahydropyrazino[2,1-c][1,4]oxazin-3-yl]-2-benzofuran-1(3H)-one |

TABLE 3-continued

| Example # | | |
|---|---|---|
| 48 | 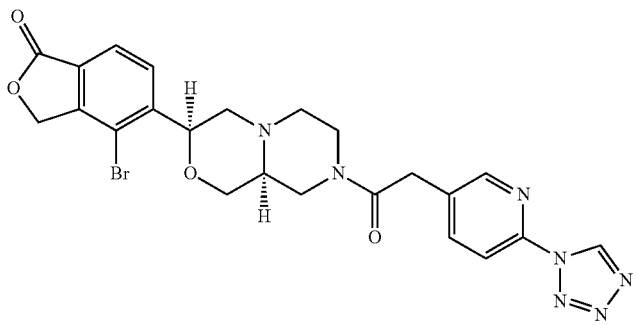 [SMILES: O=C1OCc2c1ccc([C@H]1CN3CCN(C(=O)Cc4ccc(-n5cnnn5)nc4)C[C@H]3CO1)c2Cl] | LC/MS (M + H) 540, 542<br>4-bromo-5-[(3S,9aS)-8-{[6-(1H-tetrazol-1-yl)pyridin-3-yl]acetyl}octahydropyrazino[2,1-c][1,4]oxazin-3-yl]-2-benzofuran-1(3H)-one |
| 49 | 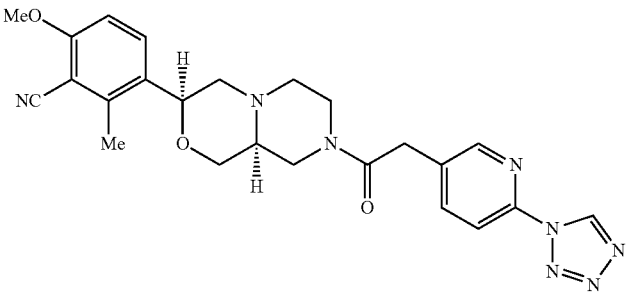 [SMILES: COc1ccc([C@H]2CN3CCN(C(=O)Cc4ccc(-n5cnnn5)nc4)C[C@H]3CO2)c(C)c1C#N] | LC/MS (M + H) 475<br>6-methoxy-2-methyl-3-[(3S,9aS)-8-{[6-(1H-tetrazol-1-yl)pyridin-3-yl]acetyl}octahydropyrazino[2,1-c][1,4]oxazin-3-yl]benzonitrile |
| 50 | 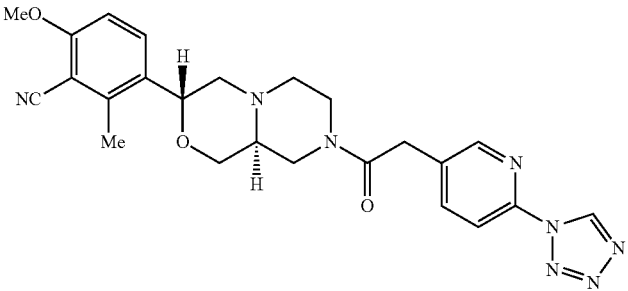 [SMILES: COc1ccc([C@@H]2CN3CCN(C(=O)Cc4ccc(-n5cnnn5)nc4)C[C@H]3CO2)c(C)c1C#N] | LC/MS (M + H) 475<br>6-methoxy-2-methyl-3-[(3R,9aS)-8-{[6-(1H-tetrazol-1-yl)pyridin-3-yl]acetyl}octahydropyrazino[2,1-c][1,4]oxazin-3-yl]benzonitrile |
| 51 | 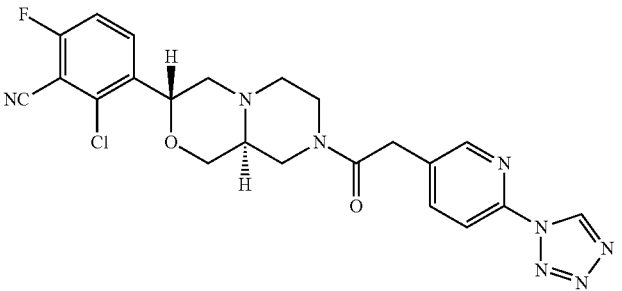 [SMILES: N#Cc1c(F)ccc([C@@H]2CN3CCN(C(=O)Cc4ccc(-n5cnnn5)nc4)C[C@H]3CO2)c1Cl] | LC/MS (M + H) 483<br>2-chloro-6-fluoro-3-[(3R,9aS)-8-{[6-(1H-tetrazol-1-yl)pyridin-3-yl]acetyl}octahydropyrazino[2,1-c][1,4]oxazin-3-yl]benzonitrile |
| 52 | 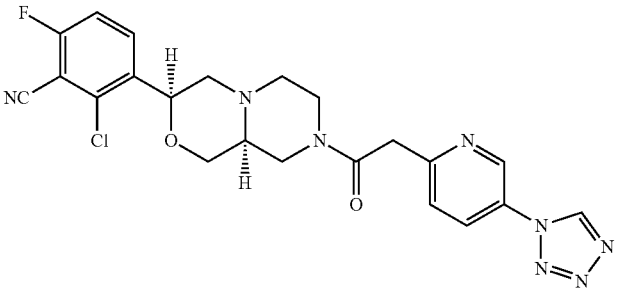 [SMILES: N#Cc1c(F)ccc([C@H]2CN3CCN(C(=O)Cc4ccc(-n5cnnn5)cn4)C[C@H]3CO2)c1Cl] | LC/MS (M + H) 483<br>2-chloro-6-fluoro-3-[(3S,9aS)-8-{[5-(1H-tetrazol-1-yl)pyridin-2-yl]acetyl}octahydropyrazino[2,1-c][1,4]oxazin-3-yl]benzonitrile |

TABLE 3-continued

| Example # | | |
|---|---|---|
| 53 | 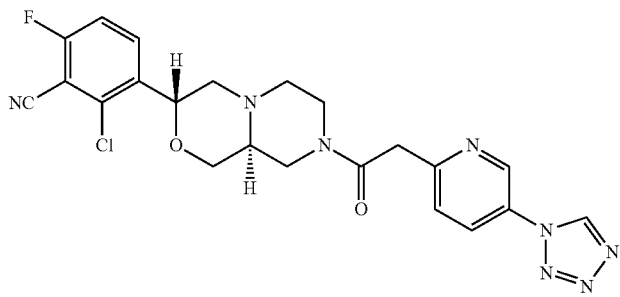 [SMILES: N#Cc1c(F)ccc([C@@H]2CN3CCN(C(=O)Cc4ccc(-n5cnnn5)cn4)C[C@H]3CO2)c1Cl] | LC/MS (M + H) 483<br>2-chloro-6-fluoro-3-[(3R,9aS)-8-{[5-(1H-tetrazol-1-yl)pyridin-2-yl]acetyl}octahydropyrazino[2,1-c][1,4]oxazin-3-yl]benzonitrile |
| 54 | 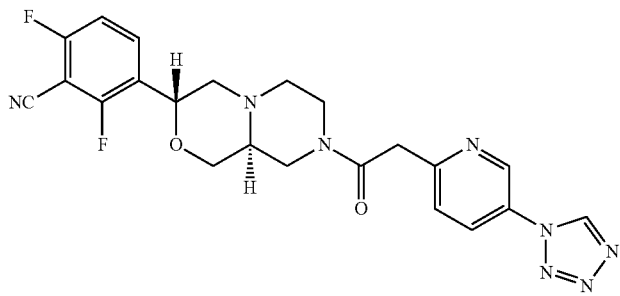 [SMILES: N#Cc1c(F)ccc([C@@H]2CN3CCN(C(=O)Cc4ccc(-n5cnnn5)cn4)C[C@H]3CO2)c1F] | LC/MS (M + H) 467<br>2,6-difluoro-3-[(3R,9aS)-8-{[5-(1H-tetrazol-1-yl)pyridin-2-yl]acetyl}octahydropyrazino[2,1-c][1,4]oxazin-3-yl]benzonitrile |
| 55 | 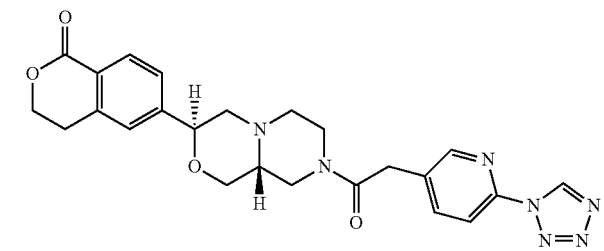 [SMILES: O=C1OCCc2cc([C@H]3CN4CCN(C(=O)Cc5ccc(-n6cnnn6)nc5)C[C@@H]4CO3)ccc21] | LC/MS (M + H) 476<br>6-[(3S,9aR)-8-{[6-(1H-tetrazol-1-yl)pyridin-3-yl]acetyl}octahydropyrazino[2,1-c][1,4]oxazin-3-yl]-3,4-dihydro-1H-isochromen-1-one |
| 56 | 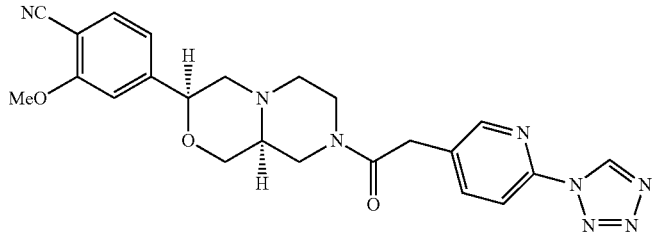 [SMILES: COc1cc([C@H]2CN3CCN(C(=O)Cc4ccc(-n5cnnn5)nc4)C[C@H]3CO2)ccc1C#N] | LC/MS (M + H) 461<br>2-methoxy-4-[(3S,9aS)-8-{[6-(1H-tetrazol-1-yl)pyridin-3-yl]acetyl}octahydropyrazino[2,1-c][1,4]oxazin-3-yl]benzonitrile |
| 57 | 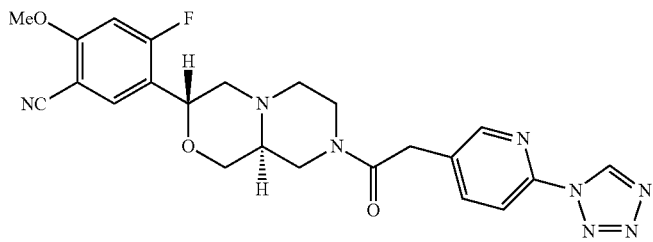 | LC/MS (M + H) 479<br>4-fluoro-2-methoxy-5-[(3R,9aS)-8-{[6-(1H-tetrazol-1-yl)pyridin-3-yl]acetyl}octahydropyrazino[2,1-c][1,4]oxazin-3-yl]benzonitrile |

TABLE 3-continued

| Example # | | |
|---|---|---|
| 58 | 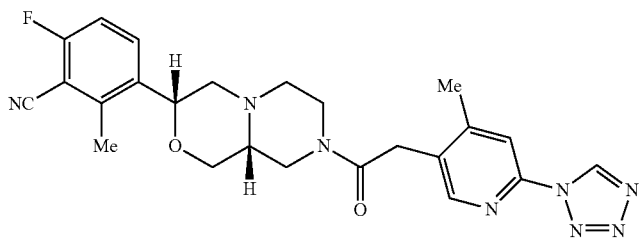 [SMILES: Cc1cc(-n2cnnn2)ncc1CC(=O)N1CCN2C[C@@H](c3ccc(F)c(C#N)c3C)OC[C@H]2C1] | LC/MS (M + H) 477<br>6-fluoro-2-methyl-3-[(3R,9aR)-8-{[4-methyl-6-(1H-tetrazol-1-yl)pyridin-3-yl]acetyl}octahydropyrazino[2,1-c][1,4]oxazin-3-yl]benzonitrile |
| 59 | 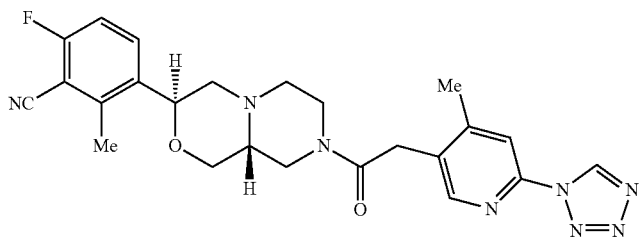 [SMILES: Cc1cc(-n2cnnn2)ncc1CC(=O)N1CCN2C[C@H](c3ccc(F)c(C#N)c3C)OC[C@H]2C1] | LC/MS (M + H) 477<br>6-fluoro-2-methyl-3-[(3S,9aR)-8-{[4-methyl-6-(1H-tetrazol-1-yl)pyridin-3-yl]acetyl}octahydropyrazino[2,1-c][1,4]oxazin-3-yl]benzonitrile |
| 60 | 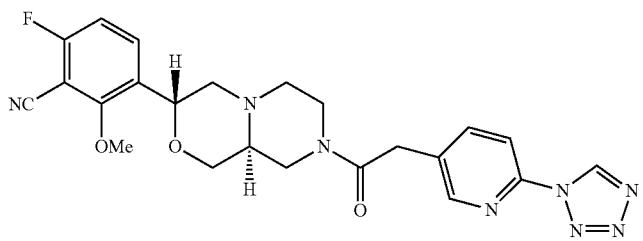 [SMILES: COc1c([C@@H]2CN3CCN(C(=O)Cc4ccc(-n5cnnn5)nc4)C[C@H]3CO2)ccc(F)c1C#N] | LC/MS (M + H) 479<br>6-fluoro-2-methoxy-3-[(3R,9aS)-8-{[6-(1H-tetrazol-1-yl)pyridin-3-yl]acetyl}octahydropyrazino[2,1-c][1,4]oxazin-3-yl]benzonitrile |
| 61 | 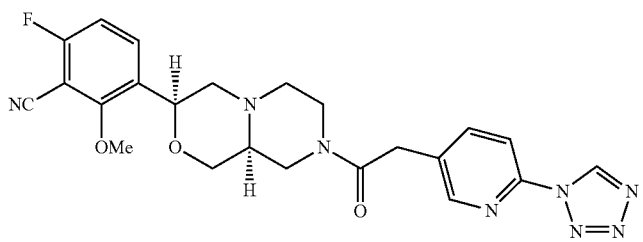 [SMILES: COc1c([C@H]2CN3CCN(C(=O)Cc4ccc(-n5cnnn5)nc4)C[C@H]3CO2)ccc(F)c1C#N] | LC/MS (M + H) 479<br>6-fluoro-2-methoxy-3-[(3S,9aS)-8-{[6-(1H-tetrazol-1-yl)pyridin-3-yl]acetyl}octahydropyrazino[2,1-c][1,4]oxazin-3-yl]benzonitrile |
| 62 | 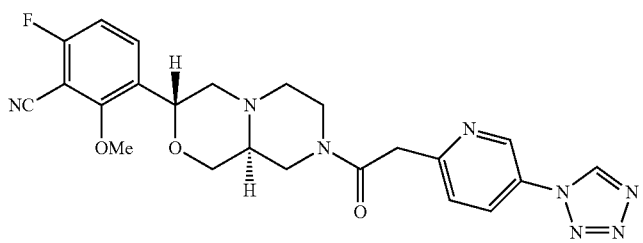 [SMILES: COc1c([C@@H]2CN3CCN(C(=O)Cc4ccc(-n5cnnn5)cn4)C[C@H]3CO2)ccc(F)c1C#N] | LC/MS (M + H) 479<br>6-fluoro-2-methoxy-3-[(3R,9aS)-8-{[5-(1H-tetrazol-1-yl)pyridin-2-yl]acetyl}octahydropyrazino[2,1-c][1,4]oxazin-3-yl]benzonitrile |
| 63 | 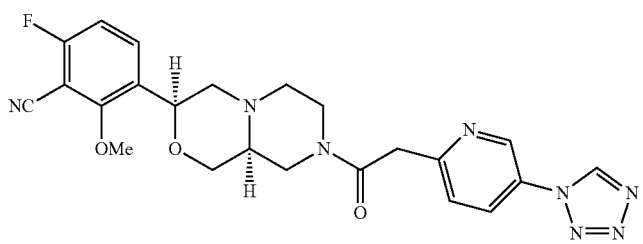 [SMILES: COc1c([C@H]2CN3CCN(C(=O)Cc4ccc(-n5cnnn5)cn4)C[C@H]3CO2)ccc(F)c1C#N] | LC/MS (M + H) 479<br>6-fluoro-2-methoxy-3-[(3S,9aS)-8-{[5-(1H-tetrazol-1-yl)pyridin-2-yl]acetyl}octahydropyrazino[2,1-c][1,4]oxazin-3-yl]benzonitrile |

TABLE 3-continued

| Example # | | |
|---|---|---|
| 64 | 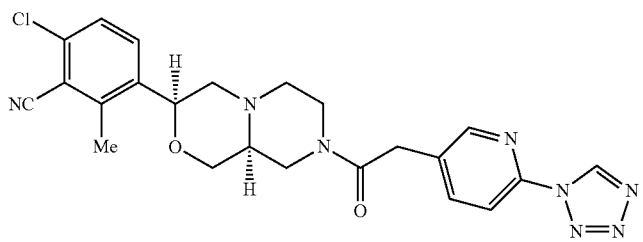 | LC/MS (M + H) 479<br>6-chloro-2-methyl-3-[(3S,9aS)-8-{[6-(1H-tetrazol-1-yl)pyridin-3-yl]acetyl}octahydropyrazino[2,1-c][1,4]oxazin-3-yl]benzonitrile |
| 65 | 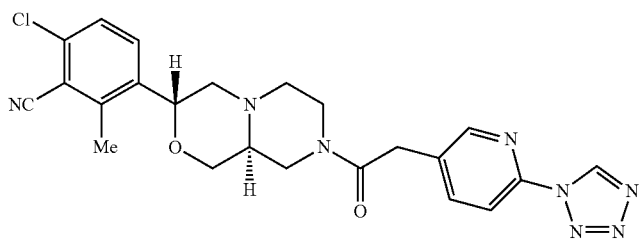 | LC/MS (M + H) 479<br>6-chloro-2-methyl-3-[(3R,9aS)-8-{[6-(1H-tetrazol-1-yl)pyridin-3-yl]acetyl}octahydropyrazino[2,1-c][1,4]oxazin-3-yl]benzonitrile |
| 66 | 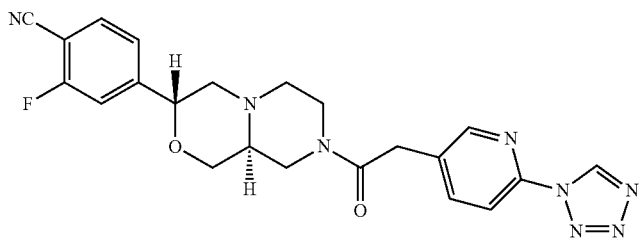 [SMILES: N#Cc1ccc([C@@H]2CN3CCN(C(=O)Cc4ccc(-n5cnnn5)nc4)C[C@H]3CO2)cc1F] | LC/MS (M + H) 449<br>2-fluoro-4-[(3R,9aS)-8-{[6-(1H-tetrazol-1-yl)pyridin-3-yl]acetyl}octahydropyrazino[2,1-c][1,4]oxazin-3-yl]benzonitrile |
| 67 | 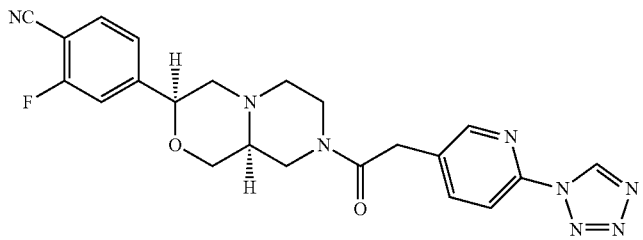 [SMILES: N#Cc1ccc([C@H]2CN3CCN(C(=O)Cc4ccc(-n5cnnn5)nc4)C[C@H]3CO2)cc1F] | LC/MS (M + H) 449<br>2-fluoro-4-[(3S,9aS)-8-{[6-(1H-tetrazol-1-yl)pyridin-3-yl]acetyl}octahydropyrazino[2,1-c][1,4]oxazin-3-yl]benzonitrile |
| 68 | 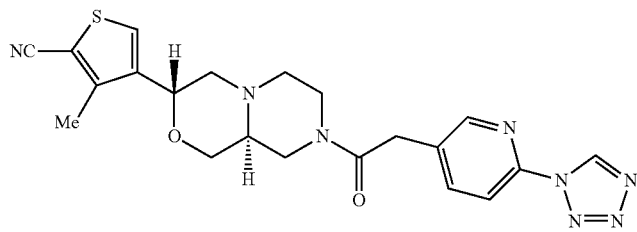 [SMILES: Cc1c([C@@H]2CN3CCN(C(=O)Cc4ccc(-n5cnnn5)nc4)C[C@H]3CO2)csc1C#N] | LC/MS (M + H) 451<br>3-methyl-4-[(3R,9aS)-8-{[6-(1H-tetrazol-1-yl)pyridin-3-yl]acetyl}octahydropyrazino[2,1-c][1,4]oxazin-3-yl]thiophene-2-carbonitrile |
| 69 | 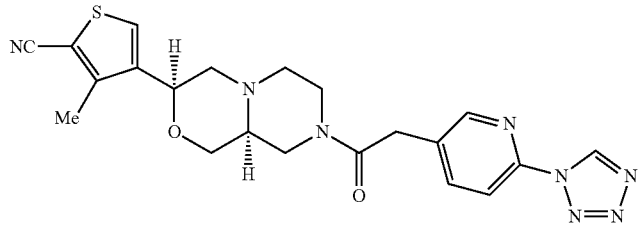 [SMILES: Cc1c([C@H]2CN3CCN(C(=O)Cc4ccc(-n5cnnn5)nc4)C[C@H]3CO2)csc1C#N] | LC/MS (M + H) 451<br>3-methyl-4-[(3S,9aS)-8-{[6-(1H-tetrazol-1-yl)pyridin-3-yl]acetyl}octahydropyrazino[2,1-c][1,4]oxazin-3-yl]thiophene-2-carbonitrile |

TABLE 3-continued

| Example # | | |
|---|---|---|
| 70 | | LC/MS (M + H) 451<br>3-methyl-4-[(3R,9aS)-8-{[5-(1H-tetrazol-1-yl)pyridin-2-yl]acetyl}octahydropyrazino[2,1-c][1,4]oxazin-3-yl]thiophene-2-carbonitrile |
| 71 | | LC/MS (M + H) 451<br>3-methyl-4-[(3S,9aS)-8-{[5-(1H-tetrazol-1-yl)pyridin-2-yl]acetyl}octahydropyrazino[2,1-c][1,4]oxazin-3-yl]thiophene-2-carbonitrile |
| 72 | | LC/MS (M + H) 476<br>6-methyl-5-[(3R,9aS)-8-{[6-(1H-tetrazol-1-yl)pyridin-3-yl]acetyl}octahydropyrazino[2,1-c][1,4]oxazin-3-yl]-2-benzofuran-1(3H)-one |
| 73 | | LC/MS (M + H) 476<br>6-methyl-5-[(3S,9aS)-8-{[6-(1H-tetrazol-1-yl)pyridin-3-yl]acetyl}octahydropyrazino[2,1-c][1,4]oxazin-3-yl]-2-benzofuran-1(3H)-one |
| 74 | | LC/MS (M + H) 446<br>4-methyl-5-[(3R,9aS)-8-{[6-(1H-tetrazol-1-yl)pyridin-3-yl]acetyl}octahydropyrazino[2,1-c][1,4]oxazin-3-yl]pyridine-3-carbonitrile |
| 75 | | LC/MS (M + H) 464<br>6-fluoro-2-methyl-3-[(3R,9aS)-8-{[5-(1H-tetrazol-1-yl)pyrazin-2-yl]acetyl}octahydropyrazino[2,1-c][1,4]oxazin-3-yl]benzonitrile |

TABLE 3-continued

| Example # | Structure | Data |
|---|---|---|
| 76 | | LC/MS (M + H) 464<br>6-fluoro-2-methyl-3-[(3S,9aS)-8-{[5-(1H-tetrazol-1-yl)pyrazin-2-yl]acetyl}octahydropyrazino[2,1-c][1,4]oxazin-3-yl]benzonitrile |
| 77 | | LC/MS (M + H) 477<br>6-fluoro-2-methyl-3-[(3R,9aS)-8-{[2-methyl-6-(1H-tetrazol-1-yl)pyridin-3-yl]acetyl}octahydropyrazino[2,1-c][1,4]oxazin-3-yl]benzonitrile |
| 78 | | LC/MS (M + H) 477<br>6-fluoro-2-methyl-3-[(3S,9aS)-8-{[2-methyl-6-(1H-tetrazol-1-yl)pyridin-3-yl]acetyl}octahydropyrazino[2,1-c][1,4]oxazin-3-yl]benzonitrile |
| 79 | | LC/MS (M + H) 491<br>6-fluoro-2-methyl-3-[(3R,9aS)-8-{2-[2-methyl-6-(1H-tetrazol-1-yl)pyridin-3-yl]propanoyl}octahydropyrazino[2,1-c][1,4]oxazin-3-yl]benzonitrile |
| 80 | | LC/MS (M + H) 477<br>6-[(3R,9aS)-8-{[5-(1H-tetrazol-1-yl)pyrazin-2-yl]acetyl}octahydropyrazino[2,1-c][1,4]oxazin-3-yl]-3,4-dihydro-1H-isochromen-1-one |
| 81 | | LC/MS (M + H) 467<br>2,4-difluoro-5-[(3R,9aS)-8-{[6-(1H-tetrazol-1-yl)pyridin-3-yl]acetyl}octahydropyrazino[2,1-c][1,4]oxazin-3-yl]benzonitrile |

TABLE 3-continued

| Example # | | |
|---|---|---|
| 82 | 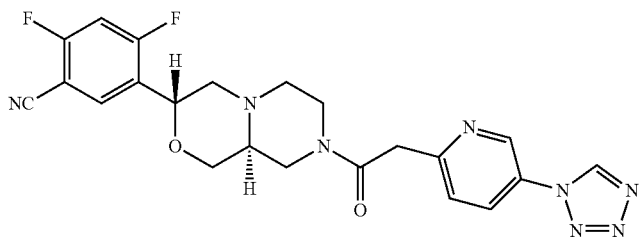 [SMILES: N#Cc1cc([C@@H]2CN3CCN(C(=O)Cc4ccc(-n5cnnn5)cn4)C[C@H]3CO2)c(F)cc1F] | LC/MS (M + H) 467<br>2,4-difluoro-5-[(3R,9aS)-8-{[5-(1H-tetrazol-1-yl)pyridin-2-yl]acetyl}octahydropyrazino[2,1-c][1,4]oxazin-3-yl]benzonitrile |
| 83 | 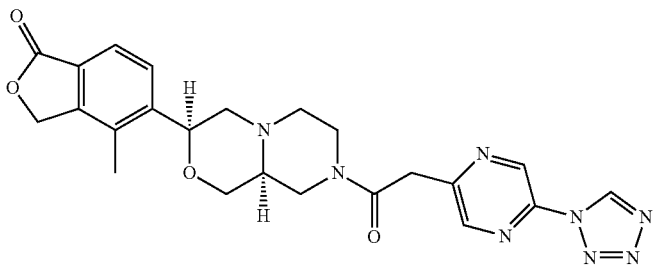 [SMILES: Cc1c([C@H]2CN3CCN(C(=O)Cc4cnc(-n5cnnn5)cn4)C[C@H]3CO2)ccc2c1COC2=O] | LC/MS (M + H) 477<br>4-methyl-5-[(3S,9aS)-8-{[5-(1H-tetrazol-1-yl)pyrazin-2-yl]acetyl}octahydropyrazino[2,1-c][1,4]oxazin-3-yl]-2-benzofuran-1(3H)-one |
| 84 | 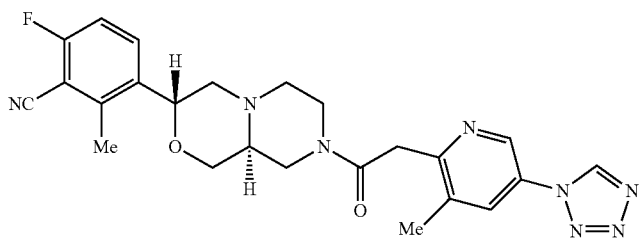 [SMILES: Cc1cc(-n2cnnn2)cnc1CC(=O)N1CCN2C[C@@H](c3ccc(F)c(C#N)c3C)OC[C@@H]2C1] | LC/MS (M + H) 477<br>6-fluoro-2-methyl-3-[(3R,9aS)-8-{[3-methyl-5-(1H-tetrazol-1-yl)pyridin-2-yl]acetyl}octahydropyrazino[2,1-c][1,4]oxazin-3-yl]benzonitrile |
| 85 | 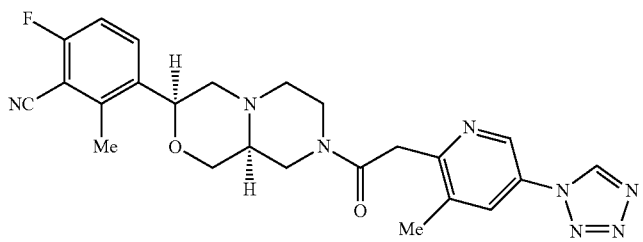 [SMILES: Cc1cc(-n2cnnn2)cnc1CC(=O)N1CCN2C[C@H](c3ccc(F)c(C#N)c3C)OC[C@@H]2C1] | LC/MS (M + H) 477<br>6-fluoro-2-methyl-3-[(3S,9aS)-8-{[3-methyl-5-(1H-tetrazol-1-yl)pyridin-2-yl]acetyl}octahydropyrazino[2,1-c][1,4]oxazin-3-yl]benzonitrile |
| 86 | 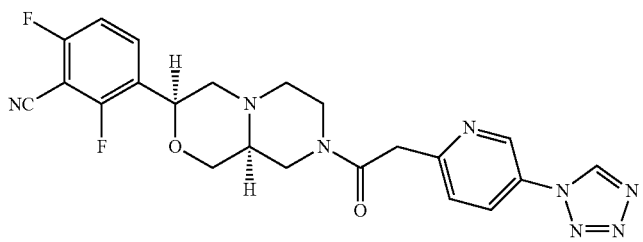 [SMILES: N#Cc1c(F)ccc([C@H]2CN3CCN(C(=O)Cc4ccc(-n5cnnn5)cn4)C[C@H]3CO2)c1F] | LC/MS (M + H) 467<br>2,6-difluoro-3-[(3S,9aS)-8-{[5-(1H-tetrazol-1-yl)pyridin-2-yl]acetyl}octahydropyrazino[2,1-c][1,4]oxazin-3-yl]benzonitrile |
| 87 | 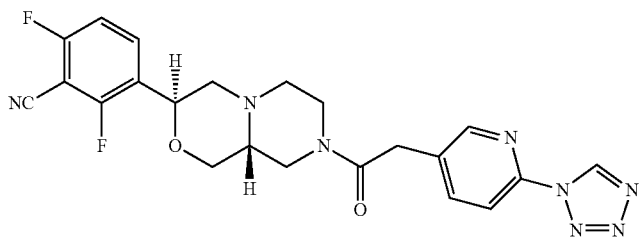 [SMILES: N#Cc1c(F)ccc([C@H]2CN3CCN(C(=O)Cc4ccc(-n5cnnn5)nc4)C[C@@H]3CO2)c1F] | LC/MS (M + H) 467<br>2,6-difluoro-3-[(3S,9aR)-8-{[6-(1H-tetrazol-1-yl)pyridin-3-yl]acetyl}octahydropyrazino[2,1-c][1,4]oxazin-3-yl]benzonitrile |

TABLE 3-continued

| Example # | | |
|---|---|---|
| 88 | 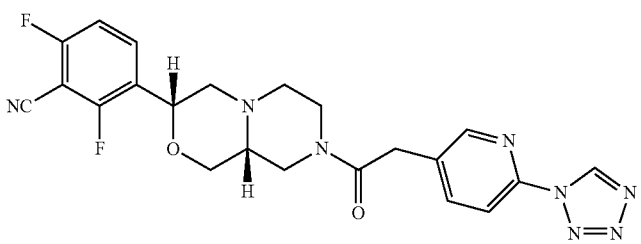 [SMILES: N#Cc1c(F)ccc([C@@H]2CN3CCN(C(=O)Cc4ccc(-n5cnnn5)nc4)C[C@@H]3CO2)c1F] | LC/MS (M + H) 467<br>2,6-difluoro-3-[(3R,9aR)-8-{[6-(1H-tetrazol-1-yl)pyridin-3-yl]acetyl}octahydropyrazino[2,1-c][1,4]oxazin-3-yl]benzonitrile |
| 89 | 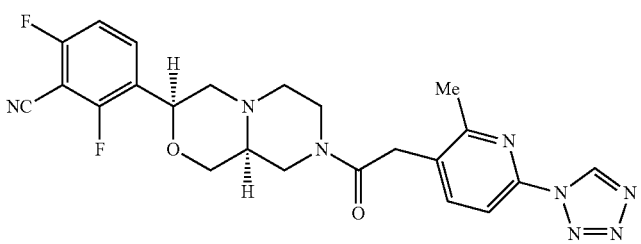 [SMILES: Cc1nc(-n2cnnn2)ccc1CC(=O)N1CCN2C[C@H](c3ccc(F)c(C#N)c3F)OC[C@@H]2C1] | LC/MS (M + H) 467<br>2,6-difluoro-3-[(3S,9aS)-8-{[2-methyl-6-(1H-tetrazol-1-yl)pyridin-3-yl]acetyl}octahydropyrazino[2,1-c][1,4]oxazin-3-yl]benzonitrile |
| 90 | 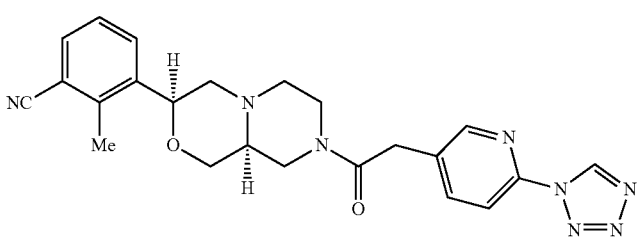 [SMILES: Cc1c(C#N)cccc1[C@H]1CN2CCN(C(=O)Cc3ccc(-n4cnnn4)nc3)C[C@H]2CO1] | LC/MS (M + H) 445<br>2-methyl-3-[(3S,9aS)-8-{[6-(1H-tetrazol-1-yl)pyridin-3-yl]acetyl}octahydropyrazino[2,1-c][1,4]oxazin-3-yl]benzonitrile |
| 91 | 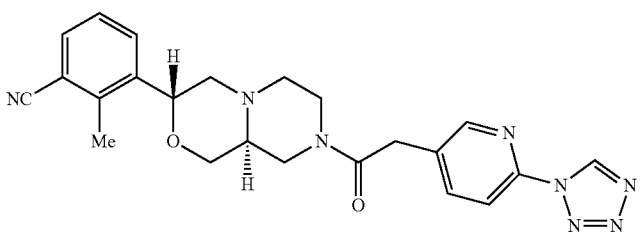 [SMILES: Cc1c(C#N)cccc1[C@@H]1CN2CCN(C(=O)Cc3ccc(-n4cnnn4)nc3)C[C@H]2CO1] | LC/MS (M + H) 445<br>2-methyl-3-[(3R,9aS)-8-{[6-(1H-tetrazol-1-yl)pyridin-3-yl]acetyl}octahydropyrazino[2,1-c][1,4]oxazin-3-yl]benzonitrile |
| 92 | 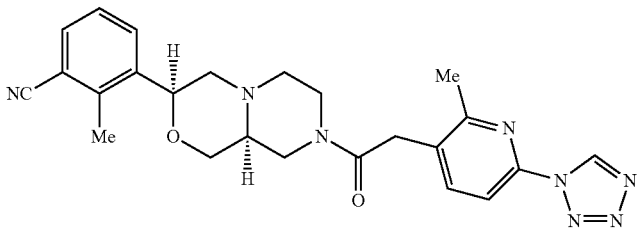 [SMILES: Cc1nc(-n2cnnn2)ccc1CC(=O)N1CCN2C[C@H](c3cccc(C#N)c3C)OC[C@@H]2C1] | LC/MS (M + H) 459<br>2-methyl-3-[(3S,9aS)-8-{[2-methyl-6-(1H-tetrazol-1-yl)pyridin-3-yl]acetyl}octahydropyrazino[2,1-c][1,4]oxazin-3-yl]benzonitrile |
| 93 | 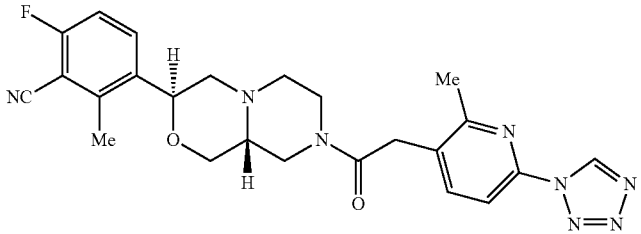 [SMILES: Cc1nc(-n2cnnn2)ccc1CC(=O)N1CCN2C[C@H](c3ccc(F)c(C#N)c3C)OC[C@H]2C1] | LC/MS (M + H) 477<br>6-fluoro-2-methyl-3-[(3S,9aR)-8-{[2-methyl-6-(1H-tetrazol-1-yl)pyridin-3-yl]acetyl}octahydropyrazino[2,1-c][1,4]oxazin-3-yl]benzonitrile |

| Example # | | |
|---|---|---|
| 94 | 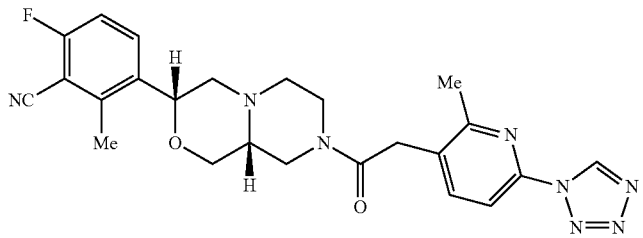 [SMILES: Cc1nc(-n2cnnn2)ccc1CC(=O)N1CCN2C[C@@H](c3ccc(F)c(C#N)c3C)OC[C@H]2C1] | LC/MS (M + H) 477<br>6-fluoro-2-methyl-3-[(3R,9aR)-8-{[2-methyl-6-(1H-tetrazol-1-yl)pyridin-3-yl]acetyl}octahydropyrazino[2,1-c][1,4]oxazin-3-yl]benzonitrile |
| 95 | 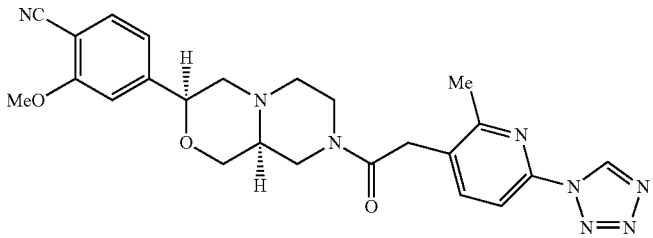 [SMILES: COc1cc([C@H]2CN3CCN(C(=O)Cc4ccc(-n5cnnn5)nc4C)C[C@H]3CO2)ccc1C#N] | LC/MS (M + H) 475<br>2-methoxy-4-[(3S,9aS)-8-{[2-methyl-6-(1H-tetrazol-1-yl)pyridin-3-yl]acetyl}octahydropyrazino[2,1-c][1,4]oxazin-3-yl]benzonitrile |
| 96 | 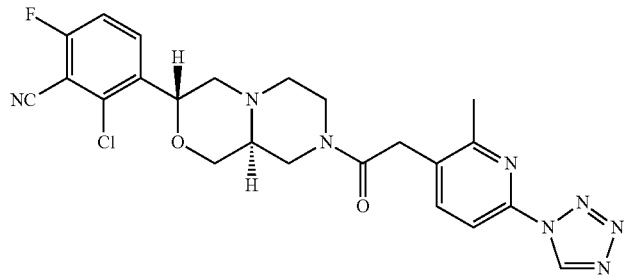 [SMILES: Cc1nc(-n2cnnn2)ccc1CC(=O)N1CCN2C[C@@H](c3ccc(F)c(C#N)c3Cl)OC[C@@H]2C1] | LC/MS (M + H) 497<br>2-chloro-6-fluoro-3-[(3S,9aS)-8-{[2-methyl-6-(1H-tetrazol-1-yl)pyridin-3-yl]acetyl}octahydropyrazino[2,1-c][1,4]oxazin-3-yl]benzonitrile |
| 97 | 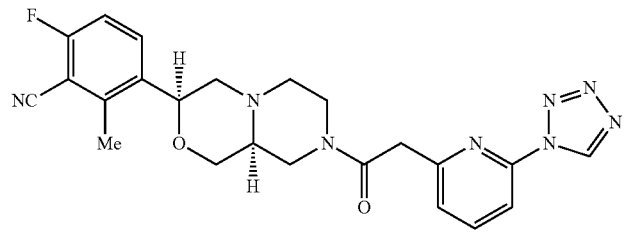 [SMILES: Cc1c([C@H]2CN3CCN(C(=O)Cc4cccc(-n5cnnn5)n4)C[C@H]3CO2)ccc(F)c1C#N] | LC/MS (M + H) 463<br>6-fluoro-2-methyl-3-[(3S,9aS)-8-{[6-(1H-tetrazol-1-yl)pyridin-2-yl]acetyl}octahydropyrazino[2,1-c][1,4]oxazin-3-yl]benzonitrile |
| 98 | 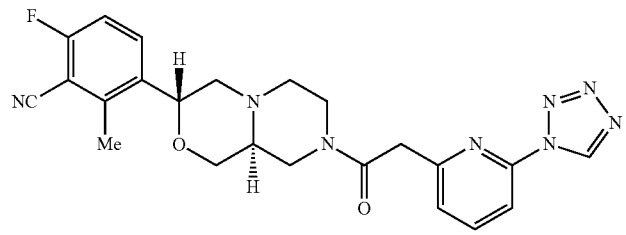 [SMILES: Cc1c([C@@H]2CN3CCN(C(=O)Cc4cccc(-n5cnnn5)n4)C[C@H]3CO2)ccc(F)c1C#N] | LC/MS (M + H) 463<br>6-fluoro-2-methyl-3-[(3R,9aS)-8-{[6-(1H-tetrazol-1-yl)pyridin-2-yl]acetyl}octahydropyrazino[2,1-c][1,4]oxazin-3-yl]benzonitrile |
| 99 | 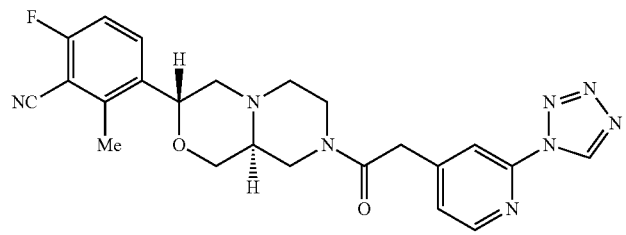 [SMILES: Cc1c([C@@H]2CN3CCN(C(=O)Cc4ccnc(-n5cnnn5)c4)C[C@H]3CO2)ccc(F)c1C#N] | LC/MS (M + H) 463<br>6-fluoro-2-methyl-3-[(3R,9aS)-8-{[2-(1H-tetrazol-1-yl)pyridin-4-yl]acetyl}octahydropyrazino[2,1-c][1,4]oxazin-3-yl]benzonitrile |

TABLE 3-continued

| Example # | | |
|---|---|---|
| 100 | | LC/MS (M + H) 463<br>6-fluoro-2-methyl-3-[(3S,9aS)-8-{[2-(1H-tetrazol-1-yl)pyridin-4-yl]acetyl}octahydropyrazino[2,1-c][1,4]oxazin-3-yl]benzonitrile |
| 101 | | LC/MS (M + H) 463<br>6-fluoro-2-methyl-3-[(3S,9aS)-8-{[5-(1H-tetrazol-1-yl)pyridin-3-yl]acetyl}octahydropyrazino[2,1-c][1,4]oxazin-3-yl]benzonitrile |
| 102 | | LC/MS (M + H) 463<br>6-fluoro-2-methyl-3-[(3R,9aR)-8-{[6-(1H-tetrazol-1-yl)pyridin-3-yl]acetyl}octahydropyrazino[2,1-c][1,4]oxazin-3-yl]benzonitrile |
| 103 | | LC/MS (M + H) 474<br>(3R,9aS)-3-[3-(1H-tetrazol-1-yl)phenyl]-8-{[6-(1H-tetrazol-1-yl)pyridin-3-yl]acetyl}octahydropyrazino[2,1-c][1,4]oxazine |
| 104 | | LC/MS (M + H) 488<br>(3R,9aS)-3-[2-methyl-3-(1H-tetrazol-1-yl)phenyl]-8-{[6-(1H-tetrazol-1-yl)pyridin-3-yl]acetyl}octahydropyrazino[2,1-c][1,4]oxazine |
| 105 | | LC/MS (M + H) 504<br>(3R)-3-methyl-6-[(3R,9aS)-3-methyl-8-{[6-(1H-tetrazol-1-yl)pyridin-3-yl]acetyl}octahydropyrazino[2,1-c][1,4]oxazin-3-yl]-3,4-dihydro-1H-isochromen-1-one |

TABLE 3-continued

| Example # | Structure | |
|---|---|---|
| 106 | 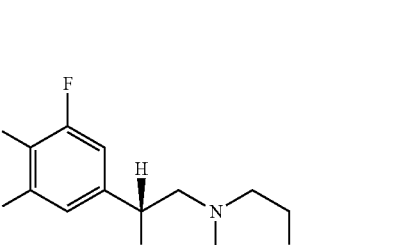 | LC/MS (M + H) 504<br>(3S)-3-methyl-6-[(3R,9aS)-3-methyl-8-{[6-(1H-tetrazol-1-yl)pyridin-3-yl]acetyl}octahydropyrazino[2,1-c][1,4]oxazin-3-yl]-3,4-dihydro-1H-isochromen-1-one |
| 107 | 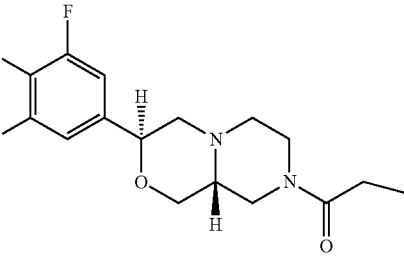 | LC/MS (M + H) 467<br>2,6-difluoro-4-[(3R,9aR)-8-{[6-(1H-tetrazol-1-yl)pyridin-3-yl]acetyl}octahydropyrazino[2,1-c][1,4]oxazin-3-yl]benzonitrile |
| 108 | 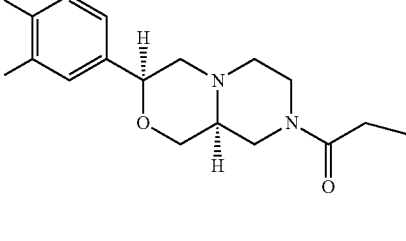 | LC/MS (M + H) 467<br>2,6-difluoro-4-[(3S,9aR)-8-{[6-(1H-tetrazol-1-yl)pyridin-3-yl]acetyl}octahydropyrazino[2,1-c][1,4]oxazin-3-yl]benzonitrile |
| 109 | 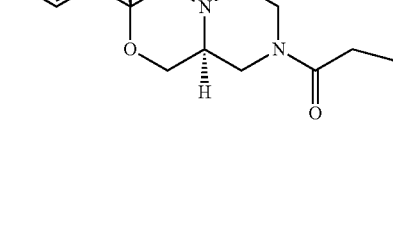 | LC/MS (M + H) 467<br>2,6-difluoro-4-[(3S,9aS)-8-{[6-(1H-tetrazol-1-yl)pyridin-3-yl]acetyl}octahydropyrazino[2,1-c][1,4]oxazin-3-yl]benzonitrile |
| 110 |  | LC/MS (M + H) 467<br>2,6-difluoro-4-[(3R,9aS)-8-{[6-(1H-tetrazol-1-yl)pyridin-3-yl]acetyl}octahydropyrazino[2,1-c][1,4]oxazin-3-yl]benzonitrile |

TABLE 3-continued

| Example # | Structure | Data |
|---|---|---|
| 111 | | LC/MS (M + H) 479<br>2-fluoro-6-methoxy-4-[(3R,9aR)-8-{[6-(1H-tetrazol-1-yl)pyridin-3-yl]acetyl}octahydropyrazino[2,1-c][1,4]oxazin-3-yl]benzonitrile |
| 112 | | LC/MS (M + H) 479<br>2-fluoro-6-methoxy-4-[(3S,9aR)-8-{[6-(1H-tetrazol-1-yl)pyridin-3-yl]acetyl}octahydropyrazino[2,1-c][1,4]oxazin-3-yl]benzonitrile |
| 113 | | LC/MS (M + H) 479<br>2-fluoro-6-methoxy-4-[(3S,9aS)-8-{[6-(1H-tetrazol-1-yl)pyridin-3-yl]acetyl}octahydropyrazino[2,1-c][1,4]oxazin-3-yl]benzonitrile |
| 114 | | LC/MS (M + H) 479<br>2-fluoro-6-methoxy-4-[(3R,9aS)-8-{[6-(1H-tetrazol-1-yl)pyridin-3-yl]acetyl}octahydropyrazino[2,1-c][1,4]oxazin-3-yl]benzonitrile |
| 115 | | LC/MS (M + H) 468<br>2,6-difluoro-4-[(3R,9aR)-8-{[2-(1H-tetrazol-1-yl)pyrimidin-5-yl]acetyl}octahydropyrazino[2,1-c][1,4]oxazin-3-yl]benzonitrile |

TABLE 3-continued

| Example # | | |
|---|---|---|
| 116 | 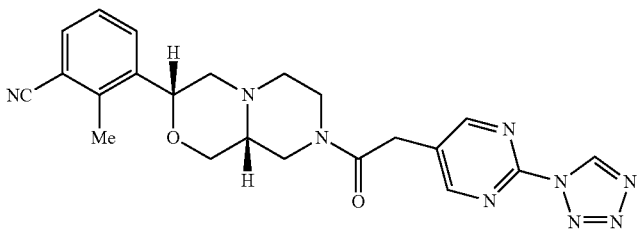 [SMILES: Cc1c(C#N)cccc1[C@@H]1CN2CCN(C(=O)Cc3cnc(-n4cnnn4)nc3)C[C@@H]2CO1] | LC/MS (M + H) 446<br>2-methyl-3-[(3R,9aR)-8-{[2-(1H-tetrazol-1-yl)pyrimidin-5-yl]acetyl}octahydropyrazino[2,1-c][1,4]oxazin-3-yl]benzonitrile |
| 117 | 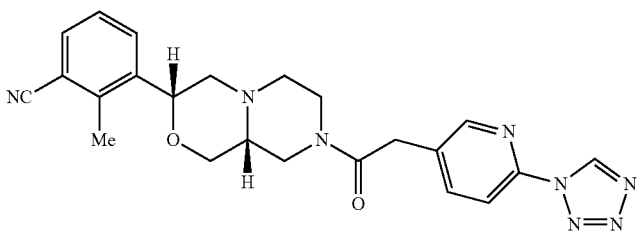 [SMILES: Cc1c(C#N)cccc1[C@@H]1CN2CCN(C(=O)Cc3ccc(-n4cnnn4)nc3)C[C@@H]2CO1] | LC/MS (M + H) 445<br>2-methyl-3-[(3R,9aR)-8-{[6-(1H-tetrazol-1-yl)pyridin-3-yl]acetyl}octahydropyrazino[2,1-c][1,4]oxazin-3-yl]benzonitrile |
| 118 | 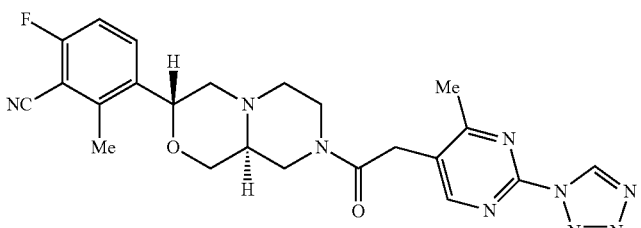 | LC/MS (M + H) 478<br>6-fluoro-2-methyl-3-[(3R,9aS)-8-{[4-methyl-2-(1H-tetrazol-1-yl)pyrimidin-5-yl]acetyl}octahydropyrazino[2,1-c][1,4]oxazin-3-yl]benzonitrile |
| 119 | 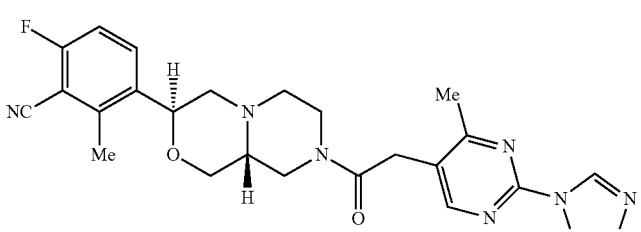 | LC/MS (M + H) 478<br>6-fluoro-2-methyl-3-[(3S,9aR)-8-{[4-methyl-2-(1H-tetrazol-1-yl)pyrimidin-5-yl]acetyl}octahydropyrazino[2,1-c][1,4]oxazin-3-yl]benzonitrile |
| 120 | 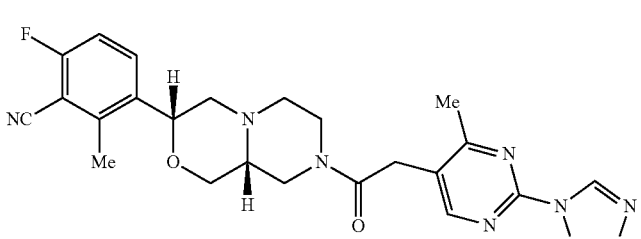 | LC/MS (M + H) 478<br>6-fluoro-2-methyl-3-[(3R,9aR)-8-{[4-methyl-2-(1H-tetrazol-1-yl)pyrimidin-5-yl]acetyl}octahydropyrazino[2,1-c][1,4]oxazin-3-yl]benzonitrile |
| 121 | 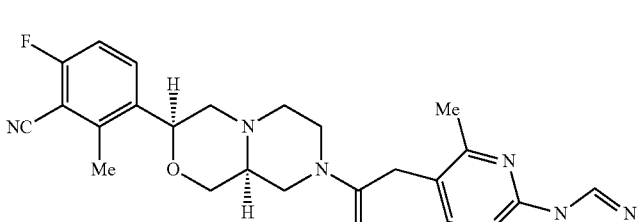 | LC/MS (M + H) 478<br>6-fluoro-2-methyl-3-[(3S,9aS)-8-{[4-methyl-2-(1H-tetrazol-1-yl)pyrimidin-5-yl]acetyl}octahydropyrazino[2,1-c][1,4]oxazin-3-yl]benzonitrile |

TABLE 3-continued

| Example # | | |
|---|---|---|
| 122 | | LC/MS (M + H) 477<br>4-methyl-5-[(3R,9aR)-8-{[2-(1H-tetrazol-1-yl)pyrimidin-5-yl]acetyl}octahydropyrazino[2,1-c][1,4]oxazin-3-yl]-2-benzofuran-1(3H)-one |
| 123 | | LC/MS (M + H) 477<br>4-methyl-5-[(3R,9aR)-8-{[5-(1H-tetrazol-1-yl)pyrazin-2-yl]acetyl}octahydropyrazino[2,1-c][1,4]oxazin-3-yl]-2-benzofuran-1(3H)-one |
| 124 | | LC/MS (M + H) 493<br>6-fluoro-3-[(3R,9aR)-8-{[3-methoxy-5-(1H-tetrazol-1-yl)pyridin-2-yl]acetyl}octahydropyrazino[2,1-c][1,4]oxazin-3-yl]-2-methylbenzonitrile |
| 125 | | LC/MS (M + H) 484<br>2-chloro-6-fluoro-3-[(3R,9aR)-8-{[2-(1H-tetrazol-1-yl)pyrimidin-5-yl]acetyl}octahydropyrazino[2,1-c][1,4]oxazin-3-yl]benzonitrile |
| 126 | | LC/MS (M + H) 484<br>2-chloro-6-fluoro-3-[(3S,9aR)-8-{[2-(1H-tetrazol-1-yl)pyrimidin-5-yl]acetyl}octahydropyrazino[2,1-c][1,4]oxazin-3-yl]benzonitrile |
| 127 | | LC/MS (M + H) 477<br>6-fluoro-2-methyl-3-[(3S,9aS)-8-{[6-methyl-5-(1H-tetrazol-1-yl)pyridin-2-yl]acetyl}octahydropyrazino[2,1-c][1,4]oxazin-3-yl]benzonitrile |

TABLE 3-continued

| Example # | | |
|---|---|---|
| 128 | | LC/MS (M + H) 477<br>6-fluoro-2-methyl-3-[(3R,9aS)-8-{[6-methyl-5-(1H-tetrazol-1-yl)pyridin-2-yl]acetyl}octahydropyrazino[2,1-c][1,4]oxazin-3-yl]benzonitrile |
| 129 | | LC/MS (M + H) 477<br>6-fluoro-2-methyl-3-[(3R,9aR)-8-{[4-methyl-5-(1H-tetrazol-1-yl)pyridin-2-yl]acetyl}octahydropyrazino[2,1-c][1,4]oxazin-3-yl]benzonitrile |
| 130 | | LC/MS (M + H) 477<br>6-fluoro-2-methyl-3-[(3S,9aS)-8-{[4-methyl-5-(1H-tetrazol-1-yl)pyridin-2-yl]acetyl}octahydropyrazino[2,1-c][1,4]oxazin-3-yl]benzonitrile |
| 131 | | LC/MS (M + H) 477<br>6-fluoro-2-methyl-3-[(3S,9aR)-8-{[6-methyl-5-(1H-tetrazol-1-yl)pyridin-2-yl]acetyl}octahydropyrazino[2,1-c][1,4]oxazin-3-yl]benzonitrile |
| 132 | | LC/MS (M + H) 477<br>6-fluoro-2-methyl-3-[(3R,9aR)-8-{[6-methyl-5-(1H-tetrazol-1-yl)pyridin-2-yl]acetyl}octahydropyrazino[2,1-c][1,4]oxazin-3-yl]benzonitrile |
| 133 | | LC/MS (M + H) 477<br>6-fluoro-2-methyl-3-[(3R,9aR)-8-{[5-methyl-6-(1H-tetrazol-1-yl)pyridin-3-yl]acetyl}octahydropyrazino[2,1-c][1,4]oxazin-3-yl]benzonitrile |

TABLE 3-continued

| Example # | | |
|---|---|---|
| 134 | | LC/MS (M + H) 477<br>6-fluoro-2-methyl-3-[(3S,9aR)-8-{[5-methyl-6-(1H-tetrazol-1-yl)pyridin-3-yl]acetyl}octahydropyrazino[2,1-c][1,4]oxazin-3-yl]benzonitrile |
| 135 | | LC/MS (M + H) 476<br>6-methoxy-2-methyl-3-[(3R,9aS)-8-{[2-(1H-tetrazol-1-yl)pyrimidin-5-yl]acetyl}octahydropyrazino[2,1-c][1,4]oxazin-3-yl]benzonitrile |
| 136 | | LC/MS (M + H) 484<br>2-chloro-6-fluoro-3-[(3R,9aS)-8-{[2-(1H-tetrazol-1-yl)pyrimidin-5-yl]acetyl}octahydropyrazino[2,1-c][1,4]oxazin-3-yl]benzonitrile |
| 137 | | LC/MS (M + H) 484<br>2-chloro-6-fluoro-3-[(3S,9aS)-8-{[2-(1H-tetrazol-1-yl)pyrimidin-5-yl]acetyl}octahydropyrazino[2,1-c][1,4]oxazin-3-yl]benzonitrile |
| 138 | | LC/MS (M + H) 498<br>2-chloro-6-fluoro-3-[(3R,9aR)-8-{[4-methyl-2-(1H-tetrazol-1-yl)pyrimidin-5-yl]acetyl}octahydropyrazino[2,1-c][1,4]oxazin-3-yl]benzonitrile |
| 139 | | LC/MS (M + H) 480<br>6-fluoro-2-methoxy-3-[(3S,9aS)-8-{[2-(1H-tetrazol-1-yl)pyrimidin-5-yl]acetyl}octahydropyrazino[2,1-c][1,4]oxazin-3-yl]benzonitrile |

TABLE 3-continued

| Example # | Structure | Data |
|---|---|---|
| 140 | 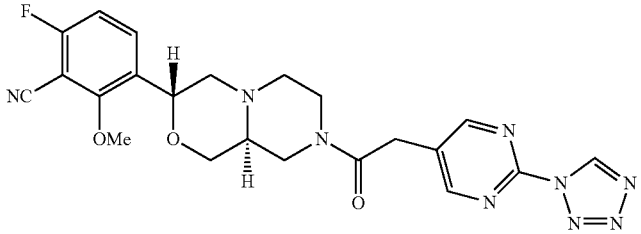 [SMILES: COc1c([C@@H]2CN3CCN(C(=O)Cc4cnc(-n5cnnn5)nc4)C[C@H]3CO2)ccc(F)c1C#N] | LC/MS (M + H) 480<br>6-fluoro-2-methoxy-3-[(3R,9aS)-8-{[2-(1H-tetrazol-1-yl)pyrimidin-5-yl]acetyl}octahydropyrazino[2,1-c][1,4]oxazin-3-yl]benzonitrile |
| 141 | 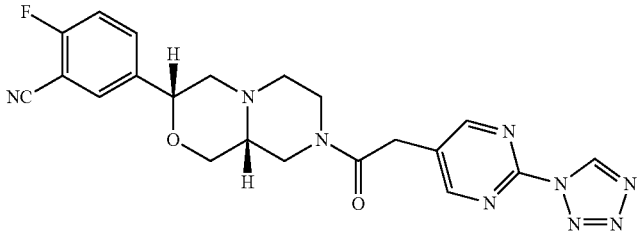 [SMILES: N#Cc1cc([C@@H]2CN3CCN(C(=O)Cc4cnc(-n5cnnn5)nc4)C[C@@H]3CO2)ccc1F] | LC/MS (M + H) 450<br>2-fluoro-5-[(3R,9aR)-8-{[2-(1H-tetrazol-1-yl)pyrimidin-5-yl]acetyl}octahydropyrazino[2,1-c][1,4]oxazin-3-yl]benzonitrile |
| 142 | 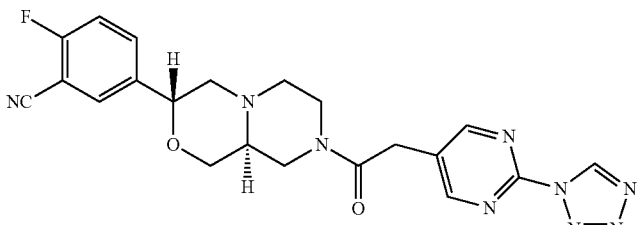 | LC/MS (M + H) 450<br>2-fluoro-5-[(3R,9aS)-8-{[2-(1H-tetrazol-1-yl)pyrimidin-5-yl]acetyl}octahydropyrazino[2,1-c][1,4]oxazin-3-yl]benzonitrile |
| 143 | 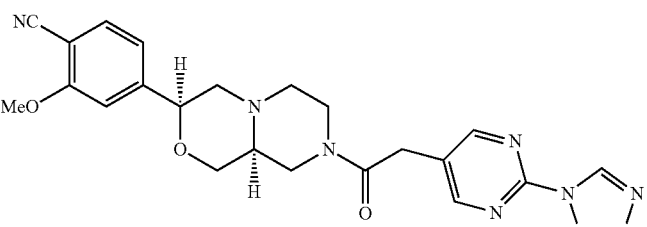 | LC/MS (M + H) 462<br>2-methoxy-4-[(3S,9aS)-8-{[2-(1H-tetrazol-1-yl)pyrimidin-5-yl]acetyl}octahydropyrazino[2,1-c][1,4]oxazin-3-yl]benzonitrile |
| 144 | 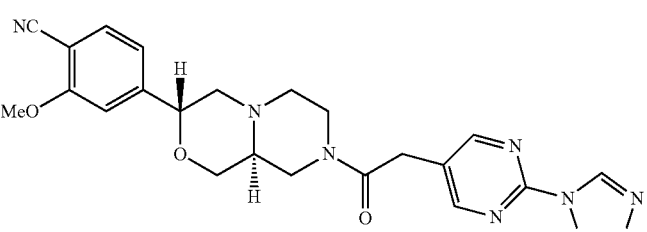 | LC/MS (M + H) 462<br>2-methoxy-4-[(3R,9aS)-8-{[2-(1H-tetrazol-1-yl)pyrimidin-5-yl]acetyl}octahydropyrazino[2,1-c][1,4]oxazin-3-yl]benzonitrile |
| 145 | 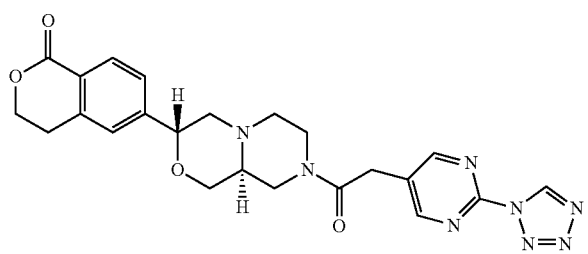 [SMILES: O=C1OCCc2cc([C@@H]3CN4CCN(C(=O)Cc5cnc(-n6cnnn6)nc5)C[C@H]4CO3)ccc21] | LC/MS (M + H) 477<br>6-[(3R,9aS)-8-{[2-(1H-tetrazol-1-yl)pyrimidin-5-yl]acetyl}octahydropyrazino[2,1-c][1,4]oxazin-3-yl]-3,4-dihydro-1H-isochromen-1-one |

TABLE 3-continued

| Example # | | |
|---|---|---|
| 146 | 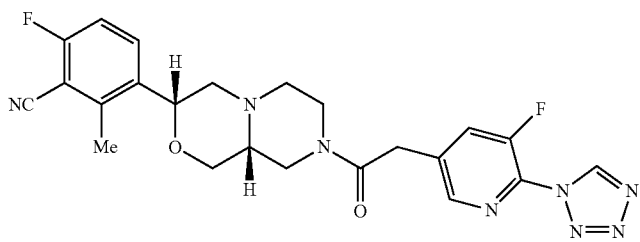 [SMILES: Cc1c([C@@H]2CN3CCN(C(=O)Cc4cnc(-n5cnnn5)c(F)c4)C[C@@H]3CO2)ccc(F)c1C#N] | LC/MS (M + H) 481<br>6-fluoro-3-[(3R,9aR)-8-{[5-fluoro-6-(1H-tetrazol-1-yl)pyridin-3-yl]acetyl}octahydropyrazino[2,1-c][1,4]oxazin-3-yl]-2-methylbenzonitrile |
| 147 | 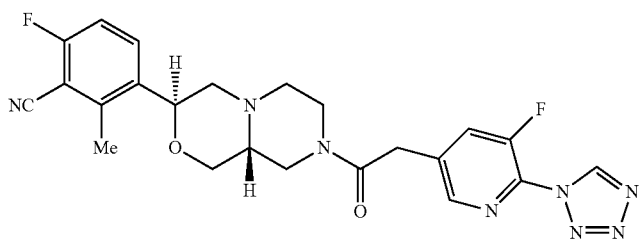 [SMILES: Cc1c([C@H]2CN3CCN(C(=O)Cc4cnc(-n5cnnn5)c(F)c4)C[C@@H]3CO2)ccc(F)c1C#N] | LC/MS (M + H) 481<br>6-fluoro-3-[(3S,9aR)-8-{[5-fluoro-6-(1H-tetrazol-1-yl)pyridin-3-yl]acetyl}octahydropyrazino[2,1-c][1,4]oxazin-3-yl]-2-methylbenzonitrile |
| 148 | 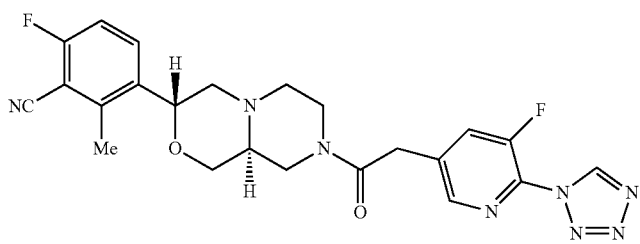 [SMILES: Cc1c([C@@H]2CN3CCN(C(=O)Cc4cnc(-n5cnnn5)c(F)c4)C[C@H]3CO2)ccc(F)c1C#N] | LC/MS (M + H) 481<br>6-fluoro-3-[(3R,9aS)-8-{[5-fluoro-6-(1H-tetrazol-1-yl)pyridin-3-yl]acetyl}octahydropyrazino[2,1-c][1,4]oxazin-3-yl]-2-methylbenzonitrile |
| 149 | 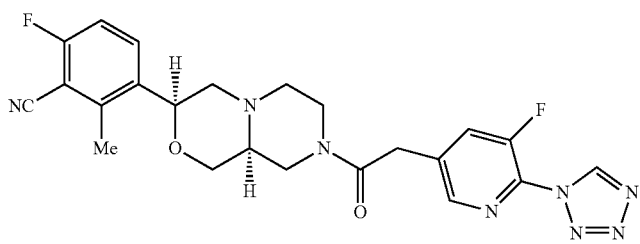 [SMILES: Cc1c([C@H]2CN3CCN(C(=O)Cc4cnc(-n5cnnn5)c(F)c4)C[C@H]3CO2)ccc(F)c1C#N] | LC/MS (M + H) 481<br>6-fluoro-3-[(3S,9aS)-8-{[5-fluoro-6-(1H-tetrazol-1-yl)pyridin-3-yl]acetyl}octahydropyrazino[2,1-c][1,4]oxazin-3-yl]-2-methylbenzonitrile |
| 150 | 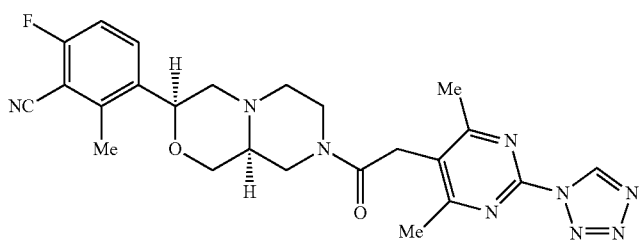 [SMILES: Cc1nc(-n2cnnn2)nc(C)c1CC(=O)N1CCN2C[C@H](c3ccc(F)c(C#N)c3C)OC[C@@H]2C1] | LC/MS (M + H) 492<br>3-[(3S,9aS)-8-{[4,6-dimethyl-2-(1H-tetrazol-1-yl)pyrimidin-5-yl]acetyl}octahydropyrazino[2,1-c][1,4]oxazin-3-yl]-6-fluoro-2-methylbenzonitrile |
| 151 | 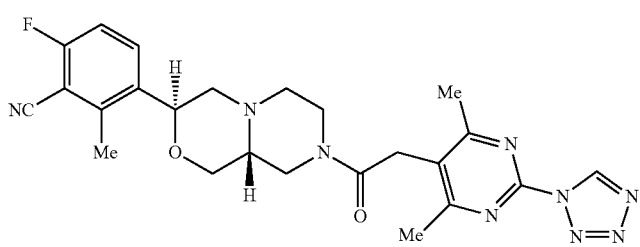 [SMILES: Cc1nc(-n2cnnn2)nc(C)c1CC(=O)N1CCN2C[C@H](c3ccc(F)c(C#N)c3C)OC[C@H]2C1] | LC/MS (M + H) 492<br>3-[(3S,9aR)-8-{[4,6-dimethyl-2-(1H-tetrazol-1-yl)pyrimidin-5-yl]acetyl}octahydropyrazino[2,1-c][1,4]oxazin-3-yl]-6-fluoro-2-methylbenzonitrile |

TABLE 3-continued

| Example # | | |
|---|---|---|
| 152 | 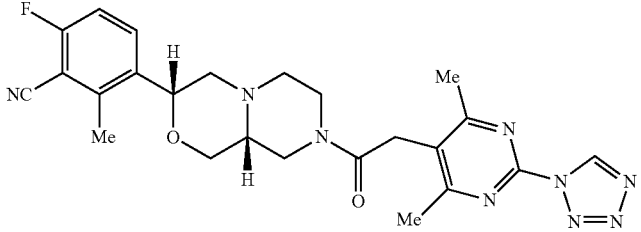 [SMILES: Cc1nc(-n2cnnn2)nc(C)c1CC(=O)N1CCN2C[C@@H](c3ccc(F)c(C#N)c3C)OC[C@H]2C1] | LC/MS (M + H) 492<br>3-[(3R,9aR)-8-{[4,6-dimethyl-2-(1H-tetrazol-1-yl)pyrimidin-5-yl]acetyl}octahydropyrazino[2,1-c][1,4]oxazin-3-yl]-6-fluoro-2-methylbenzonitrile |
| 153 | 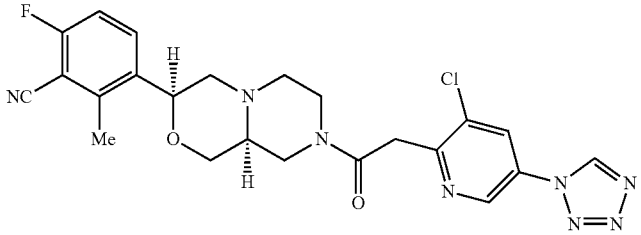 [SMILES: Cc1c([C@H]2CN3CCN(C(=O)Cc4ncc(-n5cnnn5)cc4Cl)C[C@H]3CO2)ccc(F)c1C#N] | LC/MS (M + H) 497<br>3-[(3S,9aS)-8-{[3-chloro-5-(1H-tetrazol-1-yl)pyridin-2-yl]acetyl}octahydropyrazino[2,1-c][1,4]oxazin-3-yl]-6-fluoro-2-methylbenzonitrile |
| 154 | 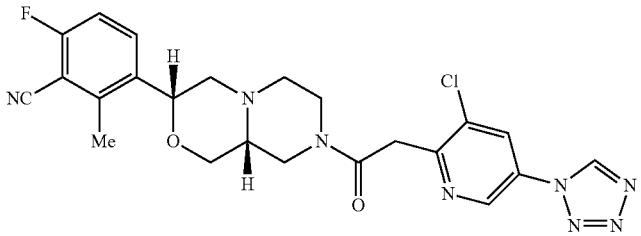 [SMILES: Cc1c([C@@H]2CN3CCN(C(=O)Cc4ncc(-n5cnnn5)cc4Cl)C[C@@H]3CO2)ccc(F)c1C#N] | LC/MS (M + H) 497<br>3-[(3R,9aR)-8-{[3-chloro-5-(1H-tetrazol-1-yl)pyridin-2-yl]acetyl}octahydropyrazino[2,1-c][1,4]oxazin-3-yl]-6-fluoro-2-methylbenzonitrile |
| 155 | 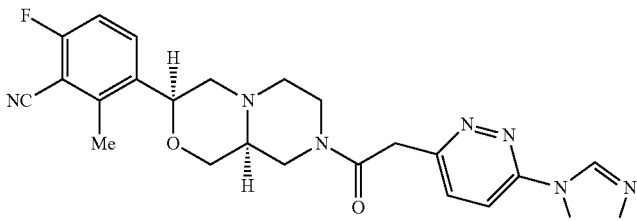 | LC/MS (M + H) 464<br>6-fluoro-2-methyl-3-[(3S,9aS)-8-{[6-(1H-tetrazol-1-yl)pyridazin-3-yl]acetyl}octahydropyrazino[2,1-c][1,4]oxazin-3-yl]benzonitrile |
| 156 | 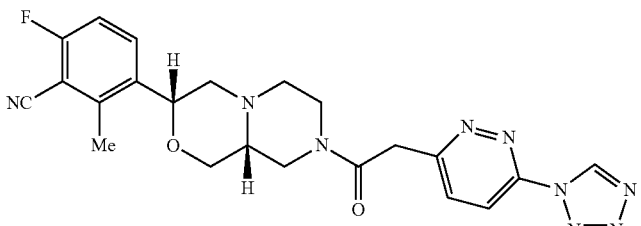 | LC/MS (M + H) 464<br>6-fluoro-2-methyl-3-[(3R,9aR)-8-{[6-(1H-tetrazol-1-yl)pyridazin-3-yl]acetyl}octahydropyrazino[2,1-c][1,4]oxazin-3-yl]benzonitrile |
| 157 | 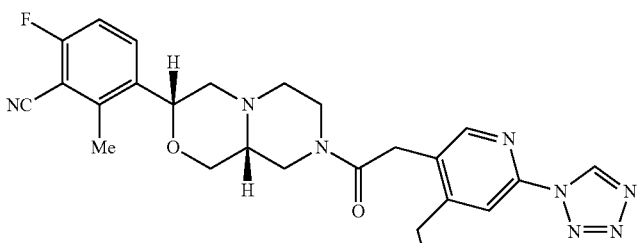 | LC/MS (M + H) 491<br>3-[(3R,9aR)-8-{[4-ethyl-6-(1H-tetrazol-1-yl)pyridin-3-yl]acetyl}octahydropyrazino[2,1-c][1,4]oxazin-3-yl]-6-fluoro-2-methylbenzonitrile |

TABLE 3-continued

| Example # | | |
|---|---|---|
| 158 | 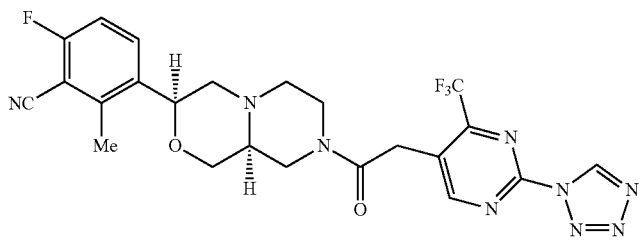 [SMILES: Cc1c([C@H]2CN3CCN(C(=O)Cc4cnc(-n5cnnn5)nc4C(F)(F)F)C[C@H]3CO2)ccc(F)c1C#N] | LC/MS (M + H) 532<br>6-fluoro-2-methyl-3-[(3S,9aS)-8-{[2-(1H-tetrazol-1-yl)-4-(trifluoromethyl)pyrimidin-5-yl]acetyl}octahydropyrazino[2,1-c][1,4]oxazin-3-yl]benzonitrile |
| 159 | 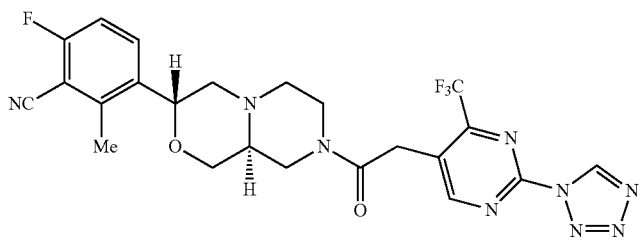 [SMILES: Cc1c([C@@H]2CN3CCN(C(=O)Cc4cnc(-n5cnnn5)nc4C(F)(F)F)C[C@H]3CO2)ccc(F)c1C#N] | LC/MS (M + H) 532<br>6-fluoro-2-methyl-3-[(3R,9aS)-8-{[2-(1H-tetrazol-1-yl)-4-(trifluoromethyl)pyrimidin-5-yl]acetyl}octahydropyrazino[2,1-c][1,4]oxazin-3-yl]benzonitrile |
| 160 | 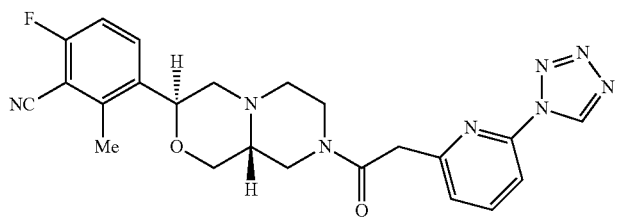 [SMILES: Cc1c([C@H]2CN3CCN(C(=O)Cc4cccc(-n5cnnn5)n4)C[C@@H]3CO2)ccc(F)c1C#N] | LC/MS (M + H) 463<br>6-fluoro-2-methyl-3-[(3S,9aR)-8-{[6-(1H-tetrazol-1-yl)pyridin-2-yl]acetyl}octahydropyrazino[2,1-c][1,4]oxazin-3-yl]benzonitrile |
| 161 | 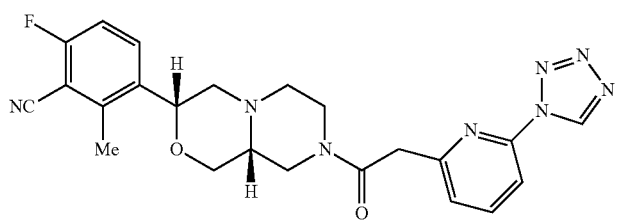 [SMILES: Cc1c([C@@H]2CN3CCN(C(=O)Cc4cccc(-n5cnnn5)n4)C[C@@H]3CO2)ccc(F)c1C#N] | LC/MS (M + H) 463<br>6-fluoro-2-methyl-3-[(3R,9aR)-8-{[6-(1H-tetrazol-1-yl)pyridin-2-yl]acetyl}octahydropyrazino[2,1-c][1,4]oxazin-3-yl]benzonitrile |
| 162 | 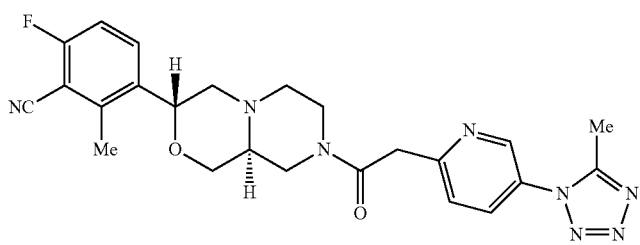 [SMILES: Cc1c([C@@H]2CN3CCN(C(=O)Cc4ccc(-n5nnnc5C)cn4)C[C@H]3CO2)ccc(F)c1C#N] | LC/MS (M + H) 477<br>6-fluoro-2-methyl-3-[(3R,9aS)-8-{[5-(5-methyl-1H-tetrazol-1-yl)pyridin-2-yl]acetyl}octahydropyrazino[2,1-c][1,4]oxazin-3-yl]benzonitrile |
| 163 | 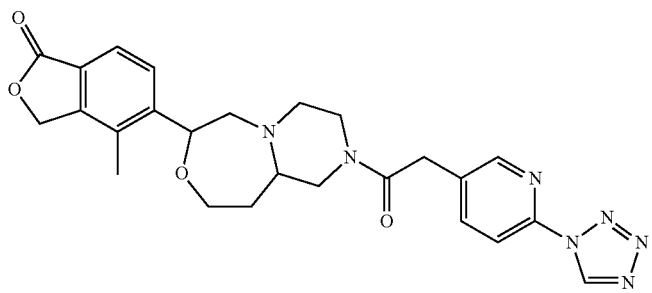 [SMILES: Cc1c(C2CN3CCN(C(=O)Cc4ccc(-n5cnnn5)nc4)CC3CCO2)ccc2c1COC2=O] | LC/MS (M + H) 490<br>Cis isomer (either R,R or S,S) separated from SFC on Chiralpak AD column, first to elute<br>4-methyl-5-(2-{[6-(1H-tetrazol-1-yl)pyridin-3-yl]acetyl}octahydro-2H-pyrazino[1,2-d][1,4]oxazepin-7-yl)-2-benzofuran-1(3H)-one |

TABLE 3-continued

| Example # | | |
|---|---|---|
| 164 | 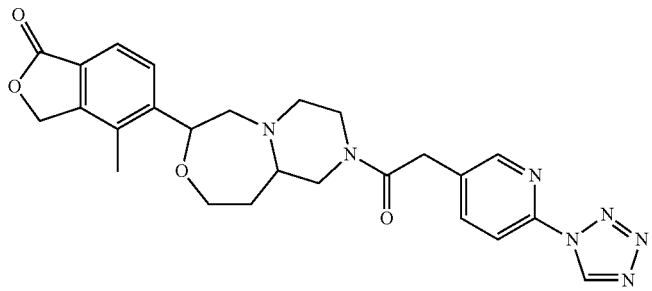 [SMILES: Cc1c(C2CN3CCN(C(=O)Cc4ccc(-n5cnnn5)nc4)CC3CCO2)ccc2c1COC2=O] | LC/MS (M + H) 490<br>Cis isomer (either R,R or S,S) separated from SFC on Chiralpak AD column, second to elute<br>4-methyl-5-(2-{[6-(1H-tetrazol-1-yl)pyridin-3-yl]acetyl}octahydro-2H-pyrazino[1,2-d][1,4]oxazepin-7-yl)-2-benzofuran-1(3H)-one |
| 165 | 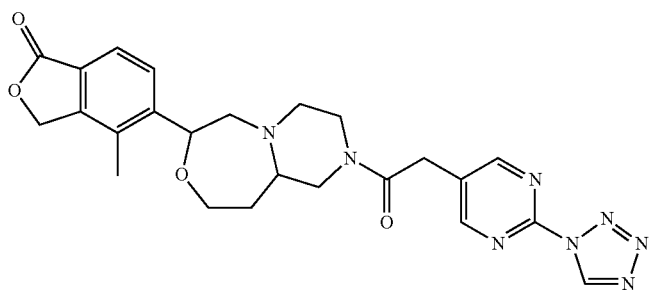 [SMILES: Cc1c(C2CN3CCN(C(=O)Cc4cnc(-n5cnnn5)nc4)CC3CCO2)ccc2c1COC2=O] | LC/MS (M + H) 491<br>Cis isomer (either R,R or S,S) separated from SFC on Chiralpak AD column, first to elute<br>4-methyl-5-(2-{[2-(1H-tetrazol-1-yl)pyrimidin-5-yl]acetyl}octahydro-2H-pyrazino[1,2-d][1,4]oxazepin-7-yl)-2-benzofuran-1(3H)-one |
| 166 | 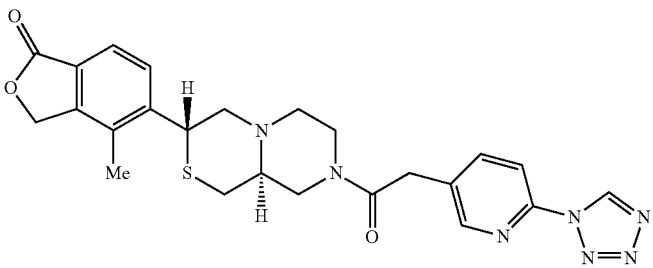 [SMILES: Cc1c([C@@H]2CN3CCN(C(=O)Cc4ccc(-n5cnnn5)nc4)C[C@H]3CS2)ccc2c1COC2=O] | LC/MS (M + H) 492<br>4-methyl-5-[(3R,9aS)-8-{[6-(1H-tetrazol-1-yl)pyridin-3-yl]acetyl}octahydropyrazino[2,1-c][1,4]thiazin-3-yl]-2-benzofuran-1(3H)-one |
| 167 | 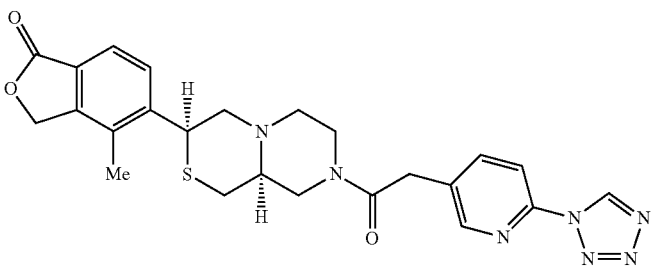 [SMILES: Cc1c([C@H]2CN3CCN(C(=O)Cc4ccc(-n5cnnn5)nc4)C[C@H]3CS2)ccc2c1COC2=O] | LC/MS (M + H) 492<br>4-methyl-5-[(3S,9aS)-8-{[6-(1H-tetrazol-1-yl)pyridin-3-yl]acetyl}octahydropyrazino[2,1-c][1,4]thiazin-3-yl]-2-benzofuran-1(3H)-one |
| 168 | 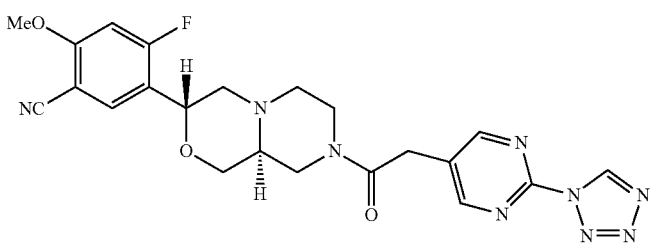 [SMILES: COc1cc(F)c([C@@H]2CN3CCN(C(=O)Cc4cnc(-n5cnnn5)nc4)C[C@H]3CO2)cc1C#N] | LC/MS (M + H) 480<br>4-fluoro-2-methoxy-5-[(3R,9aS)-8-{[2-(1H-tetrazol-1-yl)pyrimidin-5-yl]acetyl}octahydropyrazino[2,1-c][1,4]oxazin-3-yl]benzonitrile |

TABLE 3-continued

| Example # | | |
|---|---|---|
| 169 | 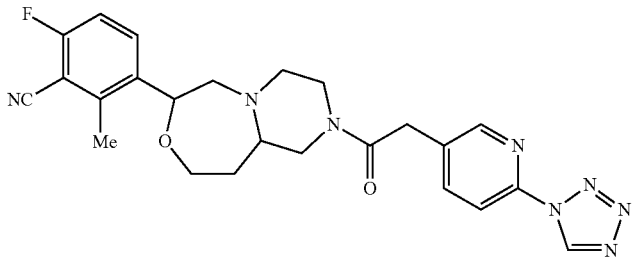<br>cis isomer | LC/MS (M + H) 477<br>cis isomer, absolute stereochemistry unknown<br>6-fluoro-2-methyl-3-[(7S,10aR)-2-{[6-(1H-tetrazol-1-yl)pyridin-3-yl]acetyl}octahydro-2H-pyrazino[1,2-d][1,4]oxazepin-7-yl]benzonitrile |
| 170 | 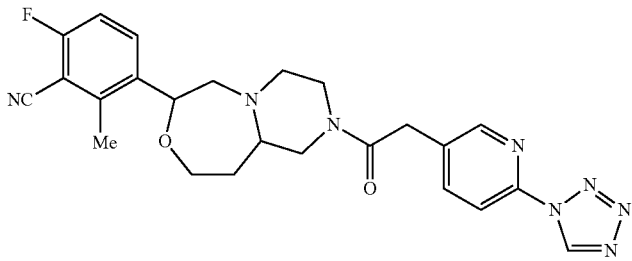<br>cis isomer | LC/MS (M + H) 477<br>cis isomer, absolute stereochemistry unknown, but opposite to that immediately above<br>6-fluoro-2-methyl-3-[(7R,10aS)-2-{[6-(1H-tetrazol-1-yl)pyridin-3-yl]acetyl}octahydro-2H-pyrazino[1,2-d][1,4]oxazepin-7-yl]benzonitrile |
| 171 | 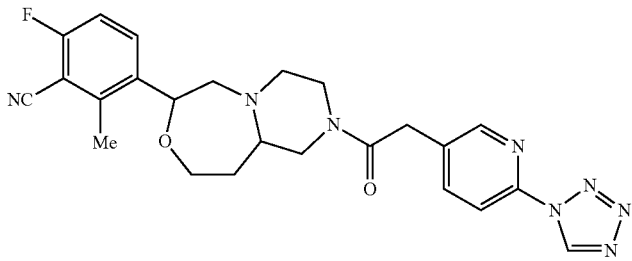<br>trans isomer | LC/MS (M + H) 477<br>trans isomer, absolute stereochemistry unknown<br>6-fluoro-2-methyl-3-[(7R,10aR)-2-{[6-(1H-tetrazol-1-yl)pyridin-3-yl]acetyl}octahydro-2H-pyrazino[1,2-d][1,4]oxazepin-7-yl]benzonitrile |
| 172 | 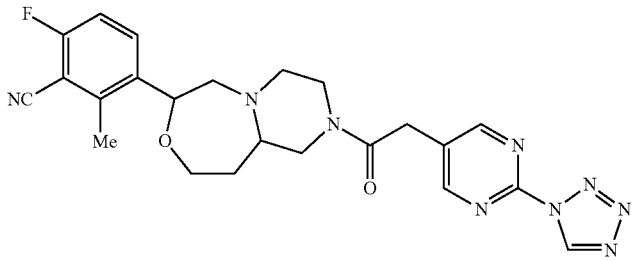<br>cis isomer | LC/MS (M + H) 478<br>cis isomer, absolute stereochemistry unknown<br>6-fluoro-2-methyl-3-[(7S,10aR)-2-{[2-(1H-tetrazol-1-yl)pyrimidin-5-yl]acetyl}octahydro-2H-pyrazino[1,2-d][1,4]oxazepin-7-yl]benzonitrile |
| 173 | 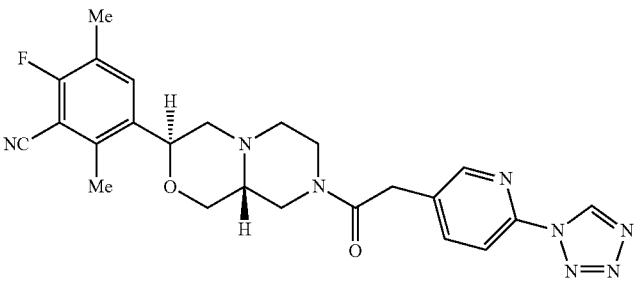 [SMILES: Cc1cc([C@H]2CN3CCN(C(=O)Cc4ccc(-n5cnnn5)nc4)C[C@@H]3CO2)c(C)c(C#N)c1F] | LC/MS (M + H) 477<br>2-fluoro-3,6-dimethyl-5-[(3S,9aR)-8-{[6-(1H-tetrazol-1-yl)pyridin-3-yl]acetyl}octahydropyrazino[2,1-c][1,4]oxazin-3-yl]benzonitrile |

TABLE 3-continued

| Example # | | |
|---|---|---|
| 174 | | LC/MS (M + H) 477<br>2-fluoro-3,6-dimethyl-5-[(3R,9aR)-8-{[6-(1H-tetrazol-1-yl)pyridin-3-yl]acetyl}octahydropyrazino[2,1-c][1,4]oxazin-3-yl]benzonitrile |
| 175 | | LC/MS (M + H) 449<br>(3R,9aS)-3-(2,1,3-benzoxadiazol-5-yl)-8-{[2-(1H-tetrazol-1-yl)pyrimidin-5-yl]acetyl}octahydropyrazino[2,1-c][1,4]oxazine |
| 176 | | LC/MS (M + H) 462<br>(3S,9aS)-3-(4-methyl-2,1,3-benzoxadiazol-5-yl)-8-{[6-(1H-tetrazol-1-yl)pyridin-3-yl]acetyl}octahydropyrazino[2,1-c][1,4]oxazine |
| 177 | | LC/MS (M + H) 462<br>(3R,9aS)-3-(4-methyl-2,1,3-benzoxadiazol-5-yl)-8-{[6-(1H-tetrazol-1-yl)pyridin-3-yl]acetyl}octahydropyrazino[2,1-c][1,4]oxazine |
| 178 | | LC/MS (M + H) 448<br>(3R,9aS)-3-(2,1,3-benzoxadiazol-5-yl)-8-{[5-(1H-tetrazol-1-yl)pyridin-2-yl]acetyl}octahydropyrazino[2,1-c][1,4]oxazine |
| 179 | | LC/MS (M + H) 448<br>(3R,9aS)-3-(2,1,3-benzoxadiazol-5-yl)-8-{[6-(1H-tetrazol-1-yl)pyridin-3-yl]acetyl}octahydropyrazino[2,1-c][1,4]oxazine |

TABLE 3-continued

| Example # | | |
|---|---|---|
| 180 | 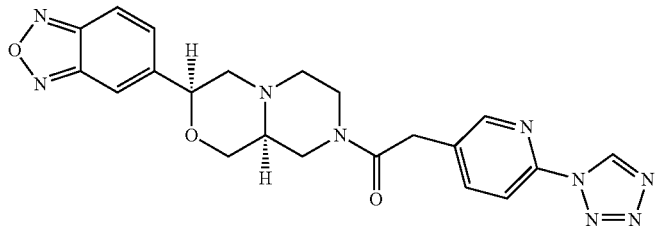 [SMILES: O=C(Cc1ccc(-n2cnnn2)nc1)N1CCN2C[C@H](c3ccc4nonc4c3)OC[C@@H]2C1] | LC/MS (M + H) 448<br>(3S,9aS)-3-(2,1,3-benzoxadiazol-5-yl)-8-{[6-(1H-tetrazol-1-yl)pyridin-3-yl]acetyl}octahydropyrazino[2,1-c][1,4]oxazine |
| 181 | 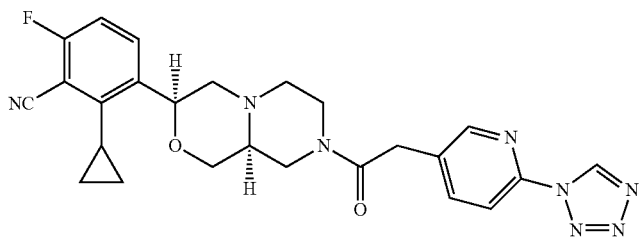 [SMILES: N#Cc1c(F)ccc([C@H]2CN3CCN(C(=O)Cc4ccc(-n5cnnn5)nc4)C[C@H]3CO2)c1C1CC1] | LC/MS (M + H) 489<br>2-cyclopropyl-6-fluoro-3-[(3S,9aS)-8-{[6-(1H-tetrazol-1-yl)pyridin-3-yl]acetyl}octahydropyrazino[2,1-c][1,4]oxazin-3-yl]benzonitrile |
| 182 | 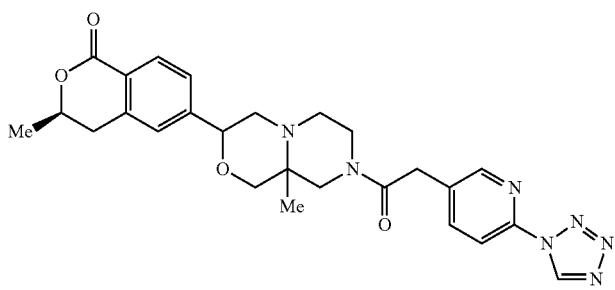 [SMILES: C[C@@H]1Cc2cc(C3CN4CCN(C(=O)Cc5ccc(-n6cnnn6)nc5)CC4(C)CO3)ccc2C(=O)O1] | LC/MS (M + H) 504<br>Either cis or trans at bicycle (mixture of two diastereomers)<br>(3R)-3-methyl-6-(9a-methyl-8-{[6-(1H-tetrazol-1-yl)pyridin-3-yl]acetyl}octahydropyrazino[2,1-c][1,4]oxazin-3-yl)-3,4-dihydro-1H-isochromen-1-one |
| 183 | 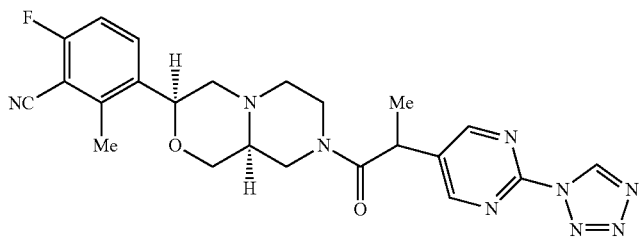 [SMILES: Cc1c([C@H]2CN3CCN(C(=O)C(C)c4cnc(-n5cnnn5)nc4)C[C@H]3CO2)ccc(F)c1C#N] | SFC HPLC on OJ column, faster eluting;<br>LC/MS 478 (M + H)+<br>6-fluoro-2-methyl-3-[(3S,9aS)-8-{2-[2-(1H-tetrazol-1-yl)pyrimidin-5-yl]propanoyl}octahydropyrazino[2,1-c][1,4]oxazin-3-yl]benzonitrile |
| 184 | 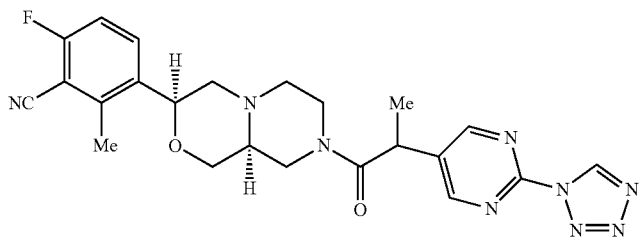 [SMILES: Cc1c([C@H]2CN3CCN(C(=O)C(C)c4cnc(-n5cnnn5)nc4)C[C@H]3CO2)ccc(F)c1C#N] | SFC HPLC on OJ column, slower eluting;<br>LC/MS 478 (M + H)+<br>6-fluoro-2-methyl-3-[(3S,9aS)-8-{2-[2-(1H-tetrazol-1-yl)pyrimidin-5-yl]propanoyl}octahydropyrazino[2,1-c][1,4]oxazin-3-yl]benzonitrile |
| 185 | 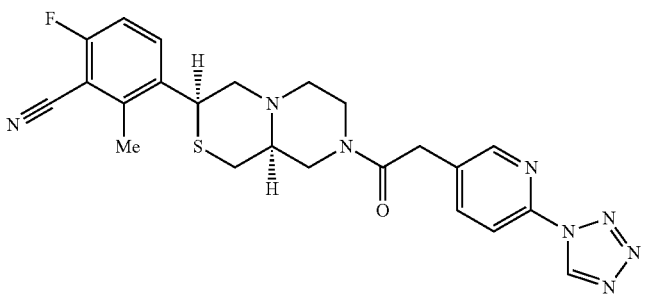 [SMILES: Cc1c([C@H]2CN3CCN(C(=O)Cc4ccc(-n5cnnn5)nc4)C[C@H]3CS2)ccc(F)c1C#N] | LC/MS 479 (M + H)+<br>6-fluoro-2-methyl-3-[(3S,9aS)-8-{[6-(1H-tetrazol-1-yl)pyridin-3-yl]acetyl}octahydropyrazino[2,1-c][1,4]thiazin-3-yl]benzonitrile |

TABLE 3-continued

| Example # | Structure | LC/MS & Name |
|---|---|---|
| 186 | (structure) | LC/MS 479 (M + H)+<br>6-fluoro-2-methyl-3-[(3S,9aS)-8-{[5-(1H-tetrazol-1-yl)pyridin-3-yl]acetyl}octahydropyrazino[2,1-c][1,4]thiazin-3-yl]benzonitrile |
| 187 | (structure) | LC/MS 511 (M + H)+<br>3-[(3S,9aS)-2,2-dioxido-8-{[6-(1H-tetrazol-1-yl)pyridin-3-yl]acetyl}octahydropyrazino[2,1-c][1,4]thiazin-3-yl]-6-fluoro-2-methylbenzonitrile |

Example 188

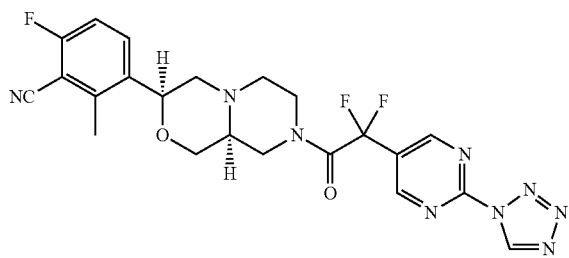 [SMILES: Cc1c([C@H]2CN3CCN(C(=O)C(F)(F)c4cnc(-n5cnnn5)nc4)C[C@H]3CO2)ccc(F)c1C#N]

3-((3S,9aS)-8-(2-(2-(1H-tetrazol-1-yl)pyrimidin-5-yl)-2,2-difluoroacetyl)octahydropyrazino[2,1-c][1,4]oxazin-3-yl)-6-fluoro-2-methylbenzonitrile Step A: Ethyl 2-(2-aminopyrimidin-5-yl)-2,2-difluoroacetate To the Schlank flask containing 2-amino-5-iodopyrimidine (2.210 g, 10.00 mmol) and copper powder (0.953 g, 15.0 mmol) in anhydrous DMSO (10 mL) was added ethyl bromodifluoroacetate (1.285 mL, 10.00 mmol). The reaction mixture was heated at 80° C. under nitrogen overnight. Reaction mixture was cooled to room temperature and diluted with dichloromethane (80 mL) and 2N aqueous ammonium chloride (150 mL). The mixture was extracted with dichloromethane (2×60 mL). The organic layer was washed with brine (2×50 mL), and concentrated. The residue was purified by Biotage SP1 column chromatography on silica gel [40+ M], eluting with 5-60% ethyl acetate/hexanes, 24 CV; 60% ethyl acetate/hexanes, 6 column volumes. $^1$H NMR (500 MHz, DMSO-$d_6$) δ 8.40 (s, 2H), 7.35 (s, 2H), 4.32 (q, J=7.1 Hz, 2H), 1.24 (t, J=7.1 Hz, 3H).

Step B: 2-(2-aminopyrimidin-5-yl)-2,2-difluoroacetic acid

Hydrolysis of the ester was achieved according to the protocol applied to 2-(2-(1H-tetrazol-1-yl)pyrimidin-5-yl)propanoic acid above.
LC/MS: [(M+1)]=190.2;

Step C: 3-((3S,9aS)-8-(2-(2-aminopyrimidin-5-yl)-2,2-difluoroacetyl)octahydropyrazino[2,1-c][1,4]oxazin-3-yl)-6-fluoro-2-methylbenzonitrile To a solution of 6-fluoro-2-methyl-3-((3S,9aS)-octahydropyrazino[2,1-c][1,4]oxazin-3-yl)benzonitrile (60 mg, 0.218 mmol) and 2-(2-aminopyrimidin-5-yl)-2,2-difluoroacetic acid (60.3 mg, 0.218 mmol) in anhydrous DMF (2724 μL) was added DIEA (133 μL, 0.763 mmol) followed by HATU (149 mg, 0.392 mmol). The mixture was stirred at RT overnight. The reaction mixture was diluted with methanol and purified on mass-directed preparative HPLC, Polar method (Column: Sunfire Prep $C_{18}$, OBD 5 um, 30×100 mm). LC/MS: [(M+1)]+=447.08; $^1$H NMR (500 MHz, DMSO-$d_6$) δ 8.36 (s, 2H), 8.11-8.17 (m, 1H), 7.30-7.39 (m, 3H), 4.83-4.92 (m, 1H), 4.07-4.27 (m, 1H), 3.43-3.76 (m, 2H), 3.00-3.37 (m, 4H), 2.72-2.96 (m, 2H), 2.58-2.68 (m, 1H), 2.16-2.55 (m, 4H).

Step D: 3-((3S,9aS)-8-(2-(2-(1H-tetrazol-1-yl)pyrimidin-5-yl)-2,2-difluoroacetyl)octahydropyrazino[2,1-c][1,4]oxazin-3-yl)-6-fluoro-2-methylbenzonitrile Trimethylsilyl trifluoroacetate (23.8 μL, 0.137 mmol) was added to a suspension of 3-((3S,9aS)-8-(2-(2-aminopyrimidin-5-yl)-2,2-difluoroacetyl)octahydropyrazino[2,1-c][1,4]oxazin-3-yl)-6-fluoro-2-methylbenzonitrile (36.1 mg, 0.081 mmol) in ethyl acetate (735 μL). The mixture was stirred for 5 min at room temperature and triethyl orthoformate (23.67 μL, 0.142 mmol) was added. After stirring for 5 more min at room temperature, azidotrimethylsilane (16.91 μL, 0.129 mmol) was added. The mixture was stirred at room temperature overnight. The reaction mixture was diluted with methanol and purified on mass-directed preparative HPLC. Appropriate fractions were collected and solvent was removed under reduced pressure. The residue was converted to hydrochloric acid salt. LC/MS: [(M+1)]⁺=500.0; ¹H NMR (500 MHz, DMSO-d₆) δ 10.33 (s, 1H), 9.35 (s, 2H), 7.85-7.94 (m, 1H), 7.43-7.54 (m, 1H), 5.14-5.27 (m, 1H), 4.01-4.60 (m, 5H), 3.13-3.95 (m, 6H), 2.53 (s, 3H).

Example 189

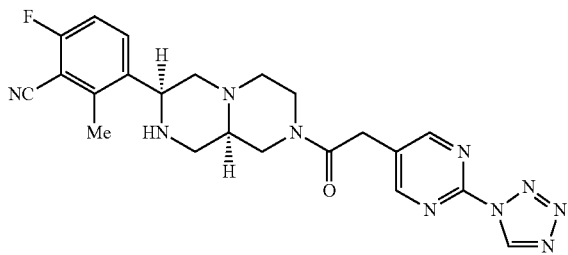 [SMILES: Cc1c([C@H]2CN3CCN(C(=O)Cc4cnc(-n5cnnn5)nc4)C[C@H]3CN2)ccc(F)c1C#N]

3-((3S,9aR)-8-(2-(2-(1H-tetrazol-1-yl)pyrimidin-5-yl)acetyl)octahydro-1H-pyrazino[1,2-a]pyrazin-3-yl)-6-fluoro-2-methylbenzonitrile Step A: (3S,9aS)-tert-butyl 8-(2-(2-(1H-tetrazol-1-yl)pyrimidin-5-yl)acetyl)-3-(3-cyano-4-fluoro-2-methylphenyl)hexahydro-1H-pyrazino[1,2-a]pyrazine-2(6H)-carboxylate To a solution of (3S,9aS)-tert-butyl 3-(3-cyano-4-fluoro-2-methylphenyl)hexahydro-1H-pyrazino[1,2-a]pyrazine-2(6H)-carboxylate (46 mg, 0.123 mmol) and 2-(2-(1H-tetrazol-1-yl)pyrimidin-5-yl)acetic acid (30.4 mg, 0.147 mmol) in DMF (2 mL) was added HATU (70.1 mg, 0.184 mmol) and diisopropylethylamine (64.4 µl, 0.369 mmol) and the resulting solution was stirred at rt for 1 h. Ethyl acetate (50 mL) was added and the organic phase was washed with brine (3×50 mL), dried over sodium sulphate, concentrated and the residue was purified on TLC using 10% methanol/methylene chloride to give title compound, LC/MS: [(M+23)]⁺=585.23; [(M+1-100-28)]⁺=435.20.

Step B: 3-((3S,9aR)-8-(2-(2-(1H-tetrazol-1-yl)pyrimidin-5-yl)acetyl)octahydro-1H-pyrazino[1,2-a]pyrazin-3-yl)-6-fluoro-2-methylbenzonitrile To the solution of (3S,9aS)-tert-butyl 8-(2-(2-(1H-tetrazol-1-yl)pyrimidin-5-yl)acetyl)-3-(3-cyano-4-fluoro-2-methylphenyl)hexahydro-1H-pyrazino[1,2-a]pyrazine-2(6H)-carboxylate (60 mg, 0.107 mmol) in methylene chloride (2 mL) was added thioanisole (50.5 µl, 0.427 mmol) and trifluoroacetic acid (3287 µl, 42.7 mmol), the resulting solution was stirred at rt for 1 h. After removing the volatile, the residue was participated between methylene chloride (100 mL) and 1N sodium hydroxide (50 mL), the alkaline phase was extracted with methylene chloride, the combined methylene chloride phase was dried over sodium sulphate, concentrated and the residue was purified on TLC using 10% methanol/methylene chloride to give title compound. ¹H NMR (500 MHz, CDCl₃) δ 9.60 (s, 1H), 8.81-8.80 (two singlets, 2H), 8.43-8.40 (m, 1H), 7.06-7.02 (m, 1H), 5.33 (s, 2H), 4.574-4.40 (m, 1H), 4.23-4.22 (m, 1H), 3.89-3.80 (m, 2H), 3.70-3.54 (m, 1H), 3.26-3.14 (m, 2H), 3.03-2.90 (m, 2H), 2.80-2.67 (m, 2H), 2.64-2.63 (two singlets, 3H), 2.59-2.38 (m, 2H); LC/MS: [(M+23)]⁺=485.13; [(M+1-28)]⁺=435.20.

The following EXAMPLES in TABLE 4 were prepared in an analagous fashion to that described for the synthesis of EXAMPLE 189 (immediately above) from the appropriate amine and carboxylic acid INTERMEDIATES (prepared as described above). Data provided includes chiral HPLC conditions (if applicable); and MS and/or HNMR characterization.

TABLE 4

| EXAMPLE # | Structure | Chiral HPLC conditions (if applicable); Characterization MS and/or HNMR; compound name |
|---|---|---|
| 190 | 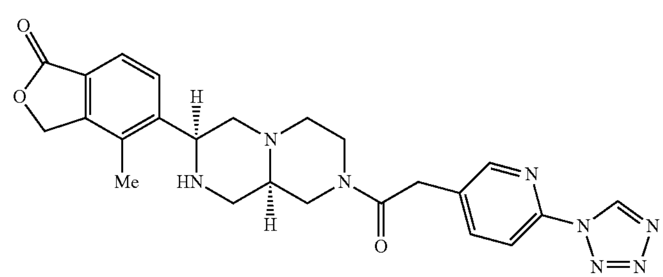 [SMILES: Cc1c([C@H]2CN3CCN(C(=O)Cc4ccc(-n5cnnn5)nc4)C[C@H]3CN2)ccc2c1COC2=O] | LC/MS (M + H) 475 4-methyl-5-[(3S,9aR)-8-{[6-(1H-tetrazol-1-yl)pyridin-3-yl]acetyl}octahydro-2H-pyrazino[1,2-a]pyrazin-3-yl]-2-benzofuran-1(3H)-one |
| 191 | 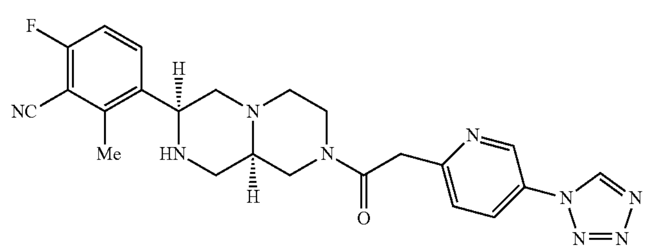 [SMILES: Cc1c([C@H]2CN3CCN(C(=O)Cc4ccc(-n5cnnn5)cn4)C[C@H]3CN2)ccc(F)c1C#N] | LC/MS (M + H) 462 6-fluoro-2-methyl-3-[(3S,9aR)-8-{[5-(1H-tetrazol-1-yl)pyridin-2-yl]acetyl}octahydropyrazino[1,2-a]pyrazin-3-yl]benzonitrile |

TABLE 4-continued

| EXAMPLE # | Structure | Chiral HPLC conditions (if applicable); Characterization MS and/or HNMR; compound name |
|---|---|---|
| 192 | 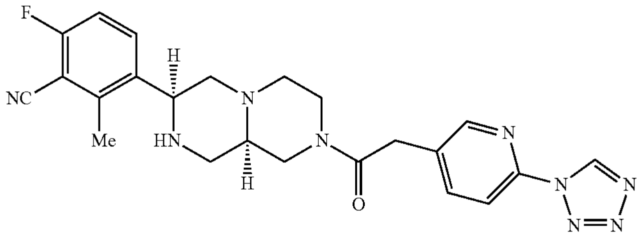 [SMILES: Cc1c([C@H]2CN3CCN(C(=O)Cc4ccc(-n5cnnn5)nc4)C[C@H]3CN2)ccc(F)c1C#N] | LC/MS (M + H) 462 6-fluoro-2-methyl-3-[(3S,9aR)-8-{[6-(1H-tetrazol-1-yl)pyridin-3-yl]acetyl}octahydro-2H-pyrazino[1,2-a]pyrazin-3-yl]benzonitrile |
| 193 | 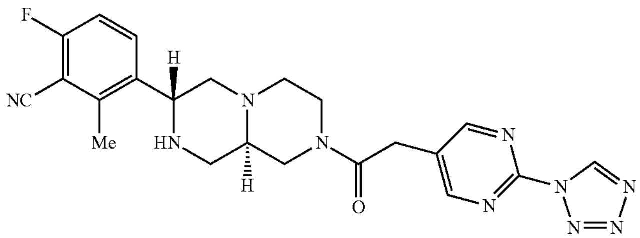 [SMILES: Cc1c([C@@H]2CN3CCN(C(=O)Cc4cnc(-n5cnnn5)nc4)C[C@H]3CN2)ccc(F)c1C#N] | LC/MS (M + H) 463 6-fluoro-2-methyl-3-[(3R,9aR)-8-{[2-(1H-tetrazol-1-yl)pyrimidin-5-yl]acetyl}octahydro-2H-pyrazino[1,2-a]pyrazin-3-yl]benzonitrile |
| 194 | 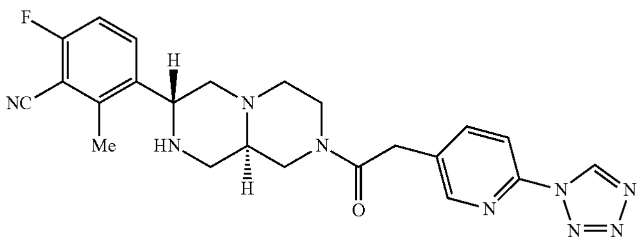 [SMILES: Cc1c([C@@H]2CN3CCN(C(=O)Cc4ccc(-n5cnnn5)nc4)C[C@H]3CN2)ccc(F)c1C#N] | LC/MS (M + H) 462 6-fluoro-2-methyl-3-[(3R,9aR)-8-{[6-(1H-tetrazol-1-yl)pyridin-3-yl]acetyl}octahydro-2H-pyrazino[1,2-a]pyrazin-3-yl]benzonitrile |
| 195 | 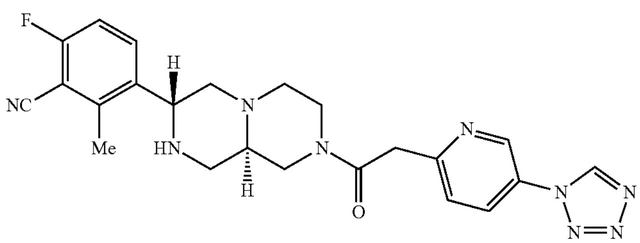 [SMILES: Cc1c([C@@H]2CN3CCN(C(=O)Cc4ccc(-n5cnnn5)cn4)C[C@H]3CN2)ccc(F)c1C#N] | LC/MS (M + H) 462 6-fluoro-2-methyl-3-[(3R,9aR)-8-{[5-(1H-tetrazol-1-yl)pyridin-2-yl]acetyl}octahydro-2H-pyrazino[1,2-a]pyrazin-3-yl]benzonitrile |
| 196 | 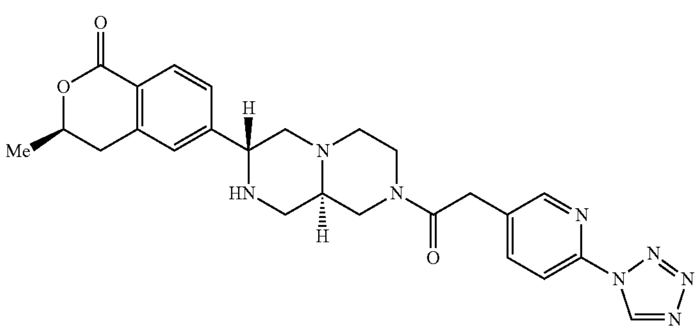 [SMILES: C[C@@H]1Cc2cc([C@@H]3CN4CCN(C(=O)Cc5ccc(-n6cnnn6)nc5)C[C@H]4CN3)ccc2C(=O)O1] | LC/MS (M + H) 489 (3R)-3-methyl-6-[(3R,9aR)-8-{[6-(1H-tetrazol-1-yl)pyridin-3-yl]acetyl}octahydro-2H-pyrazino[1,2-a]pyrazin-3-yl]-3,4-dihydro-1H-isochromen-1-one |
| 197 | 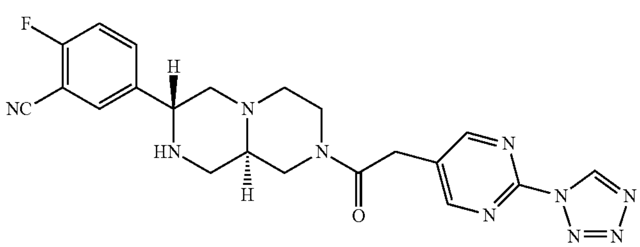 [SMILES: N#Cc1cc([C@@H]2CN3CCN(C(=O)Cc4cnc(-n5cnnn5)nc4)C[C@H]3CN2)ccc1F] | LC/MS (M + H) 449 2-fluoro-5-[(3R,9aR)-8-{[2-(1H-tetrazol-1-yl)pyrimidin-5-yl]acetyl}octahydro-2H-pyrazino[1,2-a]pyrazin-3-yl]benzonitrile |

Example 198

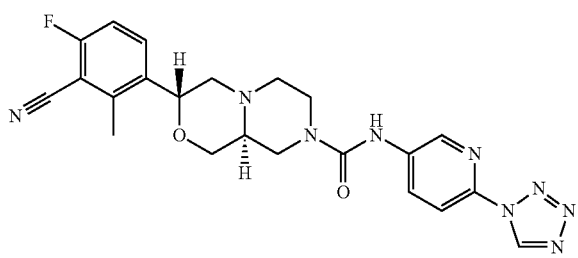 [SMILES: Cc1c([C@@H]2CN3CCN(C(=O)Nc4ccc(-n5cnnn5)nc4)C[C@H]3CO2)ccc(F)c1C#N]

(3R,9aS)-3-(3-cyano-4-fluoro-2-methylphenyl)-N-[6-(1H-tetrazol-1-yl)pyridin-3-yl]hexahydropyrazino[2,1-c][1,4]oxazine-8(1H)-carboxamide To a solution of [6-(1H-tetrazol-1-yl)pyridin-3-yl]carbamate (43.5 mg, 0.154 mmol) and 6-fluoro-2-methyl-3-(3R,9aS)-octahydropyrazino[2,1-c][1,4]oxazin-3-yl)benzonitrile (51.9 mg, 0.166 mmol) in DMSO (0.7 mL) was added aqueous 10 M NaOH (0.034 mL, 0.339 mmol). The mixture was stirred at RT overnight. Water was added and the mixture was extracted with EtOAc. The solvent was removed under reduced pressure and the residue was purified with reverse phase HPLC (10 to 100% ACN/water, both containing 0.1% TFA) to give title compound. $^1$H NMR (500 MHz, CD$_3$OD) δ 9.85 (s, 1H), 8.68 (s, 1H), 8.22 (m, 1H), 8.02 (m, 1H), 7.84 (m, 1H), 7.28 (m, 1H) 5.20 (d, J=8.2 Hz, 1H), 4.48-4.43 (m, 2H), 4.35-4.32 (m, 1H), 3.94 (t, J=11.8 Hz, 1H), 3.68-3.58 (m, 3H), 3.51-3.46 (m, 1H), 3.28-3.14 (m, 3H), 2.61 (s, 3H); LC/MS: [(M+1)]$^+$=464.16, [(M+1-28)]$^+$=436.14

The EXAMPLES in Table 5 were prepared according to the method described for the synthesis of (3R,9aS)-3-(3-cyano-4-fluoro-2-methylphenyl)-N-[6-(1H-tetrazol-1-yl)pyridin-3-yl]hexahydropyrazino[2,1-c][1,4]oxazine-8(1H)-carboxamide starting from the appropriate amines and phenylcarbamates prepared as described previously.

TABLE 5

| EXAMPLE # | Structure, Name, LC-MS |
|---|---|
| 199 | (3R,9aR)-3-(3-cyano-4-fluoro-2-methylphenyl)-N-[6-(1H-tetrazol-1-yl)pyridin-3-yl]hexahydropyrazino[2,1-c][1,4]oxazine-8(1H)-carboxamide; [(M + 1)]$^+$ 464.14 |
| 200 | (3R,9aR)-3-(3-cyano-4-fluoro-2-methylphenyl)-N-[5-(1H-tetrazol-1-yl)pyridin-2-yl]hexahydropyrazino[2,1-c][1,4]oxazine-8(1H)-carboxamide; [(M + 23)]$^+$ 486.02 |
| 201 | (3R,9aS)-3-(3-cyano-4-fluoro-2-methylphenyl)-N-[5-(1H-tetrazol-1-yl)pyridin-2-yl]hexahydropyrazino[2,1-c][1,4]oxazine-8(1H)-carboxamide; [(M + 1)]$^+$ 464.08 |

TABLE 5-continued

| EXAMPLE # | Structure, Name, LC-MS |
|---|---|
| 202 | 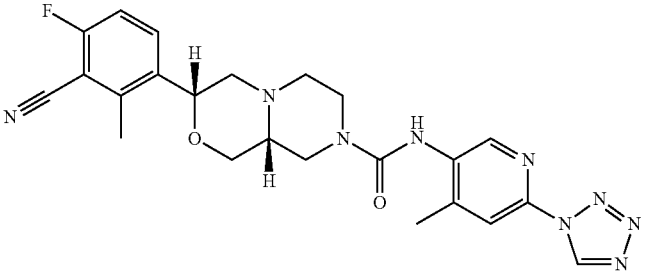<br>(3R,9aR)-3-(3-cyano-4-fluoro-2-methylphenyl)-N-[4-methyl-6-(1H-tetrazol-1-yl)pyridin-3-yl]hexahydropyrazino[2,1-c][1,4]oxazine-8(1H)-carboxamide; [(M + 23)]⁺ 478.03 |
| 203 | 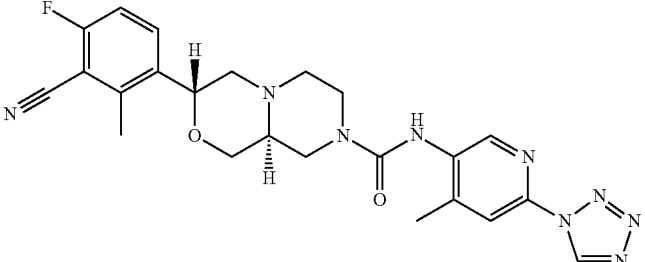<br>(3R,9aS)-3-(3-cyano-4-fluoro-2-methylphenyl)-N-[4-methyl-6-(1H-tetrazol-1-yl)pyridin-3-yl]hexahydropyrazino[2,1-c][1,4]oxazine-8(1H)-carboxamide; [(M + 23)]⁺ 500.05 |
| 204 | 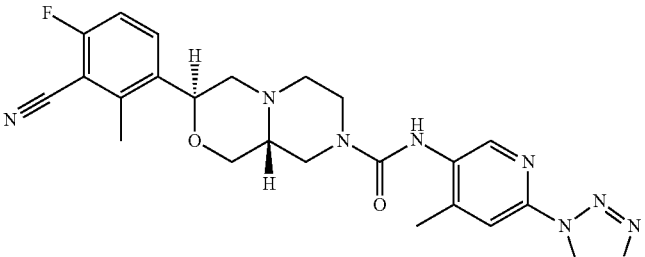<br>(3S,9aR)-3-(3-cyano-4-fluoro-2-methylphenyl)-N-[4-methyl-6-(1H-tetrazol-1-yl)pyridin-3-yl]hexahydropyrazino[2,1-c][1,4]oxazine-8(1H)-carboxamide; [(M + 1)]⁺ 478.04 |
| 205 | 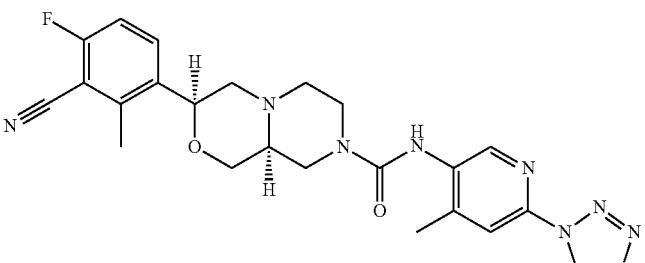<br>(3S,9aS)-3-(3-cyano-4-fluoro-2-methylphenyl)-N-[4-methyl-6-(1H-tetrazol-1-yl)pyridin-3-yl]hexahydropyrazino[2,1-c][1,4]oxazine-8(1H)-carboxamide; [(M + 1)]⁺ 477.93 |

The following Thallium Flux Assay and/or the Electrophysiology Assay were performed on the final product compounds in the Examples.

Thallium Flux Assay

Cell Culture Conditions-HEK293 cells stably expressing hROMK (hK$_{ir}$1.1) were grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 mL Calcium/Magnesium-free PBS. Add 5 mL of 1× trypsin (prepared in Ca/Mg Free PBS) to T-225 flask and return flask to 37° C./$CO_2$ incubator for 2-3 minutes. To dislodge the cell, gently bang the side of the flask with your hand. Triturate the cells completely and then transfer the cells to 25 mL complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
  FluxOR™ Reagent (Component A)
  FluxOR™ Assay Buffer (Component B)—10× Concentrate
  PowerLoad™ Concentrate (Component C)—100× Concentrate
  Probenecid (Component D)—Lyophilized sample is kept at −20° C. Water soluble, 100× after solubilization in 1 mL water. Store at 4° C.
  FluxOR™ Chloride-free Buffer (Component E)—5× Concentrate
  Potassium sulfate ($K_2SO_4$) Concentrate (Component F)—125 mM in water. Store at 4° C.
  Thallium sulfate ($Tl_2SO_4$) Concentrate (Component G)—50 mM in water. Store at 4° C.
  DMSO (dimethyl sulfoxide, Component H)—1 mL (100%)

Reagent Preparation: FluxOR Working Solutions
  1000× FluxOR™ Reagent: Reconstitute a vial of component A in 100 µl DMSO; Mix well; Store 10 µl aliquots at −20° C.
  1× FluxOR™ Assay Buffer: Dilute Component B 10-fold with water; Adjust pH to 7.4 with Hepes/NaOH; Filter and store at 4° C.
  Probenecid/Assay Buffer: 100 mL of 1× FluxOR™ Assay Buffer; 1 mL of reconstituted component D; Store at 4° C.
  Loading Buffer (per microplate): 10 µl 1000× FluxOR™ Reagent; 100 µl component C; 10 mL Probenecid/Assay Buffer
  Compound Buffer (per microplate): 20 mL Probenecid/Assay Buffer; 0.3 mM ouabain (10 mM ouabain in water can be stored in amber bottle/aluminum foil at room temperature); Test compound
  1× FluxOR™ Chloride-Free Buffer: Prepare 1× working solution in water. Can be stored at room temperature
  Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Store at 4° C. when not in use. If kept sterile, this solution is good for months.

Assay Protocol—

The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol
1. Seed HEK-hKir1.1 cells (50 µl at 20,000 cells/well) in 384-well PDL coated Microplates
2. Allow cells to adhere overnight in humidified 37° C./10% $CO_2$ incubator
3. Completely remove cell growth media from microplate and replace with 25 µl loading buffer
4. Incubate Microplate at room temperature, protected form light, for 90 min
5. Remove loading buffer and replace with 25 µl 1× Assay Buffer±test compound.
6. Incubate microplate at room temperature, protected form light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—

The fluorescence intensity of wells containing 3 µM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—

Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 µM in this assay. Alternatively, the control could be another compound (outside the scope of Formula I) that has an $IC_{50}$ potency in this assay of less than 1 µM.

Electrophysiology Assay

Block of Kir1.1 (ROMK1) currents was examined by whole cell voltage clamp (Hamill et. al. Pfluegers Archives 391:85-100 (1981)) using the IonWorks Quattro automated electrophysiology platform (Molecular Devices, Sunnyvale, Calif.). Chinese hamster ovary cells stably expressing Kir1.1 channels were maintained in T-75 flasks in cell culture media in a humidified 10% $CO_2$ incubator at 37° C. Prior to an experiment, Kir1.1 expression was induced by overnight incubation with 1 mM sodium butyrate. On the day of the experiment, cells were dissociated with 2.5 mL of Versene (Invitrogen 15040-066) for approximately 6 min at 37° C. and suspended in 10 mL of bath solution containing (in mM): 150 NaCl, 10 KCl, 2.7 $CaCl_2$, 0.5 $MgCl_2$, 5 HEPES, pH 7.4. After centrifugation, the cell pellet was resuspended in approximately 4.0 mL of bath solution and placed in the IonWorks instrument. The intracellular solution consisted of (in mM): 80 K gluconate, 40 KCl, 20 KF, 3.2 $MgCl_2$, 3 EGTA, 5 Hepes, pH 7.4.

Electrical access to the cytoplasm was achieved by perforation in 0.13 mg/mL amphotericin B for 4 min. Amphotericin B (Sigma A-4888) was prepared as a 40 mg/mL solution in DMSO. Voltage protocols and current recordings were performed using the IonWorks HT software/hardware system. Currents were sampled at 1 kHz. No correction for liquid junction potentials was used. The test pulse, consisting of a 100 ms step to 0 mV from a holding potential of −70 mV, followed by a 100 ms voltage ramp from −70 mV to +70 mV, was applied before and after a 6 min compound incubation period. Test compounds were prepared by diluting DMSO stock solutions into the bath solution at 3× the final concentration and placed in the instrument in 96-well polypropylene plates. Current amplitudes were measured using the IonWorks software. To assess compound potency, the fractional block during the voltage step to 0 mV was calculated in Microsoft Excel (Microsoft, Redmond, Calif.), and dose-response curves were fitted with Igor Pro 4.0 (WaveMetrics, Lake Oswego, Oreg.). Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 μM in this assay. Alternatively, the control could be another compound (outside the scope of Formula I) that has an $IC_{50}$ potency in this assay of less than 1 μM.

All of the final product compounds in the Examples (diastereomeric mixtures and individual diastereomers) had $IC_{50}$ potencies of 1 μM or less in one or both of the Thallium Flux Assay and the Electrophysiology Assay unless otherwise noted in the Examples section. Representative examples of data collected for compounds of the present invention using the Thallium Flux Assay and the Electrophysiology Assay are shown in Table 5 below.

TABLE 5

| EXAMPLE # | Thallium Flux $IC_{50}$ (μM) | Electrophysiology $IC_{50}$ (μM) |
|---|---|---|
| 1 | 0.08 | 0.06 |
| 2 | 0.12 | 0.07 |
| 3 | 0.09 | 0.10 |
| 4 | 0.07 | 0.04 |
| 5 | 0.05 | |
| 6 | 0.10 | 0.04 |
| 7 | | 0.07 |
| 8 | | 0.04 |
| 9 | 0.18 | |
| 10 | 0.07 | |
| 11 | 0.09 | |
| 12 | 0.12 | |
| 13 | 0.11 | 0.03 |
| 14 | 0.08 | |
| 15 | 0.14 | |
| 16 | 0.48 | |
| 17 | 0.16 | |
| 18 | 0.32 | |
| 19 | 0.16 | |
| 20 | 0.17 | |
| 21 | 0.10 | |
| 22 | 0.16 | |
| 23 | 0.07 | |
| 24 | 0.16 | |
| 25 | 0.04 | |
| 26 | | 0.06 |
| 27 | 0.10 | |
| 28 | 0.18 | |
| 29 | 0.11 | |
| 30 | 0.16 | |
| 31 | 0.16 | |
| 32 | 0.08 | |
| 33 | 0.08 | 0.08 |
| 34 | 0.58 | |
| 35 | 0.18 | |
| 36 | 0.07 | 0.15 |
| 37 | | 0.02 |
| 38 | | 0.12 |
| 39 | 0.26 | |
| 40 | 0.07 | |
| 41 | 0.23 | |
| 42 | 0.21 | |
| 43 | 0.09 | |
| 44 | 0.17 | |
| 45 | 0.25 | |
| 46 | 0.67 | |
| 47 | 0.09 | |
| 48 | 0.15 | |
| 49 | 0.29 | |
| 50 | 0.08 | 0.13 |
| 51 | 0.05 | |
| 52 | 0.11 | |
| 53 | 0.06 | |
| 54 | 0.10 | |
| 55 | 0.12 | |
| 56 | 0.12 | |
| 57 | 0.21 | 0.19 |
| 58 | 0.12 | |
| 59 | 0.14 | |
| 60 | 0.14 | |
| 61 | 0.13 | 0.07 |
| 62 | 0.46 | |
| 63 | 0.18 | |
| 64 | 0.68 | |
| 65 | 0.15 | |
| 66 | 0.37 | |
| 67 | 0.07 | |
| 68 | 0.04 | |
| 69 | 0.11 | |
| 70 | 0.27 | |
| 71 | 0.39 | |
| 72 | 0.75 | |
| 73 | 0.23 | |
| 74 | 0.39 | |
| 75 | 0.13 | |
| 76 | 0.15 | |
| 77 | 0.10 | |
| 78 | 0.12 | |
| 79 | 0.31 | |
| 80 | 0.50 | |
| 81 | 0.16 | |
| 82 | 0.34 | |
| 83 | 0.16 | |
| 84 | 0.23 | |
| 85 | 0.24 | |
| 86 | 0.29 | |
| 87 | 0.22 | |
| 88 | 0.09 | |
| 89 | 0.07 | |
| 90 | 0.13 | |
| 91 | 0.06 | |
| 92 | 0.20 | |
| 93 | 0.21 | |
| 94 | 0.14 | |
| 95 | 0.32 | |
| 96 | 0.14 | |
| 97 | 0.25 | |
| 98 | 0.56 | |
| 99 | 0.34 | |
| 100 | 0.19 | |
| 101 | 0.18 | |
| 102 | 0.15 | |
| 103 | 0.34 | |
| 104 | 0.48 | |
| 105 | 0.35 | |
| 106 | 0.42 | |
| 107 | 0.17 | |
| 108 | 0.49 | |
| 109 | 0.19 | |
| 110 | 0.37 | |
| 111 | 0.17 | |

TABLE 5-continued

| EXAMPLE # | Thallium Flux IC$_{50}$ (μM) | Electrophysiology IC$_{50}$ (μM) |
|---|---|---|
| 112 | 0.22 | |
| 113 | 0.12 | |
| 114 | 0.11 | |
| 115 | 0.27 | |
| 116 | 0.33 | |
| 117 | 0.22 | |
| 118 | 0.12 | |
| 119 | 0.33 | |
| 120 | 0.20 | |
| 121 | 0.12 | 0.09 |
| 122 | 0.39 | |
| 123 | 0.69 | |
| 124 | 0.33 | |
| 125 | 0.06 | |
| 126 | 0.14 | |
| 127 | 0.09 | |
| 128 | 0.18 | |
| 129 | 0.25 | |
| 130 | 0.19 | |
| 131 | 0.20 | |
| 132 | 0.14 | |
| 133 | 0.14 | |
| 134 | 0.28 | |
| 135 | 0.33 | |
| 136 | 0.04 | |
| 137 | 0.06 | |
| 138 | 0.14 | |
| 139 | 0.16 | |
| 140 | 0.12 | |
| 141 | 0.30 | |
| 142 | 0.10 | |
| 143 | 0.19 | |
| 144 | 0.39 | |
| 145 | 0.24 | |
| 146 | 0.09 | |
| 147 | 0.14 | |
| 148 | 0.08 | |
| 149 | 0.13 | |
| 150 | 0.29 | |
| 151 | 0.30 | |
| 152 | 0.20 | |
| 153 | 0.17 | |
| 154 | 0.20 | |
| 155 | 0.30 | |
| 156 | 0.21 | |
| 157 | 0.32 | |
| 158 | 0.20 | |
| 159 | 0.26 | |
| 160 | 0.39 | |
| 161 | 0.35 | |
| 162 | 0.17 | |
| 163 | 0.21 | |
| 164 | 0.65 | |
| 165 | 0.21 | |
| 166 | 0.38 | |
| 167 | 0.42 | |
| 168 | 0.35 | |
| 169 | 0.18 | |
| 170 | 0.24 | |
| 171 | 0.27 | |
| 172 | 0.22 | |
| 173 | 0.30 | |
| 174 | 0.35 | |
| 175 | 0.53 | |
| 176 | 0.20 | |
| 177 | 0.25 | |
| 178 | 0.35 | |
| 179 | 0.18 | |
| 180 | 0.59 | |
| 181 | 0.38 | |
| 182 | 0.32 | |
| 183 | 0.47 | |
| 184 | 0.29 | |
| 185 | 0.18 | |
| 186 | 0.27 | |
| 187 | 0.28 | |
| 188 | 0.35 | |
| 189 | 0.12 | |
| 190 | 0.39 | |
| 191 | 0.12 | |
| 192 | 0.07 | |
| 193 | 0.10 | |
| 194 | 0.06 | 0.06 |
| 195 | 0.25 | |
| 196 | 0.23 | |
| 197 | 0.24 | |
| 198 | 0.16 | |
| 199 | 0.14 | |
| 200 | 0.25 | |
| 201 | 0.32 | |
| 202 | 0.34 | |
| 203 | 0.22 | |
| 203 | 0.28 | |

Spontaneously Hypertensive Rat (SHR) Assay

The spontaneously hypertensive rat (SHR) exhibits age-dependent hypertension that does not require administration of exogenous agents to elevate blood pressure nor does it require the use of a high salt diet to elevate blood pressure. Thus it resembles human essential hypertension and provides an opportunity to assess the dose-dependence of novel agents for their ability to lower blood pressure.

Experimental protocols for evaluating blood pressure lowering efficacy of compounds of the present invention in spontaneously hypertensive rats (SHR):

Spontaneously hypertensive rats (SHR, male, 6 months, Charles River) were implanted with DSI TA 11PA-C40 telemetry device (Data Sciences, Inc., St. Paul, Minn.) under isoflurane or ketamine/metomidine anesthesia. The telemetry unit catheter was inserted into the descending aorta via the femoral artery and the telemetry device was implanted subcutaneously in the left flank area. Animals were allowed to recover from surgery for 14 days before the start of any studies. Blood pressure, heart rate, and activity signals from conscious, freely moving rats were recorded continuously for 30 seconds every 10 minutes. HCTZ (25 mg/kg/day, PO) was included as a reference diuretic at a dose giving approximately maximal efficacy in SHR. The blood pressure lowering efficacy of compounds of the present invention compared to vehicle control was evaluated following a single oral gavage each day for a typical duration of three to fourteen days. Data were collected as hourly averages, and changes in blood pressure were calculated by subtracting vehicle control baseline data on an hourly basis. Example numbers 2, 3, 4, 6, 13, 14, 36, 50, 57, 78, and 168 were evaluated at PO, QD doses of either 3 mg/kg or 10 mg/kg and resulted in typical reductions in daily (24 h) mean systolic blood pressure ranging from 7 mmHg to 25 mmHg by the last day of the studies.

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound having structural Formula I:

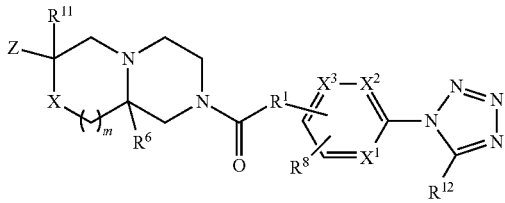

or a pharmaceutically acceptable salt thereof wherein:
X is O;
$R^1$ is —C($R^9$)($R^{10}$)— or —N($R^{13}$)—;
m is an integer selected from 1 or 2;
$X^1$, $X^2$ and $X^3$ are each independently selected from C($R^7$) or N, provided that at least one of $X^1$, $X^2$ and $X^3$ must be N and at most two of $X^1$ $X^2$ and $X^3$ are N;
Z is

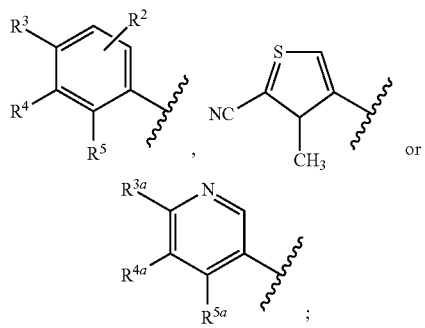

$R^2$ is —H, —F, —Cl, —$C_{1-6}$alkyl, —$C_{3-6}$cycloalkyl or —$OC_{1-6}$alkyl;
$R^3$ and $R^{3a}$ are each independently —H, —F, —Cl, —CN, —$C_{1-6}$alkyl, —$C_{3-6}$cycloalkyl or —$OC_{1-6}$alkyl;
$R^4$ and $R^{4a}$ are each independently —F, —Cl, —CN, —$C_{1-6}$alkyl, —$C_{3-6}$cycloalkyl, —$OC_{1-4}$alkyl or N-tetrazolyl;
or $R^3$ and $R^4$ are joined together with the carbon atoms in the phenyl ring to which they are attached to form:

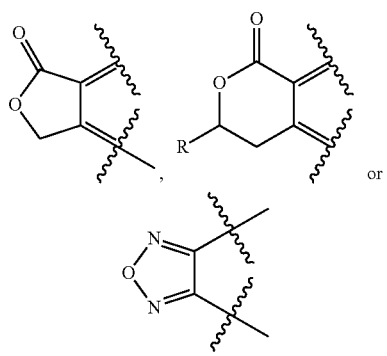

wherein R is —H or —$C_{1-4}$alkyl;
$R^5$ and $R^{5a}$ are each independently —H, —F, —Cl, —CN, —$C_{1-4}$alkyl, —$C_{3-6}$cycloalkyl or —$OC_{1-4}$alkyl;
provided that when $R^3$ and $R^4$ are not joined together, then one and only one of $R^3$, $R^4$ or $R^5$ is —CN;
and provided that one and only one of $R^{3a}$, $R^{4a}$ or $R^{5a}$ is —CN;
$R^6$ is —H or —$C_{1-4}$alkyl;
each $R^7$ is independently —H, —F, —Cl, —$CF_3$, —$C_{1-4}$alkyl or —$OC_{1-4}$alkyl;
$R^8$ is —H, —F, —Cl, —$CF_3$, —$C_{1-4}$alkyl or —$OC_{1-4}$alkyl;
$R^9$ is —H, —F or —$C_{1-4}$alkyl;
$R^{10}$ is —H or —F;
$R^{11}$ is —H or —$CH_3$;
$R^{12}$ is —H or —$CH_3$; and
$R^{13}$ is —H or —$C_{1-4}$alkyl.

2. The compound of claim 1 wherein Z is

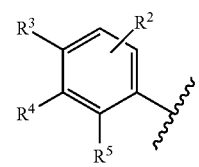

and one of $R^3$ and $R^4$ is —CN, or a pharmaceutically acceptable salt thereof.

3. The compound of claim 1 wherein Z is

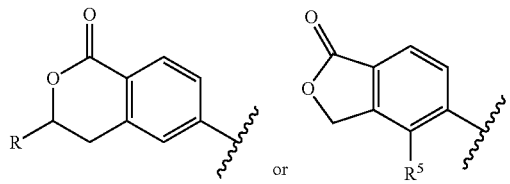

or a pharmaceutically acceptable salt thereof.

4. The compound of claim 1 wherein Z is

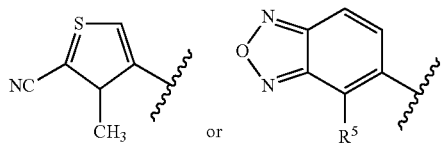

or a pharmaceutically acceptable salt thereof.

5. The compound of claim 1 or a pharmaceutically acceptable salt thereof wherein $R^1$ is —C($R^9$)($R^{10}$)—.

6. The compound of claim 1 or a pharmaceutically acceptable salt thereof wherein

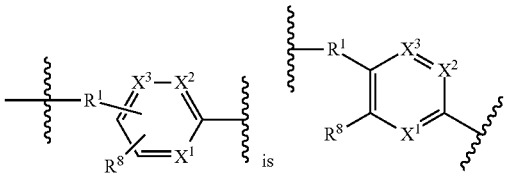

7. The compound of claim 1 or a pharmaceutically acceptable salt thereof wherein m is 1, $R^6$ is —H, $R^{11}$ is —H and $R^{12}$ is —H.

8. The compound of claim 2 having structural Formula IV

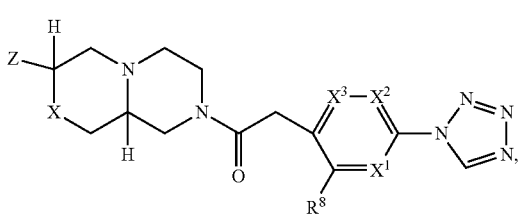

or a pharmaceutically acceptable salt thereof wherein:
X is O,
$X^1$, $X^2$ and $X^3$ are each independently selected from $C(R^7)$ or N, provided that at least one of $X^1$, $X^2$ and $X^3$ must be N and at most two of $X^1$ $X^2$ and $X^3$ are N;
Z is

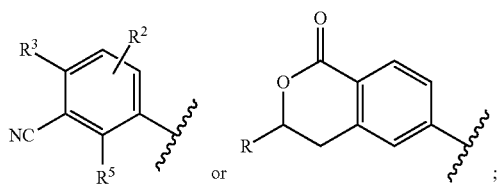

R is —H or —$C_{1-3}$ alkyl; $R^2$ is —H, —F, —Cl, —$C_{1-3}$alkyl, cyclopropyl or —$OC_{1-3}$alkyl;
$R^3$ is —H, —F, —Cl, —CN, —$C_{1-3}$alkyl, cyclopropyl or —$OC_{1-3}$alkyl; $R^5$ is —H, —F, —Cl, —CN, —$C_{1-3}$alkyl, cyclopropyl or —$OC_{1-3}$ alkyl; $R^7$ is —H, —$CH_3$, —$CH_2CH_3$, —$OCH_3$, —F, —Cl, or —$CF_3$; and
$R^8$ is —H, —$CH_3$ or —$OCH_3$.

9. The compound of claim 1 which is:
6-((3R,9aS)-8-{[4-(1H-tetrazol-1-yl)phenyl]acetyl}octahydropyrazino[2,1-c][1,4]oxazin-3-yl)-3,4-dihydro-1H-isochromen-1-one;
3-((3R,9aS)-8-(2-(5-(1H-tetrazol-1-yl)pyridin-2-yl)acetyl)octahydropyrazino[2,1-c][1,4]oxazin-3-yl)-6-fluoro-2-methylbenzonitrile;
3-((3S,9aS)-8-(2-(5-(1H-tetrazol-1-yl)pyridin-2-yl)acetyl)octahydropyrazino[2,1-c][1,4]oxazin-3-yl)-6-fluoro-2-methylbenzonitrile;
6-fluoro-2-methyl-3-[(3S,9aS)-8-{[6-(1H-tetrazol-1-yl)pyridin-3-yl]acetyl}octahydropyrazino[2,1-c][1,4]oxazin-3-yl]benzonitrile;
6-fluoro-2-methyl-3-[(3S,9aS)-8-{[2-(1H-tetrazol-1-yl)pyrimidin-5-yl]acetyl}octahydropyrazino[2,1-c][1,4]oxazin-3-yl]benzonitrile;
6-fluoro-2-methyl-3-[(3R,9aR)-8-{[2-(1H-tetrazol-1-yl)pyrimidin-5-yl]acetyl}octahydropyrazino[2,1-c][1,4]oxazin-3-yl]benzonitrile;
(3S)-3-methyl-6-[(3R,9aS)-8-{[6-(1H-tetrazol-1-yl)pyridin-3-yl]acetyl}octahydropyrazino[2,1-c][1,4]oxazin-3-yl]-3,4-dihydro-1H-isochromen-1-one;
(3R)-3-methyl-6-[(3R,9aS)-8-{[6-(1H-tetrazol-1-yl)pyridin-3-yl]acetyl}octahydropyrazino[2,1-c][1,4]oxazin-3-yl]-3,4-dihydro-1H-isochromen-1-one; 6-methoxy-2-methyl-3-[(3R,9aS)-8-{[6-(1H-tetrazol-1-yl)pyridin-3-yl]acetyl}octahydropyrazino[2,1-c][1,4]oxazin-3-yl]benzonitrile;
4-fluoro-2-methoxy-5-[(3R,9aS)-8-{[6-(1H-tetrazol-1-yl)pyridin-3-yl]acetyl}octahydropyrazino[2,1-c][1,4]oxazin-3-yl]benzonitrile;
6-fluoro-2-methoxy-3-[(3S,9aS)-8-{[6-(1H-tetrazol-1-yl)pyridin-3-yl]acetyl}octahydropyrazino[2,1-c][1,4]oxazin-3-yl]benzonitrile;
6-fluoro-2-methyl-3-[(3S,9aS)-8-{[4-methyl-2-(1H-tetrazol-1-yl)pyrimidin-5-yl]acetyl}octahydropyrazino[2,1-c][1,4]oxazin-3-yl]benzonitrile; or
6-fluoro-2-methyl-3-[(3R,9aR)-8-{[6-(1H-tetrazol-1-yl)pyridin-3-yl]acetyl}octahydro-2H-pyrazino[1,2-a]pyrazin-3-yl]benzonitrile;
or a pharmaceutically acceptable salt thereof.

10. The compound of claim 1 which is;
3-((3R,9aS)-8-(2-(5-(1H-tetrazol-1-yl)pyridin-2-yl)acetyl)octahydropyrazino[2,1-c][1,4]oxazin-3-yl)-6-fluoro-2-methylbenzonitrile;
3-((3S,9aS)-8-(2-(5-(1H-tetrazol-1-yl)pyridin-2-yl)acetyl)octahydropyrazino[2,1-c][1,4]oxazin-3-yl)-6-fluoro-2-methylbenzonitrile;
6-fluoro-2-methyl-3-[(3S,9aS)-8-{[2-(1H-tetrazol-1-yl)pyrimidin-5-yl]acetyl}octahydropyrazino[2,1-c][1,4]oxazin-3-yl]benzonitrile;
6-fluoro-2-methyl-3-[(3R,9aR)-8-{[2-(1H-tetrazol-1-yl)pyrimidin-5-yl]acetyl}octahydropyrazino[2,1-c][1,4]oxazin-3-yl]benzonitrile;
(3S)-3-methyl-6-[(3R,9aS)-8-{[6-(1H-tetrazol-1-yl)pyridin-3-yl]acetyl}octahydropyrazino[2,1-c][1,4]oxazin-3-yl]-3,4-dihydro-1H-isochromen-1-one;
(3R)-3-methyl-6-[(3R,9aS)-8-{[6-(1H-tetrazol-1-yl)pyridin-3-yl]acetyl}octahydropyrazino[2,1-c][1,4]oxazin-3-yl]-3,4-dihydro-1H-isochromen-1-one;
or a pharmaceutically acceptable salt thereof.

11. A pharmaceutical composition comprised of a compound of claim 1 and a pharmaceutically acceptable carrier.

12. A pharmaceutical composition comprised of a compound of claim 10 and a pharmaceutically acceptable carrier.

13. The pharmaceutical composition of claim 11 further comprising an additional active agent selected from losartan, valsartan, candesartan cilexetil, olmesartan medoximil, telmesartan, eprosartan mesylate, irbesartan, azilsartan medoxomil, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril, amiloride, spironolactone, eplerenone or triamterene, or a pharmaceutically acceptable salt thereof, and optionally hydrochlorothiazide.

14. A method for causing diueresis, natriuresis or both, comprising administering a compound of claim 1 in a therapeutically effective amount to a patient in need thereof.

15. A method for the treatment of hypertension comprising administering a compound of claim 1 in a therapeutically effective amount to a patient in need thereof.

16. A method for the treatment of heart failure comprising administering a compound of claim 1 in a therapeutically effective amount to a patient in need thereof.

17. A method for the treatment of one or more disorders selected from hypertension, acute heart failure, chronic heart failure or pulmonary arterial hypertension, comprising administering a compound of claim 1 in a therapeutically effective amount as appropriate, to a patient in need thereof.

18. The compound of claim 1 which is:
6-((3R,9aS)-8-{[4-(1H-tetrazol-1-yl)phenyl]acetyl}octahydropyrazino[2,1-c][1,4]oxazin-3-yl)-3,4-dihydro-1H-isochromen-1-one;
3-((3R,9aS)-8-(2-(5-(1H-tetrazol-1-yl)pyridin-2-yl)acetyl)octahydropyrazino[2,1-c][1,4]oxazin-3-yl)-6-fluoro-2-methylbenzonitrile;

3-((3S,9aS)-8-(2-(5-(1H-tetrazol-1-yl)pyridin-2-yl)
   acetyl)octahydropyrazino[2,1-c][1,4]oxazin-3-yl)-6-
   fluoro-2-methylbenzonitrile;
6-fluoro-2-methyl-3-[(3S,9aS)-8-{[6-(1H-tetrazol-1-yl)
   pyridin-3-yl]acetyl}octahydropyrazino[2,1-c][1,4]ox-
   azin-3-yl]benzonitrile;
6-fluoro-2-methyl-3-[(3R,9aS)-8-{[6-(1H-tetrazol-1-yl)
   pyridin-3-yl]acetyl}octahydropyrazino[2,1-c][1,4]ox-
   azin-3-yl]benzonitrile;
6-fluoro-2-methyl-3-[(3S,9aS)-8-{[2-(1H-tetrazol-1-yl)
   pyrimidin-5-yl]acetyl}octahydropyrazino[2,1-c][1,4]
   oxazin-3-yl]benzonitrile;
6-fluoro-2-methyl-3-[(3S,9aR)-8-{[6-(1H-tetrazol-1-yl)
   pyridin-3-yl]acetyl}octahydropyrazino[2,1-c][1,4]ox-
   azin-3-yl]benzonitrile;
6-fluoro-2-methyl-3-[(3R,9aR)-8-{[6-(1H-tetrazol-1-yl)
   pyridin-3-yl]acetyl}octahydropyrazino[2,1-c][1,4]ox-
   azin-3-yl]benzonitrile;
6-fluoro-2-methyl-3-[(3S,9aR)-8-{[2-(1H-tetrazol-1-yl)
   pyrimidin-5-yl]acetyl}octahydropyrazino[2,1-c][1,4]
   oxazin-3-yl]benzonitrile;
2-chloro-6-fluoro-3-[(3S,9aS)-8-{[6-(1H-tetrazol-1-yl)
   pyridin-3-yl]acetyl}octahydropyrazino[2,1-c][1,4]ox-
   azin-3-yl]benzonitrile;
2,6-difluoro-3-[(3R,9aS)-8-{[6-(1H-tetrazol-1-yl)pyri-
   din-3-yl]acetyl}octahydropyrazino[2,1-c][1,4]oxazin-
   3-yl]benzonitrile;
2,6-difluoro-3-[(3S,9aS)-8-{[6-(1H-tetrazol-1-yl)pyridin-
   3-yl]acetyl}octahydropyrazino[2,1-c][1,4]oxazin-3-yl]
   benzonitrile;
6-fluoro-2-methyl-3-[(3R,9aR)-8-{[2-(1H-tetrazol-1-yl)
   pyrimidin-5-yl]acetyl}octahydropyrazino[2,1-c][1,4]
   oxazin-3-yl]benzonitrile;
6-fluoro-2-methyl-3-[(3R,9aS)-8-{[2-(1H-tetrazol-1-yl)
   pyrimidin-5-yl]acetyl}octahydropyrazino[2,1-c][1,4]
   oxazin-3-yl]benzonitrile;
4-methyl-5-[(3S,9aS)-8-{[2-(1H-tetrazol-1-yl)pyrimidin-
   5-yl]acetyl}octahydropyrazino[2,1-c][1,4]oxazin-3-
   yl]-2-benzofuran-1(3H)-one;
4-methyl-5-[(3R,9aS)-8-{[2-(1H-tetrazol-1-yl)pyrimidin-
   5-yl]acetyl}octahydropyrazino[2,1-c][1,4]oxazin-3-
   yl]-2-benzofuran-1(3H)-one;
2-methyl-3-[(3R,9aS)-8-{[2-(1H-tetrazol-1-yl)pyrimidin-
   5-yl]acetyl}octahydropyrazino[2,1-c][1,4]oxazin-3-yl]
   benzonitrile;
2-methyl-3-[(3S,9aS)-8-{[2-(1H-tetrazol-1-yl)pyrimidin-
   5-yl]acetyl}octahydropyrazino[2,1-c][1,4]oxazin-3-yl]
   benzonitrile;
(3r)-3-methyl-6-[(3R,9aS)-8-{[2-(1H-tetrazol-1-yl)pyri-
   midin-5-yl]acetyl}octahydropyrazino[2,1-c][1,4]ox-
   azin-3-yl]-3,4-dihydro-1H-isochromen-1-one;
(3S)-3-methyl-6-[(3R,9aS)-8-{[2-(1H-tetrazol-1-yl)pyri-
   midin-5-yl]acetyl}octahydropyrazino[2,1-c][1,4]ox-
   azin-3-yl]-3,4-dihydro-1H-isochromen-1-one;
4-methyl-5-[(3S,9aS)-8-{[6-(1H-tetrazol-1-yl)pyridin-3-
   yl]acetyl}octahydropyrazino[2,1-c][1,4]oxazin-3-yl]-
   2-benzofuran-1(3H)-one;
4-methyl-5-[(3R,9aS)-8-{[6-(1H-tetrazol-1-yl)pyridin-3-
   yl]acetyl}octahydropyrazino[2,1-c][1,4]oxazin-3-yl]-
   2-benzofuran-1(3H)-one;
4-methyl-5-[(3R,9aR)-8-{[6-(1H-tetrazol-1-yl)pyridin-3-
   yl]acetyl}octahydropyrazino[2,1-c][1,4]oxazin-3-yl]-
   2-benzofuran-1(3H)-one;
4-methyl-5-[(3S,9aR)-8-{[6-(1H-tetrazol-1-yl)pyridin-3-
   yl]acetyl}octahydropyrazino[2,1-c][1,4]oxazin-3-yl]-
   2-benzofuran-1(3H)-one;
5-[(3R,9aS)-8-{[6-(1H-tetrazol-1-yl)pyridin-3-yl]
   acetyl}octahydropyrazino[2,1-c][1,4]oxazin-3-yl]-2-
   benzofuran-1(3H)-one;
5-[(3S,9aS)-8-{[6-(1H-tetrazol-1-yl)pyridin-3-yl]
   acetyl}octahydropyrazino[2,1-c][1,4]oxazin-3-yl]-2-
   benzofuran-1(3H)-one;
5-[(3R,9aS)-8-{[5-(1H-tetrazol-1-yl)pyridin-2-yl]
   acetyl}octahydropyrazino[2,1-c][1,4]oxazin-3-yl]-2-
   benzofuran-1(3H)-one;
5-[(3S,9aS)-8-{[5-(1H-tetrazol-1-yl)pyridin-2-yl]
   acetyl}octahydropyrazino[2,1-c][1,4]oxazin-3-yl]-2-
   benzofuran-1(3H)-one;
4-methyl-5-[(3S,9aS)-8-{[5-(1H-tetrazol-1-yl)pyridin-2-
   yl]acetyl}octahydropyrazino[2,1-c][1,4]oxazin-3-yl]-
   2-benzofuran-1(3H)-one;
6-[(3R,9aS)-8-{[2-methyl-6-(1H-tetrazol-1-yl)pyridin-3-
   yl]acetyl}octahydropyrazino[2,1-c][1,4]oxazin-3-yl]-
   3,4-dihydro-1H-isochromen-1-one;
6-fluoro-2-methyl-3-[(3S,9aR)-8-{[5-(1H-tetrazol-1-yl)
   pyridin-2-yl]acetyl}octahydropyrazino[2,1-c][1,4]ox-
   azin-3-yl]benzonitrile;
6-fluoro-2-methyl-3-[(3R,9aR)-8-{[5-(1H-tetrazol-1-yl)
   pyridin-2-yl]acetyl}octahydropyrazino[2,1-c][1,4]ox-
   azin-3-yl]benzonitrile;
(3S)-3-methyl-6-[(3R,9aS)-8-{[6-(1H-tetrazol-1-yl)pyri-
   din-3-yl]acetyl}octahydropyrazino[2,1-c][1,4]oxazin-
   3-yl]-3,4-dihydro-1H-isochromen-1-one;
(3S)-3-methyl-6-[(3S,9aS)-8-{[6-(1H-tetrazol-1-yl)pyri-
   din-3-yl]acetyl}octahydropyrazino[2,1-c][1,4]oxazin-
   3-yl]-3,4-dihydro-1H-isochromen-1-one;
(3S)-3-methyl-6-[(3S,9aR)-8-{[6-(1H-tetrazol-1-yl)pyri-
   din-3-yl]acetyl}octahydropyrazino[2,1-c][1,4]oxazin-
   3-yl]-3,4-dihydro-1H-isochromen-1-one;
(3R)-3-methyl-6-[(3R,9aS)-8-{[6-(1H-tetrazol-1-yl)pyri-
   din-3-yl]acetyl}octahydropyrazino[2,1-c][1,4]oxazin-
   3-yl]-3,4-dihydro-1H-isochromen-1-one;
2-fluoro-5-[(3R,9aS)-8-{[6-(1H-tetrazol-1-yl)pyridin-3-
   yl]acetyl}octahydropyrazino[2,1-c][1,4]oxazin-3-yl]
   benzonitrile;
2-fluoro-5-[(3R,9aS)-8-{[5-(1H-tetrazol-1-yl)pyridin-2-
   yl]acetyl}octahydropyrazino[2,1-c][1,4]oxazin-3-yl]
   benzonitrile;
2-methoxy-4-[(3S,9aR)-8-{[6-(1H-tetrazol-1-yl)pyridin-
   3-yl]acetyl}octahydropyrazino[2,1-c][1,4]oxazin-3-yl]
   benzonitrile;
2-methoxy-4-[(3R,9aR)-8-{[6-(1H-tetrazol-1-yl)pyridin-
   3-yl]acetyl}octahydropyrazino[2,1-c][1,4]oxazin-3-yl]
   benzonitrile;
2-methoxy-4-[(3R,9aS)-8-{[6-(1H-tetrazol-1-yl)pyridin-
   3-yl]acetyl}octahydropyrazino[2,1-c][1,4]oxazin-3-yl]
   benzonitrile;
4-methyl-5-[(3S,9aS)-8-{[4-methyl-6-(1H-tetrazol-1-yl)
   pyridin-3-yl]acetyl}octahydropyrazino[2,1-c][1,4]ox-
   azin-3-yl]-2-benzofuran-1(3H)-one;
6-fluoro-2-methyl-3-[(3S,9aS)-8-{[4-methyl-6-(1H-tetra-
   zol-1-yl)pyridin-3-yl]acetyl}octahydropyrazino[2,1-c]
   [1,4]oxazin-3-yl]benzonitrile;
6-[(3R,9aS)-8-{[4-methyl-6-(1H-tetrazol-1-yl)pyridin-3-
   yl]acetyl}octahydropyrazino[2,1-c][1,4]oxazin-3-yl]-
   3,4-dihydro-1H-isochromen-1-one;
2-methoxy-4-[(3R,9aR)-8-{[4-methyl-6-(1H-tetrazol-1-
   yl)pyridin-3-yl]acetyl}octahydropyrazino[2,1-c][1,4]
   oxazin-3-yl]benzonitrile;
4-chloro-5-[(3R,9aS)-8-{[6-(1H-tetrazol-1-yl)pyridin-3-
   yl]acetyl}octahydropyrazino[2,1-c][1,4]oxazin-3-yl]-
   2-benzofuran-1(3H)-one;

4-chloro-5-[(3S,9aS)-8-{[6-(1H-tetrazol-1-yl)pyridin-3-yl]acetyl}octahydropyrazino[2,1-c][1,4]oxazin-3-yl]-2-benzofuran-1(3H)-one;

4-bromo-5-[(3S,9aS)-8-{[6-(1H-tetrazol-1-yl)pyridin-3-yl]acetyl}octahydropyrazino[2,1-c][1,4]oxazin-3-yl]-2-benzofuran-1(3H)-one;

6-methoxy-2-methyl-3-[(3S,9aS)-8-{[6-(1H-tetrazol-1-yl)pyridin-3-yl]acetyl}octahydropyrazino[2,1-c][1,4]oxazin-3-yl]benzonitrile;

6-methoxy-2-methyl-3-[(3R,9aS)-8-{[6-(1H-tetrazol-1-yl)pyridin-3-yl]acetyl}octahydropyrazino[2,1-c][1,4]oxazin-3-yl]benzonitrile;

2-chloro-6-fluoro-3-[(3R,9aS)-8-{[6-(1H-tetrazol-1-yl)pyridin-3-yl]acetyl}octahydropyrazino[2,1-c][1,4]oxazin-3-yl]benzonitrile;

2-chloro-6-fluoro-3-[(3S,9aS)-8-{[5-(1H-tetrazol-1-yl)pyridin-2-yl]acetyl}octahydropyrazino[2,1-c][1,4]oxazin-3-yl]benzonitrile;

2-chloro-6-fluoro-3-[(3R,9aS)-8-{[5-(1H-tetrazol-1-yl)pyridin-2-yl]acetyl}octahydropyrazino[2,1-c][1,4]oxazin-3-yl]benzonitrile;

2,6-difluoro-3-[(3R,9aS)-8-{[5-(1H-tetrazol-1-yl)pyridin-2-yl]acetyl}octahydropyrazino[2,1-c][1,4]oxazin-3-yl]benzonitrile;

6-[(3S,9aR)-8-{[6-(1H-tetrazol-1-yl)pyridin-3-yl]acetyl}octahydropyrazino[2,1-c][1,4]oxazin-3-yl]-3,4-dihydro-1H-isochromen-1-one;

2-methoxy-4-[(3S,9aS)-8-{[6-(1H-tetrazol-1-yl)pyridin-3-yl]acetyl}octahydropyrazino[2,1-c][1,4]oxazin-3-yl]benzonitrile;

4-fluoro-2-methoxy-5-[(3R,9aS)-8-{[6-(1H-tetrazol-1-yl)pyridin-3-yl]acetyl}octahydropyrazino[2,1-c][1,4]oxazin-3-yl]benzonitrile;

6-fluoro-2-methyl-3-[(3R,9aR)-8-{[4-methyl-6-(1H-tetrazol-1-yl)pyridin-3-yl]acetyl}octahydropyrazino[2,1-c][1,4]oxazin-3-yl]benzonitrile;

6-fluoro-2-methyl-3-[(3S,9aR)-8-{[4-methyl-6-(1H-tetrazol-1-yl)pyridin-3-yl]acetyl}octahydropyrazino[2,1-c][1,4]oxazin-3-yl]benzonitrile;

6-fluoro-2-methoxy-3-[(3R,9aS)-8-{[6-(1H-tetrazol-1-yl)pyridin-3-yl]acetyl}octahydropyrazino[2,1-c][1,4]oxazin-3-yl]benzonitrile;

6-fluoro-2-methoxy-3-[(3S,9aS)-8-{[6-(1H-tetrazol-1-yl)pyridin-3-yl]acetyl}octahydropyrazino[2,1-c][1,4]oxazin-3-yl]benzonitrile;

6-fluoro-2-methoxy-3-[(3R,9aS)-8-{[5-(1H-tetrazol-1-yl)pyridin-2-yl]acetyl}octahydropyrazino[2,1-c][1,4]oxazin-3-yl]benzonitrile;

6-fluoro-2-methoxy-3-[(3S,9aS)-8-{[5-(1H-tetrazol-1-yl)pyridin-2-yl]acetyl}octahydropyrazino[2,1-c][1,4]oxazin-3-yl]benzonitrile;

6-chloro-2-methyl-3-[(3S,9aS)-8-{[6-(1H-tetrazol-1-yl)pyridin-3-yl]acetyl}octahydropyrazino[2,1-c][1,4]oxazin-3-yl]benzonitrile;

6-chloro-2-methyl-3-[(3R,9aS)-8-{[6-(1H-tetrazol-1-yl)pyridin-3-yl]acetyl}octahydropyrazino[2,1-c][1,4]oxazin-3-yl]benzonitrile;

2-fluoro-4-[(3R,9aS)-8-{[6-(1H-tetrazol-1-yl)pyridin-3-yl]acetyl}octahydropyrazino[2,1-c][1,4]oxazin-3-yl]benzonitrile;

2-fluoro-4-[(3S,9aS)-8-{[6-(1H-tetrazol-1-yl)pyridin-3-yl]acetyl}octahydropyrazino[2,1-c][1,4]oxazin-3-yl]benzonitrile;

3-methyl-4-[(3R,9aS)-8-{[6-(1H-tetrazol-1-yl)pyridin-3-yl]acetyl}octahydropyrazino[2,1-c][1,4]oxazin-3-yl]thiophene-2-carbonitrile;

3-methyl-4-[(3S,9aS)-8-{[6-(1H-tetrazol-1-yl)pyridin-3-yl]acetyl}octahydropyrazino[2,1-c][1,4]oxazin-3-yl]thiophene-2-carbonitrile;

3-methyl-4-[(3R,9aS)-8-{[5-(1H-tetrazol-1-yl)pyridin-2-yl]acetyl}octahydropyrazino[2,1-c][1,4]oxazin-3-yl]thiophene-2-carbonitrile;

3-methyl-4-[(3S,9aS)-8-{[5-(1H-tetrazol-1-yl)pyridin-2-yl]acetyl}octahydropyrazino[2,1-c][1,4]oxazin-3-yl]thiophene-2-carbonitrile;

6-methyl-5-[(3R,9aS)-8-{[6-(1H-tetrazol-1-yl)pyridin-3-yl]acetyl}octahydropyrazino[2,1-c][1,4]oxazin-3-yl]-2-benzofuran-1(3H)-one;

6-methyl-5-[(3S,9aS)-8-{[6-(1H-tetrazol-1-yl)pyridin-3-yl]acetyl}octahydropyrazino[2,1-c][1,4]oxazin-3-yl]-2-benzofuran-1(3H)-one;

4-methyl-5-[(3R,9aS)-8-{[6-(1H-tetrazol-1-yl)pyridin-3-yl]acetyl}octahydropyrazino[2,1-c][1,4]oxazin-3-yl]pyridine-3-carbonitrile;

6-fluoro-2-methyl-3-[(3R,9aS)-8-{[5-(1H-tetrazol-1-yl)pyrazin-2-yl]acetyl}octahydropyrazino[2,1-c][1,4]oxazin-3-yl]benzonitrile;

6-fluoro-2-methyl-3-[(3S,9aS)-8-{[5-(1H-tetrazol-1-yl)pyrazin-2-yl]acetyl}octahydropyrazino[2,1-c][1,4]oxazin-3-yl]benzonitrile;

6-fluoro-2-methyl-3-[(3R,9aS)-8-{[2-methyl-6-(1H-tetrazol-1-yl)pyridin-3-yl]acetyl}octahydropyrazino[2,1-c][1,4]oxazin-3-yl]benzonitrile;

6-fluoro-2-methyl-3-[(3S,9aS)-8-{[2-methyl-6-(1H-tetrazol-1-yl)pyridin-3-yl]acetyl}octahydropyrazino[2,1-c][1,4]oxazin-3-yl]benzonitrile;

6-fluoro-2-methyl-3-[(3R,9aS)-8-{2-[2-methyl-6-(1H-tetrazol-1-yl)pyridin-3-yl]propanoyl}octahydropyrazino[2,1-c][1,4]oxazin-3-yl]benzonitrile;

6-[(3R,9aS)-8-{[5-(1H-tetrazol-1-yl)pyrazin-2-yl]acetyl}octahydropyrazino[2,1-c][1,4]oxazin-3-yl]-3,4-dihydro-1H-isochromen-1-one;

2,4-difluoro-5-[(3R,9aS)-8-{[6-(1H-tetrazol-1-yl)pyridin-3-yl]acetyl}octahydropyrazino[2,1-c][1,4]oxazin-3-yl]benzonitrile;

2,4-difluoro-5-[(3R,9aS)-8-{[5-(1H-tetrazol-1-yl)pyridin-2-yl]acetyl}octahydropyrazino[2,1-c][1,4]oxazin-3-yl]benzonitrile;

4-methyl-5-[(3S,9aS)-8-{[5-(1H-tetrazol-1-yl)pyrazin-2-yl]acetyl}octahydropyrazino[2,1-c][1,4]oxazin-3-yl]-2-benzofuran-1(3H)-one;

6-fluoro-2-methyl-3-[(3R,9aS)-8-{[3-methyl-5-(1H-tetrazol-1-yl)pyridin-2-yl]acetyl}octahydropyrazino[2,1-c][1,4]oxazin-3-yl]benzonitrile;

6-fluoro-2-methyl-3-[(3S,9aS)-8-{[3-methyl-5-(1H-tetrazol-1-yl)pyridin-2-yl]acetyl}octahydropyrazino[2,1-c][1,4]oxazin-3-yl]benzonitrile;

2,6-difluoro-3-[(3S,9aS)-8-{[5-(1H-tetrazol-1-yl)pyridin-2-yl]acetyl}octahydropyrazino[2,1-c][1,4]oxazin-3-yl]benzonitrile;

2,6-difluoro-3-[(3S,9aR)-8-{[6-(1H-tetrazol-1-yl)pyridin-3-yl]acetyl}octahydropyrazino[2,1-c][1,4]oxazin-3-yl]benzonitrile;

2,6-difluoro-3-[(3R,9aR)-8-{[6-(1H-tetrazol-1-yl)pyridin-3-yl]acetyl}octahydropyrazino[2,1-c][1,4]oxazin-3-yl]benzonitrile;

2,6-difluoro-3-[(3S,9aS)-8-{[2-methyl-6-(1H-tetrazol-1-yl)pyridin-3-yl]acetyl}octahydropyrazino[2,1-c][1,4]oxazin-3-yl]benzonitrile;

2-methyl-3-[(3S,9aS)-8-{[6-(1H-tetrazol-1-yl)pyridin-3-yl]acetyl}octahydropyrazino[2,1-c][1,4]oxazin-3-yl]benzonitrile;

2-methyl-3-[(3R,9aS)-8-{[6-(1H-tetrazol-1-yl)pyridin-3-yl]acetyl}octahydropyrazino[2,1-c][1,4]oxazin-3-yl]benzonitrile;
2-methyl-3-[(3S,9aS)-8-{[2-methyl-6-(1H-tetrazol-1-yl)pyridin-3-yl]acetyl}octahydropyrazino[2,1-c][1,4]oxazin-3-yl]benzonitrile;
6-fluoro-2-methyl-3-[(3S,9aR)-8-{[2-methyl-6-(1H-tetrazol-1-yl)pyridin-3-yl]acetyl}octahydropyrazino[2,1-c][1,4]oxazin-3-yl]benzonitrile;
6-fluoro-2-methyl-3-[(3R,9aR)-8-{[2-methyl-6-(1H-tetrazol-1-yl)pyridin-3-yl]acetyl}octahydropyrazino[2,1-c][1,4]oxazin-3-yl]benzonitrile;
2-methoxy-4-[(3S,9aS)-8-{[2-methyl-6-(1H-tetrazol-1-yl)pyridin-3-yl]acetyl}octahydropyrazino[2,1-c][1,4]oxazin-3-yl]benzonitrile;
2-chloro-6-fluoro-3-[(3R,9aS)-8-{[2-methyl-6-(1H-tetrazol-1-yl)pyridin-3-yl]acetyl}octahydropyrazino[2,1-c][1,4]oxazin-3-yl]benzonitrile;
6-fluoro-2-methyl-3-[(3S,9aS)-8-{[6-(1H-tetrazol-1-yl)pyridin-2-yl]acetyl}octahydropyrazino[2,1-c][1,4]oxazin-3-yl]benzonitrile;
6-fluoro-2-methyl-3-[(3R,9aS)-8-{[6-(1H-tetrazol-1-yl)pyridin-2-yl]acetyl}octahydropyrazino[2,1-c][1,4]oxazin-3-yl]benzonitrile;
6-fluoro-2-methyl-3-[(3R,9aS)-8-{[2-(1H-tetrazol-1-yl)pyridin-4-yl]acetyl}octahydropyrazino[2,1-c][1,4]oxazin-3-yl]benzonitrile;
6-fluoro-2-methyl-3-[(3S,9aS)-8-{[2-(1H-tetrazol-1-yl)pyridin-4-yl]acetyl}octahydropyrazino[2,1-c][1,4]oxazin-3-yl]benzonitrile;
6-fluoro-2-methyl-3-[(3S,9aS)-8-{[5-(1H-tetrazol-1-yl)pyridin-3-yl]acetyl}octahydropyrazino[2,1-c][1,4]oxazin-3-yl]benzonitrile;
6-fluoro-2-methyl-3-[(3R,9aR)-8-{[6-(1H-tetrazol-1-yl)pyridin-3-yl]acetyl}octahydropyrazino[2,1-c][1,4]oxazin-3-yl]benzonitrile;
(3R,9aS)-3-[3-(1H-tetrazol-1-yl)phenyl]-8-{[6-(1H-tetrazol-1-yl)pyridin-3-yl]acetyl}octahydropyrazino[2,1-c][1,4]oxazine;
(3R,9aS)-3-[2-methyl-3-(1H-tetrazol-1-yl)phenyl]-8-{[6-(1H-tetrazol-1-yl)pyridin-3-yl]acetyl}octahydropyrazino[2,1-c][1,4]oxazine;
(3R)-3-methyl-6-[(3R,9aS)-3-methyl-8-{[6-(1H-tetrazol-1-yl)pyridin-3-yl]acetyl}octahydropyrazino[2,1-c][1,4]oxazin-3-yl]-3,4-dihydro-1H-isochromen-1-one;
(3S)-3-methyl-6-[(3R,9aS)-3-methyl-8-{[6-(1H-tetrazol-1-yl)pyridin-3-yl]acetyl}octahydropyrazino[2,1-c][1,4]oxazin-3-yl]-3,4-dihydro-1H-isochromen-1-one;
2,6-difluoro-4-[(3R,9aR)-8-{[6-(1H-tetrazol-1-yl)pyridin-3-yl]acetyl}octahydropyrazino[2,1-c][1,4]oxazin-3-yl]benzonitrile;
2,6-difluoro-4-[(3S,9aR)-8-{[6-(1H-tetrazol-1-yl)pyridin-3-yl]acetyl}octahydropyrazino[2,1-c][1,4]oxazin-3-yl]benzonitrile;
2,6-difluoro-4-[(3S,9aS)-8-{[6-(1H-tetrazol-1-yl)pyridin-3-yl]acetyl}octahydropyrazino[2,1-c][1,4]oxazin-3-yl]benzonitrile;
2,6-difluoro-4-[(3R,9aS)-8-{[6-(1H-tetrazol-1-yl)pyridin-3-yl]acetyl}octahydropyrazino[2,1-c][1,4]oxazin-3-yl]benzonitrile;
2-fluoro-6-methoxy-4-[(3R,9aR)-8-{[6-(1H-tetrazol-1-yl)pyridin-3-yl]acetyl}octahydropyrazino[2,1-c][1,4]oxazin-3-yl]benzonitrile;
2-fluoro-6-methoxy-4-[(3S,9aR)-8-{[6-(1H-tetrazol-1-yl)pyridin-3-yl]acetyl}octahydropyrazino[2,1-c][1,4]oxazin-3-yl]benzonitrile;
2-fluoro-6-methoxy-4-[(3S,9aS)-8-{[6-(1H-tetrazol-1-yl)pyridin-3-yl]acetyl}octahydropyrazino[2,1-c][1,4]oxazin-3-yl]benzonitrile;
2-fluoro-6-methoxy-4-[(3R,9aS)-8-{[6-(1H-tetrazol-1-yl)pyridin-3-yl]acetyl}octahydropyrazino[2,1-c][1,4]oxazin-3-yl]benzonitrile;
2,6-difluoro-4-[(3R,9aR)-8-{[2-(1H-tetrazol-1-yl)pyrimidin-5-yl]acetyl}octahydropyrazino[2,1-c][1,4]oxazin-3-yl]benzonitrile;
2-methyl-3-[(3R,9aR)-8-{[2-(1H-tetrazol-1-yl)pyrimidin-5-yl]acetyl}octahydropyrazino[2,1-c][1,4]oxazin-3-yl]benzonitrile;
2-methyl-3-[(3R,9aR)-8-{[6-(1H-tetrazol-1-yl)pyridin-3-yl]acetyl}octahydropyrazino[2,1-c][1,4]oxazin-3-yl]benzonitrile;
6-fluoro-2-methyl-3-[(3R,9aS)-8-{[4-methyl-2-(1H-tetrazol-1-yl)pyrimidin-5-yl]acetyl}octahydropyrazino[2,1-c][1,4]oxazin-3-yl]benzonitrile;
6-fluoro-2-methyl-3-[(3S,9aR)-8-{[4-methyl-2-(1H-tetrazol-1-yl)pyrimidin-5-yl]acetyl}octahydropyrazino[2,1-c][1,4]oxazin-3-yl]benzonitrile;
6-fluoro-2-methyl-3-[(3R,9aR)-8-{[4-methyl-2-(1H-tetrazol-1-yl)pyrimidin-5-yl]acetyl}octahydropyrazino[2,1-c][1,4]oxazin-3-yl]benzonitrile;
6-fluoro-2-methyl-3-[(3S,9aS)-8-{[4-methyl-2-(1H-tetrazol-1-yl)pyrimidin-5-yl]acetyl}octahydropyrazino[2,1-c][1,4]oxazin-3-yl]benzonitrile;
4-methyl-5-[(3R,9aR)-8-{[2-(1H-tetrazol-1-yl)pyrimidin-5-yl]acetyl}octahydropyrazino[2,1-c][1,4]oxazin-3-yl]-2-benzofuran-1(3H)-one;
4-methyl-5-[(3R,9aR)-8-{[5-(1H-tetrazol-1-yl)pyrazin-2-yl]acetyl}octahydropyrazino[2,1-c][1,4]oxazin-3-yl]-2-benzofuran-1(3H)-one;
6-fluoro-3-[(3R,9aR)-8-{[3-methoxy-5-(1H-tetrazol-1-yl)pyridin-2-yl]acetyl}octahydropyrazino[2,1-c][1,4]oxazin-3-yl]-2-methylbenzonitrile;
2-chloro-6-fluoro-3-[(3R,9aR)-8-{[2-(1H-tetrazol-1-yl)pyrimidin-5-yl]acetyl}octahydropyrazino[2,1-c][1,4]oxazin-3-yl]benzonitrile;
2-chloro-6-fluoro-3-[(3S,9aR)-8-{[2-(1H-tetrazol-1-yl)pyrimidin-5-yl]acetyl}octahydropyrazino[2,1-c][1,4]oxazin-3-yl]benzonitrile;
6-fluoro-2-methyl-3-[(3S,9aS)-8-{[6-methyl-5-(1H-tetrazol-1-yl)pyridin-2-yl]acetyl}octahydropyrazino[2,1-c][1,4]oxazin-3-yl]benzonitrile;
6-fluoro-2-methyl-3-[(3R,9aS)-8-{[6-methyl-5-(1H-tetrazol-1-yl)pyridin-2-yl]acetyl}octahydropyrazino[2,1-c][1,4]oxazin-3-yl]benzonitrile;
6-fluoro-2-methyl-3-[(3R,9aR)-8-{[4-methyl-5-(1H-tetrazol-1-yl)pyridin-2-yl]acetyl}octahydropyrazino[2,1-c][1,4]oxazin-3-yl]benzonitrile;
6-fluoro-2-methyl-3-[(3S,9aS)-8-{[4-methyl-5-(1H-tetrazol-1-yl)pyridin-2-yl]acetyl}octahydropyrazino[2,1-c][1,4]oxazin-3-yl]benzonitrile;
6-fluoro-2-methyl-3-[(3S,9aR)-8-{[6-methyl-5-(1H-tetrazol-1-yl)pyridin-2-yl]acetyl}octahydropyrazino[2,1-c][1,4]oxazin-3-yl]benzonitrile;
6-fluoro-2-methyl-3-[(3R,9aR)-8-{[6-methyl-5-(1H-tetrazol-1-yl)pyridin-2-yl]acetyl}octahydropyrazino[2,1-c][1,4]oxazin-3-yl]benzonitrile;
6-fluoro-2-methyl-3-[(3R,9aR)-8-{[5-methyl-6-(1H-tetrazol-1-yl)pyridin-3-yl]acetyl}octahydropyrazino[2,1-c][1,4]oxazin-3-yl]benzonitrile;
6-fluoro-2-methyl-3-[(3S,9aR)-8-{[5-methyl-6-(1H-tetrazol-1-yl)pyridin-3-yl]acetyl}octahydropyrazino[2,1-c][1,4]oxazin-3-yl]benzonitrile;

6-methoxy-2-methyl-3-[(3R,9aS)-8-{[2-(1H-tetrazol-1-yl)pyrimidin-5-yl]acetyl}octahydropyrazino[2,1-c][1,4]oxazin-3-yl]benzonitrile;

2-chloro-6-fluoro-3-[(3R,9aS)-8-{[2-(1H-tetrazol-1-yl)pyrimidin-5-yl]acetyl}octahydropyrazino[2,1-c][1,4]oxazin-3-yl]benzonitrile;

2-chloro-6-fluoro-3-[(3S,9aS)-8-{[2-(1H-tetrazol-1-yl)pyrimidin-5-yl]acetyl}octahydropyrazino[2,1-c][1,4]oxazin-3-yl]benzonitrile;

2-chloro-6-fluoro-3-[(3R,9aR)-8-{[4-methyl-2-(1H-tetrazol-1-yl)pyrimidin-5-yl]acetyl}octahydropyrazino[2,1-c][1,4]oxazin-3-yl]benzonitrile;

6-fluoro-2-methoxy-3-[(3S,9aS)-8-{[2-(1H-tetrazol-1-yl)pyrimidin-5-yl]acetyl}octahydropyrazino[2,1-c][1,4]oxazin-3-yl]benzonitrile;

6-fluoro-2-methoxy-3-[(3R,9aS)-8-{[2-(1H-tetrazol-1-yl)pyrimidin-5-yl]acetyl}octahydropyrazino[2,1-c][1,4]oxazin-3-yl]benzonitrile;

2-fluoro-5-[(3R,9aR)-8-{[2-(1H-tetrazol-1-yl)pyrimidin-5-yl]acetyl}octahydropyrazino[2,1-c][1,4]oxazin-3-yl]benzonitrile;

2-fluoro-5-[(3R,9aS)-8-{[2-(1H-tetrazol-1-yl)pyrimidin-5-yl]acetyl}octahydropyrazino[2,1-c][1,4]oxazin-3-yl]benzonitrile;

2-methoxy-4-[(3S,9aS)-8-{[2-(1H-tetrazol-1-yl)pyrimidin-5-yl]acetyl}octahydropyrazino[2,1-c][1,4]oxazin-3-yl]benzonitrile;

2-methoxy-4-[(3R,9aS)-8-{[2-(1H-tetrazol-1-yl)pyrimidin-5-yl]acetyl}octahydropyrazino[2,1-c][1,4]oxazin-3-yl]benzonitrile;

6-[(3R,9aS)-8-{[2-(1H-tetrazol-1-yl)pyrimidin-5-yl]acetyl}octahydropyrazino[2,1-c][1,4]oxazin-3-yl]-3,4-dihydro-1H-isochromen-1-one;

6-fluoro-3-[(3R,9aR)-8-{[5-fluoro-6-(1H-tetrazol-1-yl)pyridin-3-yl]acetyl}octahydropyrazino[2,1-c][1,4]oxazin-3-yl]-2-methylbenzonitrile;

6-fluoro-3-[(3S,9aR)-8-{[5-fluoro-6-(1H-tetrazol-1-yl)pyridin-3-yl]acetyl}octahydropyrazino[2,1-c][1,4]oxazin-3-yl]-2-methylbenzonitrile;

6-fluoro-3-[(3R,9aS)-8-{[5-fluoro-6-(1H-tetrazol-1-yl)pyridin-3-yl]acetyl}octahydropyrazino[2,1-c][1,4]oxazin-3-yl]-2-methylbenzonitrile;

6-fluoro-3-[(3S,9aS)-8-{[5-fluoro-6-(1H-tetrazol-1-yl)pyridin-3-yl]acetyl}octahydropyrazino[2,1-c][1,4]oxazin-3-yl]-2-methylbenzonitrile;

3-[(3S,9aS)-8-{[4,6-dimethyl-2-(1H-tetrazol-1-yl)pyrimidin-5-yl]acetyl}octahydropyrazino[2,1-c][1,4]oxazin-3-yl]-6-fluoro-2-methylbenzonitrile;

3-[(3S,9aR)-8-{[4,6-dimethyl-2-(1H-tetrazol-1-yl)pyrimidin-5-yl]acetyl}octahydropyrazino[2,1-c][1,4]oxazin-3-yl]-6-fluoro-2-methylbenzonitrile;

3-[(3R,9aR)-8-{[4,6-dimethyl-2-(1H-tetrazol-1-yl)pyrimidin-5-yl]acetyl}octahydropyrazino[2,1-c][1,4]oxazin-3-yl]-6-fluoro-2-methylbenzonitrile;

3-[(3S,9aS)-8-{[3-chloro-5-(1H-tetrazol-1-yl)pyridin-2-yl]acetyl}octahydropyrazino[2,1-c][1,4]oxazin-3-yl]-6-fluoro-2-methylbenzonitrile;

3-[(3R,9aR)-8-{[3-chloro-5-(1H-tetrazol-1-yl)pyridin-2-yl]acetyl}octahydropyrazino[2,1-c][1,4]oxazin-3-yl]-6-fluoro-2-methylbenzonitrile;

6-fluoro-2-methyl-3-[(3S,9aS)-8-{[6-(1H-tetrazol-1-yl)pyridazin-3-yl]acetyl}octahydropyrazino[2,1-c][1,4]oxazin-3-yl]benzonitrile;

6-fluoro-2-methyl-3-[(3R,9aR)-8-{[6-(1H-tetrazol-1-yl)pyridazin-3-yl]acetyl}octahydropyrazino[2,1-c][1,4]oxazin-3-yl]benzonitrile;

3-[(3R,9aR)-8-{[4-ethyl-6-(1H-tetrazol-1-yl)pyridin-3-yl]acetyl}octahydropyrazino[2,1-c][1,4]oxazin-3-yl]-6-fluoro-2-methylbenzonitrile;

6-fluoro-2-methyl-3-[(3S,9aS)-8-{[2-(1H-tetrazol-1-yl)-4-(trifluoromethyl)pyrimidin-5-yl]acetyl}octahydropyrazino[2,1-c][1,4]oxazin-3-yl]benzonitrile;

6-fluoro-2-methyl-3-[(3R,9aS)-8-{[2-(1H-tetrazol-1-yl)-4-(trifluoromethyl)pyrimidin-5-yl]acetyl}octahydropyrazino[2,1-c][1,4]oxazin-3-yl]benzonitrile;

6-fluoro-2-methyl-3-[(3S,9aR)-8-{[6-(1H-tetrazol-1-yl)pyridin-2-yl]acetyl}octahydropyrazino[2,1-c][1,4]oxazin-3-yl]benzonitrile;

6-fluoro-2-methyl-3-[(3R,9aR)-8-{[6-(1H-tetrazol-1-yl)pyridin-2-yl]acetyl}octahydropyrazino[2,1-c][1,4]oxazin-3-yl]benzonitrile;

6-fluoro-2-methyl-3-[(3R,9aS)-8-{[5-(5-methyl-1H-tetrazol-1-yl)pyridin-2-yl]acetyl}octahydropyrazino[2,1-c][1,4]oxazin-3-yl]benzonitrile;

4-methyl-5-(2-{[6-(1H-tetrazol-1-yl)pyridin-3-yl]acetyl}octahydro-2H-pyrazino[1,2-d][1,4]oxazepin-7-yl)-2-benzofuran-1(3H)-one;

4-methyl-5-(2-{[6-(1H-tetrazol-1-yl)pyridin-3-yl]acetyl}octahydro-2H-pyrazino[1,2-d][1,4]oxazepin-7-yl)-2-benzofuran-1(3H)-one;

4-methyl-5-(2-{[2-(1H-tetrazol-1-yl)pyrimidin-5-yl]acetyl}octahydro-2H-pyrazino[1,2-d][1,4]oxazepin-7-yl)-2-benzofuran-1(3H)-one;

4-methyl-5-[(3R,9aS)-8-{[6-(1H-tetrazol-1-yl)pyridin-3-yl]acetyl}octahydropyrazino[2,1-c][1,4]thiazin-3-yl]-2-benzofuran-1(3H)-one;

4-methyl-5-[(3S,9aS)-8-{[6-(1H-tetrazol-1-yl)pyridin-3-yl]acetyl}octahydropyrazino[2,1-c][1,4]thiazin-3-yl]-2-benzofuran-1(3H)-one;

4-fluoro-2-methoxy-5-[(3R,9aS)-8-{[2-(1H-tetrazol-1-yl)pyrimidin-5-yl]acetyl}octahydropyrazino[2,1-c][1,4]oxazin-3-yl]benzonitrile;

6-fluoro-2-methyl-3-[(7S,10aR)-2-{[6-(1H-tetrazol-1-yl)pyridin-3-yl]acetyl}octahydro-2H-pyrazino[1,2-d][1,4]oxazepin-7-yl]benzonitrile;

6-fluoro-2-methyl-3-[(7R,10aS)-2-{[6-(1H-tetrazol-1-yl)pyridin-3-yl]acetyl}octahydro-2H-pyrazino[1,2-d][1,4]oxazepin-7-yl]benzonitrile;

6-fluoro-2-methyl-3-[(7R,10aR)-2-{[6-(1H-tetrazol-1-yl)pyridin-3-yl]acetyl}octahydro-2H-pyrazino[1,2-d][1,4]oxazepin-7-yl]benzonitrile;

6-fluoro-2-methyl-3-[(7S,10aR)-2-{[2-(1H-tetrazol-1-yl)pyrimidin-5-yl]acetyl}octahydro-2H-pyrazino[1,2-d][1,4]oxazepin-7-yl]benzonitrile;

2-fluoro-3,6-dimethyl-5-[(3S,9aR)-8-{[6-(1H-tetrazol-1-yl)pyridin-3-yl]acetyl}octahydropyrazino[2,1-c][1,4]oxazin-3-yl]benzonitrile;

2-fluoro-3,6-dimethyl-5-[(3R,9aR)-8-{[6-(1H-tetrazol-1-yl)pyridin-3-yl]acetyl}octahydropyrazino[2,1-c][1,4]oxazin-3-yl]benzonitrile;

(3R,9aS)-3-(2,1,3-benzoxadiazol-5-yl)-8-{[2-(1H-tetrazol-1-yl)pyrimidin-5-yl]acetyl}octahydropyrazino[2,1-c][1,4]oxazine;

(3S,9aS)-3-(4-methyl-2,1,3-benzoxadiazol-5-yl)-8-{[6-(1H-tetrazol-1-yl)pyridin-3-yl]acetyl}octahydropyrazino[2,1-c][1,4]oxazine;

(3R,9aS)-3-(4-methyl-2,1,3-benzoxadiazol-5-yl)-8-{[6-(1H-tetrazol-1-yl)pyridin-3-yl]acetyl}octahydropyrazino[2,1-c][1,4]oxazine;

(3R,9aS)-3-(2,1,3-benzoxadiazol-5-yl)-8-{[5-(1H-tetrazol-1-yl)pyridin-2-yl]acetyl}octahydropyrazino[2,1-c][1,4]oxazine;

(3R,9aS)-3-(2,1,3-benzoxadiazol-5-yl)-8-{[6-(1H-tetrazol-1-yl)pyridin-3-yl]acetyl}octahydropyrazino[2,1-c][1,4]oxazine;

(3S,9aS)-3-(2, 1,3-benzoxadiazol-5-yl)-8-{[6-(1H-tetrazol-1-yl)pyridin-3-yl]acetyl}octahydropyrazino[2,1-c][1,4]oxazine;

2-cyclopropyl-6-fluoro-3-[(3S,9aS)-8-{[6-(1H-tetrazol-1-yl)pyridin-3-yl]acetyl}octahydropyrazino[2,1-c][1,4]oxazin-3-yl]benzonitrile;

(3R)-3-methyl-6-(9a-methyl-8-{[6-(1H-tetrazol-1-yl)pyridin-3-yl]acetyl}octahydropyrazino[2,1-c][1,4]oxazin-3-yl)-3,4-dihydro-1H-isochromen-1-one;

6-fluoro-2-methyl-3-[(3S,9aS)-8-{2-[2-(1H-tetrazol-1-yl)pyrimidin-5-yl]propanoyl}octahydropyrazino[2,1-c][1,4]oxazin-3-yl]benzonitrile;

6-fluoro-2-methyl-3-[(3S,9aS)-8-{2-[2-(1H-tetrazol-1-yl)pyrimidin-5-yl]propanoyl}octahydropyrazino[2,1-c][1,4]oxazin-3-yl]benzonitrile;

6-fluoro-2-methyl-3-[(3S,9aS)-8-{[6-(1H-tetrazol-1-yl)pyridin-3-yl]acetyl}octahydropyrazino[2,1-c][1,4]thiazin-3-yl]benzonitrile;

6-fluoro-2-methyl-3-[(3S,9aS)-8-{[5-(1H-tetrazol-1-yl)pyridin-2-yl]acetyl}octahydropyrazino[2,1-c][1,4]thiazin-3-yl]benzonitrile;

3-[(3S,9aS)-2,2-dioxido-8-{[6-(1H-tetrazol-1-yl)pyridin-3-yl]acetyl}octahydropyrazino[2,1-c][1,4]thiazin-3-yl]-6-fluoro-2-methylbenzonitrile;

3-43S,9aS)-8-(2-(2-(1H-tetrazol-1-yl)pyrimidin-5-yl)-2,2-difluoroacetyl)octahydropyrazino[2,1-c][1,4]oxazin-3-yl)-6-fluoro-2-methylbenzonitrile;

3-((3S,9aR)-8-(2-(2-(1H-tetrazol-1-yl)pyrimidin-5-yl)acetyl)octahydro-1H-pyrazino[1,2-a]pyrazin-3-yl)-6-fluoro-2-methylbenzonitrile;

4-methyl-5-[(3S,9aR)-8-{[6-(1H-tetrazol-1-yl)pyridin-3-yl]acetyl}octahydro-2H-pyrazino[1,2-a]pyrazin-3-yl]-2-benzo furan-1 (314)-one;

6-fluoro-2-methyl-3-[(3S,9aR)-8-{[5-(1H-tetrazol-1-yl)pyridin-2-yl]acetyl}octahydro-2H-pyrazino[1,2-a]pyrazin-3-yl]benzonitrile;

6-fluoro-2-methyl-3-[(3S,9aR)-8-{[6-(1H-tetrazol-1-yl)pyridin-3-yl]acetyl}octahydro-2H-pyrazino[1,2-a]pyrazin-3-yl]benzonitrile;

6-fluoro-2-methyl-3-[(3R,9aR)-8-{[2-(1H-tetrazol-1-yl)pyrimidin-5-yl]acetyl}octahydro-2H-pyrazino[1,2-a]pyrazin-3-yl]benzonitrile;

6-fluoro-2-methyl-3-[(3R,9aR)-8-{[6-(1H-tetrazol-1-yl)pyridin-3-yl]acetyl}octahydro-2H-pyrazino[1,2-a]pyrazin-3-yl]benzonitrile;

6-fluoro-2-methyl-3-[(3R,9aR)-8-{[5-(1H-tetrazol-1-yl)pyridin-2-yl]acetyl}octahydro-2H-pyrazino[1,2-a]pyrazin-3-yl]benzonitrile;

(3R)-3-methyl-6-[(3R,9aR)-8-{[6-(1H-tetrazol-1-yl)pyridin-3-yl]acetyl}octahydro-2H-pyrazino[1,2-a]pyrazin-3-yl]-3,4-dihydro-1H-isochromen-1-one;

2-fluoro-5-[(3R,9aR)-8-{[2-(1H-tetrazol-1-yl)pyrimidin-5-yl]acetyl}octahydro-2H-pyrazino[1,2-a]pyrazin-3-yl]benzonitrile;

(3R,9aS)-3-(3-cyano-4-fluoro-2-methylphenyl)-N-[6-(1H-tetrazol-1-yl)pyridin-3-yl]hexahydropyrazino[2,1-c][1,4]oxazine-8(1H)-carboxamide;

(3R,9aR)-3-(3-cyano-4-fluoro-2-methylphenyl)-N-[6-(1H-tetrazol-1-yl)pyridin-3-yl]hexahydropyrazino[2,1-c][1,4]oxazine-8(1H)-carboxamide;

(3R,9aR)-3-(3-cyano-4-fluoro-2-methylphenyl)-N-[5-(1H-tetrazol-1-yl)pyridin-2-yl]hexahydropyrazino[2,1-c][1,4]oxazine-8(1H)-carboxamide;

(3R,9aS)-3-(3-cyano-4-fluoro-2-methylphenyl)-N-[5-(1H-tetrazol-1-yl)pyridin-2-yl]hexahydropyrazino[2,1-c][1,4]oxazine-8(1H)-carboxamide;

(3R,9aR)-3-(3-cyano-4-fluoro-2-methylphenyl)-N-[4-methyl-6-(1H-tetrazol-1-yl)pyridin-3-yl]hexahydropyrazino[2,1-c][1,4]oxazine-8(1H)-carboxamide;

(3R,9aS)-3-(3-cyano-4-fluoro-2-methylphenyl)-N-[4-methyl-6-(1H-tetrazol-1-yl)pyridin-3-yl]hexahydropyrazino[2,1-c][1,4]oxazine-8(1H)-carboxamide;

(3S,9aR)-3-(3-cyano-4-fluoro-2-methylphenyl)-N-[4-methyl-6-(1H-tetrazol-1-yl)pyridin-3-yl]hexahydropyrazino[2,1-c][1,4]oxazine-8(1H)-carboxamide;

(3S,9aS)-3-(3-cyano-4-fluoro-2-methylphenyl)-N-[4-methyl-6-(1H-tetrazol-1-yl)pyridin-3-yl]hexahydropyrazino[2,1-c][1,4]oxazine-8(1H)-carboxamide;

or a pharmaceutically acceptable salt thereof.

\* \* \* \* \*